US010851339B1

(12) United States Patent
Belgrader et al.

(10) Patent No.: US 10,851,339 B1
(45) Date of Patent: **\*Dec. 1, 2020**

(54) INSTRUMENTS, MODULES, AND METHODS FOR IMPROVED DETECTION OF EDITED SEQUENCES IN LIVE CELLS

(71) Applicant: Inscripta, Inc., Boulder, CO (US)

(72) Inventors: Phillip Belgrader, Pleasanton, CA (US); Don Masquelier, Boulder, CO (US); Andrew Garst, Boulder, CO (US); Richard Fox, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,360

(22) Filed: Sep. 4, 2020

Related U.S. Application Data

(63) Continuation of application No. 16/930,269, filed on Jul. 15, 2020, now Pat. No. 10,801,008, which is a (Continued)

(51) Int. Cl.
*C12M 1/00* (2006.01)
*C12M 3/00* (2006.01)
*C12M 1/26* (2006.01)
*C12N 15/87* (2006.01)
*B01D 63/08* (2006.01)
(Continued)

(52) U.S. Cl.
CPC ............ *C12M 47/04* (2013.01); *C12M 23/44* (2013.01); *C12M 29/04* (2013.01); *C12M 33/00* (2013.01); *C12M 47/02* (2013.01); *C12N 15/87* (2013.01); *B01D 63/08* (2013.01); *B01D 69/06* (2013.01);
(Continued)

(58) Field of Classification Search
CPC .... B01D 63/08; B01D 63/082; B01D 63/084; B01D 63/088; B01D 69/06; B01D 71/02; B01D 71/028; B01D 2201/0407; B01D 2201/184; B01D 25/00; B01D 25/002; B01D 25/003; B01D 25/02; B01D 25/12; B01D 25/164; B01D 25/176; B01D 25/19; B01D 25/21; B01D 25/22; B01D 2313/04; B01D 2313/08; B01D 2313/086; B01D 2313/105; B01D 2313/20; B01D 2313/50; B01D 61/18; B01D 63/087; B01L 2200/0668; B01L 2300/0681; B01L 2300/0829; B01L 2300/0883; B01L 3/502707; B01L 3/502761; C12N 15/1003; C12N 15/102; C12N 15/87; C12M 1/12; C12M 47/04; C12M 47/02; C12M 29/04; C12M 23/44; C12M 33/00
See application file for complete search history.

(56) References Cited

U.S. PATENT DOCUMENTS

| | | | | |
|---|---|---|---|---|
| 6,022,742 | A | * | 2/2000 | Kopf ..................... B01D 61/32 210/791 |
| 2012/0184940 | A1 | * | 7/2012 | Ying ................... A61M 1/3403 604/508 |
| 2013/0005025 | A1 | * | 1/2013 | Church ................. C12N 15/87 435/285.1 |

\* cited by examiner

*Primary Examiner* — Pranav N Patel
(74) *Attorney, Agent, or Firm* — Sarah Brashears; Dianna L. DeVore

(57) ABSTRACT

The present disclosure provides instruments, modules and methods for improved detection of edited cells following nucleic acid-guided nuclease genome editing. The disclosure provides improved automated instruments that perform methods—including high throughput methods—for screening cells that have been subjected to editing and identifying cells that have been properly edited.

18 Claims, 52 Drawing Sheets

Related U.S. Application Data continuation of application No. 16/820,292, filed on Mar. 16, 2020, now Pat. No. 10,723,995, which is a continuation of application No. 16/597,826, filed on Oct. 9, 2019, now Pat. No. 10,633,626, which is a continuation of application No. 16/454,865, filed on Jun. 27, 2019, now Pat. No. 10,550,363, which is a continuation of application No. 16/399,988, filed on Apr. 30, 2019, now Pat. No. 10,533,152.

(60) Provisional application No. 62/735,365, filed on Sep. 24, 2018, provisional application No. 62/781,112, filed on Dec. 18, 2018, provisional application No. 62/779,119, filed on Dec. 13, 2018, provisional application No. 62/718,449, filed on Aug. 14, 2018.

(51) Int. Cl.
*B01D 71/02* (2006.01)
*B01D 69/06* (2006.01)

(52) U.S. Cl.
CPC ...... *B01D 71/02* (2013.01); *B01D 2201/0407* (2013.01)

Digital growth of E.coli in microwells
Low magnification

Darker microwells = growth

Top view of microwells
Medium magnification

Darker microwells = growth

Microwells with membrane removed
High magnification

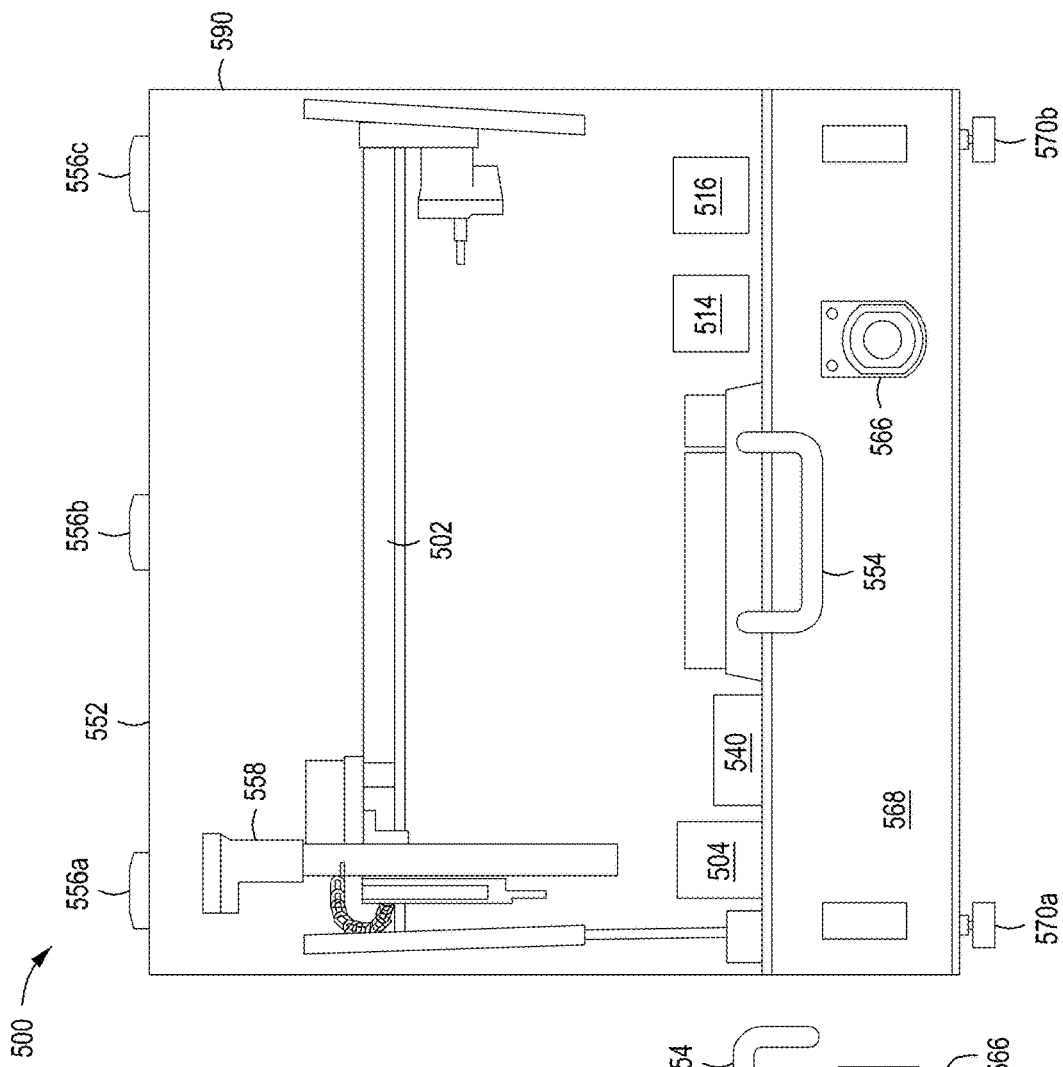
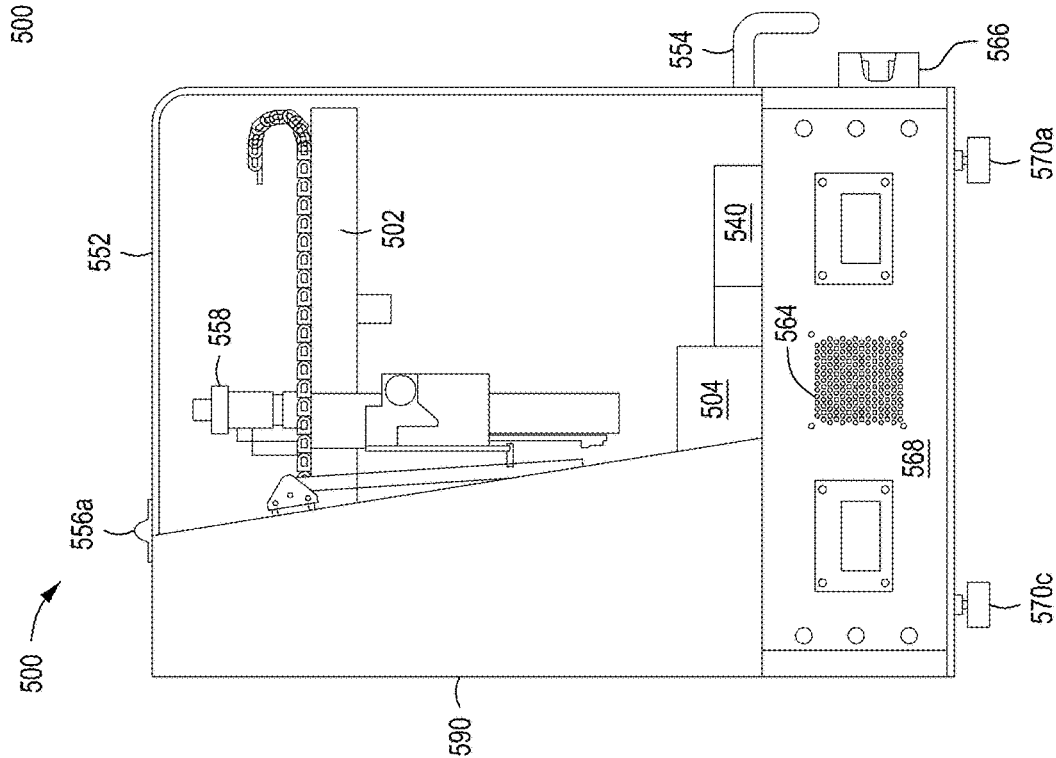
FIG. 5D
FIG. 5C

INSTRUMENTS, MODULES, AND METHODS FOR IMPROVED DETECTION OF EDITED SEQUENCES IN LIVE CELLS

RELATED APPLICATIONS

This application is a continuation of U.S. Ser. No. 16/930,269, filed 15 Jul. 2020; which is a continuation U.S. Ser. No. 16/820,292, filed 16 Mar. 2020, now U.S. Pat. No. 10,723,995; which is a continuation of U.S. Ser. No. 16/597,826, filed 9 Oct. 2019, now U.S. Pat. No. 10,633,626; which is a continuation of U.S. Ser. No. 16/454,865, filed 27 Jun. 2019, now U.S. Pat. No. 10,550,363; which is a continuation of U.S. Ser. No. 16/399,988, filed 30 Apr. 2019, now U.S. Pat. No. 10,533,152; which claims priority to U.S. Provisional Applications Nos. 62/718,449, filed 14 Aug. 2018; 62/735,365, filed 24 Sep. 2018; 62/781,112, filed 18 Dec. 2018; and 62/779,119, filed 13 Dec. 2018.

FIELD OF THE INVENTION

This invention relates to improved instruments, modules, and methods to screen, select and thus optimize detection of genome edits in live cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences, and hence gene function. The nucleases include nucleic acid-guided nucleases, which enable researchers to generate permanent edits in live cells. Current protocols employing nucleic acid-guided nuclease systems typically utilize constitutively-expressed nuclease components to drive high efficiency editing. However, in pooled or multiplex formats constitutive expression of editing components can lead to rapid depletion of edited cell types and selective enrichment of cells that have not been edited. This occurs in most cell types because only a small fraction (<1-5%) of cells survive the introduction of double-strand DNA (dsDNA) breaks and thus these cells contribute fewer numbers to viable cell counts in the resulting populations compared to unedited cells that did not experience a dsDNA break.

There is thus a need in the art of nucleic acid-guided nuclease gene editing for improved instruments, modules and methods for creating genome edits and for identifying and enriching cells that have been edited. The present invention satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following Detailed Description including those aspects illustrated in the accompanying drawings and defined in the appended claims.

The present disclosure provides instruments, modules and methods for tightly-regulated expression of nucleic acid-guided nuclease editing system components that allow for separation of the processes of transformation and genome editing. The compositions and methods employ inducible guide RNA (gRNA) constructs leading to increased observed transformation efficiency and automation-friendly control over the timing and duration of the editing process. Further, the instruments, modules, and methods enable automated high-throughput and extremely sensitive screening to identify edited cells. The instruments, modules, and methods take advantage of singulation or substantial singulation, where the term "singulation" in this context refers to the process of separating cells and growing them into clonally-isolated formats. The term "substantial singulation" refers to the process of separating cells in a population of cells into "groups" of 2 to 100, or 2 to 50, and preferably 2 to 10 cells. Singulation, followed by an initial period of growth, induction of editing, and growth normalization leads to enrichment of edited cells. Further, the instruments, modules, and methods described herein facilitate "cherry picking" of edited cell colonies, allowing for direct selection of edited cells. Singulation or substantial singulation assists in overcoming the growth bias from unedited cells that occurs under competitive growth regimes such as in bulk liquid culture. Indeed, it has been determined that removing growth rate bias via singulation or substantial singulation, induction and normalization improves the observed editing efficiency by up to 4× (from, e.g., 10% to 40% absolute efficiency at population scale) or more over conventional methods, and further that cherry-picking colonies using the methods described herein brings the observed editing efficiency up to 8× (from, e.g., 10% to 80% absolute efficiency at population scale) over conventional methods. Thus, the combination of singulation or substantial singulation, growth, induction of editing, and either normalization or cherry picking improves observed editing efficiency by up to 8× over conventional methods where singulation or substantial singulation, growth, induction of editing and either normalization or cherry picking are not employed.

One particularly facile module or device for singulation or substantial singulation is a solid wall device where cells are substantially isolated, grown in a clonal format, editing is induced, and either normalization or cherry picking is employed. The solid wall devices or modules and the use thereof are described in detail herein. The instruments, modules and methods in some embodiments allow for normalization of edited and unedited cell colonies. Normalization refers to growing colonies of cells whether edited or unedited—to terminal size; that is, growing the cells until the cells in the colonies enter senescence due to, e.g., nutrient exhaustion or constrained space for further growth. Normalization of cell colonies enriches for edited cells as edited cells get "equal billing" with unedited cells. Additionally, the instruments, modules, and methods facilitate "cherry picking" of colonies. Cherry picking allows for direct selection of edited cells by taking advantage of edit-induced growth delay in edited colonies. Cherry picking colonies using the instruments, modules, and methods described herein may more than double the observed editing efficiency as the result of singulation or substantial singulation.

Certain embodiments of the instruments, modules, and methods provide for enriching for edited cells during nucleic acid-guided nuclease editing, where the methods comprise transforming cells with one or more vectors comprising a promoter driving expression of a nuclease, a promoter driving transcription of a guide nucleic acid, and a donor DNA sequence, wherein one or both of the promoters driving transcription of the nuclease or guide nucleic acid is an inducible promoter; diluting the transformed cells to a cell concentration sufficient to substantially singulate the transformed cells on a substrate; growing the substantially singulated cells on the substrate; initiating editing by inducing the inducible promoter(s); and either 1) growing the cell colonies resulting from the induced cells to colonies of terminal size (e.g., normalizing the cell colonies) and harvesting the normalized cell colonies; or 2) monitoring the growth of cells colonies on the substrate then selecting slow-growing colonies.

A solid wall isolation, induction and normalization (SWIIN) module comprising: a retentate member comprising: an upper surface and a lower surface and a first and second end, an upper portion of a serpentine channel defined by raised areas on the lower surface of the retentate member, wherein the upper portion of the serpentine channel traverses the lower surface of the retentate member for about 50% to about 90% of the length and width of the lower surface of the retentate member; at least one port fluidically connected to the upper portion of the serpentine channel; and a reservoir cover at the first end of the retentate member; a permeate member disposed under the retentate member comprising: an upper surface and a lower surface and a first and second end, a lower portion of a serpentine channel defined by raised areas on the upper surface of the permeate member, wherein the lower portion of the serpentine channel traverses the upper surface of the permeate member for about 50% to about 90% of the length and width of the upper surface of the permeate member, and wherein the lower portion of the serpentine channel is configured to mate with the upper portion of the serpentine channel to form a mated serpentine channel; at least one port fluidically connected to the lower portion of the serpentine channel; and a first and second reservoir at the first end of the permeate member, wherein the first reservoir is fluidically connected to the at least one port in the retentate member and the second reservoir is fluidically connected to the at least one port in the permeate member; a perforated member comprising at least 25,000 perforations disposed under and adjacent to the retentate member; a filter disposed disposed under and adjacent to the perforated member and above and adjacent to the permeate member; and a gasket disposed on top of the reservoir cover of the retentate member, wherein the gasket comprises a reservoir access aperture and a pneumatic access aperture for each reservoir.

In some aspects of this embodiment, the permeate member further comprises ultrasonic tabs disposed on the raised areas on the upper surface of the permeate member and at the first and second end of the permeate member, the retentate member further comprises recesses for the ultrasonic tabs disposed in the raised areas on the lower surface and at the first and second end of the retentate member, the ultrasonic tabs are configured to mate with the recesses for the ultrasonic tabs, and the permeate member, retentate member, the perforated member and the filter are coupled together by ultrasonic welding. In other aspects of this embodiment, the permeate member, retentate member, the perforated member and the filter are coupled together by solvent bonding.

In some aspects, the first and second reservoirs are each fluidically coupled to a reservoir port into which fluids and/or cells flow from outside the SWIIN module into the first and second reservoirs and are each pneumatically coupled to a pressure source In some aspects of this embodiment, the SWIIN module further comprises a third and a fourth reservoir, wherein the third reservoir is 1) fluidically coupled to a second port in the retentate member, 2) fluidically coupled to a reservoir port into which fluids and/or cells flow from outside the SWIIN module into the third reservoir, and 3) pneumatically coupled to a pressure source; and wherein the fourth reservoir is 1) fluidically coupled to a second port in the permeate member, 2) fluidically coupled to a reservoir port into which fluids and/or cells flow from outside the SWIIN module into the fourth reservoir, and 3) pneumatically coupled to a pressure source.

In some aspects of this embodiment, the perforated member comprises at least 100,000 perforations, or at least 200,000 perforations, or at least 400,000 perforations.

In some aspects, the retentate member is fabricated from polycarbonate, cyclic olefin co-polymer, or poly(methyl methylacrylate).

In some aspects of the SWIIN module, a serpentine channel portion of each of the retentate and permeate members is from 75 mm to 350 mm in length, from 50 mm to 250 mm in width, and from 2 mm to 15 mm in thickness, and from 150 mm to 250 mm in length, from 100 mm to 150 mm in width, and from 4 mm to 8 mm in thickness.

In some aspects, the volume of the mated serpentine channel is from 4 to 40 mL, or from 6 mL to 30 mL, or from 10 mL to 20 mL.

In some aspects of the SWIIN module, there is a support on each end of the permeate member configured to elevate the permeate and retentate members above the at least one port in the in retentate member and the at least one port in the permeate member.

Certain embodiments of the SWIIN module further comprises imaging means to detect cells growing in the wells, and in some aspects, the imaging means is a camera with means to backlight the serpentine channel portion of the SWIIN. In some aspects, the SWIIN module is part of a SWIIN assembly comprising a heated cover, a heater, a fan, and a thermoelectric control device.

Also provided herein is an automated multi-module cell editing instrument comprising: a SWIIN module, a housing configured to house all of some of the modules; a receptacle configured to receive cells; one or more receptacles configured to receive nucleic acids; a growth module; a transformation module configured to introduce the nucleic acids into the cells; and a processor configured to operate the automated multi-module cell editing instrument based on user input and/or selection of a pre-programmed script.

In some aspects of this embodiment, the SWIIN module also serves as a recovery module and a curing module. In some aspects, the automated multi-module cell editing instrument further comprises a cell concentration module. In some aspects, the transformation module comprises a flow-through electroporation device.

Other embodiments provide a method for enriching edited cells during nucleic acid-guided nuclease editing comprising: transforming cells with one or more vectors comprising a promoter driving transcription of a coding sequence for a nuclease, a promoter driving transcription of a guide nucleic acid, and a DNA donor sequence; diluting the transformed cells to a cell concentration to substantially isolate the transformed cells on a substrate; growing the cells and initiating editing by inducing the inducible promoter driving transcription of the guide nucleic acid; growing the induced cells into colonies; and selecting induced cells from the substantially isolated colonies from the substrate, wherein the induced substantially isolated colonies are enriched for edited cells. In optional aspects of this method, the gRNA is under the control of an inducible promoter and 1) the cells are allowed to grow from 2-200 doublings after singulation, and 2) there is an inducing step after the growth step and prior to the editing step.

Other embodiments provide a method for enriching edited cells during nucleic acid-guided nuclease editing comprising: transforming cells with one or more vectors comprising comprising a promoter driving transcription of a coding sequence for a nuclease, a promoter driving transcription of a guide nucleic acid, and a DNA donor sequence; diluting the transformed cells to a cell concentration to substantially isolate the transformed cells on a substrate; growing the cells and allowing the cells to edit; growing the cells to form colonies; and selecting small colonies from the substantially isolated colonies from the substrate, wherein the induced substantially isolated colonies are enriched for edited cells. In optional aspects of this method, the gRNA is under the control of an inducible promoter and 1) the cells are allowed to grow from 2-200 doublings after singulation, and 2) there is an inducing step after the growth step and prior to the editing step.

Other embodiments provide a method for enriching edited cells during nucleic acid-guided nuclease editing comprising: transforming cells with one or more vectors comprising a promoter driving transcription of a coding sequence for a nuclease, a promoter driving transcription of a guide nucleic acid, and a DNA donor sequence; diluting the transformed cells to a cell concentration to substantially isolate the transformed cells on a first substrate; growing the cells and allowing the cells to edit; and growing the cells to form colonies of terminal size. In some aspects, the terminal-size cell colonies are pooled, and in some aspects, the terminal-size colonies are picked. In optional aspects of this method, the gRNA is under the control of an inducible promoter and 1) the cells are allowed to grow from 2-200 doublings after singulation, and 2) there is an inducing step after the growth step and prior to the editing step.

Thus in some embodiments there is provided a singulation assembly for a solid wall singulation or substantial singulation, growth, induction of editing, and normalization or cherry-picking ("solid wall insolation/induction/normalization module" or "SWIIN") module comprising: a retentate member comprising an upper surface and a lower surface, wherein the retentate member comprises at least one retentate distribution channel which traverses the retentate member from its upper surface to its lower surface and for most of the length of retentate member; wherein the lower surface of the retentate member comprises retentate ridges between which are retentate flow directors; wherein the retentate member further comprises one or more retentate member ports configured to supply cells and fluid to and remove cells and fluid from the retentate member; and wherein the retentate member ports are fluidically-connected to the retentate distribution channel and retentate flow directors; a perforated member with an upper surface and a lower surface, wherein the upper surface of the perforated member is positioned beneath and adjacent to the lower surface of the retentate member and wherein the perforated member comprises at least 25,000 perforations; a filter with an upper surface and a lower surface, wherein the upper surface of the filter is positioned beneath and adjacent to the lower surface of the perforated member and wherein the lower surface of the filter is positioned above and adjacent to an upper surface of a permeate member; a gasket surrounding the perforated member and the filter; and the permeate member comprising the upper surface and a lower surface, wherein the permeate member comprises at least one permeate distribution channel which traverses the permeate member from its lower surface to its upper surface and for most of the length of permeate member; wherein the upper surface of the permeate member comprises permeate ridges between which are permeate flow directors; wherein the permeate member further comprises one or more permeate member ports configured to supply fluid to and remove fluid from the permeate member; and wherein the permeate member ports are fluidically-connected to the permeate distribution channel and permeate flow directors; and means to couple the retentate member, perforated member, filter, gasket and permeate member.

In some aspects of the singulation assembly embodiment the means to couple the retentate member, perforated member, filter, gasket and permeate member comprises ultrasonic welding and in other aspects, the means comprises pressure sensitive adhesive, solvent bonding, mated fittings, or a combination of adhesives, welding, solvent bonding, and mated fittings; and other such fasteners and couplings. In some aspects of the singulation assembly, the perforated member comprises at least 50,000; 100,000; 150,000; 200,000, 250,000 perforations or more, and in some aspects, the SWIIN is a compound SWIIN and each part of the compound SWIIN comprises a perforated member with at least 50,000; 100,000; 150,000; 200,000, 250,000 perforations. In some aspects, the retentate and permeate members are fabricated from polycarbonate, cyclic olefin co-polymer, or poly(methyl methylacrylate); and in some aspects, the retentate and permeate members are from 75 mm to 350 mm in length, from 50 mm to 250 mm in width, and from 2 mm to 15 mm in thickness. In some aspects of the singulation assembly, the retentate and permeate members are from 150 mm to 250 mm in length, from 100 mm to 150 mm in width, and from 4 mm to 8 mm in thickness. In some aspects of the singulation assembly, there are two permeate distribution channels and/or two retentate distribution channels, and in some aspects the retentate distribution channels and or permeate distribution channels are approximately 150 mm in length and 1 mm in width. In some aspects, the retentate and/or permeate ridges are approximately 0.5 mm in height and 80 mm in length, and in some aspects, the retentate and/or permeate flow directors are approximately 5 mm across. In some aspects, the volume of the singulation assembly is from 15 mL to 100 mL.

Some embodiments of the disclosure provide a SWIIN module comprising the singulation assembly and further comprising: a reservoir assembly comprising at least two reservoirs wherein a first reservoir is 1) fluidically-coupled to at least one reservoir port into which fluids and/or cells flow from outside the SWIIN module into the first reservoir, 2) fluidically-coupled to a reservoir/channel port from which fluids and/or cells flow into the one or more retentate member ports; and 3) pneumatically-coupled to a pressure source; a second reservoir is 1) fluidically-coupled to at least one reservoir port into which fluids flow from outside the SWIIN module into the second reservoir, 2) fluidically-coupled to a reservoir/channel port from which fluids flow into the one or more permeate member ports; and 3) pneumatically-coupled to a pressure source; and a SWIIN cover. In some aspects of the SWIIN module embodiment, the SWIIN module further comprises two additional reservoirs wherein a first and third reservoir are 1) fluidically-coupled to at least two reservoir ports into which fluids and/or cells flow from outside the SWIIN module into the first and third reservoirs, 2) fluidically-coupled to a reservoir/channel port from which fluids and/or cells flow into the at least two retentate member ports; and 3) pneumatically-coupled to a pressure source; and a second and fourth reservoir are 1) fluidically-coupled to at least two reservoir ports into which fluids flow from outside the SWIIN module into the second and fourth reservoirs, 2) fluidically-coupled to a reservoir/ channel port from which fluids flow into the at least two permeate member ports; and 3) pneumatically-coupled to a pressure source.

In some aspects of the SWIIN module embodiment, the SWIIN cover comprises a reservoir cover portion of the SWIIN cover, and wherein the reservoir cover portion comprises 1) at least two reservoir access apertures, wherein the reservoir access apertures provide access to the reservoir ports, and 2) at least two pneumatic access apertures, wherein the pneumatic access apertures provide access to the at least two reservoirs and provide negative and positive pressure to the at least two reservoirs. In some aspects the SWIIN module is configured to monitor cell colony growth after inducing editing, and further comprises means for cherry picking slow growing cell colonies. In some aspects of the SWIIN module, editing is induced by an inducible promoter that is a temperature inducible promoter, and temperature to induce transcription of the nuclease and/or guide nucleic acid is provided to the SWIIN module by a Peltier device.

Other embodiments of the disclosure provide an automated multi-module cell editing instrument comprising: the SWIIN module; a housing configured to house all of some of the modules; a receptacle configured to receive cells; one or more receptacles configured to receive nucleic acids; a growth module; a transformation module configured to introduce the nucleic acids into the cells; and a processor configured to operate the automated multi-module cell editing instrument based on user input and/or selection of a pre-programmed script.

In some aspects of the automated multi-module cell editing instrument, the transformation module comprises a flow-through electroporation device; and in some aspects the automated multi-module cell editing instrument further comprises a cell concentration module. In some aspects the cell concentration module is a tangential flow filtration module. In some aspects a liquid handling system transfers liquids between the modules. And in some aspects, the automated multi-module cell processing system performs the processes of growing cells, concentrating and rendering the cells electrocompetent, transforming the cells with nucleic acid-guided nuclease editing components, singulating the transformed cells, inducing editing in the singulated cells, and growing and enriching the cells, all without human intervention.

In yet other embodiments, there is provided an automated multi-module cell editing instrument comprising: the SWIIN module; a housing configured to house all of some of the modules; a receptacle configured to receive cells; one or more receptacles configured to receive nucleic acids; a transformation module configured to introduce the nucleic acids into the cells; a cell concentration module; and a processor configured to operate the automated multi-module cell editing instrument based on user input and/or selection of a pre-programmed script. In some aspects of the automated multi-module cell processing instrument, and a liquid handling system to transfer reagents to and between the modules, and the SWIIN module. In some aspects the stand-alone, integrated, automated multi-module cell processing system comprises a growth module which comprising a rotating growth vial, a nucleic acid assembly module, or a reagent cartridge. And in some aspects, the automated multi-module cell processing system performs the processes of growing cells, concentrating and rendering the cells electrocompetent, transforming the cells with nucleic acid-guided nuclease editing components, singulating the transformed cells, inducing editing in the singulated cells, and growing and enriching the cells, all without human intervention. As with other embodiments, this embodiment of an automated multi-module cell editing instrument comprises a liquid handling system to transfer liquids between the modules.

In yet an additional embodiment, there is provided a method for enriching edited cells during nucleic acid-guided nuclease editing comprising: transforming cells with one or more vectors comprising an inducible promoter driving expression of a nuclease, an inducible promoter driving transcription of a guide nucleic acid, and a DNA donor sequence; diluting the transformed cells to a cell concentration to substantially singulate the transformed cells on a substrate; growing the cells on the substrate for 2-200 doublings; initiating editing by inducing the inducible promoter(s) driving transcription of the guide nucleic acid and nuclease; growing the induced cells into colonies; and selecting induced cells from the substantially singulated colonies from the substrate, wherein the induced substantially singulated colonies are enriched for edited cells.

In some aspects of this method embodiment, the inducible driving transcription the guide nucleic acid is a pL promoter, and the inducible promoter driving expression of the nuclease is a pL promoter. In some aspects, all of the nuclease, guide nucleic acid and DNA donor sequence are on the same vector. In yet other aspects, the nuclease is on a first vector and the guide nucleic acid and DNA donor sequence are on a second vector and two transforming steps are required. In some aspects, the DNA donor sequence further comprises a PAM-altering sequence, and in some aspects, the one or more vectors each further comprise a gene for a selectable marker. In some aspects, the method further comprises adding selective agents to medium of the substrate to select for the selectable marker(s) on the one or more vectors. In some aspects, the induced substantially singulated colonies selected are small colonies, yet in other aspects, the cells are grown into colonies of terminal size.

Also presented in one method embodiment is a method for enriching edited cells during nucleic acid-guided nuclease editing comprising: transforming cells with one or more vectors comprising a promoter driving expression of a nuclease, an inducible promoter driving transcription of a guide nucleic acid, and a DNA donor sequence; diluting the transformed cells to a cell concentration to substantially singulate the transformed cells on a first substrate; growing the cells to form colonies on the first substrate; selecting cells from the substantially singulated colonies from the first substrate and arraying the selected cells on a second substrate; making a replica of the second substrate forming a third substrate; growing and inducing cells on the second substrate; growing and inducing cells on the third substrate under conditions that do not allow genome repair; comparing cell growth on the second and third substrates; and selecting cells that grow on the second substrate but do not grow on the third substrate.

In some aspects of the method embodiments, the promoter driving transcription the guide nucleic acid is a pL promoter, and in some aspects, the promoter driving expression of the nuclease is an inducible promoter. In some aspects, the inducible promoter driving expression of each of the guide nucleic acid and the nuclease is the same inducible promoter, and it is a pL promoter. In some aspects, the DNA donor sequence further comprises a PAM-altering sequence, and the method further comprises adding selective agents to medium of the first substrate to select for the one or more vectors. In some aspects, the guide nucleic acid is a guide RNA, and in some aspects the cells are bacteria cells and the engine vector further comprises a recombineering system.

Yet another embodiment of a method provides a method for enriching edited cells during nucleic acid-guided nuclease editing comprising: transforming cells with one or more vectors comprising a promoter driving expression of a nuclease, an inducible promoter driving transcription of a guide nucleic acid, and a DNA donor sequence; diluting the transformed cells to a cell concentration to substantially singulate the transformed cells on a substrate; growing the cells on the substrate for between 2 and 200 doublings; initiating editing by inducing the inducible promoter and growing the cells to form colonies; and selecting small colonies from the substantially singulated colonies from the substrate, wherein the induced substantially singulated colonies are enriched for edited cells.

And yet an additional embodiment provides a method for enriching edited cells during nucleic acid-guided nuclease editing comprising: transforming cells with one or more vectors comprising a promoter driving expression of a nuclease, an inducible promoter driving transcription of a guide nucleic acid, and a DNA donor sequence; diluting the transformed cells to a cell concentration to substantially singulate the transformed cells on a first substrate; growing the cells on the first substrate for between 2 and 200 doublings; initiating editing by inducing the inducible promoter; and growing the cells to form colonies of terminal size. Some aspects of this embodiment further comprise pooling the terminal-size colonies, and some aspects of this embodiment further comprise picking the terminal-size colonies.

These aspects and other features and advantages of the invention are described below in more detail.

BRIEF DESCRIPTION OF THE FIGURES

FIG. 2B depicts a protocol for functional deconvolution of the editing process, either by arraying cells in 96-well plates containing different media or by arraying cells on a culture dish containing different media. FIG. 2C depicts a protocol for picking colonies from a culture dish, arraying the colonies on a 96-well plate, then performing functional deconvolution. FIG. 2E depicts a protocol for cherry picking, and FIG. 2F depicts a protocol used for confirming that cherry-picking is extremely effective for selecting for edited cells.

FIGS. 4AA and 4BB depict compound SWIIN modules comprising two (FIG. 4AA) or four (FIG. 4BB) singulation assemblies. FIG. 4CC is an exemplary pneumatic architecture diagram for the SWIIN module described in relation to FIGS. 4A-4Z. Finally, FIG. 4DD is an exemplary pneumatic architecture diagram for a double layer SWIIN.

FIGS. 5A-5D depict a stand-alone, integrated, automated multi-module instrument and components thereof, including a singulation module, with which to generate and identify edited cells.

DETAILED DESCRIPTION

Figure 1A:
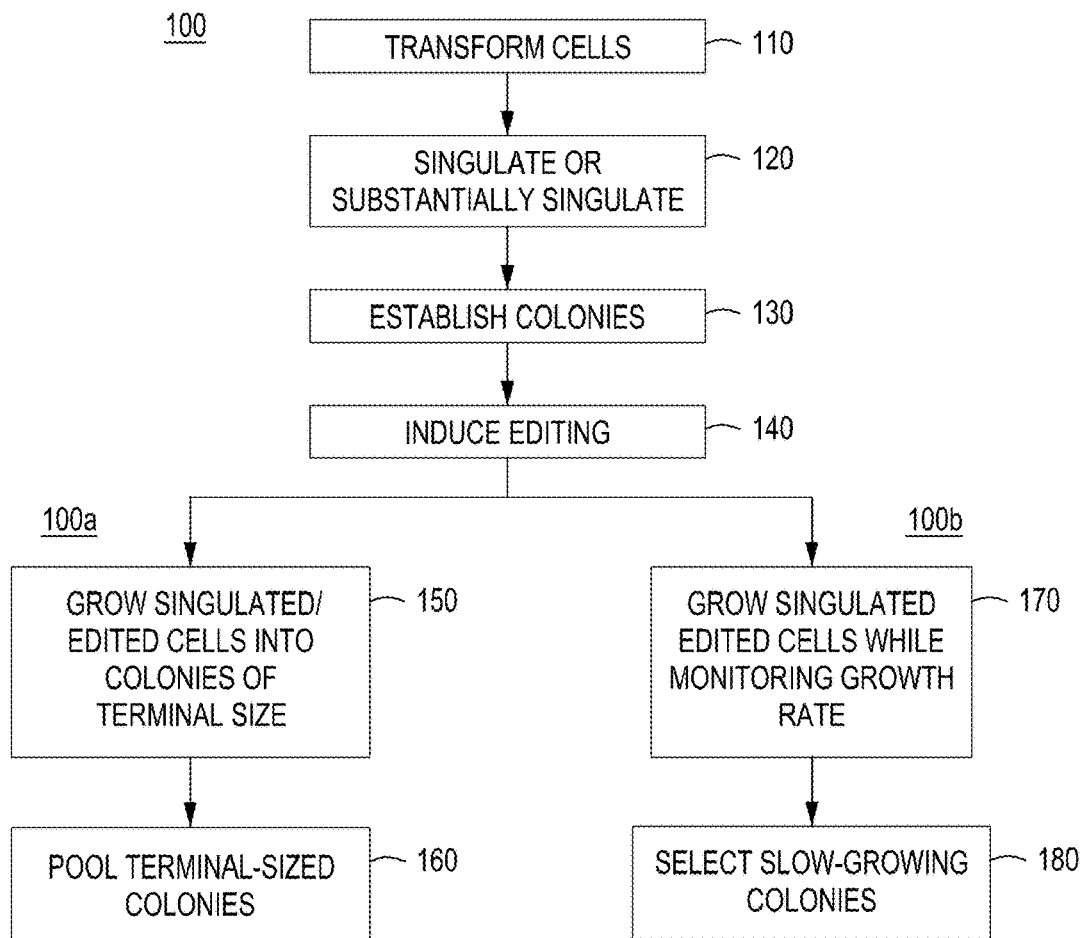
FIG. 1A is a simplified flow chart of exemplary methods for enriching and selecting edited cells.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., eds., *Genome Analysis: A Laboratory Manual Series* (Vols. I-IV) (1999); Weiner, Gabriel, Stephens, eds., *Genetic Variation: A Laboratory Manual* (2007); Dieffenbach, Dveksler, eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); Stryer, Biochemistry (4th Ed.) W.H. Freeman, New York N.Y. (1995); Gait, "*Oligonucleotide Synthesis: A Practical Approach*" (1984), IRL Press, London; Nelson and Cox, *Lehninger, Principles of Biochemistry* $3^{rd}$ Ed., W. H. Freeman Pub., New York, N.Y. (2000); Berg et al., Biochemistry, $5^{th}$ Ed., W.H. Freeman Pub., New York, N.Y. (2002); Doyle & Griffiths, eds., Cell and Tissue Culture: Laboratory Procedures in Biotechnology, Doyle & Griffiths, eds., John Wiley & Sons (1998); G. Hadlaczky, ed. *Mammalian Chromosome Engineering—Methods and Protocols*, Humana Press (2011); and Lanza and Klimanskaya, eds., *Essential Stem Cell Methods*, Academic Press (2011), all of which are herein incorporated in their entirety by reference for all purposes. CRISPR-specific techniques can be found in, e.g., Appasani and Church, *Genome Editing and Engineering From TALENs and CRISPRs to Molecular Surgery* (2018); and Lindgren and Charpentier, CRISPR: *Methods and Protocols* (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," and/or "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Additionally, the terms "approximately," "proximate," "minor," and similar terms generally refer to ranges that include the identified value within a margin of 20%, 10% or preferably 5% in certain embodiments, and any values therebetween.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, features and procedures well known to those skilled in the art have not been described in order to avoid obscuring the invention.

The term "complementary" as used herein refers to Watson-Crick base pairing between nucleotides and specifically refers to nucleotides that are hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. For example, the donor DNA will have at least one region of sequence homology (e.g., one homology arm) to the genomic target locus. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 35, 40, 50, 75, 100, 150, 200, 300, 400, or 500 or more base pairs of the target sequence. The donor DNA optionally further includes an alteration to the target sequence, e.g., a PAM mutation, that prevents binding of the nuclease at the PAM or spacer in the target sequence after editing has taken place.

As used herein, "enrichment" refers to enriching for edited cells by singulation or substantial singulation of cells, initial growth of cells into cell colonies, inducing editing, and growing the cell colonies into terminal-sized colonies (e.g., saturation or normalization of colony growth). As used herein, "cherry picking" or "selection of edited cells" refers to the process of using a combination of singulation or substantial singulation, initial growth of cells into colonies, induction of editing, then using cell growth-measured by colony size, concentration of metabolites or waste products, or other characteristics that correlate with the rate of growth of the cells—to select for cells that have been edited based on editing-induced growth delay.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive, or inducible. In the methods described herein the promoters driving transcription of the gRNAs is inducible.

As used herein the term "selectable marker" refers to a gene introduced into a cell, which confers a trait suitable for artificial selection. General use selectable markers are well-known to those of ordinary skill in the art. Drug selectable markers such as ampilcillin/carbenicillin, kanamycin, chloramphenicol, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine);

human glutathione S-transferase alpha (GSTA1; conjugates glutathione to the stem cell selective alkylator busulfan; chemoprotective selectable marker in CD34+ cells); CD24 cell surface antigen in hematopoietic stem cells; rhamnose; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by MAb-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

As used herein, the terms "singulation" or "singulate" mean to separate individual cells so that each cell (and the colonies formed from each cell) will be separate from other cells; for example, a single cell in a single microwell, or 100 single cells each in its own microwell. "Singulation" or "singulated cells" result in one embodiment, from a Poisson distribution in arraying cells. The terms "substantially singulated", "largely singulated", and "substantial singulation" mean cells are largely separated from one another, in small groups or batches. That is, when 2, 3, 4, 5, 6, 7, 8, 9, 10, 11, 12, 13, 14, 15, 16, 17, 18, 19, 20, 21, 22, 23, 24, 25, 26, 27, 28, 29, 30 or up to 50—but preferably 10 or less cells—are delivered to a microwell. "Substantially singulated" or "largely singulated" result, in one embodiment, from a "substantial Poisson distribution" in arraying cells. With more complex libraries of edits—or with libraries that may comprise lethal edits or edits with greatly-varying fitness effects—it is preferred that cells be singulated via a Poisson distribution.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, YACs, BACs, mammalian synthetic chromosomes, and the like. As used herein, the phrase "engine vector" comprises a coding sequence for a nuclease—optionally under the control of an inducible promoter—to be used in the nucleic acid-guided nuclease systems and methods of the present disclosure. The engine vector may also comprise, in a bacterial system, the λ Red recombineering system or an equivalent thereto, as well as a selectable marker. As used herein the phrase "editing vector" comprises a donor nucleic acid, including an alteration to the target sequence which prevents nuclease binding at a PAM or spacer in the target sequence after editing has taken place, and a coding sequence for a gRNA under the control of an inducible promoter. The editing vector may also comprise a selectable marker and/or a barcode. In some embodiments, the engine vector and editing vector may be combined; that is, the contents of the engine vector may be found on the editing vector.

Inducible Editing in Nucleic Acid-Guided Nuclease Genome Systems Generally

The present disclosure provides instruments, modules and methods for nucleic acid-guided nuclease genome editing that provide 1) enhanced observed editing efficiency of nucleic acid-guided nuclease editing methods, and 2) improvement in screening for and detecting cells whose genomes have been properly edited, including high-throughput screening techniques. In current protocols employing nuclease systems, constitutively-expressed nuclease components typically are used to drive high-efficiency editing. However, in pooled or multiplex formats, constitutive expression of editing components can lead to selective enrichment of cells that are not edited due to the lack of double-strand DNA breaks that occur during editing. Moreover, constitutively-expressed nucleic acid-guided nuclease components (e.g., the nuclease and guide nucleic acid) expose the freshly-transformed, physiologically fragile cells to editing immediately, resulting in compromised viability. Presented herein are tools for tightly-regulated expression of nucleic acid-guided nuclease editing system components including tight regulation of transcription of the guide nucleic acid and, optionally and preferably, the nuclease (or the nuclease and, optionally and preferably, the guide nucleic acid)—allowing for separation of the processes of transformation and editing. Additionally, the methods described herein take advantage of singulation (separating cells and growing them into clonal colonies) and either normalization of cell colonies or cherry picking of slow-growing colonies. Singulation or substantial singulation, initial growth, followed by induction of editing and normalization overcomes growth bias from unedited cells, and substituting cherry picking for normalization allows for direct selection of edited cells. The instruments, modules, and methods may be applied to all cell types including, archaeal, prokaryotic, and eukaryotic (e.g., yeast, fungal, plant and animal) cells.

The instruments, modules, and methods described herein employ editing cassettes comprising a guide RNA (gRNA) sequence covalently linked to a donor DNA sequence where the gRNA is under the control of an inducible promoter the editing cassettes are CREATE cassettes; see U.S. Pat. No. 9,982,278, issued 29 May 2019 and Ser. No. 10/240,167, issued 26 Mar. 2019; Ser. No. 10/266,849, issued 23 Apr. 2019; and US Pub. Ser. No. 15/948,785, filed 9 Apr. 2018; Ser. No. 16/275,439, filed 14 Feb. 2019; and Ser. No. 16/275,465, filed 14 Feb. 2019, all of which are incorporated by reference in their entirety), The editing cassettes provide increased transformation efficiency and control over the timing and duration of the editing process. The disclosed methods allow for cells to be transformed, substantially singulated, grown for several doublings, after which editing in the cells is induced. The combination of process effectively negates the effect of unedited cells taking over the cell population. The combination of substantially singulating cells, then allowing for initial growth followed by inducing transcription of the gRNA (anchor nuclease) and either normalization of cell colonies or cherry picking cells leads to 2-250×, 10-225×, 25-200×, 40-175×, 50-150×, 60-100×, or 50-100× gains in identifying edited cells over prior art methods and allows for generation of arrayed or pooled edited cells comprising cell libraries with edited genomes. Additionally, the methods may be leveraged to create iterative editing systems to generate combinatorial libraries of cells with two to many edits in each cellular genome. The inducible gRNA constructs (and/or inducible nuclease constructs) and methods for using "pulsed" exposure of the cells to active editing components 1) allow for the cells to be arrayed (e.g., largely singulated.) prior to initiation of the editing procedure, 2) decrease off-target activity, 3) allow for identification of rare cell edits, and 4) enrich for edited cells or permit high-throughput screening applications to identify editing activity using cell growth as a proxy for editing, by, e.g., measuring optical density, colony size, or metabolic by-products or other characteristics thereby enriching the edited cell population.

The instruments, compositions and methods described herein improve CRISPR editing systems in which nucleic acid-guided nucleases (e.g., RNA-guided nucleases) are used to edit specific target regions in an organism's genome. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences or a single guide nucleic acid that does not require a tracrRNA. In the compositions and methods described herein, if two separate RNA molecules are combined to function as a guide nucleic acid, at least one of the guide nucleic acid components is under the control of an inducible promoter. If a single guide nucleic acid is employed, the single guide nucleic acid is under the control of an inducible promoter.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA is encoded by a DNA sequence on a polynucleotide molecule such as a plasmid, linear construct, or resides within an editing cassette and is preferably under the control of an inducible promoter.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence (the portion of the guide nucleic acid that hybridizes with the target sequence) is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be expressed from a plasmid or vector and comprises both the guide sequence and the scaffold sequence as a single transcript under the control of an inducible promoter. Alternatively, the guide nucleic acids may be transcribed from two separate sequences, at least one of which is under the control of an inducible promoter. The guide nucleic acid can be engineered to target a desired target DNA sequence by altering the guide sequence so that the guide sequence is complementary to the target DNA sequence, thereby allowing hybridization between the guide sequence and the target DNA sequence. In general, to generate an edit in the target DNA sequence, the gRNA/nuclease complex binds to a target sequence as determined by the guide RNA, and the nuclease recognizes a protospacer adjacent motif (PAM) sequence adjacent to the target sequence. The target sequence can be any polynucleotide (either DNA or RNA) endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) and/or a non-coding sequence (e.g., a regulatory polynucleotide, an intron, a PAM, or "junk" DNA).

The guide nucleic acid may be part of an editing cassette that encodes the donor nucleic acid; that is, the editing cassette may be a CREATE cassette (see, e.g U.S. Pat. No. 9,982,278, issued 29 May 2019 and Ser. No. 10/240,167, issued 26 Mar. 2019; Ser. No. 10/266,849, issued 23 Apr. 2019; and U.S. Pub. Ser. No. 15/948,785, filed 9 Apr. 2018; Ser. No. 16/275,439, filed 14 Feb. 2019; and Ser. No. 16/275,465, filed 14 Feb. 2019, all of which are incorporated by reference in their entirety). The guide nucleic acid and the donor nucleic acid may be and typically are under the control of a single (in this case, preferably inducible) promoter. Again, note that either the guide nucleic acid or the nuclease must be under the control of an inducible promoter, and in some embodiments and preferably, both the guide nucleic acid and nuclease are under the control of an inducible promoter. Indeed, it is important that the inducible promoter(s) controlling transcription of the guide nucleic acid and/or—most preferably, and—the nuclease are tightly controlled. In particular, it is important that the nuclease activity be controlled to avoid significant bias and loss in efficiency prior to singulation and singulated outgrowth. Thus, the extent to which the editing machinery is able to achieve "OFF" status is important independent of the singulation or substantial singulation process. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid. In other cases, the donor nucleic acid can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments and preferably, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, and increase the versatility of a nucleic acid-guided nuclease. In certain embodiments, the genome editing of a target sequence both introduces a desired DNA change to a target sequence, e.g., the genomic DNA of a cell, and removes, mutates, or renders inactive a proto-spacer (PAM) region in the target sequence; that is, the donor DNA often includes an alteration to the target sequence that prevents binding of the nuclease at the PAM in the target sequence after editing has taken place. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the methods disclosed herein allow for identification of edited cells in a large background of unedited cells, the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease component of the nucleic acid-guided nuclease editing system, the polynucleotide sequence encoding the nucleic acid-guided nuclease can be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/Cpfl, MAD2, or MAD7 or other MADzymes. As with the guide nucleic acid, the nuclease may be encoded by a DNA sequence on a vector (e.g., the engine vector) and be under the control of a constitutive or, preferably, an inducible promoter. Again, at least one of and preferably both of the nuclease and guide nucleic acid are under the control of an inducible promoter. In some embodiments, the sequence encoding the nuclease is under the control of an inducible promoter, and the inducible promoter may be separate from but the same as the inducible promoter controlling transcription of the guide nucleic acid; that is, a separate inducible promoter drives the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter. Again, note that it is important that the inducible promoter(s) controlling transcription of the guide nucleic acid and the nuclease are tightly controlled. In particular, it is important that the nuclease activity be controlled to avoid significant bias and loss in efficiency prior to singulation and the singulated outgrowth process. Thus, the extent to which the editing machinery is able to achieve "OFF" status is important independent of the singulation or substantial singulation process.

Another component of the nucleic acid-guided nuclease system is the donor nucleic acid. In some embodiments, the donor nucleic acid is on the same polynucleotide (e.g., vector or editing (CREATE) cassette) as the guide nucleic acid. The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 30, 35, 40, 45, 50, 75, 100, 150, 200, 500, 1000, 2500, 5000 nucleotides or more in length. In certain preferred aspects, the donor nucleic acid can be provided as an oligonucleotide of between 40-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 10, 15, 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where the guide nucleic acids are under the control of separate, different promoters, separate, like promoters, or where all guide nucleic acid/donor nucleic acid pairs are under the control of a single promoter. (See, e.g., U.S. Ser. No. 16/275,465, filed 14 Feb. 2019, drawn to multiple CREATE cassettes.) The promoter driving transcription of the gRNA and the donor nucleic acid (or driving more than one gRNA/donor nucleic acid pair) is preferably an inducible promoter and the promoter driving transcription of the nuclease is optionally an inducible promoter as well. That is, at least one of—and preferably both—the guide nucleic acid (gRNA) and the nuclease is under control of an inducible promoter.

Inducible editing is advantageous in that substantially or largely singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells (e.g., the process of "normalization" or growing colonies to "terminal size"; see, e.g., FIG. 1B described infra).

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

Also, as described above, the donor nucleic acid may comprise—in addition to the at least one mutation relative to a target sequence—one or more PAM sequence alterations that mutate, delete or render inactive the PAM site in the target sequence. The PAM sequence alteration in the target sequence renders the PAM site "immune" to the nucleic acid-guided nuclease and protects the target sequence from further editing in subsequent rounds of editing if the same nuclease is used.

The editing cassette also may comprise a barcode. A barcode is a unique DNA sequence that corresponds to the donor DNA sequence such that the barcode can identify the edit made to the corresponding target sequence. The barcode can comprise greater than four nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid design is associated with a different barcode, or, alternatively, each different cassette molecule is associate with a different barcode.

Additionally, in some embodiments, an expression vector or cassette encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

Exemplary Workflows for Editing, Enrichment, and Selection of Edited Cells

The methods described herein provide enhanced observed editing efficiency of nucleic acid-guided nuclease editing methods as the result of a combination of singulation or substantial singulation, initial cell growth, induction of editing, and either normalization of the resulting cell colonies or cherry picking slow-growing cell colonies. The combination of the singulation or substantial singulation, initial cell growth, induction of editing and normalization processes overcomes the growth bias in favor of unedited cells—and the fitness effects of editing (including differential editing rates)—thus allowing all cells "equal billing" with one another. The combination of singulation or substantial singulation, initial cell growth, induction of editing, and cherry picking allows for direct selection of edited colonies of cells. The result of the methods described herein is that even in nucleic acid-guided nuclease systems where editing is not optimal—such as in systems where non-canonical PAMs are targeted—there is an increase in the observed editing efficiency; that is, edited cells can be identified even in a large background of unedited cells. Observed editing efficiency can be improved up to 80% or more. Singulating, initial growth, induction of editing, and normalization of cell colonies or cherry picking of cell colonies leads to 2-250×, 10-225×, 25-200×, 40-175×, 50-150×, 60-100×, or 5-100× gains in identifying edited cells over prior art methods and allows for the generation of arrayed or pooled edited cells comprising genome libraries. Additionally, the instruments, modules and methods may be leveraged to create iterative editing systems to generate combinatorial libraries, identify rare cell edits, and enable high-throughput enrichment applications to identify editing activity.

FIG. 1A shows simplified flow charts for two alternative exemplary methods 100a and 100b for singulating cells for enrichment (100a) and for cherry picking (100b). Looking at FIG. 1A, method 100 begins by transforming cells 110 with the components necessary to perform nucleic acid-guided nuclease editing. For example, the cells may be transformed simultaneously with separate engine and editing vectors; the cells may already be transformed with an engine vector expressing the nuclease (e.g., the cells may have already been transformed with an engine vector or the coding sequence for the nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell 110. These delivery systems include the use of yeast systems, lipofection systems, microinjection systems, biolistic systems, virosomes, liposomes, immunoliposomes, polycations, lip-id:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of interest, particularly in the context of an automated multi-module cell editing instrument is the use of electroporation, particularly flow-through electroporation (either as a stand-alone instrument or as a module in an automated multi-module system) as described in, e.g., U.S. Ser. No. 16/147,120, filed 28 Sep. 2018; Ser. No. 16/147,353, filed 28 Sep. 2018; Ser. No. 16/147,865, filed 30 Sep. 2018; and Ser. No. 16/147,871, filed 30 Sep. 2018. If the solid wall singulation or substantial singulation/growth/induction of editing and normalization module is one module in an automated multi-module cell editing instrument as described herein infra, the cells are likely transformed in an automated cell transformation module.

After the cells are transformed with the components necessary to perform nucleic acid-guided nuclease editing, the cells are substantially or largely singulated 120; that is, the cells are diluted (if necessary) in a liquid culture medium so that the cells, when delivered to a substrate for singulation, are substantially separated from one another and can form colonies that are substantially separated from one another. For example, if a solid wall device is used (described infra in relation to FIGS. 3A-3E and 4A-4CC), the cells are diluted such that when delivered to the solid wall device the cells fill the microwells of the solid wall device in a Poisson or substantial Poisson distribution. In one example (illustrated in FIG. 3A), singulation is accomplished when an average of ½ cell is delivered to each microwell; that is, where some microwells contain one cell and other microwells contain no cells. Alternatively, a substantial Poisson distribution of cells occurs when two to several (2, 3, 4, 5, 6, 7, 8, 9, 10, 11, 12, 13, 14, 15, 16, 17, 18, 19, 20, 21, 22, 23, 24, 25, 26, 27, 28, 29, 30 or up to 50, but preferably 10 or less, or preferably 5 or less) cells are delivered to a microwell (illustrated in FIG. 3B).

Once the cells have been substantially or largely singulated 120, the cells are allowed to grow to, e.g., between 2 and 130, or between 5 and 120, or between 10 and 100 doublings, establishing clonal colonies 140. After colonies are established, editing is induced 130, e.g., where one or more inducible promoters driving transcription of one or both of the gRNA and the nuclease (preferably both), as well as, e.g., the λ red recombination system components in bacterial systems. For an exemplary inducible system, see FIG. 1C described in detail infra. Once editing is complete, in enrichment method 100a the cells are grown into colonies of terminal size 150; that is, the colonies arising from the substantially or largely singulated cells are grown into colonies to a point where cell growth has peaked and is normalized or saturated for both edited and unedited cells. Normalization occurs as the nutrients in the medium around a growing cell colony are depleted and/or cell growth fills the microwells and further growth is physically constrained. The terminal-size colonies are pooled 160 by, e.g., scraping the colonies off a plate comprising solid medium or other substrate or by flushing clonal cell colonies from microwells in a solid wall device or module to pool the cells from the normalized cell colonies. Again, because singulation or substantial singulation overcomes growth bias from unedited cells or cells exhibiting fitness effects as the result of edits made, singulation or substantial singulation, initial growth, induction of editing, and normalization alone enriches the total population of cells with cells that have been edited; that is, singulation or substantial singulation combined with initial cell growth, induced editing and normalization (e.g., growing colonies to terminal size) allows for high-throughput enrichment of edited cells.

Method 100b shown in FIG. 1A is similar to the method 100a in that cells of interest are transformed 110 with the components necessary to perform nucleic acid-guided nuclease editing. As described above, the cells may be transformed simultaneously with both the engine and editing vectors, the cells may already be expressing the nuclease (e.g., the cells may have already been transformed with an engine vector or the coding sequence for the nuclease may be stably integrated into the cellular genome) such that only the editing vector needs to be transformed into the cells, or the cells may be transformed with a single vector comprising all components required to perform nucleic acid-guided nuclease genome editing. Further, if the singulation or substantial singulation of cells, initial cell growth, induced editing, and either normalization or cherry-picking module ("solid wall isolation/induction/normalization module" or "SWIIN") is one module in an automated multi-module cell editing instrument, cell transformation may be performed in an automated transformation module as described in relation to FIGS. 8A-8E below.

After the cells are transformed 110 with the components necessary to perform nucleic acid-guided nuclease editing, the cells are diluted (if necessary) in liquid medium so that the cells, when delivered to a singulation device or module, are separated from one another and can form colonies that are separated from one another. For example, if a solid wall device is used (described in relation to FIGS. 3A-3E and 4A-4CC) the cells are diluted such that when delivered to the solid wall device, the cells fill the microwells of the solid wall device in a Poisson or substantial Poisson distribution.

Once the cells have been substantially or largely singulated 120, the cells grown to, e.g., between 2 and 150, or between 5 and 120, or between 10 and 100 doublings, establishing clonal colonies 130. After colonies are established, editing is induced 140 by, e.g., activating inducible promoters that control transcription of at least one of the gRNA and nuclease (as described above, preferably both), and, in the case of bacteria, a recombineering system. Once editing is induced 140, many of the edited cells in the clonal colonies die due to the double-strand DNA breaks that occur during the editing process; however, in a percentage of edited cells, the genome is edited and the double-strand break is properly repaired. When allowed to recover, these edited cells start growing and re-establish cell populations within each isolated partition or colony; however, the growth of edited colonies tends to lag behind the growth of clonal colonies where an edit has not taken place (e.g., cell "escapees"). If growth of these colonies is monitored 170, the small or slow-growing colonies (edited cells) may be identified and then selected or cherry picked 180 based on the observable size differentials of the colonies.

Figure 1B:
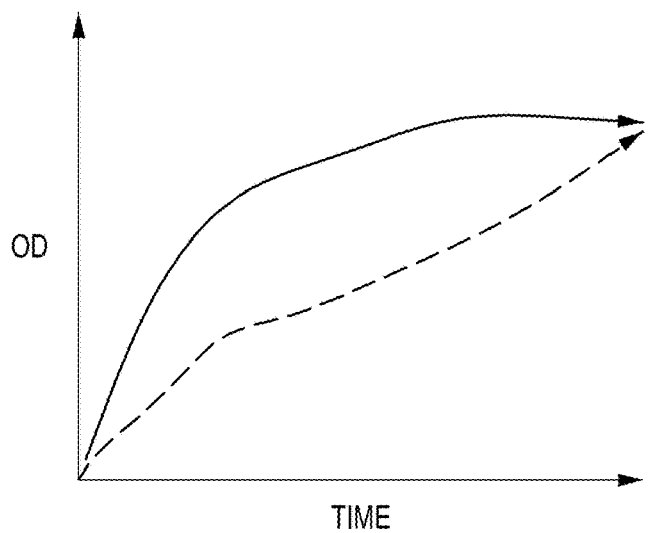
FIG. 1B is a plot of optical density vs. time showing the growth curves for edited cells (dotted line) and unedited cells (solid line).

FIG. 1B is a plot of OD versus time for unedited cells (solid line) versus edited cells (dashed line). FIG. 1B shows how normalization of edited and non-edited colonies takes place. Note that the OD (e.g., growth) of the edited cells lags behind the unedited cells initially, but eventually catches up due, e.g., to unedited cells exhausting the nutrients in the medium, becoming physically constrained within a microwell or other confined growth area (such as a droplet), or otherwise exiting log-phase growth. The cell colonies are allowed to grow long enough for the growth of the edited colonies to catch up with (approximate the size of, e.g., number of cells in) the unedited colonies.

Figure 1C:
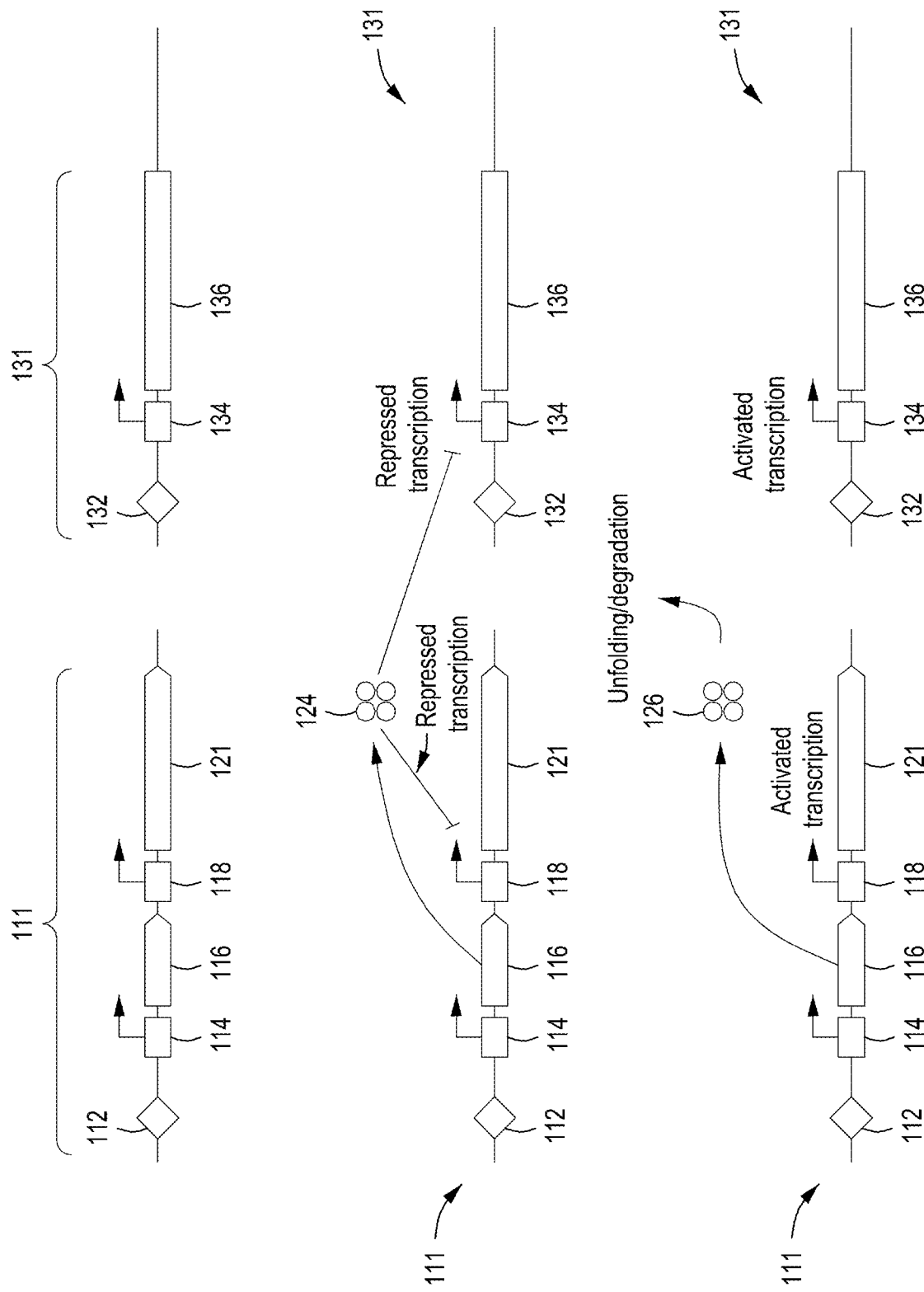
FIG. 1C depicts an exemplary inducible expression system for regulating gRNA and/or nuclease transcription.

FIG. 1C depicts an exemplary inducible expression system—in this example, the pL inducible system—for regulating gRNA activity. At the top of FIG. 1C there is shown a portion of an exemplary engine vector 111 comprising an origin of replication 112, a promoter 114 driving expression of the c1857 repressor gene 116, and a first pL promoter 118 driving expression of a nuclease 121. At the top of FIG. 1C there is also seen a portion of an exemplary editing vector 131, comprising an origin of replication 132, and a second pL promoter 134 driving transcription of an editing cassette 136 (e.g., a CREATE cassette) which includes a coding sequences for both a gRNA and a donor DNA. The middle illustration of FIG. 1C depicts the product 124 of the c1857 repressor gene 116 on the engine vector 111 actively repressing the first pL promoter 118 driving transcription of the nuclease 121 and the second pL promoter 134 driving transcription of the editing cassette 136 on the editing vector 131. Finally, the bottom illustration of FIG. 1C depicts the protein product 126 of the c1857 repressor gene 116 on the engine vector 111 unfolding/degrading due to increased temperature. The unfolded or degraded protein product 126 cannot bind first pL promoter 118 or second pL promoter 134; thus, pL promoter 118 is active and drives transcription of the nuclease 121 on engine vector 111 and pL promoter 134 is active and drives transcription of the editing cassette 136 on the editing vector 131.

In FIG. 1C, transcription of both the nuclease and the gRNA are under control of a pL promoter; however, in other embodiments, different inducible promoters may be used to drive transcription of the nuclease and gRNA or in some embodiments only one of the nuclease and gRNA are under control of an inducible promoter. For example, the pL and pBAD promoters are shown in relation to the exemplary engine and editing vectors in FIGS. 11A and 11B, and a number of gene regulation control systems have been developed for the controlled expression of genes in plant, microbe and animal cells, including mammalian cells. These systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); and U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others. However, the pL promoter is a particularly useful inducible promoter because the pL promoter is activated by an increase in temperature, to, e.g., 42° C., and deactivated by returning the temperature to, e.g., 30° C. With other inducible systems that are activated by the presence or absence of a particular molecular compound, activating the inducible promoter requires addition of or removal of a molecular compound from the culture medium, thus requiring liquid handling, medium exchange, wash steps and the like.

Figures 2A, 2C:
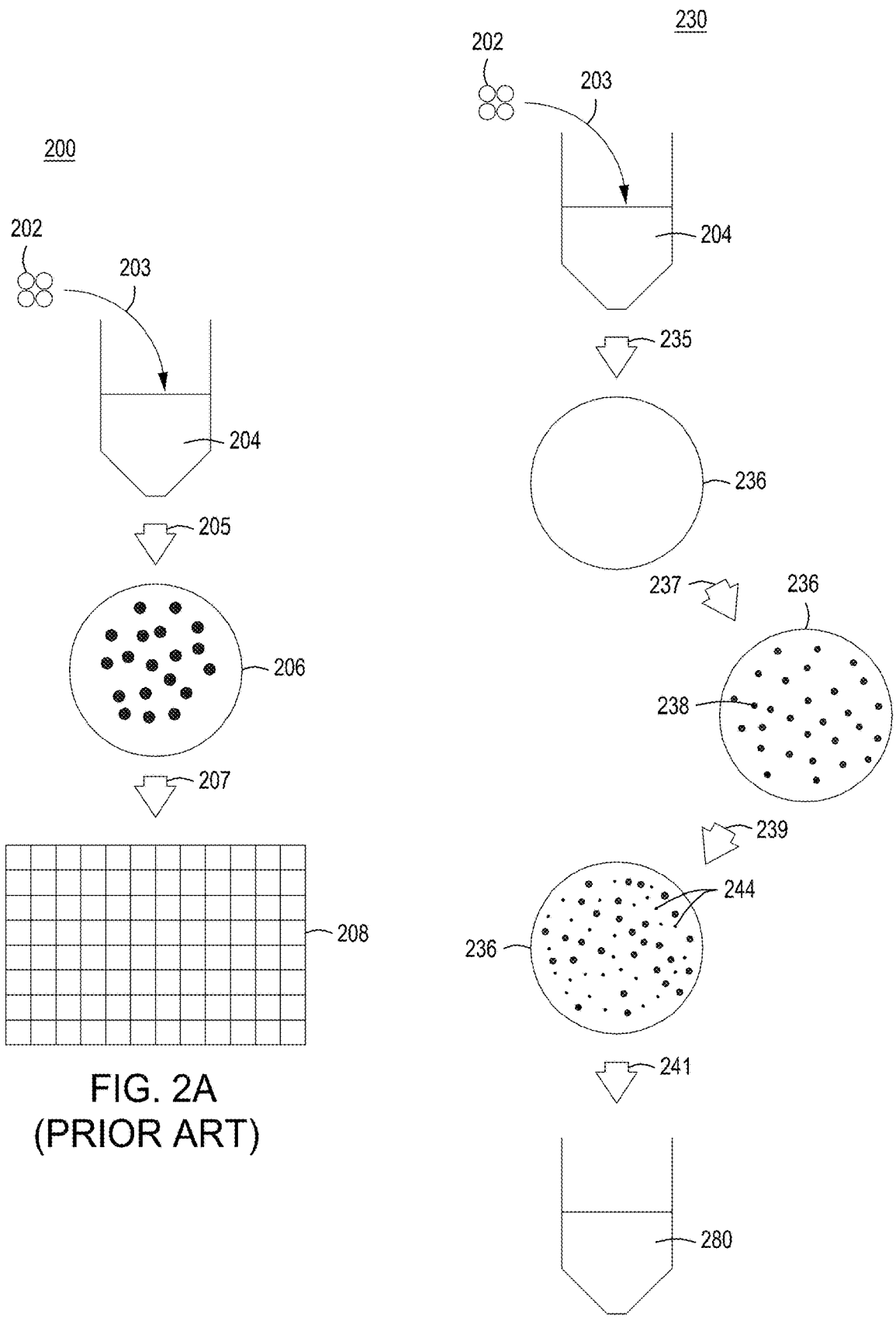
FIG. 2A depicts a prior art, standard protocol for performing nucleic acid-guided nuclease genome editing.
FIGS. 2B-2F depict improved protocols employing singulation or substantial singulation, induction, and either normalization or cherry picking (e.g., selection) for identifying edited cells in a population of cells that have undergone nucleic acid-guided nuclease genome editing.

FIG. 2A depicts a standard, conventional, prior art protocol 200 for performing nucleic acid-guided nuclease genome editing where constitutively-expressed nuclease components typically are used to drive high efficiency editing. In FIG. 2A, a library or collection of editing vectors 202 is introduced 203 (e.g., electroporated) into cultured cells 204 that comprise a coding sequence for a nuclease under the control of a constitutive or inducible promoter. In some embodiments, the coding sequence for the nuclease is contained on an "engine vector", although in other embodiments the coding sequence for the nuclease may be integrated into the cell genome. In yet another alternative, the components of the engine and editing vectors may be combined. The editing vectors 202 comprise an editing sequence comprising a sequence for a desired edit in a nucleic acid sequence endogenous to the cell as well as an optional PAM-altering sequence (most often a sequence that disables the PAM at the target sequence in the genome), a coding sequence for a gRNA under the control of a constitutive promoter, and a selectable marker. Once the cells have been transformed with the editing vectors, the cells are plated 205 on selective medium 206 to select for cells that have both the engine and editing vectors and the cells are grown until colonies form. Cells are then picked 207 from the colonies and grown in, e.g., 96-well plates 208 to be prepared for genome or plasmid sequencing. The cells that grow on plate 206 with the selective medium should comprise both the engine and editing vectors; however, it is likely that in some cells the nucleic acid-guided editing components may be non-functional. In pooled or multiplex formats, there is likely to be selective enrichment of the cells with a non-functional editing system since un-edited cells are not subjected to the double-strand DNA breaks that occur during editing. The strong selection for cells with non-functional nucleic acid-guided nuclease editing systems leads to a disproportionate representation of non-edited cells in the final cell population and compromises the integrity of libraries generated via multiplexed nuclease editing systems.

Figure 2B:
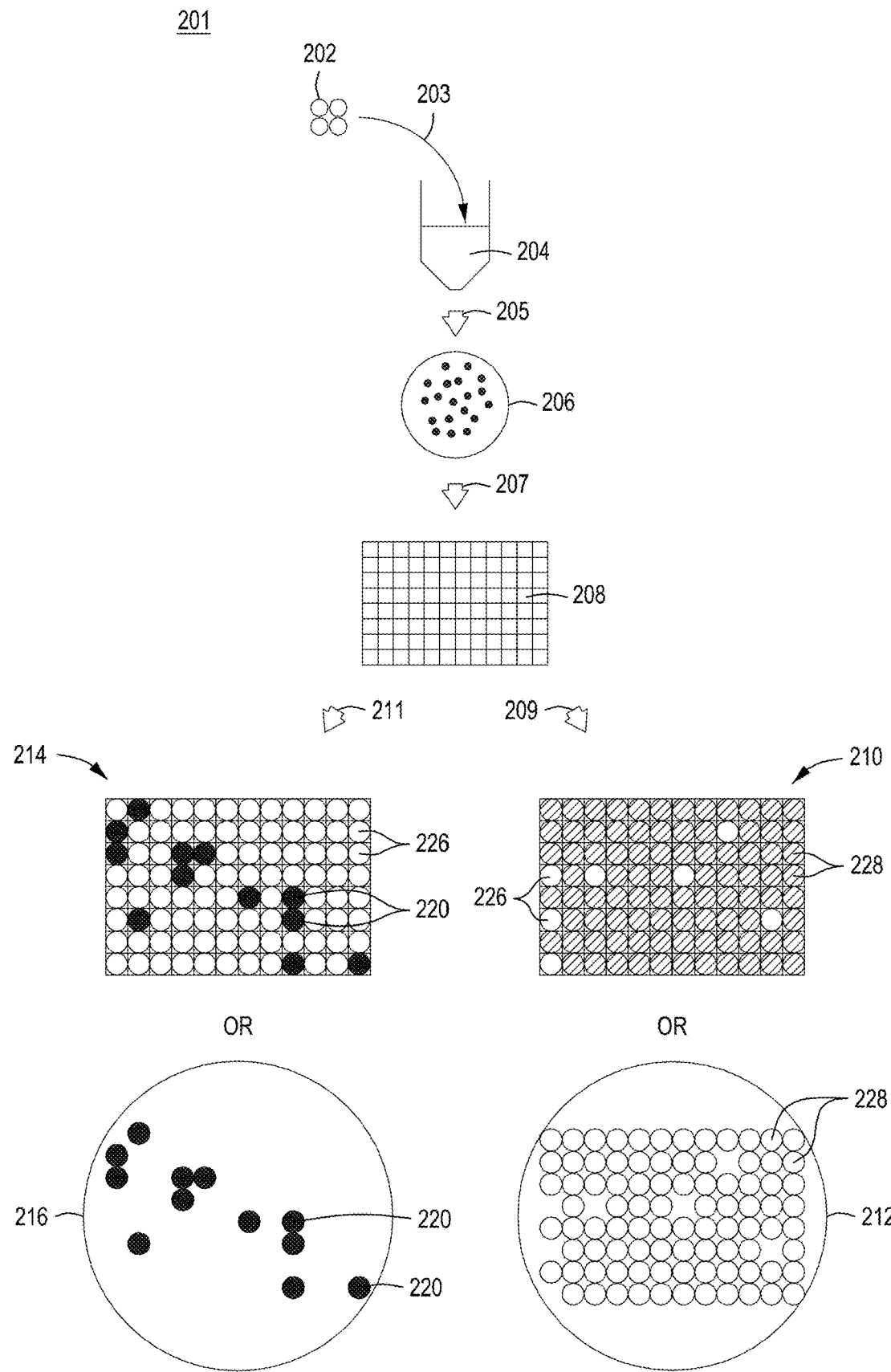

FIGS. 2B-2F depict improved protocols for performing nucleic acid-guided nuclease genome editing. FIG. 2B depicts a first embodiment 201 of an improved protocol for performing nucleic acid-guided nuclease genome editing using an inducible promoter to drive expression of the gRNA. In FIG. 2B, a library or collection of editing vectors 202 is introduced 203 (e.g., electroporated) into cultured cells 204 that comprise a coding sequence for a nuclease under the control of a constitutive or inducible promoter; however, the tightest regulation of the nucleic acid-guided nuclease system is achieved by using an inducible promoter to drive expression of the nuclease, thus it is preferred that an inducible promoter is used to drive transcription of the nuclease. In some embodiments, the coding sequence for the nuclease is contained on an "engine plasmid" (most often along with, e.g., a selectable marker) that has already been transformed into the cells, although in other embodiments the coding sequence for the nuclease may be integrated into the genome of the cells. In yet other embodiments, the coding sequence for the nuclease may be located on the editing vector (that is, a combined engine and editing vector). The editing vectors 202 comprise an editing sequence, which optionally includes a PAM-altering sequence (most often a sequence that disables the PAM at the target site in the genome), a coding sequence for a gRNA under the control of an inducible promoter, and a selectable marker.

Once the cells 204 have been transformed with the editing vectors, the cells are plated 205 on selective medium to select for cells that have both the engine and the editing vectors and grown until colonies 206 form. Cells are then picked 207 from the colonies and grown overnight in, e.g., first 96-well plate 208 in medium that selects for both the engine and editing vectors. In a next step 209, the cells from the first 96-well plate 208 are replicated into a second 96-well plate 210 into medium containing an additional selective component such as, e.g., arabinose, to drive strong induction of the λ red recombineering system (the homologous repair machinery). The inducible pBAD promoter—induced by the presence of arabinose in the growth medium—controls the λ red recombineering system and is described in relation to FIG. 11A below. Again, though a recombineering system is exemplified here in a bacterial editing system, recombineering systems generally are not needed in eukaryotic editing systems. After initial cell growth at 30° C., cutting and editing of the cellular genome is induced by increasing the temperature to 42° C. in the second 96-well plate 210 for, e.g., one-half to approximately two hours (depending on cell type), to activate the pL inducible promoters which drive transcription of the nuclease and the gRNA. Following induction of cutting and editing—e.g., for approximately 2 hours—the temperature is returned to 30° C. to allow the cells to recover.

In addition, in a step 211 cells from the first 96-well plate 208 are replicated into a third 96-well plate 214 into medium that does not contain the selective component that induces the homologous repair machinery (here, arabinose, such that the λ Red recombineering system is not activated). However, the third 96-well plate 214—aside from not having arabinose added to the growth medium—is subjected to the same conditions as the second 96-well plate; that is, initial cell growth at 30° C., increasing the temperature to 42° C. for, e.g., two hours to activate the pL inducible promoter driving the expression of the nuclease and the gRNA, then reducing the temperature to 30° C. to allow the cells to recover. As an alternative to 96-well plates 210 and 214, shown are two agar plates 212 and 216, where cells from plate 206 are arrayed. Plate 212 corresponds to the second 96-well plate 210, containing growth medium with arabinose, and plate 216 corresponds to the third 96-well plate 214, containing growth medium without arabinose. Note that as an alternative to performing the method depicted in FIG. 2B with +/− arabinose, one may perform the method with −/+ temperature induction of cutting. For example, in a +/− temperature induction experiment, plate 210 would be the uninduced culture plate (no temp) and culture plate 214 would be the temperature-induced culture plate. The same overall interpretation applies; however, cut activity is isolated to avoid having to deconvolute cut from paste.

Looking at the second and third 96-well plates (210 and 214, respectively) and at plates 212 and 216, colonies of cells can be seen. Looking first at second 96-well plate 210, there are two types of colonies: 226 (white wells) and 228 (hatched wells). Looking at third 96-well plate 214, there are two types of colonies: 220 (black wells) and 226 (white wells). Replicate plating of cells from the first 96-well plate into the second and third 96-well plates with differential media allows for functional deconvolution of the resulting cell populations. In third 96-well plate 214, cells were cultured in a medium without arabinose. With no arabinose, the λ Red recombineering system is not active, and cells that have active gRNA and nuclease expression (induced by increasing the temperature of the cultured cells to 42° C.) are not viable due to the double-strand cuts made by the active gRNA and nuclease yet without repair by the λ Red recombineering system. These cell colonies 222 are denoted by white wells. The cell colonies 220 denoted by black wells represent cells that have inactive gRNAs, such that the genomes of cells in these colonies are not cut by the gRNA and nuclease complex. Inactive gRNAs occur at a frequency of approximately 2-15% in a typical cell editing experiment, and typically are the result of errors in the guide sequence portion (homology portion) of the gRNA.

In second 96-well plate 210, the cells were cultured in a medium with arabinose, thereby activating the λ Red recombineering system. Cells that have active gRNA and nuclease expression (induced by increasing the temperature of the cultured cells to 42° C.) are cut, edited, and the λ Red recombineering system repairs the double-strand DNA breaks and thus these cells are viable. However, also viable are cells with inactive gRNAs (or less frequently, inactive nucleases). All viable colonies in plate 210 are denoted by hatched wells 228. Finally, cells that have active gRNAs but are not edited appropriately (due to, e.g., an inactive recombineering system) are denoted by white wells 226. By comparing the second 96-well plate to the third 96-well plate, the function of the nucleic acid-guided nuclease system in each colony can be determined. For example, if colonies of cells grow without arabinose (plate 214, black wells 220) and with arabinose (plate 210, hatched wells 228), the cells must not have an active gRNA. If the cells had an active gRNA, they would not have been viable in medium without arabinose (e.g., without an active λ Red recombineering system). If colonies of cells fail to grow in medium without arabinose (plate 214, white wells 226) and do grow when arabinose is added to the culture medium (plate 210, hatched wells 228), the cells in these wells comprise an active nucleic acid-guided nuclease system—with active gRNA and nuclease components—and are very likely to have been properly edited. Finally, if the colonies of cells fail to grow either without arabinose (plate 214, white wells 226) or with arabinose (plate 210, white wells 226), the gRNA is active, but the cells are not able to repair the cut for some reason. Thus, the method depicted in FIG. 2B allows for identification of edited cell colonies via functional deconvolution of the various components of the editing "machinery" in one experiment.

In plates 212 and 216 the phenotypic readout is the same as in 96-well plates 210 and 214. Like 96-well plate 210, the medium in culture dish 212 contains arabinose, and like 96-well plate 214, the medium in culture dish 216 does not contain arabinose. Thus, in culture dish 216 cells with inactive gRNAs grow, as there is no edit (double-strand break) to repair. However, in cells with an active gRNA, editing takes place but there is no active repair machinery to repair the edits, and the cells are not viable and do not form colonies. In culture dish 212 that contains arabinose, cells that have inactive gRNAs form colonies, as do cells that have active gRNAs but are properly edited. Cells that are not viable for whatever reason do not form colonies. As with 96-well plates 210 and 214, comparison of culture dishes 212 and 214 allow one to deconvolute the various components of the editing machinery. If cells grow on both culture dishes 212 and 214, the gRNA is likely inactive. If cells grow on culture dish 212 but not on culture dish 214, the gRNA is likely active and proper editing has taken place. If cells fail to grow on either culture dish 212 or 214, the cells likely have an active gRNA but the edit is not repaired properly.

Thus, the method 201 depicted in FIG. 2B allows for identification of cells with nonfunctional gRNAs that, due to the lack of double-strand DNA breaks, have a growth advantage. Most importantly, the method 201 depicted in FIG. 2B allows for identification of cells that have been properly edited. An aliquot of the colonies 228 from either second 96-well plate 210 or agar plate 212—the colonies confirmed to have an active gRNA—can be picked and sequenced to confirm editing. 96-well plate 210 or agar plate 212 may be retained so that once proper editing is confirmed by, e.g., sequencing, one can go back to plate 210 or 212 and retrieve the properly-edited cells. Plates 210 and 212 may be referred to, e.g., as "cell hotels" or "cell repositories." Note that the method 201 depicted in FIG. 2B first substantially or largely singulates the cells by plating them on selective medium at an appropriate dilution such that single cells form single colonies. Again, singulation or substantial singulation overcomes growth the bias that is characteristic of unedited cells. The method then allows for functional deconvolution of the different colonies by replica plating colonies in 96-well microtiter plates under different section media to allow positive identification of edited colonies. A specific protocol for this exemplary method is described in Example 6 below.

FIG. 2C depicts a second exemplary embodiment of an improved protocol 230 for performing nucleic acid-guided nuclease genome editing using an inducible promoter to drive expression of the gRNA, and, preferably, the nuclease as well. In FIG. 2C as in FIG. 2B, a library or collection of editing vectors 202 is introduced 203 (e.g., electroporated) into cultured cells 204 that comprise a coding sequence for a nuclease under the control of a constitutive or inducible promoter; however, the tightest regulation of the nucleic acid-guided nuclease system is achieved by using an inducible promoter to drive expression of the nuclease and thus is preferred. Also like FIG. 2B, in some embodiments, the coding sequence for the nuclease is contained on an "engine plasmid" (most often along with, e.g., a selectable marker) that has already been transformed into the cells, although in other embodiments, the coding sequence for the nuclease may be integrated into the genome of the cells. In yet other embodiments, the coding sequence for the nuclease may be located on the editing vector (that is, a combined engine and editing vector). The editing vectors 202 comprise an editing sequence with a desired edit vis-à-vis an endogenous nucleic acid sequence in the cell along with a PAM-altering sequence (most often a sequence that disables the PAM at the target site in the genome), a coding sequence for a gRNA under the control of, preferably, an inducible promoter, and a selectable marker.

Once the cells 204 have been transformed with the editing vectors, the cells are plated 235 on selective medium on substrate or plate 236 to select for cells that have both the engine and the editing vectors. The cells are diluted before plating such that the cells are substantially or largely singulated—separated enough so that they and the colonies they form are separated from other cell colonies—and the cells are then grown 237 on plate or substrate 236 until colonies 238 begin to form. The cells are allowed to grow at, e.g., 30° C. for, e.g., between 2 and 150, or between 5 and 120, or between 10 and 50 doublings, establishing clonal colonies. This initial growth of cells is to accumulate enough clonal cells in a colony to survive induction of editing. Once colonies are established, cutting and editing of the cellular genome is induced by inducing or activating the promoters driving one or both of the gRNA and nuclease, and the λ Red recombineering system (if present). If the λ Red recombineering system is present and under the control of an inducible promoter, preferably this inducible promoter is different from the inducible promoter driving transcription of the gRNA and nuclease and is activated (induced) before induction of the gRNA and nuclease. The λ Red recombineering system works as the "band aid" or repair system for double-strand breaks in bacteria, and in some species of bacteria must be present for the double-strand breaks that occur during editing to resolve. The λ Red recombineering system may be under the control of, e.g., a pBAD promoter. The pBAD promoter, like the pL promoter, is an inducible promoter; however, the pBAD promoter is regulated (induced) by the addition of arabinose to the growth medium. Thus, if there is arabinose contained in the selective medium of substrate or plate 236, the λ Red recombineering system will be activated when the cells are grown 237. As for induction of editing 239, if transcription of the gRNA and nuclease are both under control of the pL promoter, transcription of the gRNA and nuclease is induced by increasing the temperature to 42° C. for, e.g., a half-hour to two hours (or more, depending on the cell type), which activates the pL inducible promoter. Following induction of cutting and editing and a two-hour 42° C. incubation, the temperature is returned to 30° C. to allow the cells to recover and to disable the pL promoter system.

Once the cells have recovered and are growing at 30° C., the cells are grown on substrate or plate 236 into colonies of terminal size 244; that is, the colonies arising from the substantially or largely singulated cells are grown into colonies to a point where cell growth has peaked and becomes normalized (e.g., saturated) for both edited and unedited cells. As described supra, normalization occurs as the nutrients in the medium around a growing cell colony are depleted and/or cell growth fills the microwells or is otherwise constrained; that is, the cells are in senescence. The terminal-size colonies are then pooled 241 by, e.g., scraping the colonies off the substrate or plates (or by, e.g., flushing the clonal cell colonies from microwells in a solid wall device) to pool 280 the cells from the normalized cell colonies. Note that the method 240 illustrated and described for FIG. 2C utilizes singulation or substantial singulation, initial growth, induction, normalization and pooling of the resulting cell colonies. Again, because singulation or substantial singulation overcomes growth bias from unedited cells or cells exhibiting fitness effects as the result of edits made, the combination of singulation or substantial singulation, initial growth, induction of editing, and normalization enriches the total population of cells with cells that have been edited. Note, however, unlike the methods 201, 250 depicted in FIG. 2B and FIG. 2D respectively, method 240 in FIG. 2C takes no steps to deconvolute the editing "machinery."

Figure 2D:
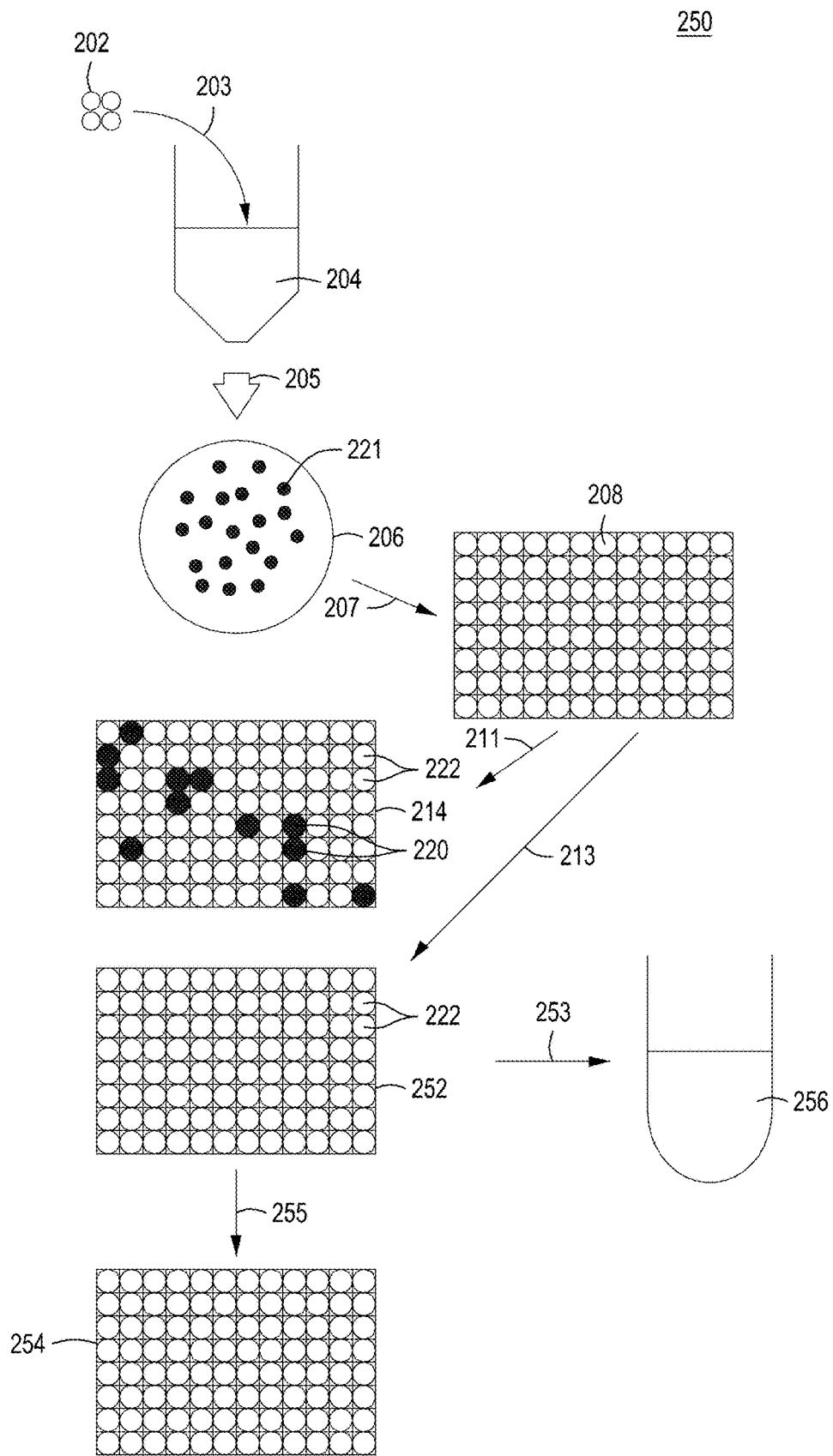

FIG. 2D depicts a third exemplary embodiment of an improved protocol 250 for performing nucleic acid-guided nuclease genome editing using an inducible promoter to drive expression of the gRNA, and in some embodiments and preferably, the nuclease as well. FIG. 2D depicts a protocol 250 for activity-based error correction and re-arraying. In FIG. 2D as in FIGS. 2B and 2C, a library or collection of editing vectors 202 is introduced 203 (e.g., electroporated) into cultured cells 204 that comprise a coding sequence for a nuclease under the control of a constitutive or inducible promoter (preferably inducible), either contained on an "engine plasmid" (e.g., along with, e.g., a selectable marker) that has already been transformed into the cells, or integrated into the genome of the cells. Alternatively, the coding sequence for the nuclease may be located on the editing vector. The editing vectors 202 comprise an editing sequence, a PAM-altering sequence (most often a sequence that disables the PAM at the target site in the genome), a coding sequence for a gRNA under the control of, preferably, an inducible promoter, and a selectable marker.

Once the cells have been transformed with the editing vectors, the cells are diluted and plated 205 on selective medium 206 to select for cells that have both the engine and the editing vectors (e.g., medium with chloramphenicol and carbenicillin) and grown until colonies form 221, again in a process that substantially or largely singulates the cells. Cells are then picked 207 from the colonies 221 and grown overnight in, e.g., first 96-well plate 208 in medium that does not comprise a selective medium. In a next step, the cells from the first 96-well plate are replicated 211 into a second 96-well plate 214 in medium without arabinose, resulting in wells with colonies (black wells 220), and wells without cells colonies (white wells 222). This process identifies cells with active gRNAs, as cells with active gRNAs will not survive because without arabinose the λ Red recombineering system is not active to repair the cuts in the genome made by the gRNA. Thus, the wells 222 likely denote wells with active gRNAs. The colonies that do grow in this second 96-well plate 214 likely have inactive gRNAs, and thus there is no cut to repair and the cells remain viable (denoted by black wells 220).

Once the cells with the active gRNAs are identified (wells 222), these cells are then "cherry-picked" 213 from the first 96-well plate and arrayed into a third 96-well plate 252 to be kept as a cell repository or "cell hotel." All colonies in the third 96-well plate 252 are cells that have been identified as likely having active gRNAs 222. With this cell repository 252, aliquots of these "cherry-picked" cells (e.g., here cells with active gRNAs) can then be arrayed 255 into a fourth 96-well plate 254 in medium with arabinose. After an initial growth period, the cells in this fourth 96-well plate 254 are subjected to cutting and editing conditions, e.g., increasing the temperature to 42° C. for, e.g., two hours, to induce the pL inducible promoter driving the expression of the nuclease and the gRNA. Once the cutting and editing processes take place, colonies containing cells that have been properly edited can be identified by monitoring growth of the colonies and selecting slow-growing colonies or by targeted or whole genome sequencing taking cells from plate 254. Once cells with desired edits are identified, the cells with the desired edits can be retrieved from 96-well plate 252 (e.g., the cell repository or "cell hotel"). Alternatively, the cells colonies with the putatively active gRNAs on plate 252 can be pooled 253 into a mixed cell culture 256 and either analyzed or subjected to an additional round of editing.

Figure 2E:
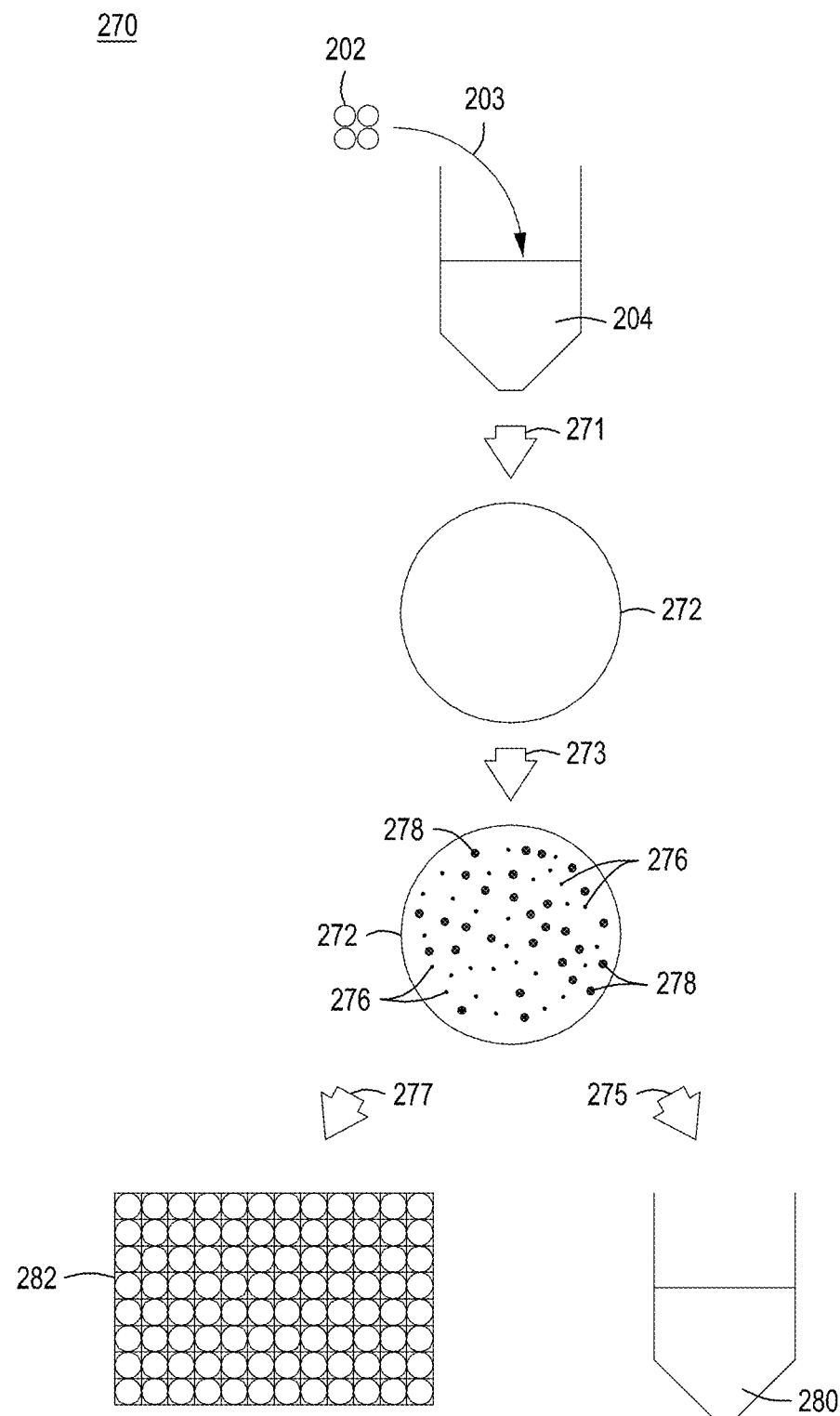

FIG. 2E depicts yet another exemplary embodiment of an improved protocol 270 for performing nucleic acid-guided nuclease genome editing using an inducible promoter to drive expression of one or more of the gRNA and/or the nuclease. The protocol 270 in FIG. 2D does not entail functional deconvolution of the editing "machinery" of the cells but depicts a protocol for high-throughput screening using colony morphology to identify edited cells. Again, in edited cells, cell viability is compromised in the period after editing is induced. The present method takes advantage of the growth lag in colonies of edited cells to identify edited cells. In some embodiments, the colony size of the edited cells is 20% smaller than colonies of non-edited cells. In some aspects, the colony size of the edited cells is 30%, 40%, 50%, 60%, 70%, 80% or 90% smaller than the colonies of non-edited cells. In many embodiments, the colony size of the edited cells is 30-80% smaller than colonies of non-edited cells, and in some embodiments, the colony size of the edited cells is 40-70% smaller than colonies of non-edited cells.

In FIG. 2E as in FIGS. 2B-2D, a library or collection of editing vectors 202 is introduced 203 (e.g., electroporated) into cultured cells 204 that comprise a coding sequence for a nuclease under the control of a constitutive or inducible promoter (preferably an inducible promoter), contained 1) on an "engine plasmid" (most often along with a selectable marker) that has already been transformed into the cells; 2) integrated into the genome of the cells being transformed; or 3) the coding sequence for the nuclease may be located on the editing vector. The editing vectors 202 comprise an editing sequence and optionally include a PAM-altering sequence (e.g., a sequence that disables the PAM at the target site in the genome), a coding sequence for a gRNA under the control of, preferably, an inducible promoter, and a selectable marker. In many embodiments, an inducible promoter is included in the editing vector backbone, and an editing cassette is inserted 3' of the inducible promoter where the editing cassette comprises, from 5' to 3': a coding sequence for a gRNA, and a donor DNA comprising a desired edit for a target sequence and the PAM-altering sequence (e.g., a CREATE cassette). Note again, that transcription of one or both of the gRNA and nuclease must be under the control of an inducible promoter. It is preferred, however, that transcription of both the gRNA and the nuclease is under the control of an inducible promoter.

At step 271, the transformed cells are diluted and plated (e.g., substantially or largely singulated) onto selective medium 272 that selects for both the engine and editing vectors (e.g., medium containing both chloramphenicol and carbenicillin) and further contains arabinose so as to activate the λ Red recombineering system. Once plated, the cells are grown 273 at 30° C. for 6-8 hours so that the cells initially establish colonies, then the temperature is increased to 42° C. for, e.g., on-half to two hours to induce expression of the nuclease and gRNA for cutting and editing. Once sufficient time for editing has taken place, the temperature is returned to 30° C. so that the cells grow to re-establish colonies on plate 272. Once colonies appear, there are large 278 and small 276 colonies. The colonies with small size 276 are indicative of an active gRNA and likely to have been edited as the double-strand cuts caused by active editing are largely toxic to the cells, resulting both in cell death in the edited colonies as well as a lag in growth for the edited cells that do survive but must repair and recover following editing. The small colonies (edited cells) are cherry picked 277 and are arrayed on a 96-well plate 282. Cells in the 96-well plate 282 can be cultured, and aliquots from this 96-well plate 282 can be sequenced and colonies with desired edits identified. This 96-well plate may be kept as a cell hotel or cell repository, and once cells that have been properly edited are identified, one can retrieve the cells with the desired edit from "cell hotel" 96-well plate 282.

Alternatively, small colonies 276 may be picked and pooled 275 for additional rounds of editing since the edited cells have been selected in the first round of editing and likely comprise edits from the first round. Note again, that this method does not provide functional deconvolution of the editing machinery; however, the method depicted in FIG. 2E employs both singulation or substantial singulation and cherry picking and thus enables for a high-throughput diagnostic method to identify cells based on the colony size morphology that have a high likelihood of being edited, and once identified, the edited cell population can be enriched. Screening out a large proportion of the cells with non-functional gRNAs allows for identification of edited cells more readily. It has been determined that removing growth rate bias via singulation or substantial singulation improves the observed editing efficiency by up to 2×, 3×, 4× or more over conventional methods, and further that cherry-picking colonies using the methods described herein increases by 1.5×, 1.75×, 2.0×, or 2.5× or more the observed editing efficiency of singulation. Thus, the combination of substantial singulation and cherry picking improve observed editing efficiency by 8× over conventional methods. Example 9 below provides materials and methods for this embodiment.

While the method for screening for edited cells using cell growth as a proxy for editing has been described herein in the context of measuring colony size of cell colonies on an agar plate, the optical density (OD) of growing cell colonies, such as in a microtiter plate or in a series of tubes may be measured instead. Moreover, other cell growth parameters can be measured in addition to or instead of cell colony size or OD. For example, spectroscopy using visible, UV, or near infrared (NIR) light allows monitoring the concentration of nutrients and/or wastes in the cell culture. Additionally, spectroscopic measurements may be used to quantify multiple chemical species simultaneously. Nonsymmetric chemical species may be quantified by identification of characteristic absorbance features in the NIR. Conversely, symmetric chemical species can be readily quantified using Raman spectroscopy. Many critical metabolites, such as glucose, glutamine, ammonia, and lactate have distinct spectral features in the IR, such that they may be easily quantified. The amount and frequencies of light absorbed by the sample can be correlated to the type and concentration of chemical species present in the sample. Each of these measurement types provides specific advantages. FT-NIR provides the greatest light penetration depth and so can be used for thicker sample so that they provide a higher degree of light scattering. FT-mid-IR (MIR) provides information that is more easily discernible as being specific for certain analytes as these wavelengths are closer to the fundamental IR absorptions. FT-Raman is advantageous when the interference due to water is to be minimized. Other spectral properties can be measured via, e.g., dielectric impedance spectroscopy, visibly fluorescence, fluorescence polarization, or luminescence. Additionally, sensors for measuring, e.g., dissolved oxygen, carbon dioxide, pH, and/or conductivity may be used to assess the rate of cell growth.

Figure 2F:
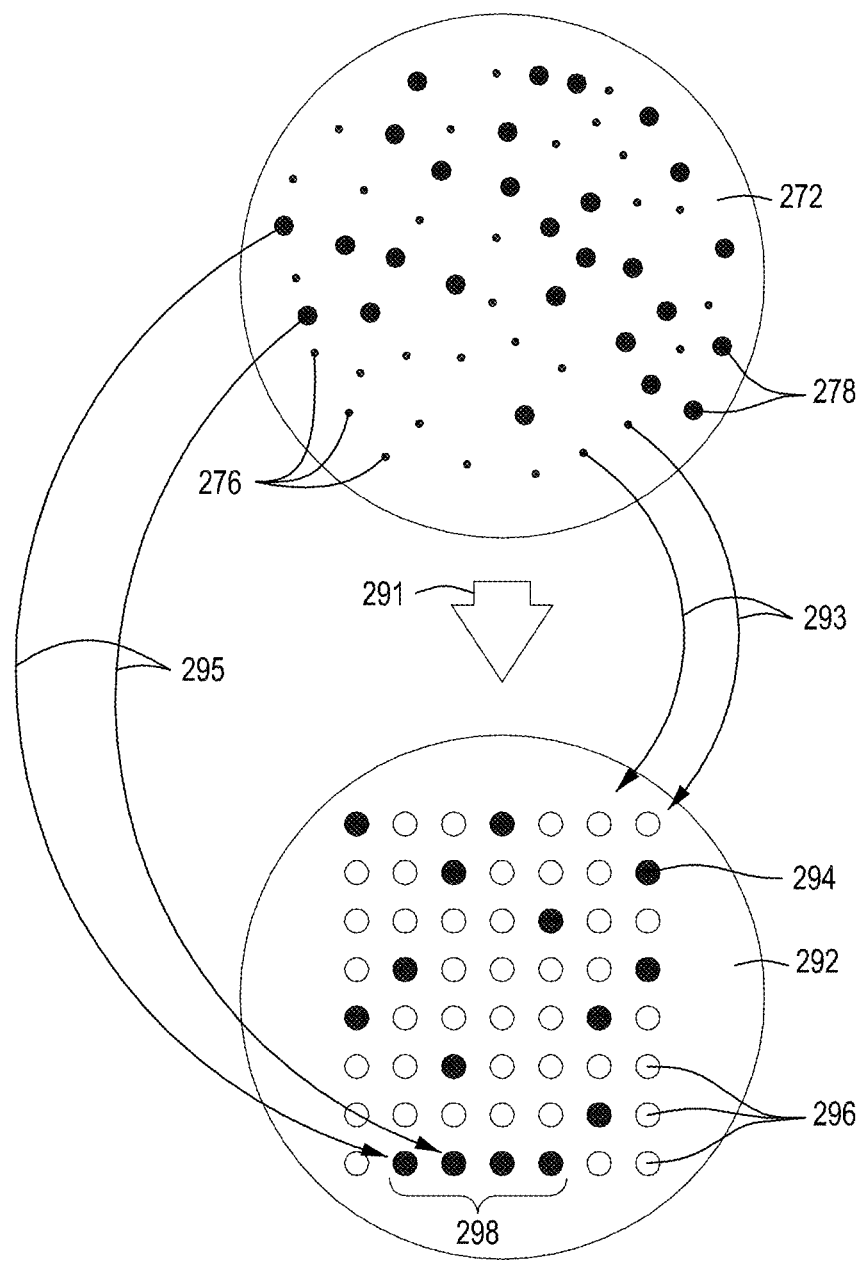

FIG. 2F depicts additional detail of the exemplary embodiment shown in FIG. 2E, using a specific example based on experiments performed (see Example 1, infra). FIG. 2F shows high-throughput screening 290 using colony morphology to identify or cherry pick edited cells. As described above, in edited cells cell viability is compromised in the period after editing is induced. The present method takes advantage of the growth lag in colonies of edited cells to identify edited cells. In FIG. 2F, transformed cells are diluted and plated on medium containing arabinose and grown for a period of time at, e.g., 30° C. Editing is initiated by, e.g., raising the temperature to 42° C. for a period of time, then the temperature is lowered to 30° C. (e.g., the transformed cells are substantially or largely singulated). Colonies are allowed to grow and both small 276 and large 278 colonies result. Colonies from this plate are picked 291 and arrayed on a second plate 292 containing selective medium, e.g., a medium to select for successful editing of galK, resulting in white (versus red) colonies when plated on MacConkey agar supplemented with galactose as the sole carbon source. Note that picking small colonies 293 from the first plate results primarily in edited cells 296 (white colonies, shown here as open circles) and—at a much lower frequency—some cells in which the gRNA is inactive 294 (red colonies, shown here as filled-in circles). Confirmation of colonies in which the gRNA is inactive is shown by picking 295 large colonies 278 from the first plate and plating them on the second plate (colonies 298) where these cells result in red colonies when grown on MacConkey agar supplemented with galactose as the sole carbon source thus confirming an inactive gRNA or other part of the editing machinery. Thus, using small and large colony morphology as a proxy for edited and non-edited cells, respectively, provides a high throughput and facile screening method for edited cells. Note that the methods depicted in FIGS. 2E and 2F employ both singulation or substantial singulation and cherry-picking strategies.

The exemplary workflows described herein employ the concept of singulation. Singulation overcomes the growth bias in favor of unedited cells, thus allowing edited cells "equal billing" with unedited cells. Further, the methods take advantage of a tightly-regulated inducible system to screen edited cells from non-edited cells (both cells where the gRNA is non-functional, and cells where the gRNAs are functional but some component of the nucleic acid-guided nuclease system is not functional). Screening may be performed using replica plates and identifying "escapees" or cells in which the gRNA is non-functional, screening may be performed by taking advantage of the growth lag of edited cells in comparison to non-edited cells, or enrichment can be performed by using a combination of singulation or substantial singulation, initial growth, induction of editing and normalization. The result of the methods is that even in nucleic acid-guided nuclease systems where editing is not optimal (such as in systems where non-canonical PAMs are targeted), there is an increase in the observed editing efficiency; that is, edited cells can be identified even in a large background of unedited cells.

Note that the methods depicted in FIGS. 2B-2F show cell colony singulation, initial growth, and induction of editing on solid medium in cell culture dishes or in 96-well plates. It should be recognized by one of ordinary skill in the art given the discussion herein that singulation, initial growth, and induction of editing can be performed in other formats, such as, e.g., in the solid wall devices described in relation to FIG. 3A-3F and 4A-4CC, or as described in U.S. Ser. No. 62/735,365, entitled "Detection of Nuclease Edited Sequences in Automated Modules and Systems", filed 24 Sep. 2018, and U.S. Ser. No. 62/781,112, entitled "Improved Detection of Nuclease Edited Sequences in Automated Modules and Systems," filed 18 Dec. 2018, which include descriptions of singulation or substantial singulation by isolating cells on functionalized islands, singulation or substantial singulation within aqueous droplets carried in a hydrophobic carrier fluid or Gel Beads-in-Emulsion (GEMs, see, e.g., 10× Genomics, Pleasanton, Calif.), or singulation or substantial singulation within a polymerized alginate scaffold (for this embodiment of singulation, also see U.S. Ser. No. 62/769,805, entitled "Improved Detection of Nuclease Edited Sequences in Automated Modules and Instruments via Bulk Cell Culture", filed 20 Nov. 2018).

Exemplary Modules for Editing, Enrichment, and Selection of Edited Cells

The instruments, methods, and modules described herein enable enhanced observed editing efficiency of nucleic acid-guided nuclease editing methods as the result of singulation or substantial singulation, initial cell growth, induction of editing, and normalization. The combination of the singulation or substantial singulation, initial growth, induction of editing and normalization processes overcomes the growth bias in favor of unedited cells—and the fitness effects of editing (including differential editing rates)—thus allowing all cells "equal billing" with one another. The result of the instruments, modules, and methods described herein is that even in nucleic acid-guided nuclease systems where editing is not optimal (such as in systems where non-canonical PAMs are targeted), there is an increase in the observed editing efficiency; that is, edited cells can be identified even in a large background of unedited cells. Observed editing efficiency can be improved up to 80% or more.

Figure 3A:
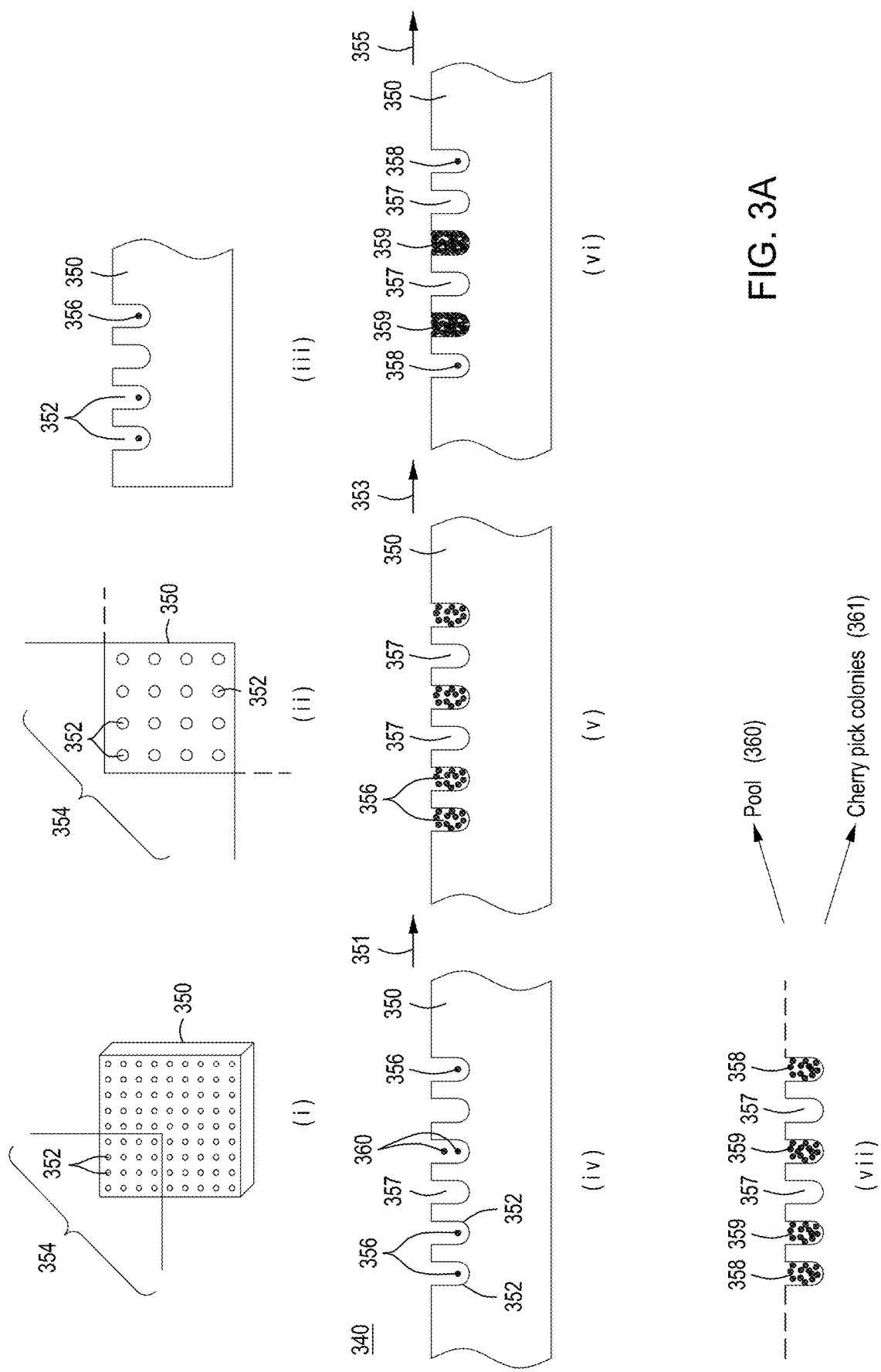
FIG. 3A depicts a simplified graphic of a workflow for singulating, editing and normalizing cells in a solid wall device. 3B depicts a simplified graphic of a workflow variation for substantially singulating, editing and normalizing cells in a solid wall device.

FIG. 3A depicts a solid wall device 350 and a workflow for singulating cells in microwells in the solid wall device, where in this workflow one or both—preferably both—of the gRNA and nuclease are under the control of an inducible promoter. At the top left of the figure (i), there is depicted solid wall device 350 with microwells 352. A section 354 of substrate 350 is shown at (ii), also depicting microwells 352. At (iii), a side cross-section of solid wall device 350 is shown, and microwells 352 have been loaded, where, in this embodiment, Poisson or substantial Poisson loading has taken place; that is, each microwell has one or no cells, and the likelihood that any one microwell has more than one cell is low. At (iv), workflow 340 is illustrated where substrate 350 having microwells 352 shows microwells 356 with one cell per microwell, microwells 357 with no cells in the microwells, and one microwell 360 with two cells in the microwell. In step 351, the cells in the microwells are allowed to double approximately 2-150 times to form clonal colonies (v), then editing is induced 353 by heating the substrate (e.g., for temperature-induced editing) or flowing chemicals under or over the substrate (e.g., sugars, antibiotics for chemical-induced editing) or by moving the solid wall device to a different medium, particularly facile if the solid wall device is placed on a membrane which forms the bottom of microwells 352 (membrane not shown).

After induction of editing 353, many cells in the colonies of cells that have been edited die as a result of the double-strand cuts caused by active editing and there is a lag in growth for the edited cells that do survive but must repair and recover following editing (microwells 358), where cells that do not undergo editing thrive (microwells 359) (vi). All cells are allowed to continue grow 355 to establish colonies and normalize, where the colonies of edited cells in microwells 358 catch up in size and/or cell number with the cells in microwells 359 that do not undergo editing (vii). Once the cell colonies are normalized, either pooling 360 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 358) are identified and selected 361 (e.g., "cherry picked") resulting in even greater enrichment of edited cells.

In growing the cells, the medium used will depend, of course, on the type of cells being edited—e.g., bacterial, yeast or mammalian. For example, medium for bacterial growth includes LB, SOC, M9 Minimal medium, and Magic medium; medium for yeast cell growth includes TPD, YPG, YPAD, and synthetic minimal medium; and medium for mammalian cell growth includes MEM, DMEM, IMDM, RPMI, and Hanks. For culture of adherent cells, cells may be disposed on beads or another type of scaffold suspended in medium. Most normal mammalian tissue-derived cells— except those derived from the hematopoietic system—are anchorage dependent and need a surface or cell culture support for normal proliferation. In the rotating growth vial described herein, microcarrier technology is leveraged. Microcarriers of particular use typically have a diameter of 100-300 μm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), HLX 11-170 (polystyrene-based); collagen or ECM (extracellular matrix)-coated carriers, such as Cytodex 3 (dextran-based, GE Healthcare) or HyQ-sphere Pro-F 102-4 (polystyrene-based, Thermo Scientific); non-charged carriers, like HyQspheres P 102-4 (Thermo Scientific); or macroporous carriers based on gelatin (Cultisphere, Percell Biolytica) or cellulose (Cytopore, GE Healthcare).

Figure 3B:
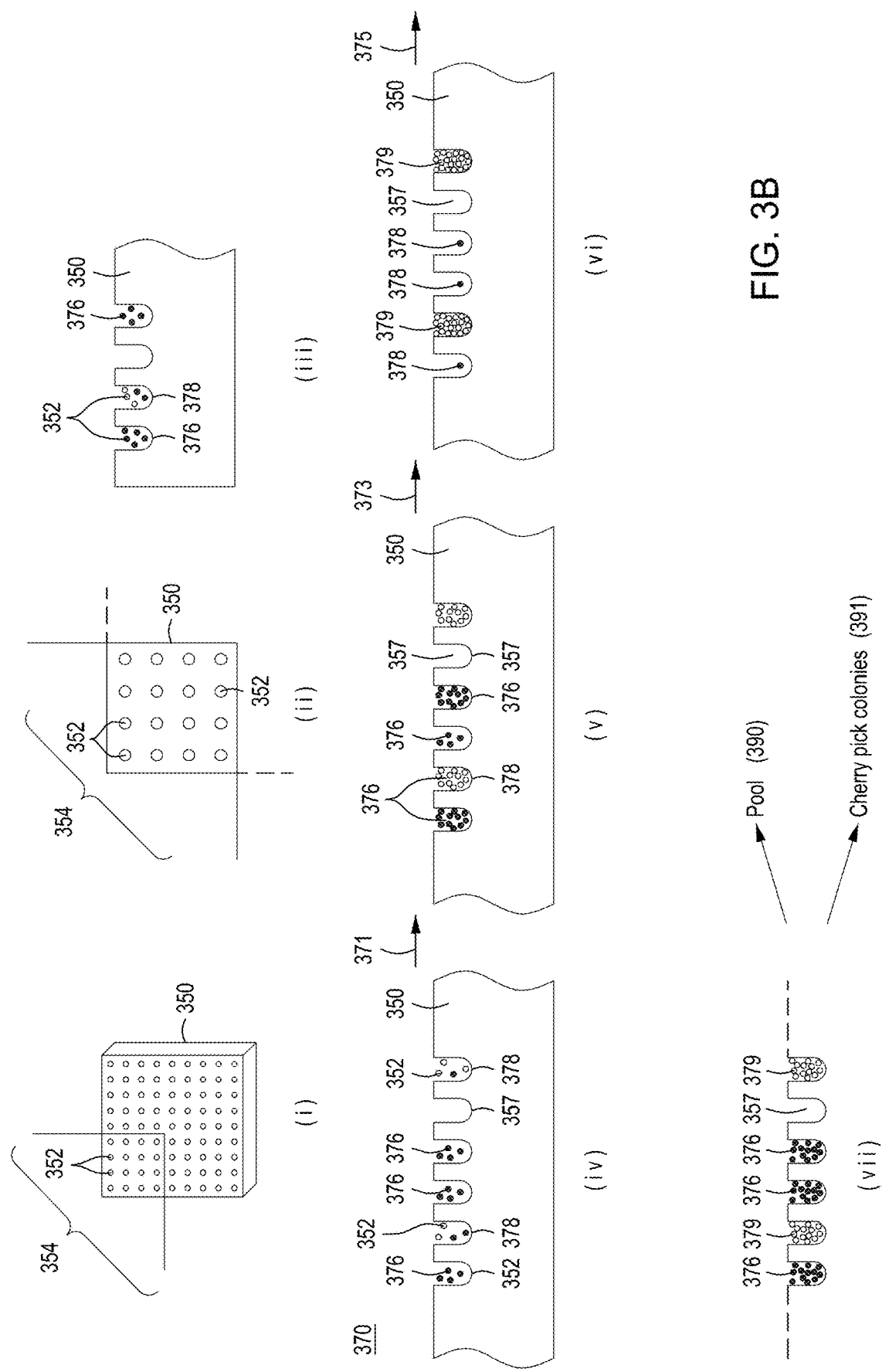
FIG. 3C is a photograph of one embodiment of a solid wall device.
FIGS. 3D-3F are photographs of E. coli cells largely singulated (via substantial Poisson distribution) and grown into colonies in microwells in a solid wall device with a permeable bottom at low, medium, and high magnification, respectively.

FIG. 3B depicts a solid wall device 350 and a workflow for substantially singulating cells in microwells in a solid wall device, where in this workflow (as in the workflow depicted in FIG. 3A) one or both—preferably both—of the gRNA and nuclease is under the control of an inducible promoter. At the top left of the figure (i), there is depicted solid wall device 350 with microwells 352. A section 354 of substrate 350 is shown at (ii), also depicting microwells 352. At (iii), a side cross-section of solid wall device 350 is shown, and microwells 352 have been loaded, where, in this embodiment, substantial Poisson loading has taken place; that is, some microwells 357 have no cells, and some microwells 376, 378 have a few cells. In FIG. 3B, cells with active gRNAs are shown as solid circles, and cells with inactive gRNAs are shown as open circles. At (iv), workflow 370 is illustrated where substrate 350 having microwells 352 shows three microwells 376 with several cells all with active gRNAs, microwell 357 with no cells, and two microwells 378 with some cells having active gRNAs and some cells having inactive gRNAs. In step 371, the cells in the microwells are allowed to double approximately 2-150 times to form clonal colonies (v), then editing is induced 373 by heating the substrate (e.g., for temperature-induced editing) or flowing chemicals under or over the substrate (e.g., sugars, antibiotics for chemical-induced editing) or by moving the solid wall device to a different medium, particularly facile if the solid wall device is placed on a membrane which forms the bottom of microwells 352.

After induction of editing 373, many cells in the colonies of cells that have been edited die as a result of the double-strand cuts caused by active editing and there is a lag in growth for the edited cells that do survive but must repair and recover following editing (microwells 376), where cells that do not undergo editing thrive (microwells 378) (vi). Thus, in microwells 376 where only cells with active gRNAs reside (cells depicted by solid circles), most cells die off; however, in microwells 378 containing cells with inactive gRNAs (cells depicted by open circles), cells continue to grow and are not impacted by active editing. The cells in each microwell (376 and 378) are allowed to grow 375 to continue to establish colonies and normalize, where the colonies of edited cells in microwells 376 catch up in size and/or cell number with the unedited cells in microwells 379 that do not undergo editing (vii). Note that in this workflow 370, the colonies of cells in the microwells are not clonal; that is, not all cells in a well arise from a single cell. Instead, the cell colonies in the well may be mixed colonies, arising in many wells from two to several different cells. Once the cell colonies are normalized, either pooling 390 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 376) are identified and selected 391 (e.g., "cherry picked") resulting in even greater enrichment of edited cells.

Figure 3C:
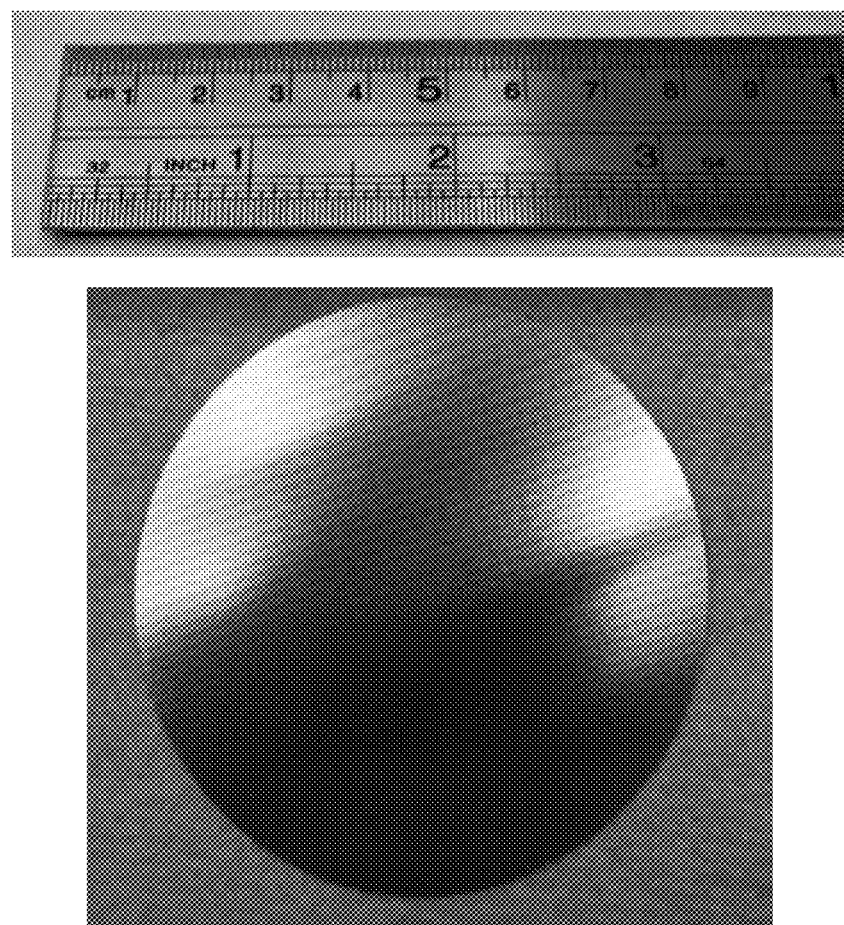

FIG. 3C is a photograph of one embodiment of a solid wall substrate comprising microwells for singulating cells. As can be seen from the photo, the solid wall substrate is a perforated disk of metal and is approximately 2 inches (~47 mm) in diameter. The perforated disk seen in this photograph is fabricated 316 stainless steel, where the perforations form the walls of the microwells, and a filter or membrane is used to form the bottom of the microwells. Use of a filter or membrane (such as a 0.22 μm PVDF Duropore™ woven membrane filter) allows for medium and/or nutrients to enter the microwells but prevents the cells from flowing down and out of the microwells. Filter or membrane members that may be used in the solid wall singulation or substantial singulation/initial growth/induction of editing and normalization or cherry picking devices and modules are those that are solvent resistant, are contamination free during filtration, and are able to retain the types and sizes of cells of interest. For example, in order to retain small cell types such as bacterial cells, pore sizes can be as low as 0.10 μm, however for other cell types, the pore sizes can be as high as 0.5 μm. Indeed, the pore sizes useful in the cell concentration device/module include filters with sizes from 0.10 μm, 0.11 μm, 0.12 μm, 0.13 μm, 0.14 μm, 0.15 μm, 0.16 μm, 0.17 μm, 0.18 μm, 0.19 μm, 0.20 μm, 0.21 μm, 0.22 μm, 0.23 μm, 0.24 μm, 0.25 μm, 0.26 μm, 0.27 μm, 0.28 μm, 0.29 μm, 0.30 μm, 0.31 μm, 0.32 μm, 0.33 μm, 0.34 μm, 0.35 μm, 0.36 μm, 0.37 μm, 0.38 μm, 0.39 μm, 0.40 μm, 0.41 μm, 0.42 μm, 0.43 μm, 0.44 μm, 0.45 μm, 0.46 μm, 0.47 μm, 0.48 μm, 0.49 μm, 0.50

µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

In the photograph shown in FIG. 3C, the perforations are approximately 150 µm-200 µm in diameter, resulting in the microwells having a volume of approximately 2.5 nl, with a total of approximately 30,000 microwells. The distance between the microwells is approximately 279 nm center-to-center. Though here the microwells have a volume of approximately 2.5 nl, the volume of the microwells may be from 1 to 25 nl, or preferably from 2 to 10 nl, and even more preferably from 2 to 4 nl. The preferred size/volume of the microwells will depend of cell type (e.g., bacterial, yeast, mammalian). The perforated disk shown here is made of 316 stainless steel; however other bio-compatible metals and materials may be used. The solid wall device may be disposable or it may be reusable. The solid wall device shown in FIG. 3C is round, but can be of any shape, for example, square, rectangular, oval, etc. (See, e.g., FIG. 4A.) Round perforated disks are useful if petri dishes are used to supply the solid wall module with nutrients via solid medium in, e.g., a petri or other cell culture dish. The filters used to form the bottom of the microwells of the solid wall device include 0.22 µm PVDF Durapore™ woven membrane filters. Further, though a 2-inch (~47 mm) diameter perforated disk is shown, the perforated disks may be smaller or larger as desired and the configuration of the solid wall module will depend on how nutrients are supplied to the solid wall module, and how media exchange is performed. For example, see the perforated member of FIG. 4A and the embodiments of a solid wall module in FIGS. 4F-4BB.

Figure 3D:
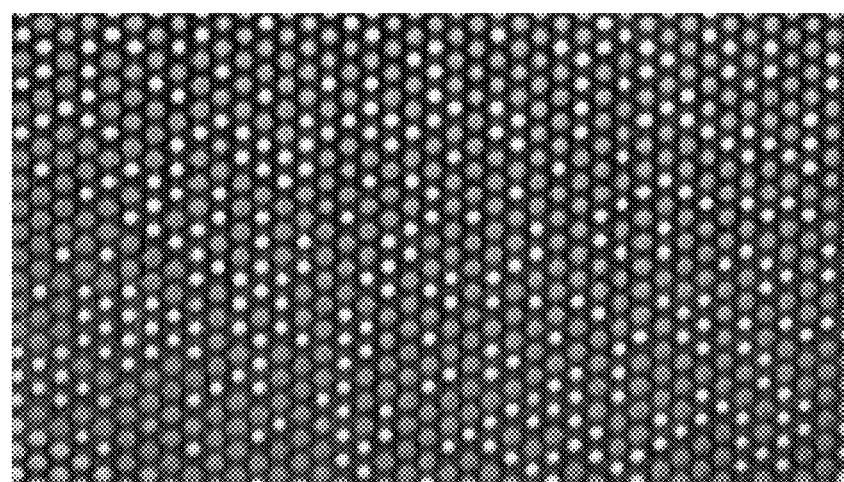
Figure 3E:
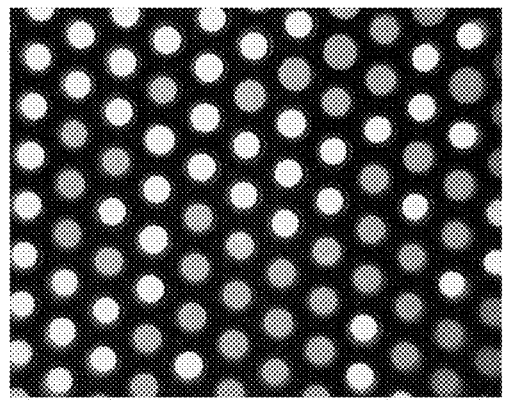
Figure 3F:
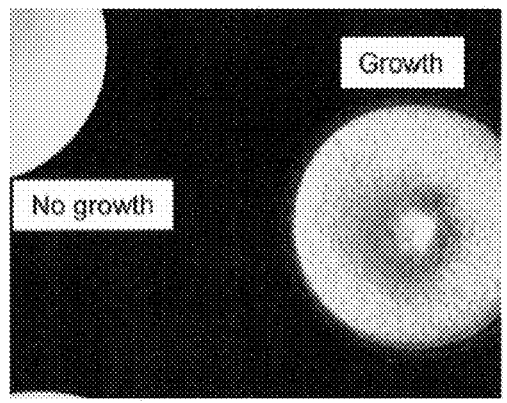
Figure 3F:
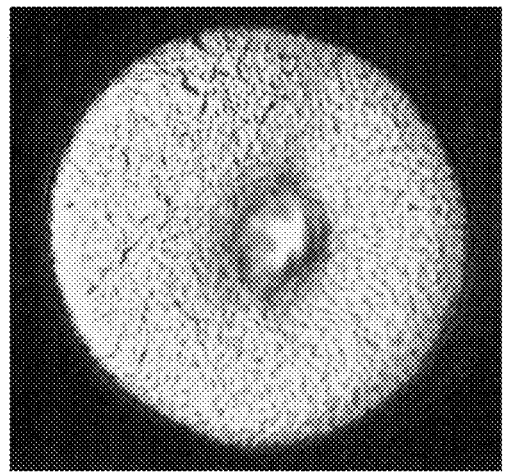

FIGS. 3D-3F are photographs of *E. coli* cells substantially or largely singulated via Poisson or substantial Poisson distribution in microwells or perforations in a perforated disk with a membrane bottom at low, medium and high magnification, respectively. FIG. 3D shows digital growth at low magnification where the darker microwells are microwells where cells are growing. FIG. 3E is a top view of microwells in a perforated disk where the darker microwells are microwells where cells are growing. FIG. 3F is a photograph of microwells where the membrane (e.g., the permeable membrane that forms the bottom of the microwells) has been removed, where unpatterned (smooth) microwells are microwells where cells are not growing, and microwells with irregular pigment/patterned are microwells where cells are growing, and, in this photograph, have filled the microwells in which they are growing. In these photographs, a 0.2 µm filter (membrane) was swaged against the perforated disk under high pressure such as the round perforated disk depicted in FIG. 3C. The perforated disk formed the walls of the microwells, and the 0.2 µm filter formed the bottom of the microwells. To load the perforated disk+filter, the *E. coli* cells were pulled into the microwells using a vacuum (see Example 6 for methods). The perforated disk+filter was then placed on an LB agar plate membrane-side down, and the cells were grown overnight at 30° C., then two days at room temperature. The membrane was removed and the bottomless microwells were photographed by light microscopy. Note the ease with which different selective media can be used to select for certain cell phenotypes; that is, one need only transfer the perforated disk+filter to a different plate or petri dish comprising a desired selective medium. Generally the number of cells loaded into a singulation device or singulation assembly ranges from between approximately 0.1× to 2.5× the number of perforations or microwells, or from between approximately 0.3× to 2.0× the number of perforations or microwells, or from between approximately 0.5× to 1.5× the number of perforations or microwells.

Figure 4A:
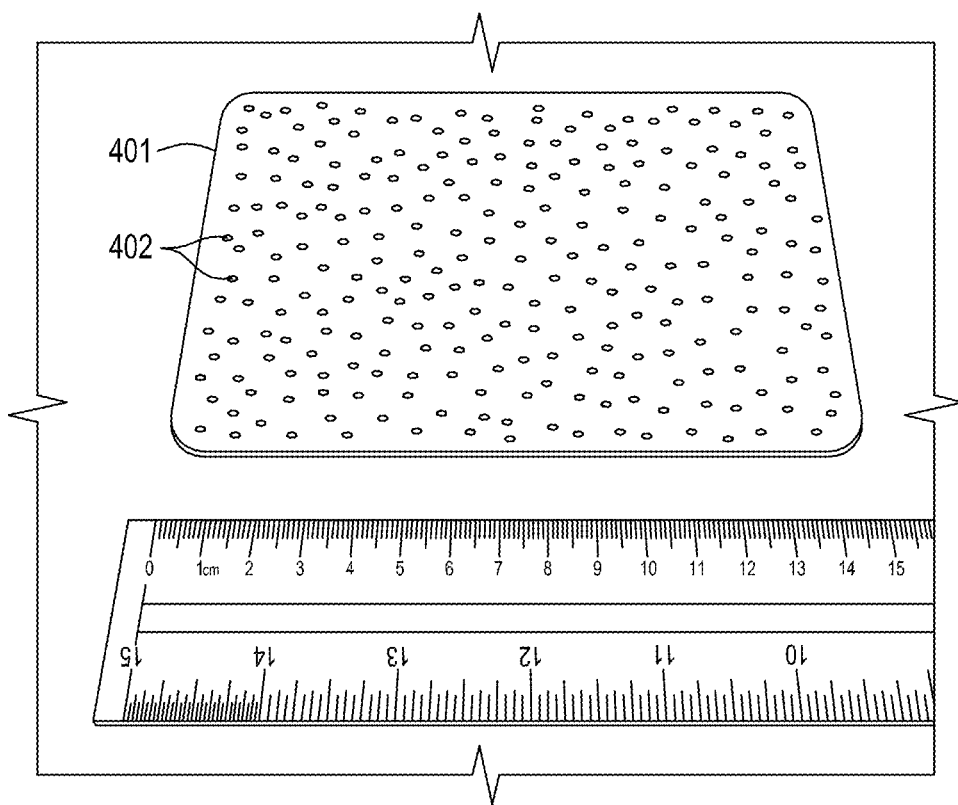
FIGS. 4A-4E are photographs of the perforated member and the microwells therein.
Figure 4B:
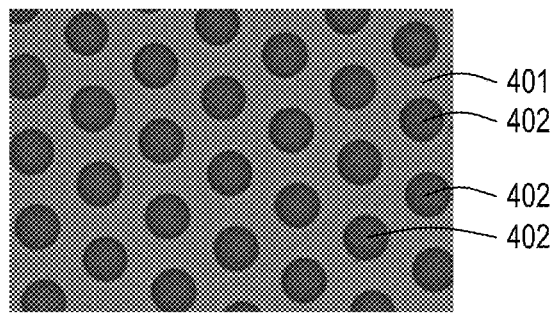

FIGS. 4A through 4BB depict various components of different embodiments and components of a solid wall singulation or substantial singulation, growth, induction of editing and either normalization or cherry picking module ("solid wall isolation/induction/normalization module" or "SWIIN") suitable for singulating (or substantially singulating) cells of all types, growing cells for an initial, e.g., 2-150 rounds of cell division, inducing editing, and either normalizing or cherry picking the resulting cell colonies. The SWIIN modules presented may be stand-alone devices, or, often, one module in an automated multi-module cell processing instrument. FIG. 4A is a representation of a perforated metal sheet or perforated member 401 that is generally rectangular in shape. The perforations are not represented at scale. As with the perforated disk described in relation to FIGS. 3C-3F, perforated member 401 is fabricated from 316 stainless steel, where the perforations form the walls of microwells, and a filter or membrane (not seen in this FIG. 4A) is used to form the bottom of the microwells.

In the scanning electromicrograph shown in FIG. 4B the perforations (microwells) are approximately 150 µm-200 µm in diameter, and the perforated member is approximately 125 deep, resulting in microwells having a volume of approximately 2.5 nl, with a total of approximately 200,000 microwells. The distance between the microwells is approximately 279 µm center-to-center. Though here the microwells have a volume of approximately 2.5 nl, the volume of the microwells may be from 1 to 25 nl, or preferably from 2 to 10 nl, and even more preferably from 2 to 4 nl. The perforated member pictured in FIG. 4A is approximately 14 cm long and 10 cm (140 mm×100 mm) wide; however, smaller perforated members (such as shown in FIG. 3C) or larger perforated members may be used depending on the density of microwells in the perforated member and the number of microwells or partitions required. For example, the larger the plexity (e.g., complexity) of the library being used to edit a population of cells, a larger number of microwells or partitions is preferred. If, for example, a 10,000-plex library is used to edit a population of cells, a perforated member with 200,000 microwells or partitions would be more than adequate; however, if a 50,000-plex library is used to edit a population of cells, a perforated member (or two or more members) with a total of 400,000 or more microwells or partitions may be preferred. Generally the number of cells loaded into a singulation device or singulation assembly ranges from between approximately 0.1× to 2.5× the number of perforations or microwells, or from between approximately 0.3× to 2.0× the number of perforations or microwells, or from between approximately 0.5× to 1.5× the number of perforations or microwells; thus, the number of cells loaded onto a perforated member comprising approximately 200,000 perforations would range from about 20,000 cells to about 500,000 cells, or from about 60,000 cells to about 400,000 cells, or from about 100,000 cells to about 300,000 cells. The preferred size/volume of the microwells will depend on the cell type (e.g., archeal, bacterial, yeast, non-mammalian eukaryotic, and/or mammalian being edited). The perforated member shown here is made of 316 stainless steel; however other bio-compatible metals and materials may be used, such as titanium, cobalt-based alloys, and ceramics. The SWIIN may be disposable or it may be reusable. If reused, the SWIIN may be heated to 55° C. or greater to sterilize the SWIIN alternatively, antibiotics mabe flushed through the SWIIN.

Figure 4C:
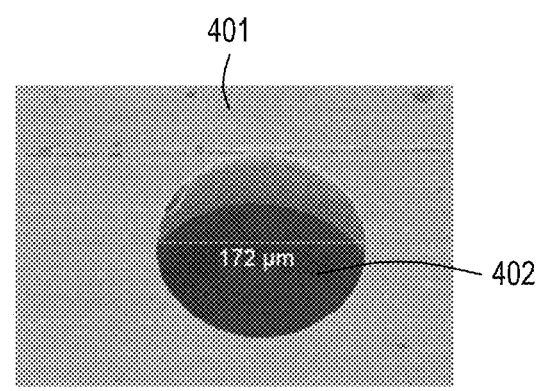
Figure 4D:
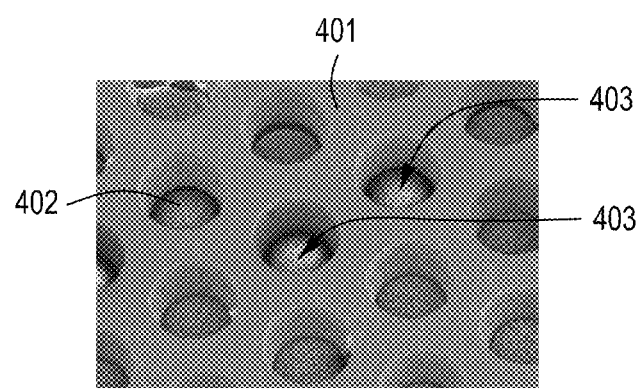
Figure 4E:
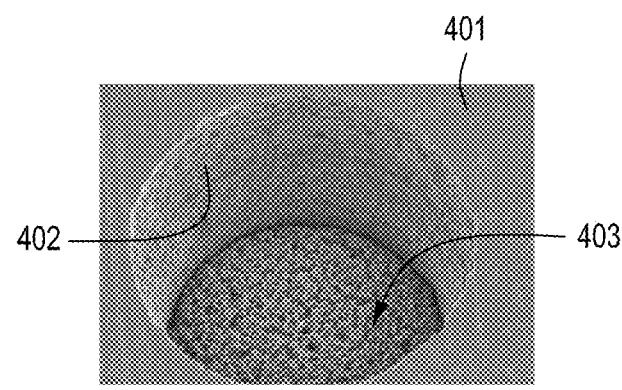

FIGS. 4B-4E are scanning electromicrographs of a portion of a perforated member 401 (FIG. 4B), a close up of one microwell 402 without (FIG. 4C) and with (FIGS. 4D and 4E) a filter membrane forming the bottom of the microwell 402. FIG. 4B shows perforated member 401 and 30 or so microwells 402. FIG. 4C also shows perforated member 401 and a single microwell 402, where this microwell is approximately 172 μm in diameter. FIG. 4D shows perforated member 401 and approximately 8 microwells 402, each of which has a portion of a filter or membrane 403 forming the bottom of the microwell 402. FIG. 4E is a higher magnification micrograph of one of the microwells 402 from the perforated member 401 shown in FIG. 4D. As described above in relation to FIGS. 3C-3F, use of a filter or membrane (such as a 0.22 μm PVDF Duropore™ woven membrane filter) allows for medium and/or nutrients to enter the microwells but prevents cells from flowing down and out of the microwells. Filter or membrane members that may be used to form the bottom of the microwells of a perforated member in a solid wall singulation or substantial singulation/initial growth/induction of editing and normalization/cherry picking module are those that are solvent resistant, are contamination free during filtration, do not tear under pressures required to exchange media and load cells, and are able to retain the types and sizes of cells of interest. For example, in order to retain small cell types such as bacterial cells, pore sizes can be as low as 0.2 μm, however for other cell types, the pore sizes can be as high as 0.5 μm or larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber. The perforated member 401 and filter 403 are swaged together; that is, the perforated member 401 and filter 403 are pressed together under high pressure (e.g., 20 kpsi). In some embodiments, the holes or partitions in the perforated member are etched with a slight taper and the filter material is pressed into the opening then relaxed to form an effective swage, allowing for an adhesive-free coupling. As an alternative, an adhesive could be employed.

Figure 4F:
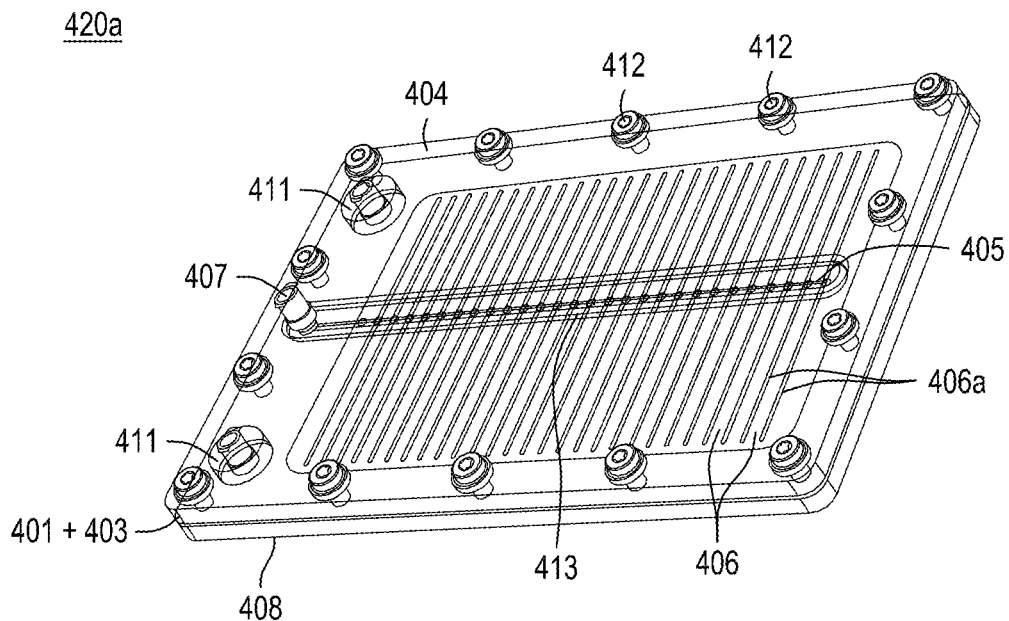
FIG. 4F-4R depict the components of three exemplary embodiments of a singulation assembly comprising retentate and permeate members, as well as a perforated member/filter/gasket assembly.

FIG. 4F depicts one embodiment of a singulation assembly 420a from a top perspective view, which presents the "retentate side" of singulation assembly 420a. As used herein a "singulation assembly" comprises a retentate member 404 as a top member, a permeate member 408 as a bottom member, with a gasket 416 surrounding a perforated member 401 and a filter 403, where gasket 416, perforated member 401 and filter 403 are sandwiched between retentate member 404 and permeate member 408. Retentate and permeate members 404 and 408, respectively, in the embodiments exemplified in FIGS. 4F-4Q and 4Y are transparent, and are approximately 200 mm long, 130 mm wide, and 4 mm thick, though in other embodiments, the retentate and permeate members can be from 75 mm to 350 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. In the embodiments depicted in FIGS. 4F-4BB, the retentate members are fabricated from PMMA (poly(methyl methacrylate); however, other materials may be used, including polycarbonate, cyclic olefin co-polymer (COC), glass, poly-vinyl chloride, polyethylene, polyamide, polypropylene, polysulfone, polyurethane, and co-polymers of these and other polymers. Gasket 416 is flat, circumferentially surrounds perforated member 401 and filter 403, and is made from rubber, silicone, nitrile rubber, polytetrafluoroethylene, a plastic polymer such as polychlorotrifluoroethylene, or other readily compressible material.

Retentate member 404 comprises a generally smooth upper surface; a single distribution channel 405 (here, located centrally) which traverses retentate member 404 from its top surface to its bottom surface and for most of the length of retentate member 404 (details of which are described in relation to FIG. 4I); and ridges 406a, which here are disposed on the bottom surface of retentate member 404 (e.g., adjacent perforated member 401) where the ridges 406a traverse the bottom of retentate member 404 from side-to-side (e.g., left to right) (in this embodiment, there are approximately 28 ridges 406a). As used herein with respect to the distribution channels in the retentate member or permeate member, "most of the length" means about 95% of the length of the retentate member or permeate member, or about 90%, 85%, 80%, 75%, or 70% of the length of the retentate member or permeate member. Flow directors 406 are formed between ridges 406a. In addition, retentate member 404 has a single port 407, which allows for cells to be introduced into singulation assembly 420a; and there is also a distribution channel cover 413, which covers the single distribution channel 405 in retentate member 404. In this embodiment, distribution channel 405 is approximately 150 mm long and 1 mm wide; retentate member ridges 406a are approximately 0.5 mm in height and 80 mm in length; and retentate member flow directors 406 are approximately 5 mm across. The volume of fluid in the singulation assembly ranges from 5 mL to 100 mL, or from 7.5 mL to 60 mL, or from 10 mL to 40 mL (note this is for a 200K perforation singulation assembly).

In addition to retentate member 404, also seen in FIG. 4F are fasteners 412, a center "sandwich" layer comprising a gasket 416 surrounding a perforated member 401 disposed above a filter or membrane 403 (the individual components are not seen in this FIG. 4F). The bottom layer of singulation assembly 420a seen in FIG. 4F is formed by a permeate member 408. The permeate member 408, like retentate member 404, comprises one or more permeate member distribution channels, permeate member ridges, permeate member flow directors, and one or more ports (none of which are shown in FIG. 4F but see FIG. 4G). The singulation assemblies 420 and SWIIN modules 400 comprising the singulation assemblies 420 are fabricated from material that withstand temperature of 4° C. to 60° C. Heating and cooling of the SWIIN modules is provided by a Peltier device or thermoelectric cooler; or a combination of systems may be employed in, e.g., multi-layer SWIIN modules (see, e.g., FIGS. 4BB and 4CC) such as reverse Rankine vapor-compression refrigeration or absorption heat pumps.

In the solid wall singulation or substantial singulation, growth, induction of editing and normalization and/or cherry-picking modules ("solid wall isolation/induction/normalization module" or "SWIIN") described in FIGS. 4A-4CC, cells and medium (at a dilution appropriate for Poisson or substantial Poisson distribution of the cells in the microwells of the perforated member) are flowed into distribution channel 405 from one or more ports (in FIG. 4F, there is one port 407) in retentate member 404, and the cells settle in the microwells, again, in a Poisson or substantial Poisson distribution of the cells in the microwells. The cells are retained in the microwells as they cannot travel through filter 403. After cell loading, an appropriate medium may then be introduced into the singulation assembly via the retentate member; that is, medium is introduced through ports 411 (FIG. 4G), and the medium travels into distribution channels 409 (FIG. 4G) in permeate member 408, then is distributed throughout flow directors 410 (FIG. 4G) in permeate member 408. The medium in permeate member 408 can flow upward through filter 403 so as to nourish the cells loaded into the microwells. In operation, once the cells are deposited into the microwells, they are grown for an initial, e.g., 2-100 or so doublings, editing is induced by, e.g., raising the temperature of the SWIIN to 42° C. to induce a temperature inducible promoter or by removing growth medium from the permeate member (back through ports 411, see FIG. 4G) and by replacing the growth medium with a medium comprising a chemical component that induces an inducible promoter. Once editing has taken place, the temperature or the SWIIN may be decreased, or the inducing medium may be removed and replaced with fresh medium lacking the chemical component and thus deactivating the inducible promoter. The cells then are allowed to continue to grow in the SWIIN until the growth of the cell colonies in the microwells is normalized. Once normalization has taken place, the colonies are flushed from the microwells (e.g., by applying pressure to permeate member 408 and thus filter 403) and the cells in the colonies are pooled; or, alternatively, the growth of the cell colonies in the microwells is monitored, and slow-growing colonies are directly selected by, e.g., pooling the cells from the slow-growing colonies by pipetting slow-growing cells from the microwells into a tube or other vessel, or colonies from individuals microwells can be selected and pipetted into, e.g., individual wells in a 96-well or 384-well plate.

Colony growth in the singulation assembly (and thus in the SWIIN module) can be monitored by automated devices such as those sold by JoVE (ScanLag™ system, Cambridge, Mass.) (also see Levin-Reisman, et al., Nature Methods, 7:737-39 (2010)). Cell growth for, e.g., mammalian cells may be monitored by, e.g., the growth monitor sold by IncuCyte (Ann Arbor, Mich.) (see also, Choudhry, PLos One, 11(2):e0148469 (2016)). Further, automated colony pickers may be employed, such as those sold by, e.g., TECAN (Pickolo™ system, Mannedorf, Switzerland); Hudson Inc. (RapidPick™, Springfield, N.J.); Molecular Devices (QPix 400™ system, San Jose, Calif.); and Singer Instruments (PIXL™ system, Somerset, UK).

Figure 4G:
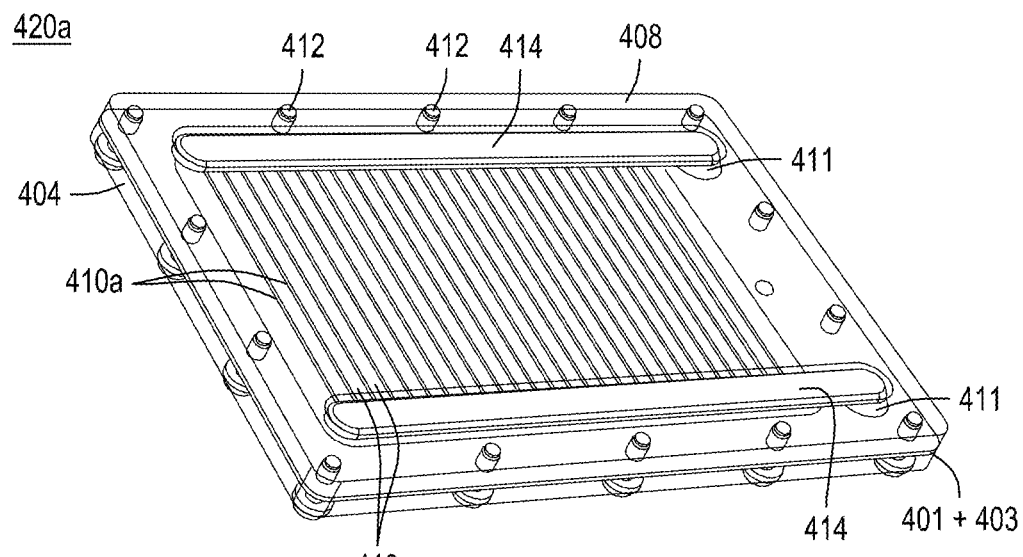

FIG. 4G depicts the embodiment of the singulation assembly 420a in FIG. 4F from a bottom perspective view, which presents the bottom of the permeate member 408 of singulation assembly 420a. Permeate member 408 comprises a generally smooth lower surface (which in FIG. 4G, because singulation assembly 420a is viewed from the bottom, is toward the top of FIG. 4G); two distribution channels (not shown) covered by distribution channel covers 414 here, located on either side (left side/right side) of the bottom of permeate member 408. Also seen are ridges 410a, which here are disposed on the top surface of permeate member 408 (where the top surface of the permeate member 408 in FIG. 4G is facing down) and traverse the top of permeate member 408 from right-to-left (in this embodiment, there are approximately 28 ridges 410a), with flow directors 410 formed ridges 410a. In addition, permeate member 408 has two ports 411, which deliver fluids to and remover fluids from the distribution channels (not seen here as they are covered by distribution channel covers 414).

In addition to permeate member 404, also seen in FIG. 4F are fasteners 412, a center "sandwich" layer comprising a gasket 416 surrounding a perforated member 401 swaged with a filter or membrane 403 (the individual components are not seen in this FIG. 4G). The bottom-most layer of singulation assembly 420a seen in FIG. 4G is retentate member 404. It should be noted that in the embodiments depicted in FIGS. 4F-4CC, fasteners 412 are exemplified; however, other means can be used to secure retentate member 404, gasket 416, perforated member 401, filter 403, and permeate member 408, such as adhesives—such as a pressure sensitive adhesive, ultrasonic welding or bonding, solvent bonding, mated fittings, or a combination of adhesives, welding, solvent bonding, and mated fittings; and other such fasteners and couplings.

Figure 4H:
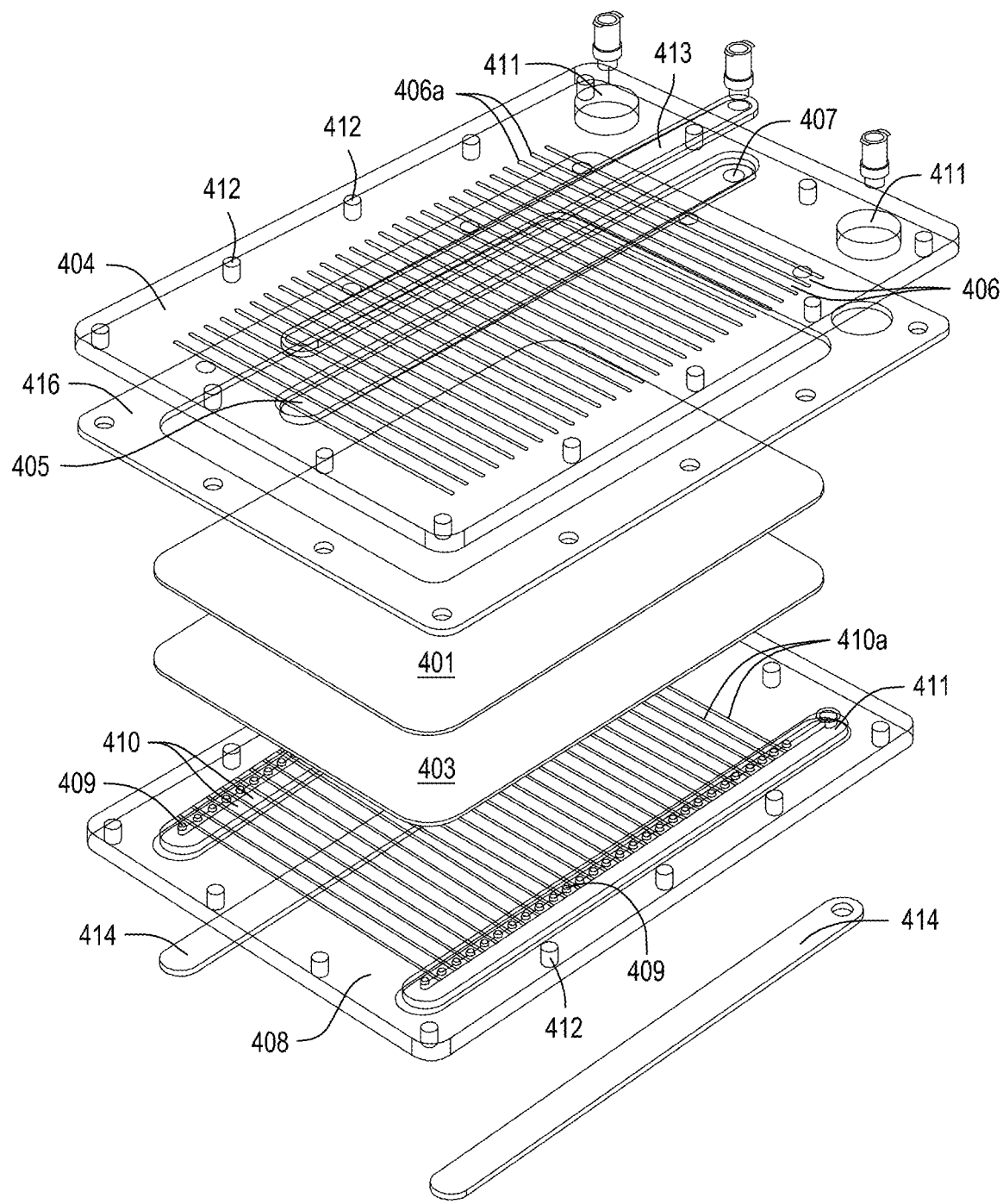

FIG. 4H depicts the embodiment of the singulation assembly 420a of FIGS. 4F and 4G from a side exploded perspective view. From the top of FIG. 4H, is seen retentate member 404 comprising single distribution channel 405 which traverses retentate member 404 from its top surface to its bottom surface and for most of the length of retentate member 404 (details of which are described in relation to FIG. 4I); ridges 406a, which are disposed on the bottom surface of retentate member 404 and traverse the bottom surface of retentate member 404 from left-to-right (in this embodiment, there are approximately 26 ridges 406a), and flow directors 406 that are formed between ridges 406a. In addition, retentate member 404 has a single port 407, which allows for cells and other fluids to be introduced into and removed from retentate member 404 and thus into or out of singulation assembly 420a. There is also a distribution channel cover 413, which is configured to fit into and cover single distribution channel 405.

Gasket 416, perforated member 401 and filter 403 can be seen more clearly in this exploded view of singulation assembly 420a, where perforated member 401 and filter 403 are of very similar size—if not the same size—and gasket 416 is configured to surround perforated member 401 and filter 403 and to provide a leak-proof seal between retentate member 404 and permeate member 408. In FIG. 4H, permeate member 408 is seen from the top down where permeate member 408 comprises two distribution channels 409 located lengthwise on either side (left-right) of permeate member 408, ridges 410a, which here are disposed on the top surface of permeate member 408 and traverse the top of permeate member 408 from side-to-side (left to right) (in this embodiment, there are approximately 28 ridges 410a), and flow directors 410 that are formed between ridges 410a in permeate member 408. In addition, permeate member 408 has two ports 411 (only one of which is seen in this FIG. 4H), where ports 411 deliver fluids and remove fluids from distribution channels 409. Also seen are distribution channel covers 414 that are not in place covering distribution channels 409. Also seen in FIG. 4H are fasteners 412, although again, other means for securing the components of singulation assembly 420a may be used and preferably are used for production singulation assemblies.

Figure 4I:
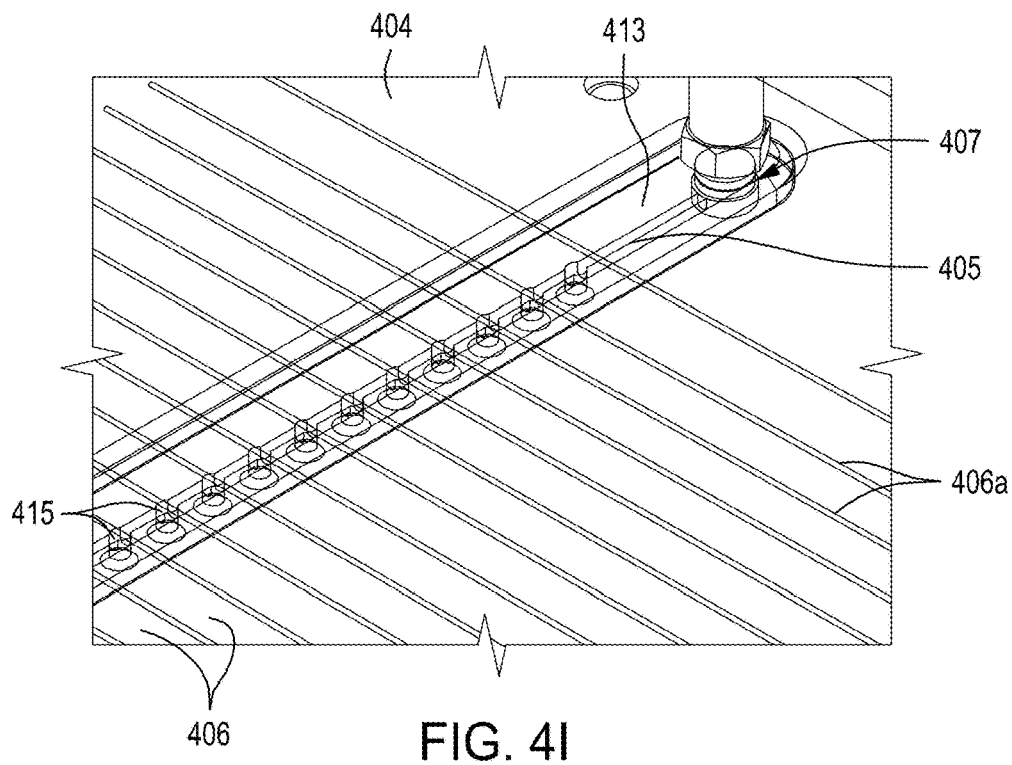

FIG. 4I is a close-up side perspective view of the top surface of retentate member 404, including port 407 (here with a luer connection from a fluid source to port 407 in retentate member 404), distribution channel 405, which traverses retentate member 404 from its top surface to its bottom surface and for most of the length of retentate member 404 and is configured to deliver fluids to (and remove fluids from) flow directors 406 on the bottom surface of retentate member 408. Distribution channel 405 comprises flow director holes 415 that correspond to flow directors 406, as flow directors 415 are positioned in distribution channel 405 between retentate member ridges 406a.

Distribution channel cover 413 is disposed upon the top surface of retentate member 404, covering (and forming the top surface of) distribution channel 405.

Figure 4J:
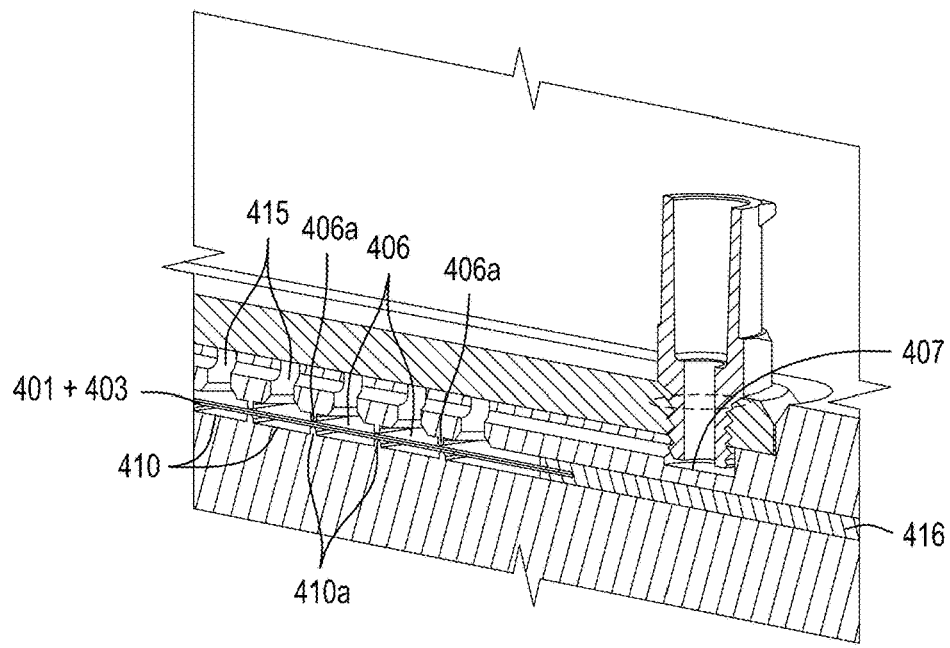

FIG. 4J is a close-up side cross sectional view of singulation assembly 420a. In FIG. 4J, retentate port 407 is seen (with a luer connection from a fluid source to port 407), as is gasket 416, and perforated member 401 and filter 403 swaged together and disposed between retentate member 404 and permeate member 408. Also seen are ridges 406a, which are disposed on the bottom surface of retentate member 404, and flow directors 406 that are formed between ridges 406a. In addition, seen are ridges 410a permeate member 408, as well as flow directors 410 that are formed between ridges 410a. Note that ridges 406a on retentate member 404 and ridges 410a on permeate member 408 meet and are coincident with one another separated only by perforated member 401 and filter 403, thus flow directors 406 and flow directors 410 are also coincident with one another. Also seen are flow director holes 415 that correspond to flow directors 406, as they are positioned between retentate member ridges 406a. Ridges 406a on retentate member 404 and ridges 410a on permeate member 408 not only form flow directors 406 and 410 in retentate member 404 and permeate member 408, respectively, but provide support to the singulation assembly 420 by distributing pressure throughout the singulation assembly 420 and preventing tears in filter or membrane 403.

Figure 4K:
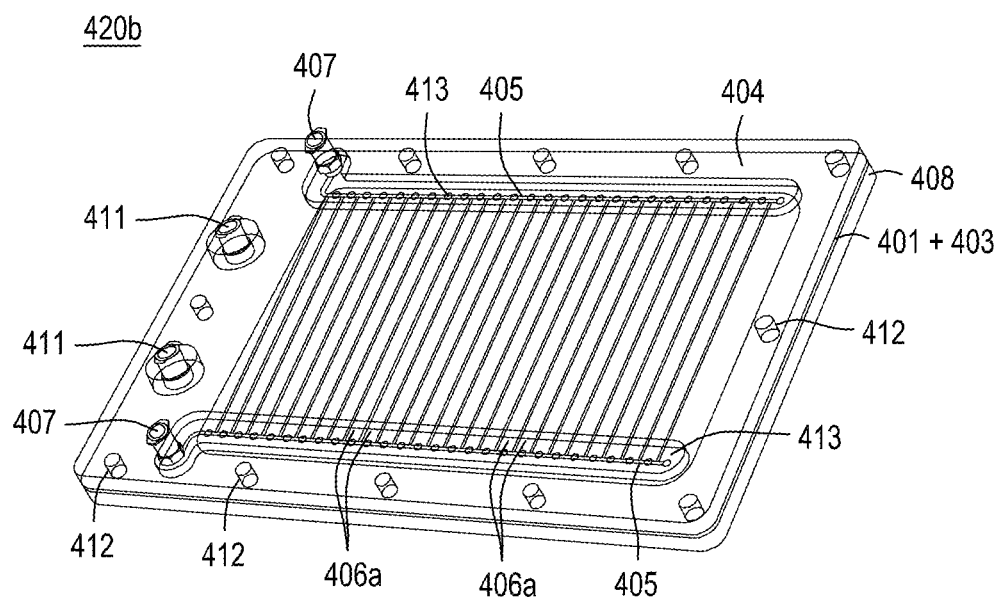

FIG. 4K depicts another embodiment of a singulation assembly 420b from a top perspective view, which presents "retentate side" of singulation assembly 420b. The singulation assembly 420b embodiment seen in FIG. 4K differs from singulation assembly 420a seen in FIGS. 4F-4H in that the retentate member 404 in FIGS. 4K-4M has two distribution channels 405 disposed lengthwise on either side (left-right) of retentate member 404 instead of a single distribution channel 405 disposed lengthwise down the middle of retentate member 404. As in FIGS. 4F-4H, retentate member 404 of FIGS. 4J-4M comprises a generally smooth upper surface; two distribution channels 405 which traverse retentate member 404 from its top surface to its bottom surface and for most of the length of retentate member 404; and ridges 406a, which are disposed on the bottom surface of retentate member 404 and traverse the bottom of retentate member 404 from side-to-side, left-to-right (in this embodiment, there are approximately 28 retentate member ridges 406a). Flow directors 406 are formed between ridges 406a on retentate member 404. In addition, retentate member 404 has two ports 407, which allow for cells and medium to be introduced into (and removed from) singulation assembly 420b. There are also distribution channel covers 413, which cover the two distribution channels 405 and actually provide the top surface of distribution channels 405.

In addition to retentate member 404, also seen in FIG. 4K are fasteners 412, the center "sandwich" layer comprising a gasket 416 surrounding perforated member 401 swaged with (and positioned above) filter or membrane 403 (the individual components are not seen in this FIG. 4K). The bottom layer of singulation assembly 420b seen in FIG. 4K is formed by a permeate member 408. Permeate member 408, like retentate member 404, comprises one or more (as seen in FIG. 4L, there are two) permeate member distribution channels, a multiplicity of ridges, and flow directors, and one or more ports (none of which are shown in FIG. 4K but see FIG. 4L).

As described before in relation to FIGS. 4F-4H, in the solid wall singulation or substantial singulation, growth, induction of editing and either normalization or cherry picking modules ("solid wall isolation/induction/normalization module" or "SWIIN") described in FIGS. 4F-4CC, cells and medium (at a dilution appropriate for Poisson or substantial Poisson distribution of the cells in the microwells of the perforated member) are flowed into distribution channels 405 from the two ports 407 in retentate member 404, and the cells settle in the microwells, again, in a Poisson or substantial Poisson distribution of the cells in the microwells. The cells are retained in the microwells of perforated member 401 as the cells cannot travel through filter 403. An appropriate medium is introduced into singulation assembly 420b through permeate member 408. The medium flows upward through filter 403 to nourish the cells. Thus, in operation, the cells are deposited into the microwells, are grown for an initial, e.g., 2-100 doublings, editing is induced by, e.g., raising the temperature of the SWIIN to 42° C. to induce a temperature inducible promoter or by removing growth medium from the permeate member and replacing the growth medium with a medium comprising a chemical component that induces an inducible promoter. Once editing has been allowed to take place, the temperature of the SWIIN may be decreased, or the inducing medium may be removed and replaced with fresh medium lacking the chemical component thereby activating the inducible promoter. The cells then are allowed to continue to grow in the SWIIN until the growth of the cell colonies in the microwells is normalized. Once the colonies are normalized, the colonies are flushed from the microwells (by applying pressure to the permeate member channels and flow directors and thus to the filter) and pooled; alternatively, the growth of the cell colonies in the microwells is monitored, and slow-growing colonies are directly selected by, e.g., pooling the cells from the slow-growing colonies.

Figure 4L:
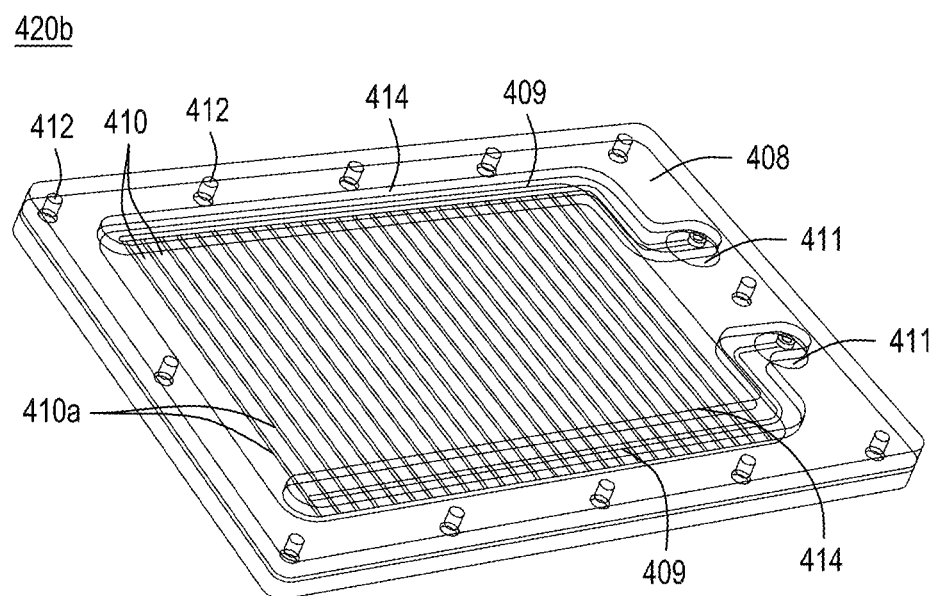

FIG. 4L depicts the embodiment of the singulation assembly 420b in FIG. 4K from a bottom perspective view, which presents the bottom of the permeate member 408 of singulation assembly 420b. Permeate member 408 comprises a generally smooth lower surface (which in FIG. 4L, because singulation assembly 420b is viewed from the bottom, is toward the top of FIG. 4L); two distribution channels (not shown) covered by distribution channel covers 414 (here, located on either side (left-right) of permeate member 408), ridges 410a, which are disposed on the top surface of permeate member 408 (where the top surface of the permeate member 408 in FIG. 4L is facing down) and traverse the top of permeate member 408 from side-to-side (in this embodiment, there are approximately 28 ridges 410a), and flow directors 410 that are formed between ridges 410a. In addition, permeate member 408 has two ports 411, which deliver fluids to (and remove fluids from) the distribution channels (not seen here as they are covered by distribution channel covers 414) and then to flow directors 410.

In addition to permeate member 404, also seen in FIG. 4L are fasteners 412, a center "sandwich" layer comprising a gasket 416 surrounding a perforated member 401 swaged with and positioned above a filter or membrane 403 (the individual components are not seen in this FIG. 4L), and the bottom-most layer of singulation assembly 420b seen in FIG. 4L is retentate member 404. Again, it should be noted that in the embodiments depicted in FIGS. 4F-4CC, fasteners are exemplified; however, other means can be used to secure retentate member 408, gasket 416, perforated member 401, filter 403, and permeate member 408, such as adhesives, ultrasonic welding or bonding, solvent bonding, mated fittings, or a combination of adhesives, welding, solvent bonding, and mated fittings; and other such fasteners and couplings.

Figure 4M:
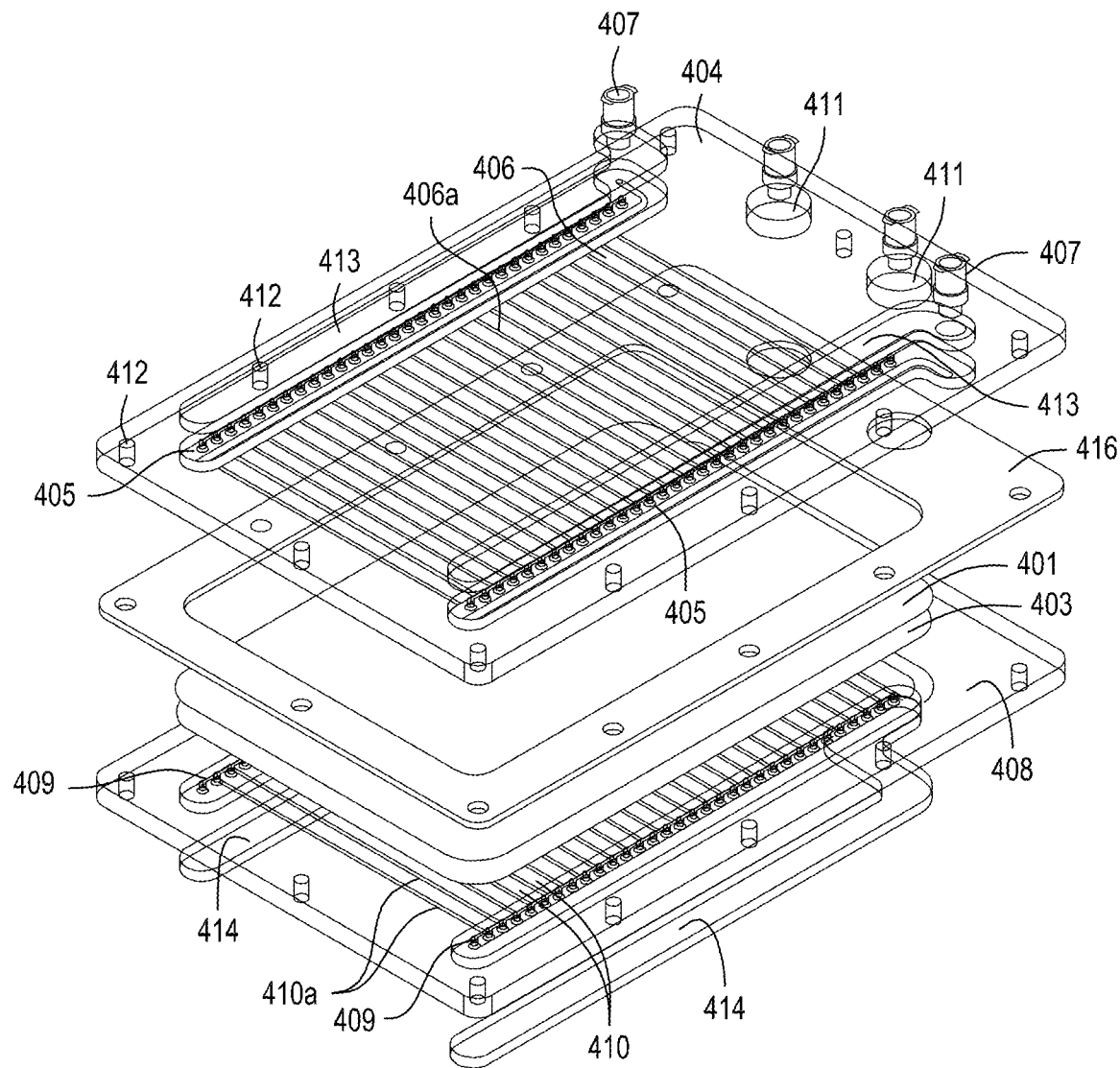

FIG. 4M depicts the embodiment of the singulation assembly 420b of FIGS. 4K and 4L from a side exploded perspective view. From the top of FIG. 4M is seen retentate member 404 comprising two distribution channels 405 located on either side (left-right) of retentate member 404, both of which traverse retentate member 404 from its top surface to its bottom surface and for most of the length of retentate member 404; ridges 406a, which are disposed on the bottom surface of retentate member 404 and traverse the bottom surface of retentate member 404 from side-to-side (in this embodiment, there are approximately 28 ridges 406a), and flow directors 406 that are formed between ridges 406a. In addition, retentate member 404 has two ports 407, which allow for cells and other fluids to be introduced into (and removed from) singulation assembly 420a through distribution channels 405. There is also two distribution channel covers 413, which are configured to fit into and cover the two distribution channels 405.

Gasket 416, perforated member 401 and filter 403 can be seen more clearly in this exploded view of singulation assembly 420b, where perforated member 401 and filter 403 are of very similar size and gasket 416 is configured to surround perforated member 401 and filter 403, to secure perforated member 401 and filter 403, and to provide a leak-proof seal between retentate member 404 and permeate member 408. In FIG. 4M, permeate member 408 is seen from the top down where permeate member 408 comprises two distribution channels 409 located lengthwise on either side (left-right) of permeate member 408, both of which traverse permeate member 408 from its bottom surface to its top surface and for most of the length of permeate member 408, ridges 410a, which here are disposed on the top surface of permeate member 408 and traverse the top of permeate member 408 from side-to-side, and flow directors 410 that are formed between ridges 410a. In addition, permeate member 408 has two ports 411, seen in this FIG. 4M as ports on retentate member 404, which when singulation assembly 420b is assembled are fluidically connected to distribution channels 409 on permeate member 408, which are connected to flow distributors 410, and thus to filter 403 disposed upon permeate member 408. Also seen are distribution channel covers 414 that are separate from singulation assembly 420b in this exploded view and not inserted into permeate member 408 to cover distribution channels 409. Also seen in FIG. 4M are holes for fasteners 412 (fasteners not shown), although again, other means aside from fasteners may be used for securing the components of singulation assembly 420b.

Figure 4N:
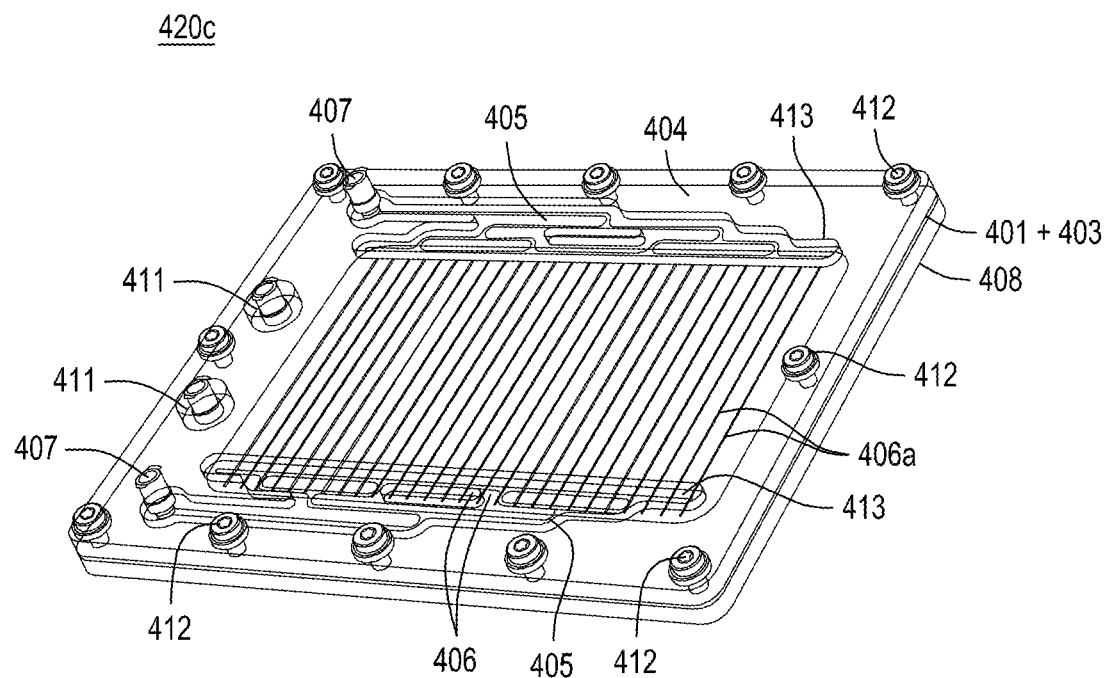
Figure 4O:
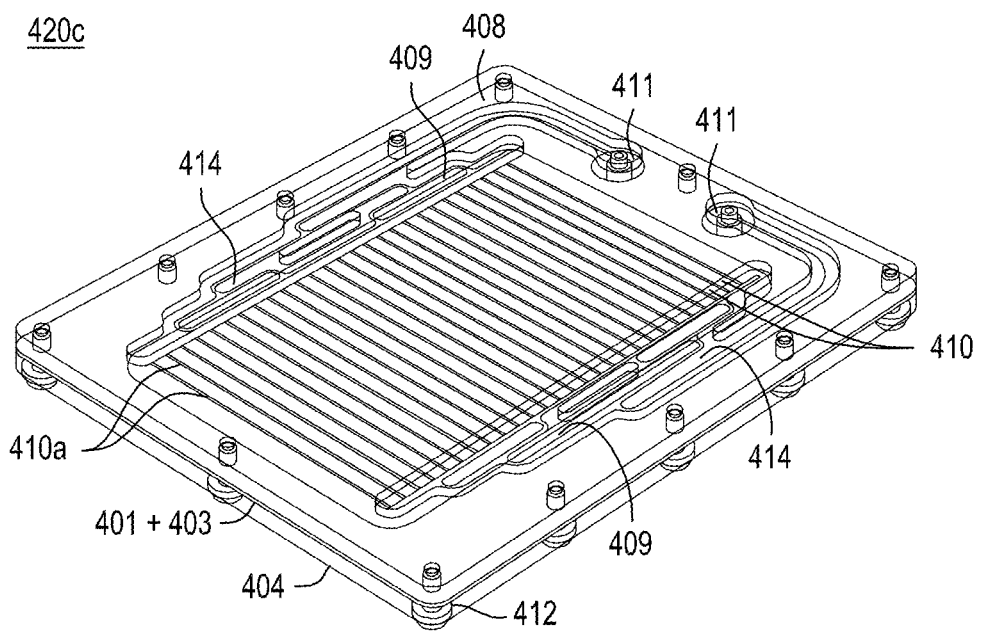
Figure 4P:
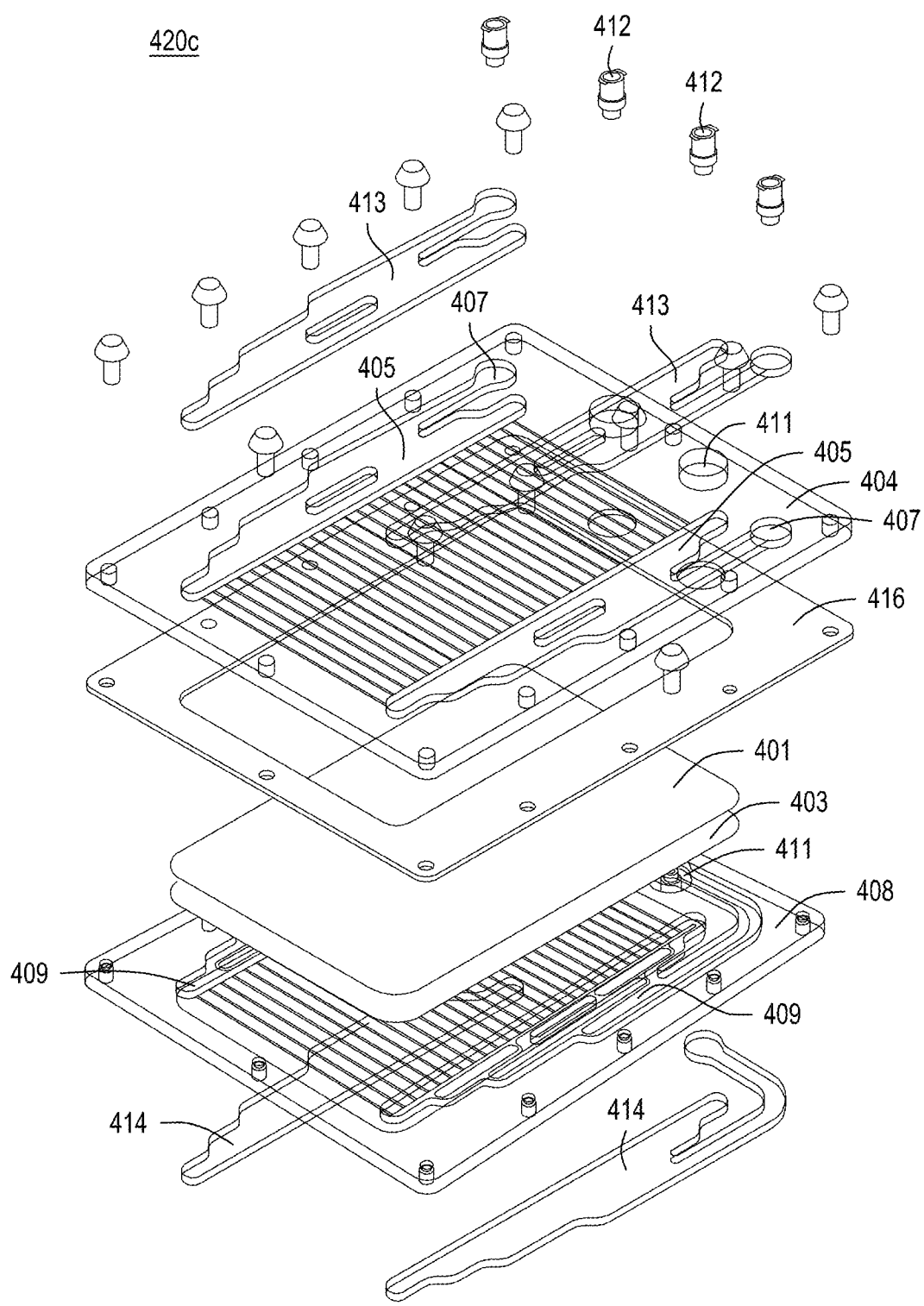

FIG. 4N depicts another embodiment of a singulation assembly 420c from a top perspective view, which presents the "retentate side" of singulation assembly 420c. The singulation assembly 420c embodiment seen in FIG. 4N differs from singulation assembly 420a seen in FIGS. 4F-4H in that the retentate member 404 in FIGS. 4N-4P has two distribution channels 405 disposed lengthwise on either side (left-right) of retentate member 404 instead of a single distribution channel 405 disposed lengthwise down the middle of retentate member 404. The singulation assembly 420c embodiment seen in FIG. 4N differs from singulation assembly 420b seen in FIGS. 4K-4M in that the configuration of the distribution channels 405 in retentate member 404 (and distribution channels 409 in permeate member 408) in FIGS. 4N-4P is different from that in FIGS. 4K-4M. The distribution channels 405 (and distribution channels 409) in FIGS. 4N-4P are branched; that is, instead of a port 407 delivering fluids directly into a distribution channel 405 at the point where port 407 intersects directly with distribution channel 405, in the embodiment of the singulation assembly shown in FIGS. 4N-4P, fluids flow into ports 407, then into branched distribution channels 405 on either side (left-right) of retentate member 407. The branched distribution channels have a first conduit which terminates approximately half-way down the length of retentate member 404, where the first conduit then branches into two secondary conduits, the two secondary conduits branch into four tertiary conduits, and these tertiary conduits deliver fluids to a final conduit that travels the length of the retentate member, evenly distributing delivering fluids to the flow directors 406.

Note that any configuration of distribution channels (e.g., distribution channels 405 on retentate member 404 and distribution channels 409 on permeate member 408) may be used on retentate member 404 or permeate member 408, as long as the distribution channels adequately distribute fluids to flow directors 406 or flow directors 410. As seen in FIGS. 4F-4H, the configuration of distribution channels 405 on retentate member 404 and distribution channels 409 on permeate member 408 may be different, or as seen in FIGS. 4K-4M and FIGS. 4N-4P, the configuration of distribution channels 405 on retentate member 404 and permeate member distribution channels 409 on permeate member 408 may be the same. As in FIGS. 4K-4M, retentate member 404 of FIGS. 4N-4P comprises a generally smooth upper surface; two distribution channels 405 one of the left and one on the right of retentate member 404 which traverse retentate member 404 from its top surface to its bottom surface and are branched thus distributing fluid the length of retentate member 404.

Retentate member 404 also comprises ridges 406a, which are disposed on the bottom surface of retentate member 404 and traverse the bottom of retentate member 404 from side-to-side. In addition—and as in previous embodiments—there are flow directors 406 that are formed between ridges 406a on retentate member 404; and two ports 407, which introduce and distribute cells and medium into (and remove cells and medium from) retentate member 404 of singulation assembly 420c. Also seen are distribution channel covers 413, which cover the two branched distribution channels 405 on retentate member 404 and actually provide the top surface of branched distribution channels 405. Note that the branching for distribution channels 405 is a part of retentate member 404 in this embodiment; however, retentate member 404 may not comprise the branches and the branching may be featured on distribution channel covers 413, which are mated to retentate member 404.

In addition to retentate member 404, also seen in FIG. 4N are fasteners 412, the center "sandwich" layer comprising a gasket 416 surrounding perforated member 401 swaged with and positioned above filter or membrane 403. The bottom layer of singulation assembly 420c seen in FIG. 4N is formed by permeate member 408. Permeate member 408, like retentate member 404, comprises one or more (as seen in FIG. 4O, there are two) distribution channels (here, they are branched), ridges, flow directors, and one or more ports (none of which are shown in FIG. 4N but see FIG. 4O).

FIG. 4O depicts the embodiment of the singulation assembly 420c in FIG. 4N from a bottom perspective view, which presents the bottom of the permeate member 408 of singulation assembly 420c. Permeate member 408 comprises a generally smooth lower surface (which in FIG. 4O, because singulation assembly 420c is viewed from the bottom, is toward the top of FIG. 4O); two branched distribution channels 409 covered by distribution channel covers 414, ridges 410a, disposed on the top surface of permeate member 408 (where the top surface of the permeate member 408 in FIG. 4O is facing down) and traverse the top surface of permeate member 408 from side-to-side, and flow directors 410 that are formed between ridges 410a. In addition, permeate member 408 has two ports 411, which deliver fluids to the branched distribution channels 409 and to flow directors 410. As with retentate member 404 and distribution channel covers 413, the branching for distribution channels 409 in permeate member 408 is a part of permeate member 408; however, permeate member 408 may not comprise the branches and the branching may instead be featured on distribution channel covers 414, which are mated to permeate member 408.

In addition to permeate member 404, also seen in FIG. 4O are fasteners 412, a center "sandwich" layer comprising a gasket 416 surrounding a perforated member 401 disposed above a filter or membrane 403 (the individual components are not seen in this FIG. 4M), and bottom-most layer of singulation assembly 420a seen in FIG. 4O is the retentate member 404.

FIG. 4P depicts the embodiment of the singulation assembly 420c of FIGS. 4N and 4O from a side exploded perspective view. From the top of FIG. 4P is seen retentate member 404 comprising two branched distribution channels 405 located on either side (left-right) of retentate member 404, both of which traverse retentate member 404 from its top surface to its bottom surface where the branches traverse most of the length of retentate member 404; ridges 406a, which are disposed on the bottom surface of retentate member 404 and traverse the bottom surface of retentate member 404 from side-to-side, and flow directors 406 that are formed between ridges 406a. In addition, retentate member 404 has two ports 407, which are fluidically coupled to branched distribution channels 405 and flow directors 406 and are configured to introduce cells and other fluids into (and remover cells and other fluids from) singulation assembly 420a. There are also distribution channel covers 413, which are configured to fit into and cover the two branched distribution channels 405.

Gasket 416, perforated member 401 and filter 403 can be seen clearly in this exploded view of singulation assembly 420c, where perforated member 401 and filter 403 are of very similar size and gasket 416 is configured to surround perforated member 401 and filter 403 and to provide a leak-proof seal between retentate member 404 and permeate member 408. In FIG. 4P, permeate member 408 is seen from the top down where permeate member 408 comprises two branched distribution channels 409 located lengthwise on either side (left-right) of permeate member 408, both of which traverse permeate member 408 from its bottom surface to its top surface and provide branched conduits for most of the length of permeate member 408. Permeate member 408 further comprises ridges 410a, which here are disposed on the top surface of permeate member 408 and traverse the top of permeate member 408 from side-to-side and flow directors 410 that are formed between permeate member ridges 410a. In addition, permeate member 408 has two ports 411 (only one port 411 can be seen in FIG. 4P). Also seen are distribution channel covers 414 that are separate from singulation assembly 420c in this exploded view and not inserted to cover branched distribution channels 409. Also seen in FIG. 4N are fasteners 412, although again, other means aside from fasteners may be used for securing the components of singulation assembly 420c.

Figure 4Q:
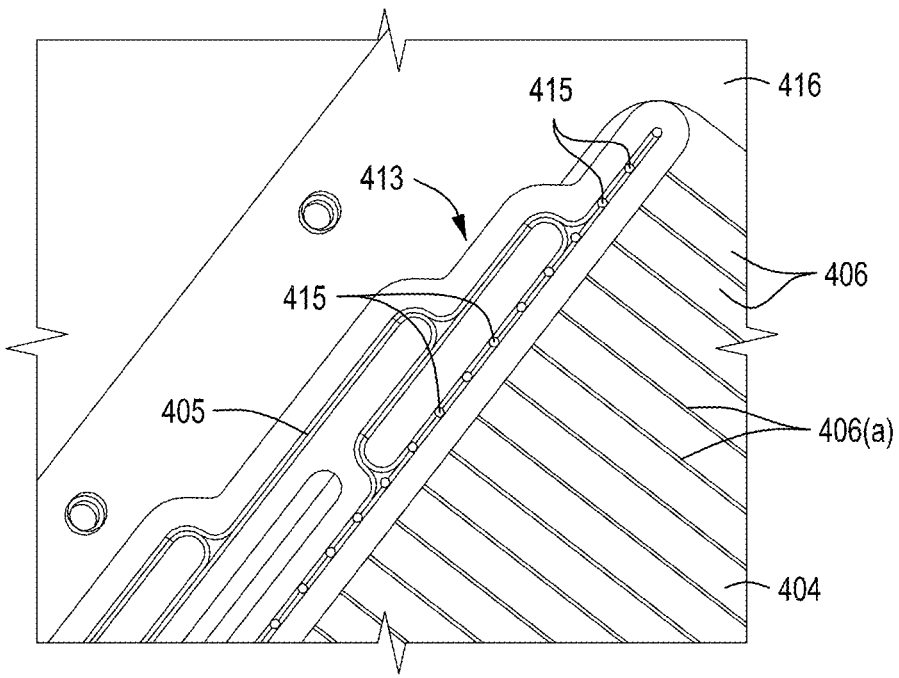

FIG. 4Q is a close-up top view from the top of retentate member 404 as shown in FIGS. 4N and 4P. Seen are ridges 406a, which are disposed on the bottom surface of retentate member 404 and traverse the bottom surface of retentate member 404 from side-to-side, and flow directors 406 that are formed between ridges 406a. Additionally seen is distribution channel 405 comprising flow director holes configured to distribute fluid into flow directors 406, where distribution channel 405 is covered by distribution channel cover 413.

Figure 4R:
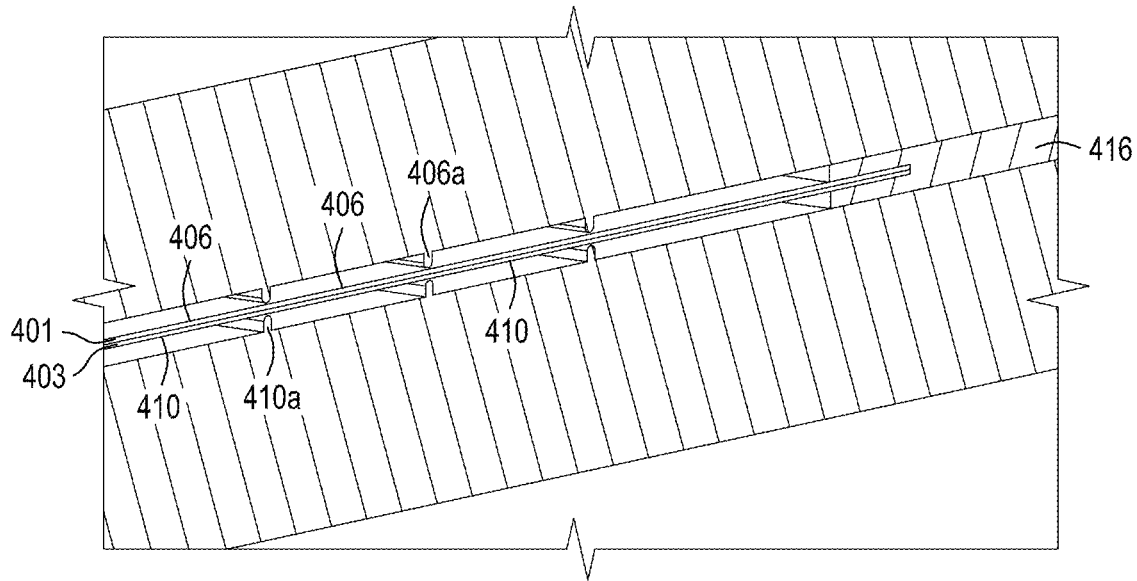

FIG. 4R is a close-up cross-sectional view of retentate member 404, with ridges 406a and flow directors 406 that are formed between ridges 406a. Also seen is permeate member 408, with ridges 410a and flow directors 410 that are formed between permeate member ridges 410a. Interposed between retentate member 404 and permeate member 408 are gasket 416, perforated member 401, and filter 403. Note that ridges 406a on retentate member 404 and ridges 410a are coincident with one another, separated only by perforated member 401 and filter 403. As stated previously, ridges 406a and ridges 410a provide support to perforated member 401 and filter 403 and reduce the likelihood that filter 403 will tear during, e.g., cell loading or medium exchange.

Figure 4S:
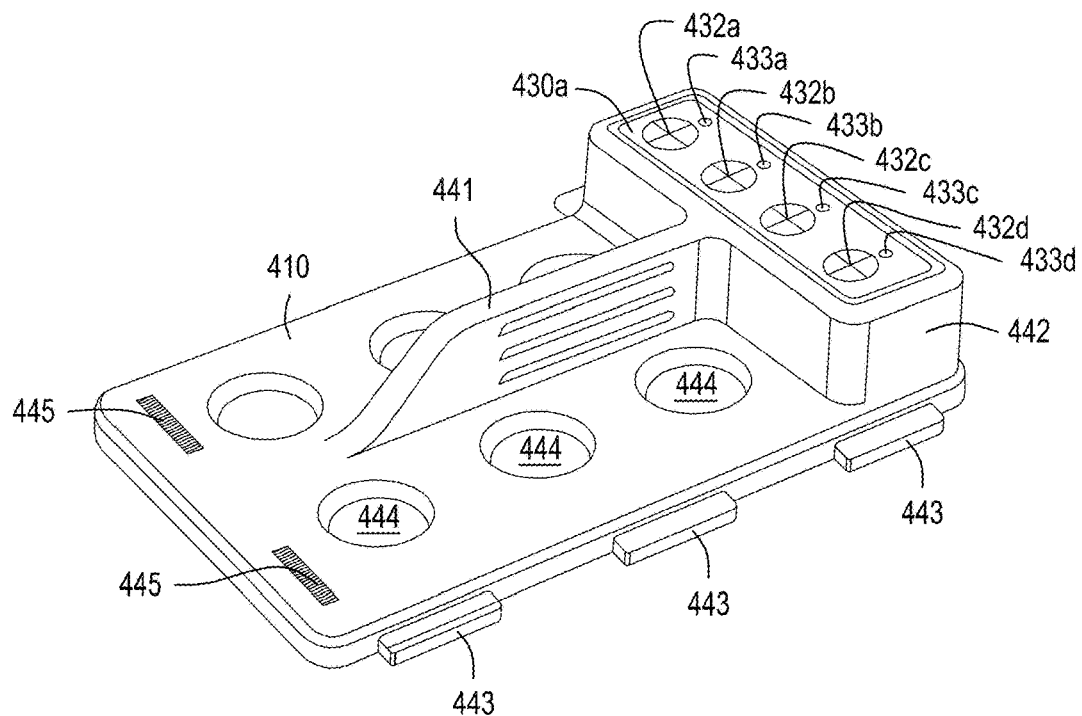
FIG. 4S-4Z depict an assembled singulation, growth, induction of editing and either normalization or cherry-picking module (e.g., "solid wall isolation/induction/normalization module" or "SWIIN").

FIGS. 4S-4W depict different views of one embodiment of a solid wall singulation or substantial singulation, growth, induction of editing and either normalization and cherry picking (SWIIN) module 400. FIG. 4S presents a side perspective view of SWIIN module 400. SWIIN module 400 comprises, e.g., one of the exemplary singulation assemblies seen in FIGS. 4F-4H, 4K-4M and 4N-4P which are housed in a SWIIN cover 440 and are one part of the SWIIN module. Various components of SWIIN cover 440 include reservoir cover 442, grip 441, windows 444 (shown are six windows, 444a, 444b, 444c, 444d, 444e, 444f), feet 443, and barcode (or other identifying information) 445. Note that in the embodiments depicted in FIGS. 4S-4Z the windows are round; however, it should be recognized by one of ordinary skill in the art that the windows can be any shape. Typically, it is desirable for 30% or more of the retentate member be available for viewing to get a reasonable sub-sample statistic on cell loading. Also seen is reservoir assembly cover 430a, which in this embodiment is not molded with SWIIN cover 440 but resides within the reservoir cover portion 442 of SWIIN cover 440. Reservoir assembly cover 430a comprises four reservoir access apertures (432a, 432b, 432c, and 432d) and four pneumatic access apertures (433a, 433b, 433c, and 433d). Pneumatic access apertures 433a, 433b, 433c, and 433d in most embodiments include filters to prevent contamination.

Windows 444 may be used to monitor cell loading and/or cell growth via camera (e.g., video camera). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Figure 4T:
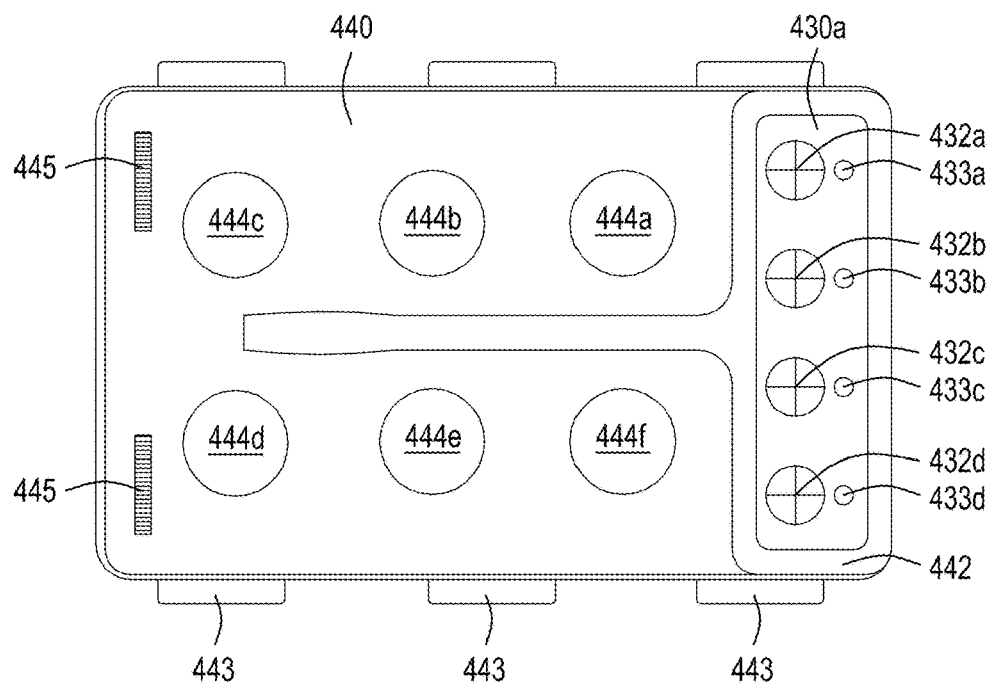

FIG. 4T is a top-down view of SWIIN module 400, showing SWIIN cover 440 and various components thereof including reservoir cover 442, grip 441, windows 444 (shown are six windows), feet 443, and barcode (or other identifying information) 445. Also seen is reservoir assembly cover 430a residing within the reservoir cover portion 442 of SWIIN cover 440, where reservoir assembly cover 430a comprises four reservoir access apertures (432a, 432b, 432c, and 432d) and four pneumatic access apertures (433a, 433b, 433c, and 433 d).

Figure 4U:
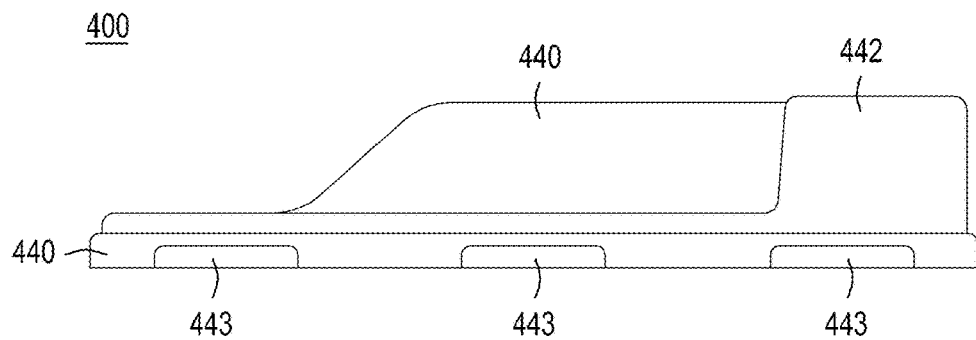
Figure 4V:
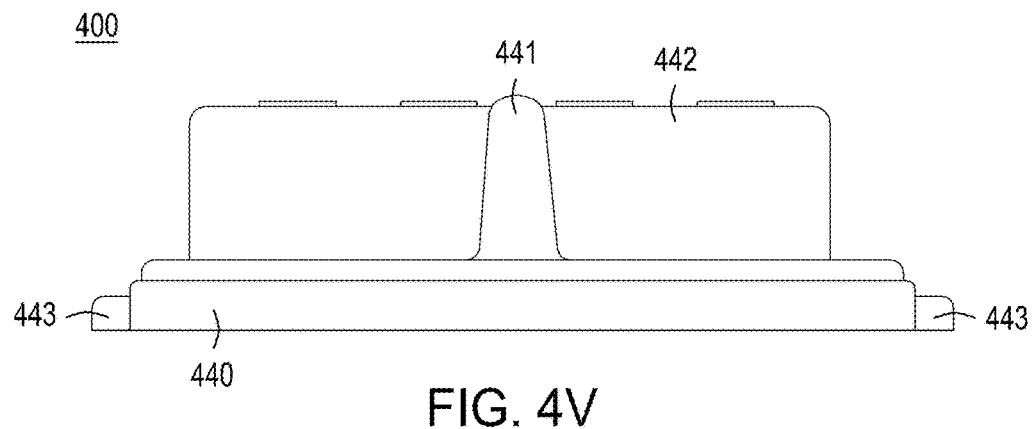
Figure 4W:
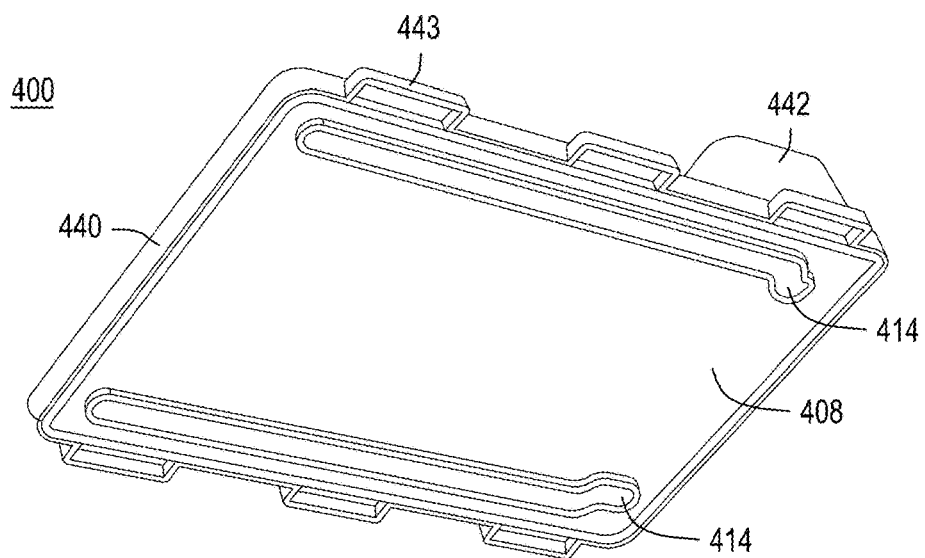

FIG. 4U is a side view of SWIIN module 400, depicting SWIIN cover 440, reservoir cover 442, grip 441, and feet 443. FIG. 4V is a view from the barcode "end" of SWIIN module 400 toward the reservoir "end" of SWIIN module 400. Seen are SWIIN cover 400, reservoir cover 442, grip 441, and feet 443. FIG. 4W is a bottom perspective view of SWIIN module 400, showing SWIIN cover 440, reservoir cover 442, feet 443, as well as distribution channel covers 414 disposed on the bottom of permeate member 408.

Figure 4X:
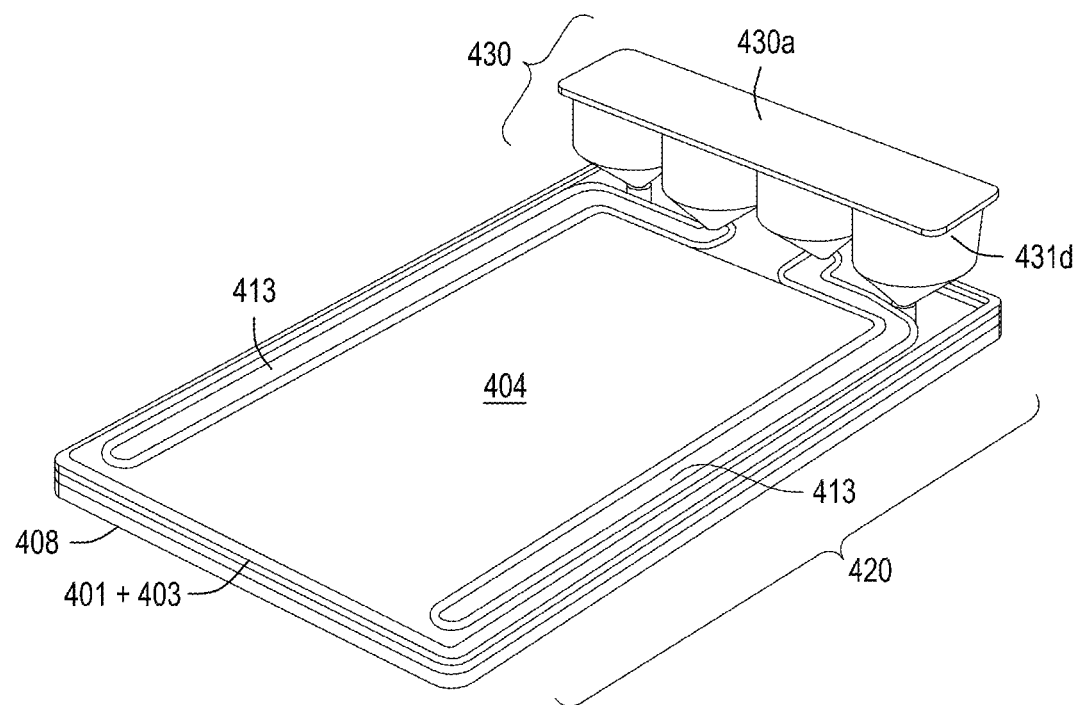
Figure 4Y:
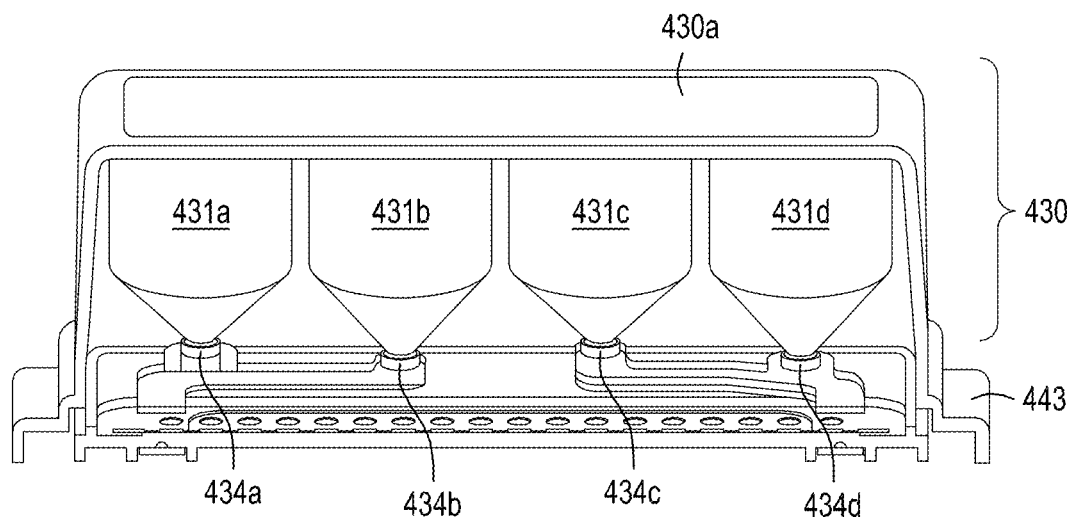
Figure 4Z:
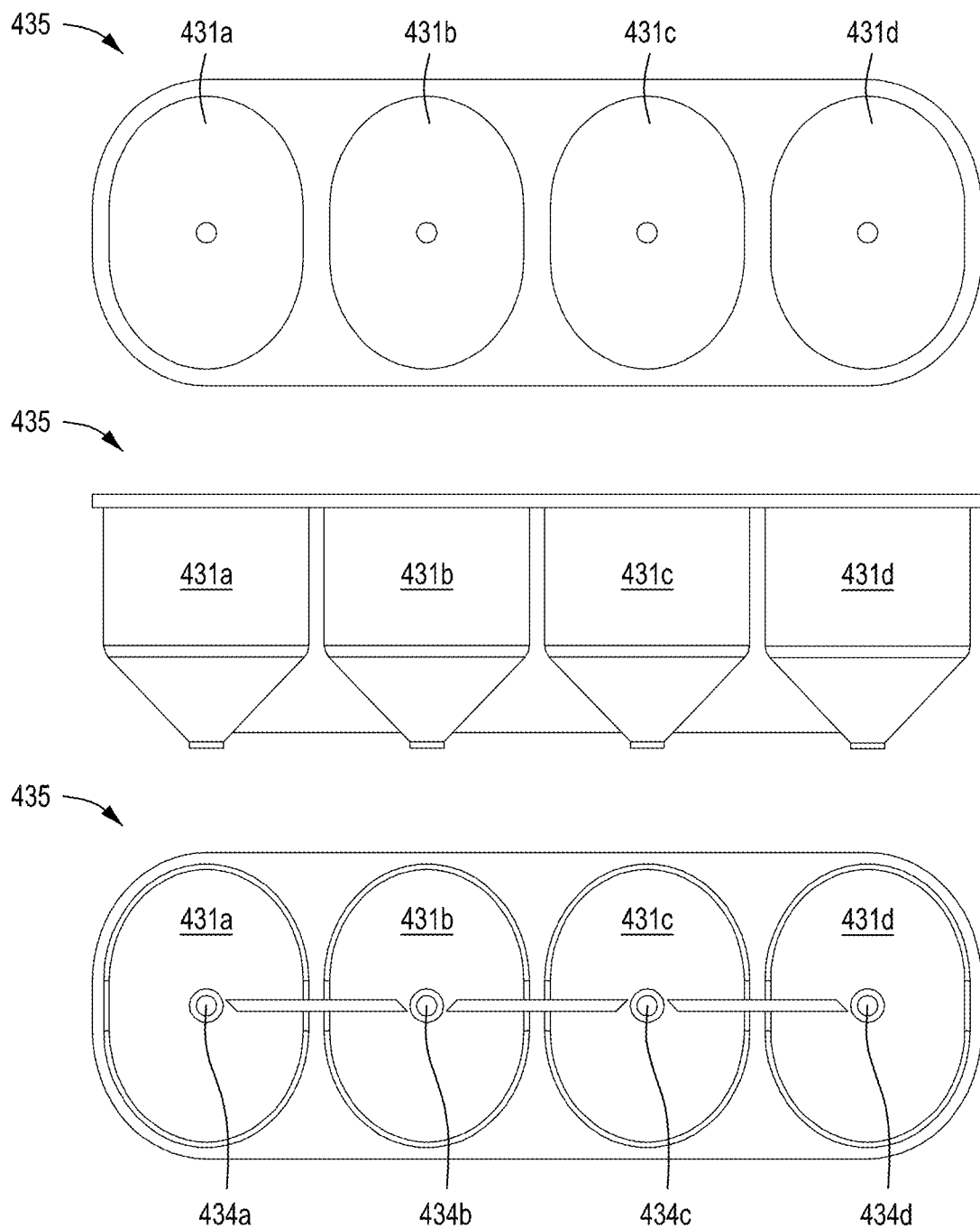
Figure 4A:
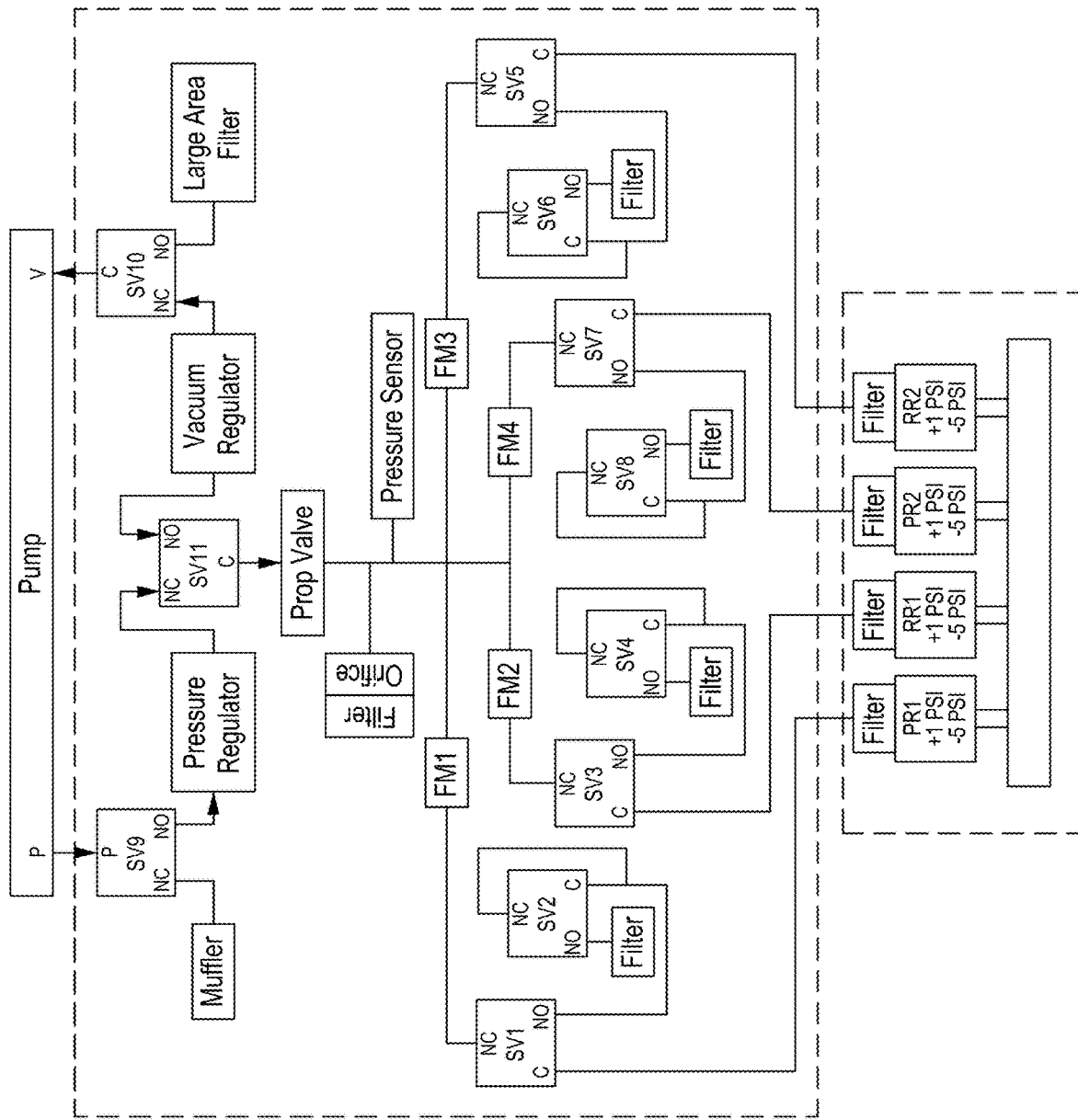
Figure 4B:
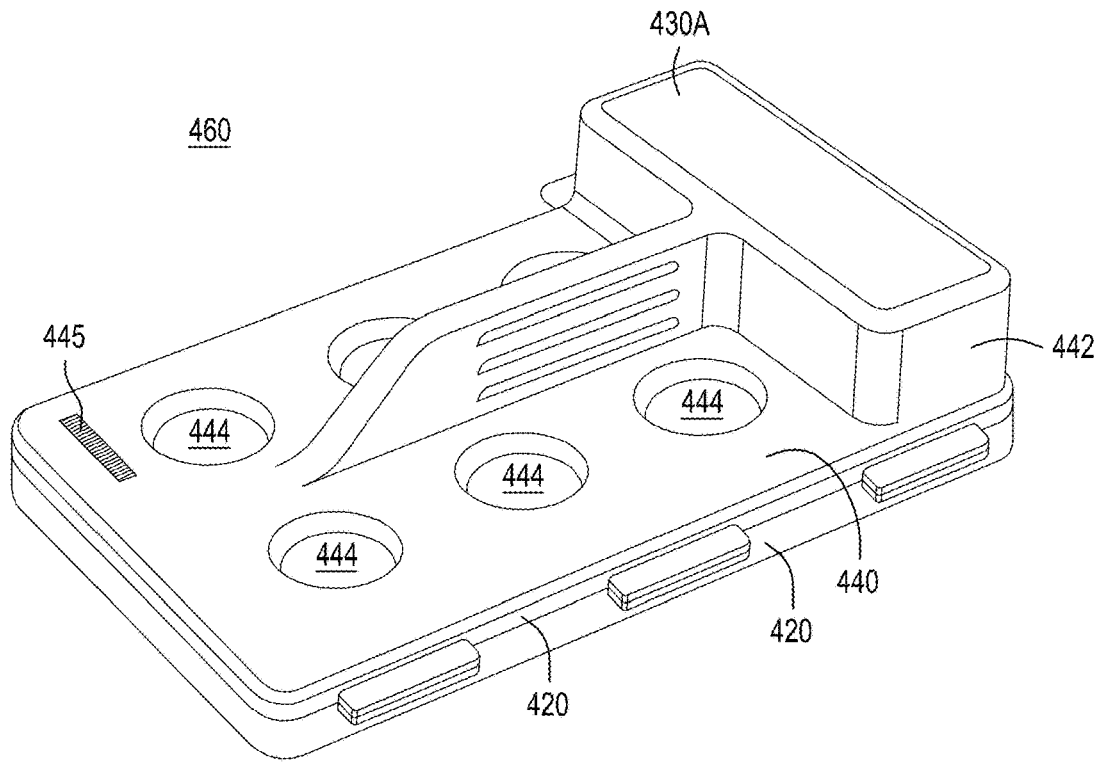
Figure 4C:
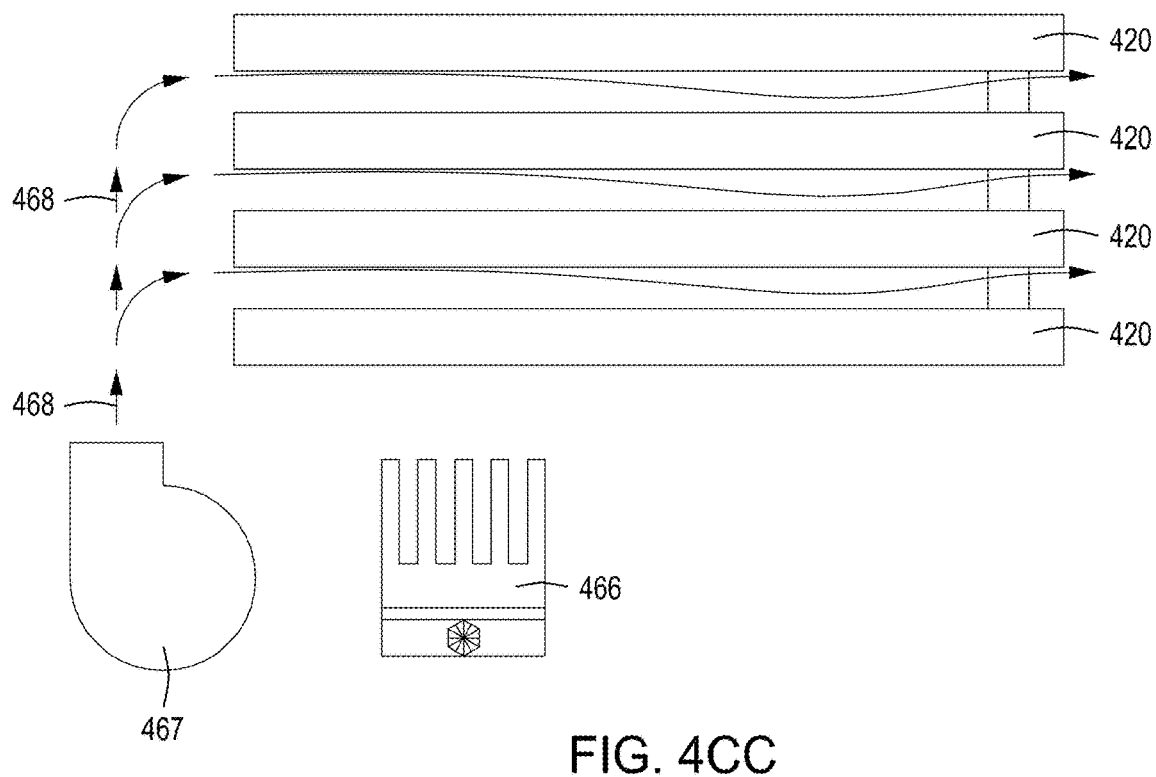
Figure 4D:
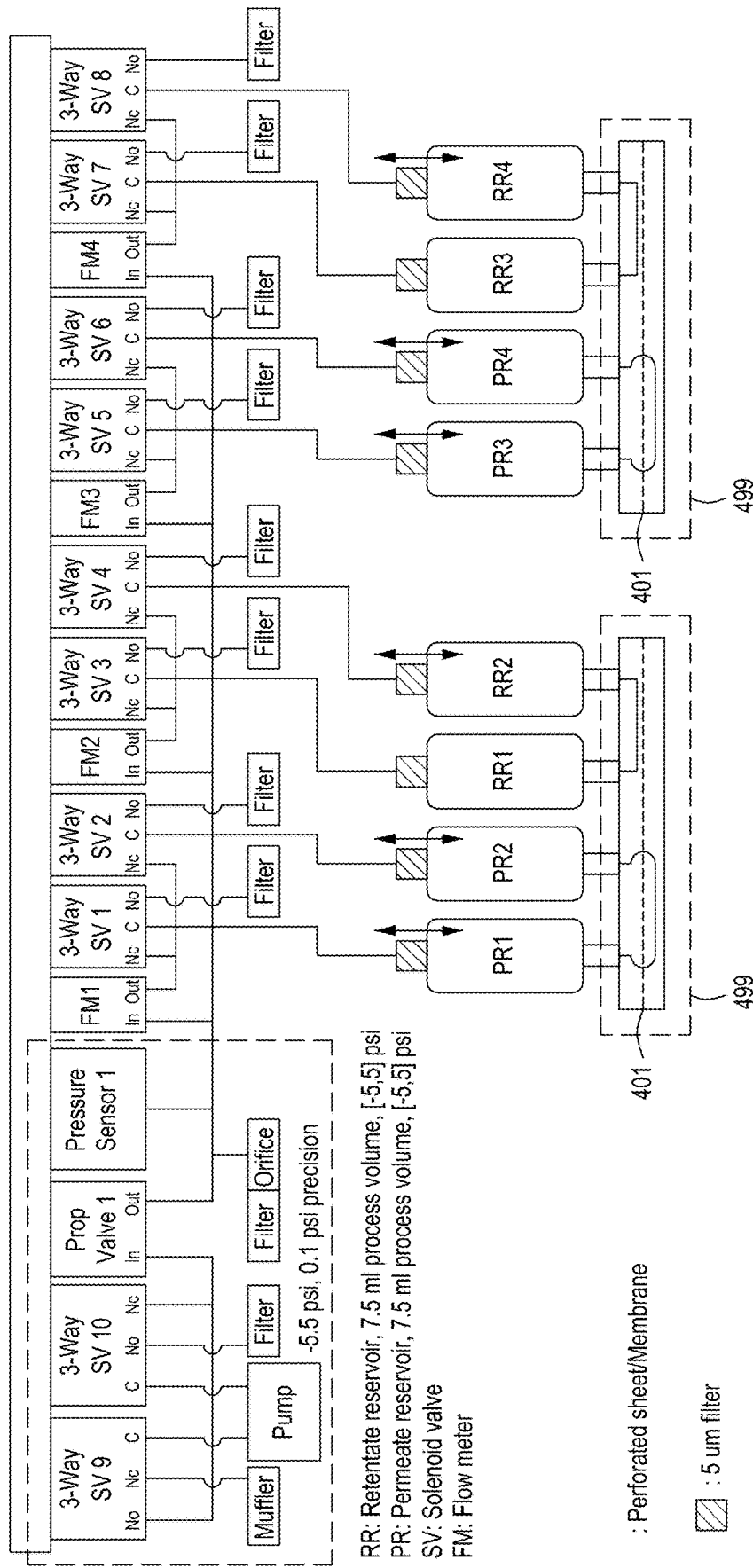

FIGS. 4X-4Z depict views of a reservoir assembly 430. In FIG. 4X, reservoir assembly 430 is disposed upon a singulation assembly 420 comprising retentate member 404; distribution channel covers 413; a gasket, perforated member, and filter assembly (not shown clearly), and a permeate member (also not shown clearly) Reservoir assembly 430 comprises reservoir assembly cover 430a, where reservoir assembly cover 430a comprises four reservoir access apertures (432a, 432b, 432c, and 432d) and four pneumatic access apertures (433a, 433b, 433c, and 433d).

FIG. 4Y is a top perspective view of a cross section of reservoir assembly 430 taken through the "reservoir" end of SWIIN cover 440. Seen are feet 443 of SWIIN cover 440. Reservoirs 431a, 431b, 431c, and 431d are seen, as well as reservoir/channel ports 434a, 434b, 434c, and 434d. Reservoirs 431b and 431c are fluidically coupled to conduits that either are fluidically coupled to distribution channels on the retentate member or distribution channels on the permeate member, and reservoirs 431a and 431d are fluidically coupled to conduits that either are fluidically coupled to distribution channels on the retentate member or distribution channels on the permeate member; that is if reservoirs 431b and 431c are fluidically coupled to conduits that are coupled to distribution channels on the retentate member, then reservoirs 431a and 431d are fluidically coupled to conduits that are coupled to distribution channels on the permeate member. However, any reservoir may be configured to deliver fluids to and remove fluids from either retentate member 404 or permeate member 408. Reservoirs 431a, 431b, 431c, and 431d typically have a volume of from 5.0 to 100 mL, or from 7.5 to 60 mL, or from 10 to 40 mL (these volumes are for the 200K singulation assembly). Note that reservoirs 431a, 431b, 431c, and 431d are funnel-shaped in the portion of the reservoir leading to reservoir/channel ports 434a, 434b, 434c, and 434d and aid in delivery of fluids from reservoirs 431a, 431b, 431c, and 431d.

FIG. 4Z shows three different views of four co-joined reservoirs 435. The top figure is a top-down view of co-joined reservoirs 435, the middle figure is a side view of co-joined reservoirs 435, and the bottom figure is a bottom-up view of co-joined reservoirs 435. Reservoirs 431a, 431b, 431c, and 431d are seen in all figures, and reservoir/channel ports 434a, 434b, 434c, and 434d are seen in the top and bottom figures.

FIG. 4AA is an exemplary pneumatic block diagram suitable for the SWIIN module depicted in FIGS. 44S-4W and, e.g., utilizing the singulation assemblies described in relation to FIGS. 4F-4R. Note that there are two solenoid valves (SV) for each reservoir-two retentate reservoirs (RR1 and RR2) and two permeate reservoirs (PR1 and PR2)—where one of the valves is for pneumatic actuation, and one of the valves serves to block the line. Note there is a flow meter for each pair of solenoid valves. Also, in this embodiment there is a single manifold serving all reservoirs; however, other embodiments may employ two manifolds, with PR1 and RR1 served by one manifold and PR2 and RR2 served by another manifold, or each reservoir (PR1, RR1, PR2, RR2) served by a separate manifold.

FIG. 4BB shows a double-layer SWIIN module 460, with a housing that comprises two singulation assemblies (singulation assemblies are not seen in this FIG. 4AA). FIG. 4CC graphically depicts a quadruple layer SWIIN module 465 comprising four singulation assemblies 420. FIG. 4BB graphically depicts a peltier device 466 and a fan 467 with forced airflow 468 that can be used to keep the four singulation assemblies 420 at a desired temperature; however, note that in multi-layer SWIINs, a combination of systems may be used such as reverse-Rankine vapor-compression refrigeration, or absorption heat pumps.

FIG. 4DD is an exemplary pneumatic architecture diagram for a double layer SWIIN showing, along with Tables 5 and 6, one embodiment of pneumatics employed to singulate or substantially singulate, grow, initiate editing, and normalize cells in the SWIIN module described in relation to FIG. 4BB. Looking at FIG. 4DD, four permeate reservoirs are seen (PR1, PR2, PR3, and PR4) and four retentate reservoirs are seen (RR1, RR2, RR3 and RR4). There are four flow meters (FM1, FM2, FM3 and FM4), ten 3-way solenoid valves ("3-way SV"), a pressure sensor, a prop valve to adjust pressure, and a pump capable of delivering pressures of −5 to 5 psi. The designation NC is for "normally closed", NO is for "normally open", and C is "closed". Table 5 provides, for each step of the cell concentration process, the status of each valve shown in FIG. 4CC and the pressure detected by pressure sensors 1 and 2. In Table 5, for the pump, 1=on, and 0=off. For the solenoid valves, 1=energized, and 0=de-energized. Table 6 provides, for each step of the cell concentration process, the volume in mL of fluid in each reservoir (i.e., the four retentate reservoirs and the four permeate reservoirs). Perforated member 401 is shown, as is temperature zone 499.

In addition to the solid wall cell singulation device (SWIIN) described in relation to FIGS. 3A-3E and 4A-4BB, other cell singulation (or substantial singulation) devices may be employed in the multi-module cell processing instrument, such as those described in U.S. Ser. No. 62/735,365, entitled "Detection of Nuclease Edited Sequences in Automated Modules and Systems", filed 24 Sep. 2018, and U.S. Ser. No. 62/781,112, entitled "Improved Detection of Nuclease Edited Sequences in Automated Modules and Systems", filed 18 Dec. 2018, including singulation or substantial singulation by plating on agar, singulation or substantial singulation by isolating cells on functionalized islands, singulation or substantial singulation within aqueous droplets carried in a hydrophobic carrier fluid or Gel Beads-in-Emulsion (GEMs, see, e.g., 10λ Genomics, Pleasanton, Calif.), or singulation or substantial singulation within a polymerized alginate scaffold (for this embodiment of singulation, also see U.S. Ser. No. 62/769,805, entitled "Improved Detection of Nuclease Edited Sequences in Automated Modules and Instruments via Bulk Cell Culture", filed 20 Nov. 2018).

Figure 5A:
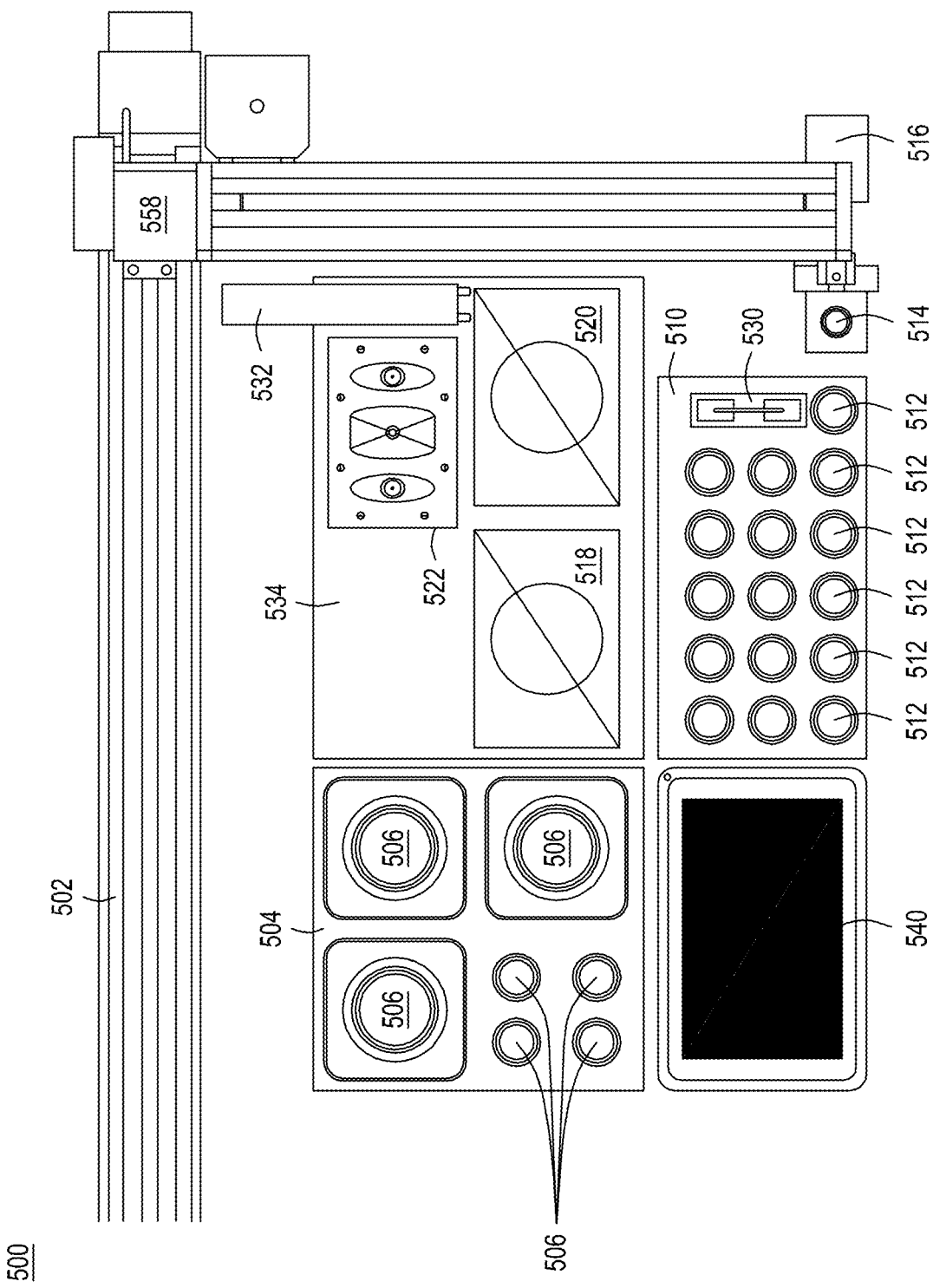

Automated Cell Editing Instruments and Modules
Automated Cell Editing Instruments FIG. 5A depicts an exemplary automated multi-module cell processing instrument 500 to, e.g., perform one of the exemplary workflows described infra, comprising one or more reagent cartridges as described herein. The instrument 500, for example, may be and preferably is designed as a stand-alone desktop instrument for use within a laboratory environment. The instrument 500 may incorporate a mixture of reusable and disposable components for performing the various integrated processes in conducting automated genome cleavage and/or editing in cells. Illustrated is a gantry 502, providing an automated mechanical motion system (actuator) (not shown) that supplies XYZ axis motion control to, e.g., an automated (i.e., robotic) liquid handling system 558 including, e.g., an air displacement pipettor 532 which allows for cell processing among multiple modules without human intervention. In some automated multi-module cell processing instruments, the air displacement pipettor 532 is moved by gantry 502 and the various modules and reagent cartridges remain stationary; however, in other embodiments, the liquid handling system 558 may stay stationary while the various modules and reagent cartridges are moved. Also included in the automated multi-module cell processing instrument 500 is reagent cartridge 510 comprising reservoirs 512 and transformation module 530 (e.g., a flow-through electroporation device as described in detail in relation to FIGS. 8A-8E), as well as a wash cartridge 504 comprising reservoirs 506. The wash cartridge 504 may be configured to accommodate large tubes, for example, wash solutions, or solutions that are used often throughout an iterative process. In one example, wash cartridge 504 may be configured to remain in place when two or more reagent cartridges 510 are sequentially used and replaced. Although reagent cartridge 510 and wash cartridge 504 are shown in FIG. 5A as separate cartridges, the contents of wash cartridge 504 may be incorporated into reagent cartridge 510. The reagent cartridge 510 and wash cartridge 504 may be identical except for the consumables (reagents or other components contained within the various inserts) inserted therein. Note in this embodiment transformation module 530 is contained within reagent cartridge 510; however, in alternative embodiments transformation module 530 is contained within its own module or may be part of another module, such as a growth module.

In some implementations, the wash and reagent cartridges 504 and 510 comprise disposable kits (one or more of the various inserts and reagents) provided for use in the automated multi-module cell processing/editing instrument 500. For example, a user may open and position each of the reagent cartridge 510 and the wash cartridge 504 comprising various desired inserts and reagents within a chassis of the automated multi-module cell editing instrument 500 prior to activating cell processing.

Also illustrated in FIG. 5A is the robotic liquid handling system 558 including the gantry 502 and air displacement pipettor 532. In some examples, the robotic handling system 558 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips may be provided in a pipette transfer tip supply (not shown) for use with the air displacement pipettor 532.

Inserts or components of the wash and reagent cartridges 504, 510, in some implementations, are marked with machine-readable indicia (not shown), such as bar codes, for recognition by the robotic handling system 558. For example, the robotic liquid handling system 558 may scan one or more inserts within each of the wash and reagent cartridges 504, 510 to confirm contents. In other implementations, machine-readable indicia may be marked upon each wash and reagent cartridge 504, 510, and a processing system (not shown, but see element 526 of FIG. 5B) of the automated multi-module cell editing instrument 500 may identify a stored materials map based upon the machine-readable indicia. The exemplary automated multi-module cell processing instrument 500 of FIG. 5A further comprises a cell growth module 534. (Note, all modules recited briefly here are described in greater detail below.) In the embodiment illustrated in FIG. 5A, the cell growth module 534 comprises two cell growth vials 518, 520 (described in greater detail below in relation to FIGS. 6A-6D) as well as a cell concentration module 522 (described in detail in relation to FIGS. 7A-7H). In alternative embodiments, the cell concentration module 522 may be separate from cell growth module 534, e.g., in a separate, dedicated module. Also illustrated as part of the automated multi-module cell processing instrument 500 of FIG. 5A is a singulation module 540, served by, e.g., robotic liquid handing system 558 and air displacement pipettor 532. Also seen are an optional nucleic acid assembly/desalting module 514 comprising a reaction chamber or tube receptacle (not shown) and a magnet 516 to allow for purification of nucleic acids using, e.g., magnetic solid phase reversible immobilization (SPRI) beads (Applied Biological Materials Inc., Richmond, BC. The cell growth module, cell concentration module, transformation module, reagent cartridge, and nucleic acid assembly module are described in greater detail infra, and an exemplary singulation module is described in detail in relation to FIGS. 3A-3E and 4A-4BB supra.

Figure 5B:
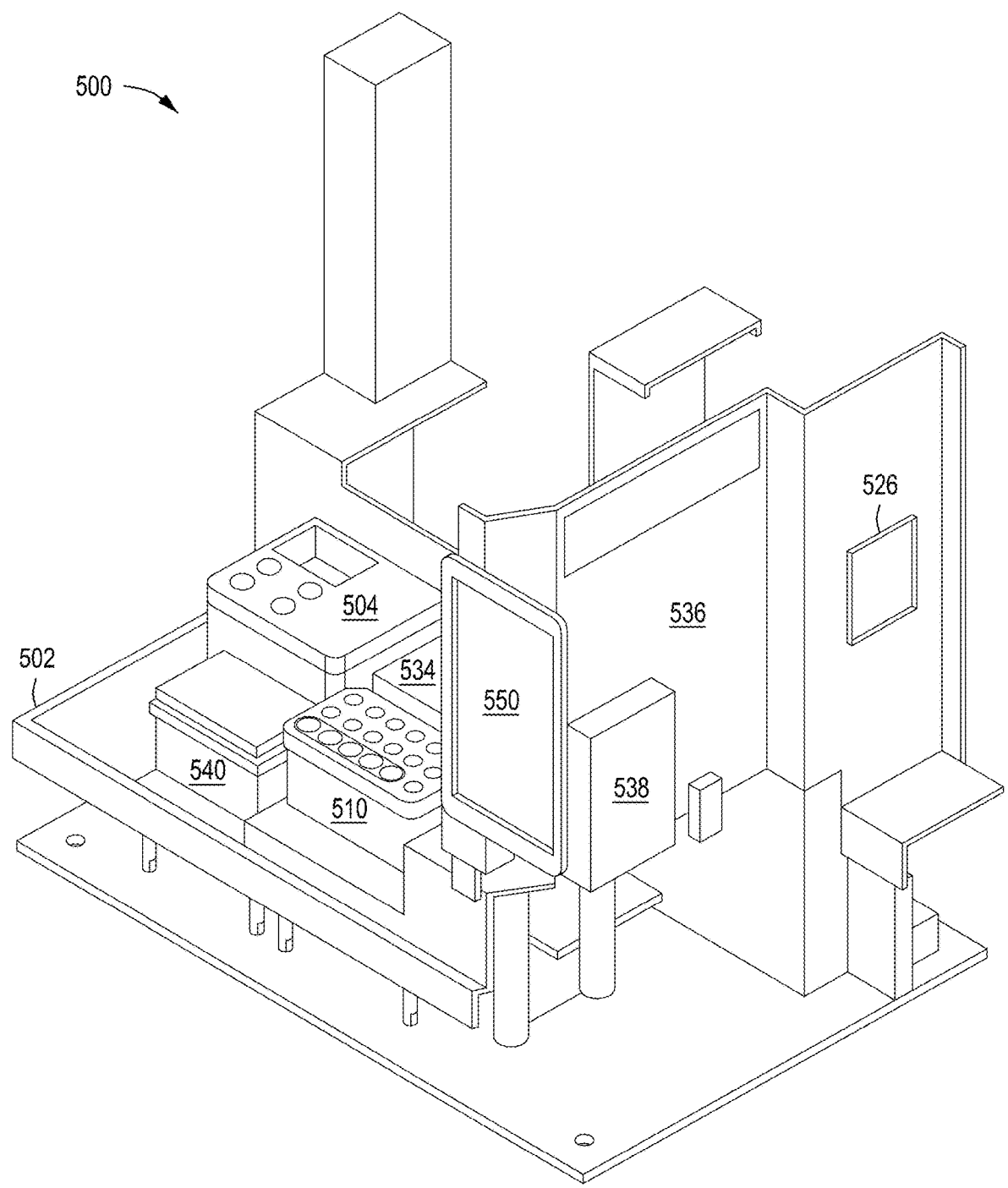

FIG. 5B is a plan view of the front of the exemplary multi-module cell processing instrument 500 depicted in FIG. 5A. Cartridge-based source materials (such as in reagent cartridge 510), for example, may be positioned in designated areas on a deck 502 of the instrument 500 for access by a robotic handling instrument (not shown in this figure). As illustrated in FIG. 5B, the deck may include a protection sink such that contaminants spilling, dripping, or overflowing from any of the modules of the instrument 500 are contained within a lip of the protection sink. In addition to reagent cartridge 510, also seen in FIG. 5B is wash cartridge 504, singulation module 540, and a portion of growth module 534. Also seen in this view is touch screen display 550, transformation module controls 538, electronics rack 536, and processing system 526.

FIGS. 5C through 5D illustrate side and front views, respectively, of multi-module cell processing instrument 500 comprising chassis 590 for use in desktop versions of the automated multi-module cell editing instrument 500. For example, the chassis 590 may have a width of about 24-48 inches, a height of about 24-48 inches and a depth of about 24-48 inches. Chassis 590 may be and preferably is designed to hold all modules and disposable supplies used in automated cell processing and to perform all processes required without human intervention (that is, chassis 590 is configured to provide an integrated, stand-alone automated multi-module cell processing instrument). Chassis 590 may mount a robotic liquid handling system 558 for moving materials between modules. As illustrated in FIG. 5C, the chassis 590 includes a cover 552 having a handle 554 and hinge 556*a* (hinges 556*b* and 556*c* are seen in FIG. 5D) for lifting the cover 552 and accessing the interior of the chassis 590. A cooling grate 564 (FIG. 5C) allows for air flow via an internal fan (not shown). Further, the chassis 590 is lifted by adjustable feet 570*a*, 570*c* (feet 570, 570*b* are shown in FIG. 5D). Adjustable feet 570*a*-570*c*, for example, may provide additional air flow beneath the chassis 590. A control button 566, in some embodiments, allows for single-button automated start and/or stop of cell processing within the automated multi-module cell processing instrument 500.

Inside the chassis 590, in some implementations, a robotic liquid handling system 558 is disposed along a gantry 502 above wash cartridge 504 (reagent cartridge 510 is not seen in these figures). Control circuitry, liquid handling tubes, air pump controls, valves, thermal units (e.g., heating and cooling units) and other control mechanisms, in some embodiments, are disposed below a deck of the chassis 590, in a control box region 568. Also seen in both FIGS. 5C and 5D is singulation device or module 540. Nucleic acid assembly module 514 comprising a magnet 516 is seen in FIG. 5D.

Although not illustrated, in some embodiments a display screen may be positioned on the front face of the chassis 590, for example covering a portion of the cover (e.g., see display 550 in FIG. 5B). The display screen may provide information to the user regarding the processing status of the automated multi-module cell editing instrument 500. In another example, the display screen may accept inputs from the user for conducting the cell processing.

The Rotating Growth Module

Figure 6A:
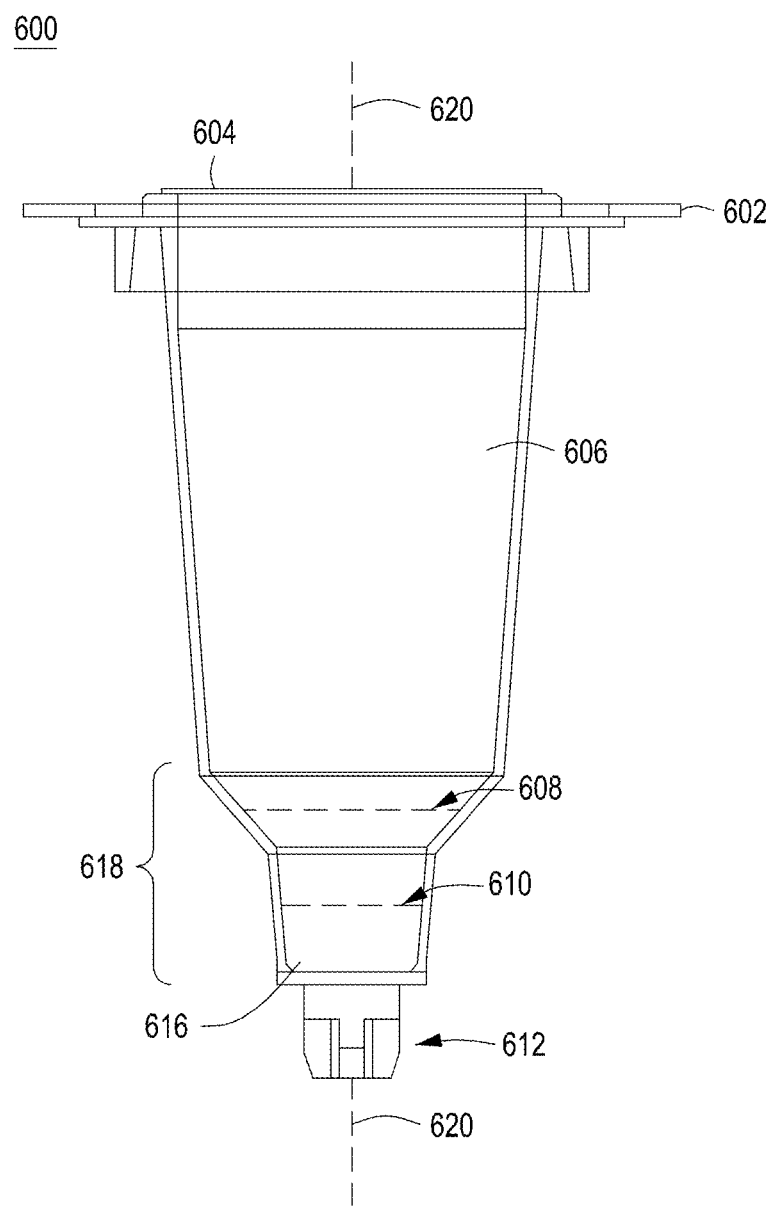
FIG. 6A depicts one embodiment of a rotating growth vial for use with the cell growth module described herein.

FIG. 6A shows one embodiment of a rotating growth vial 600 for use with the cell growth device described herein. The rotating growth vial 600 is an optically-transparent container having an open end 604 for receiving liquid media and cells, a central vial region 606 that defines the primary container for growing cells, a tapered-to-constricted region 618 defining at least one light path 610, a closed end 616, and a drive engagement mechanism 612. The rotating growth vial 600 has a central longitudinal axis 620 around which the vial rotates, and the light path 610 is generally perpendicular to the longitudinal axis of the vial. The first light path 610 is positioned in the lower constricted portion of the tapered-to-constricted region 618. Optionally, some embodiments of the rotating growth vial 600 have a second light path 608 in the tapered region of the tapered-to-constricted region 618. Both light paths in this embodiment are positioned in a region of the rotating growth vial that is constantly filled with the cell culture (cells+growth media) and are not affected by the rotational speed of the growth vial. The first light path 610 is shorter than the second light path 608 allowing for sensitive measurement of OD values when the OD values of the cell culture in the vial are at a high level (e.g., later in the cell growth process), whereas the second light path 608 allows for sensitive measurement of OD values when the OD values of the cell culture in the vial are at a lower level (e.g., earlier in the cell growth process).

The drive engagement mechanism 612 engages with a motor (not shown) to rotate the vial. In some embodiments, the motor drives the drive engagement mechanism 612 such that the rotating growth vial 600 is rotated in one direction only, and in other embodiments, the rotating growth vial 600 is rotated in a first direction for a first amount of time or periodicity, rotated in a second direction (i.e., the opposite direction) for a second amount of time or periodicity, and this process may be repeated so that the rotating growth vial 600 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 600 may be oscillated at a first periodicity (e.g., every 60 seconds), and then a later stage of cell growth the rotating growth vial 600 may be oscillated at a second periodicity (e.g., every one second) different from the first periodicity.

The rotating growth vial 600 may be reusable or, preferably, the rotating growth vial is consumable. In some embodiments, the rotating growth vial is consumable and is presented to the user pre-filled with growth medium, where the vial is hermetically sealed at the open end 604 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 604 may optionally include an extended lip 602 to overlap and engage with the cell growth device. In automated systems, the rotating growth vial 600 may be tagged with a barcode or other identifying means that can be read by a scanner or camera (not shown) that is part of the automated system.

The volume of the rotating growth vial 600 and the volume of the cell culture (including growth medium) may vary greatly, but the volume of the rotating growth vial 600 must be large enough to generate a specified total number of cells. In practice, the volume of the rotating growth vial 600 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 600. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 600 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 6B:
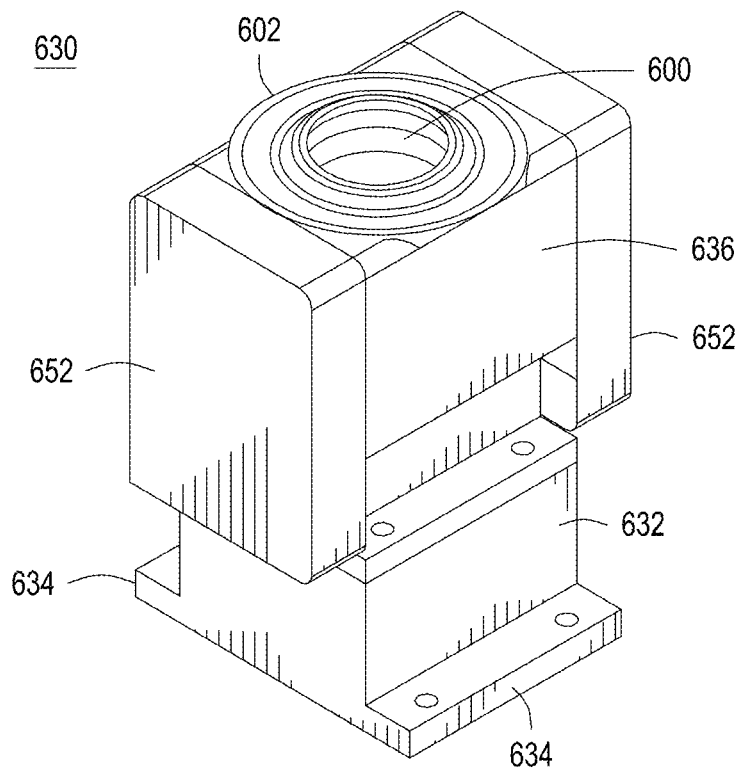
FIG. 6B illustrates a perspective view of one embodiment of a rotating growth device in a cell growth module housing.
Figure 6C:
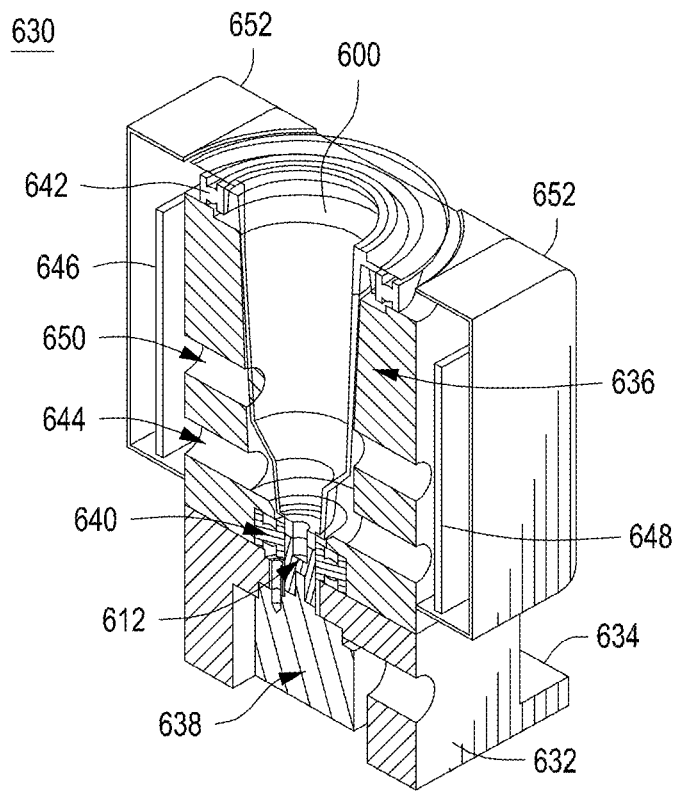
FIG. 6C depicts a cut-away view of the cell growth module from FIG. 6B.

FIG. 6B is a perspective view of one embodiment of a cell growth device 630. FIG. 6C depicts a cut-away view of the cell growth device 630 from FIG. 6B. In both figures, the rotating growth vial 600 is seen positioned inside a main housing 636 with the extended lip 602 of the rotating growth vial 600 extending above the main housing 636. Additionally, end housings 652, a lower housing 632 and flanges 634 are indicated in both figures. Flanges 634 are used to attach the cell growth device 630 to heating/cooling means or other structure (not shown). FIG. 6C depicts additional detail. In FIG. 6C, upper bearing 642 and lower bearing 640 are shown positioned within main housing 636. Upper bearing 642 and lower bearing 640 support the vertical load of rotating growth vial 600. Lower housing 632 contains the drive motor 638. The cell growth device 630 of FIG. 6C comprises two light paths: a primary light path 644, and a secondary light path 650. Light path 644 corresponds to light path 610 positioned in the constricted portion of the tapered-to-constricted portion of the rotating growth vial 600, and light path 650 corresponds to light path 608 in the tapered portion of the tapered-to-constricted portion of the rotating growth via 600*l*. Light paths 610 and 608 are not shown in FIG. 6C but may be seen in FIG. 6A. In addition to light paths 644 and 640, there is an emission board 648 to illuminate the light path(s), and detector board 646 to detect the light after the light travels through the cell culture liquid in the rotating growth vial 600.

The motor 638 engages with drive mechanism 612 and is used to rotate the rotating growth vial 600. In some embodiments, motor 638 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 638 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 636, end housings 652 and lower housing 632 of the cell growth device 630 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 600 is envisioned in some embodiments to be reusable, but preferably is consumable, the other components of the cell growth device 630 are preferably reusable and function as a stand-alone benchtop device or as a module in a multi-module cell processing system.

The processor (not shown) of the cell growth device 630 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 630—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 630, where the second spectrophotometer is used to read a blank at designated intervals.

Figure 6D:
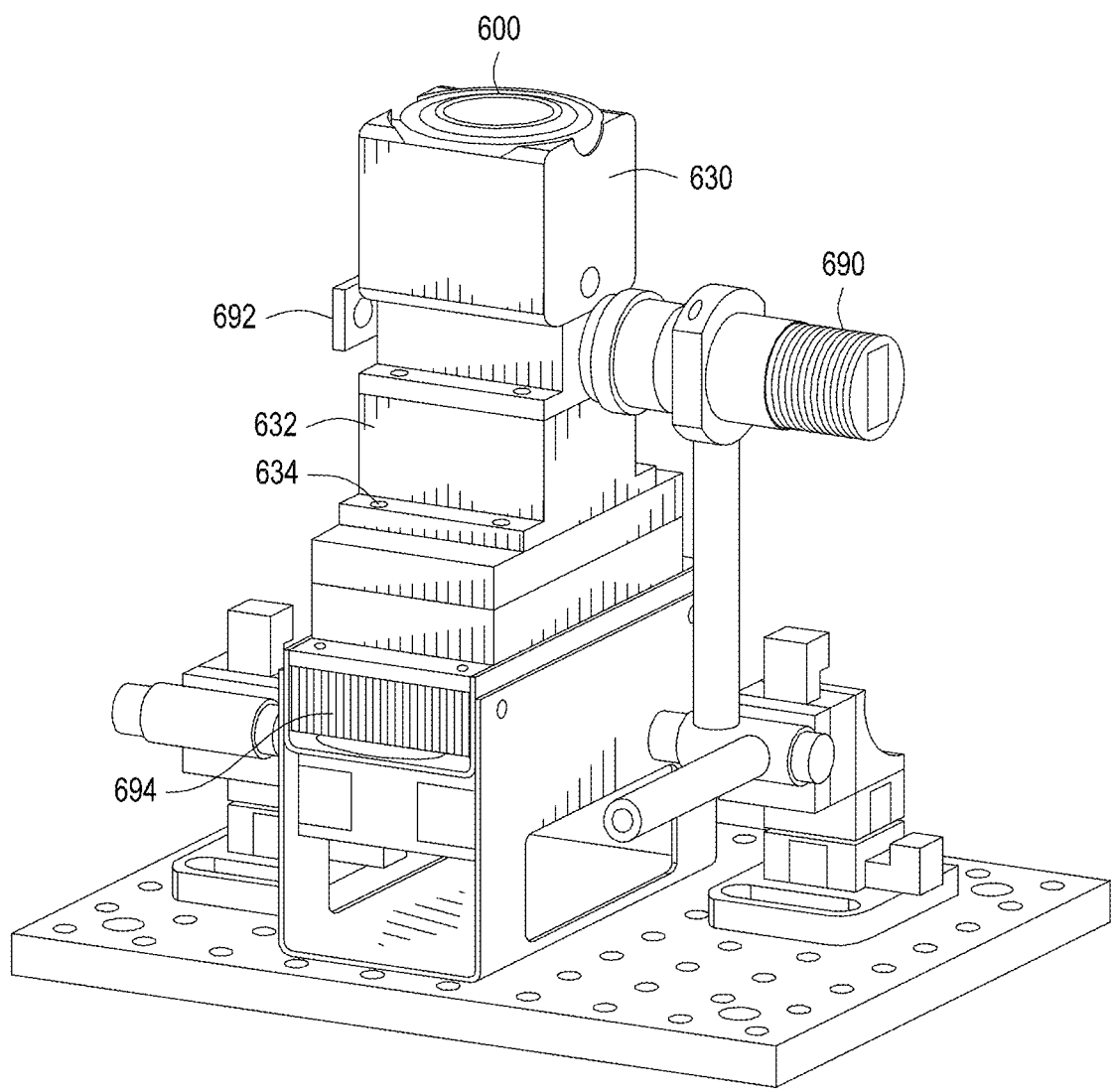
FIG. 6D illustrates the cell growth module of FIG. 6B coupled to LED, detector, and temperature regulating components.

FIG. 6D illustrates a cell growth device 630 as part of an assembly comprising the cell growth device 630 of FIG. 6B coupled to light source 690, detector 692, and thermal components 694. The rotating growth vial 600 is inserted into the cell growth device. Components of the light source 690 and detector 692 (e.g., such as a photodiode with gain control to cover 5-log) are coupled to the main housing of the cell growth device. The lower housing 632 that houses the motor that rotates the rotating growth vial 600 is illustrated, as is one of the flanges 634 that secures the cell growth device 630 to the assembly. Also, the thermal components 694 illustrated are a Peltier device or thermoelectric cooler. In this embodiment, thermal control is accomplished by attachment and electrical integration of the cell growth device 630 to the thermal components 694 via the flange 634 on the base of the lower housing 632. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 600 is controlled to approximately +/−0.5° C.

In use, cells are inoculated (cells can be pipetted, e.g., from an automated liquid handling system or by a user) into pre-filled growth media of a rotating growth vial 600 by piercing though the foil seal or film. The programmed software of the cell growth device 630 sets the control temperature for growth, typically 30° C., then slowly starts the rotation of the rotating growth vial 600. The cell/growth media mixture slowly moves vertically up the wall due to centrifugal force allowing the rotating growth vial 600 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 630 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 630 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 630 may include additional sensors for measuring, e.g., dissolved oxygen, carbon dioxide, pH, conductivity, and the like.

Cell Concentration Module

Included in the automated multi-module cell processing instrument depicted in FIGS. 5A-5D, is a cell concentration module 522. FIGS. 7A-7H depict variations of one embodiment of a cell concentration/buffer exchange module that utilizes tangential flow filtration. The cell concentration module described herein operates using tangential flow filtration (TFF), also known as cross-flow filtration, in which the majority of the feed flows tangentially over the surface of the filter thereby reducing cake (retentate) formation as compared to dead-end filtration, in which the feed flows into the filter. Secondary flows relative to the main feed are also exploited to generate shear forces that prevent filter cake formation and membrane fouling thus maximizing particle recovery, as described below.

Figure 7A:
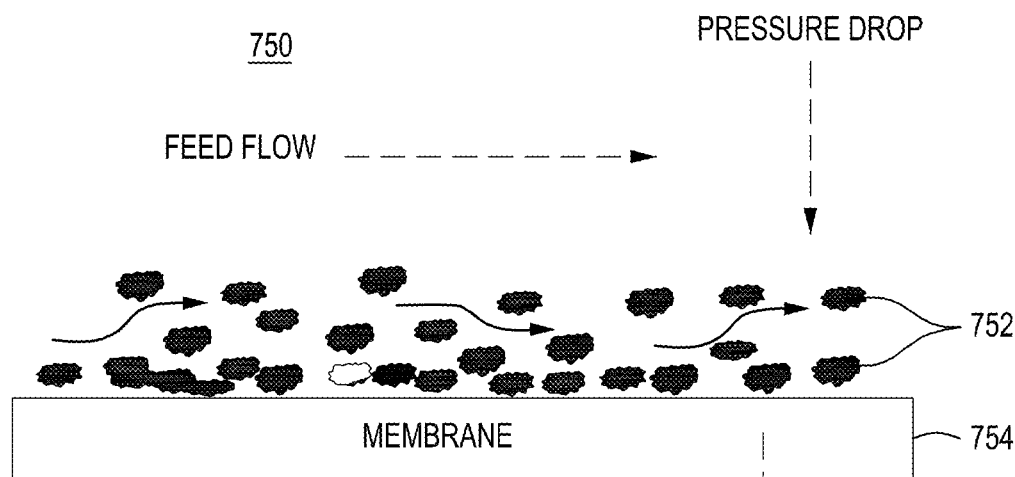
FIG. 7A is a model of the process of tangential flow filtration that is used in the TFF module presented herein.

The TFF device described herein was designed to take into account two primary design considerations. First, the geometry of the TFF device leads to filtering the cell culture over a large surface area so as to minimize processing time. Second, the design of the TFF device is configured to minimize filter fouling. FIG. 7A is a general model 750 of tangential flow filtration. The TFF device operates using tangential flow filtration, also known as cross-flow filtration. FIG. 7A shows cells flowing over a membrane 754, where the feed flow of the cells 752 in medium or buffer is parallel to the membrane 754. TFF is different from dead-end filtration where both the feed flow and the pressure drop are perpendicular to a membrane or filter.

Figure 7B:
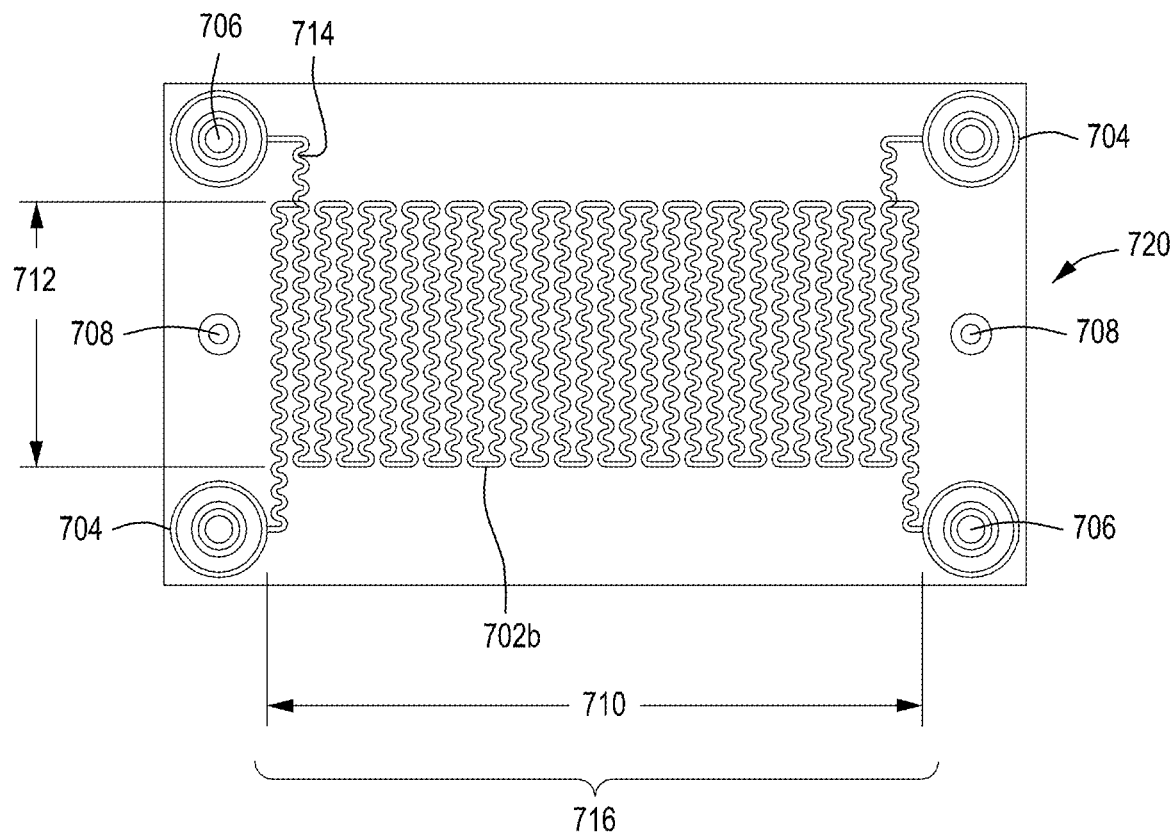
FIG. 7B depicts a top view of a lower member of one embodiment of an exemplary TFF device/module.

FIG. 7B depicts a top view of a lower member 720 of one embodiment of an exemplary TFF device/module providing tangential flow filtration. As can be seen in FIG. 7B, the lower member 720 of the TFF device module comprises a channel structure 716 comprising a flow channel through which a cell culture is flowed. The channel structure 716 comprises a single flow channel 702b. (Note, that the flow channel generally is designated 702, the portion of the flow channel in the upper member 722 of the TFF device is designated 702a, and the portion of the flow channel in the lower member 720 of the TFF device is designated 702b.) This particular embodiment comprises a channel configuration 714, e.g., an undulating serpentine geometry (i.e., the small "wiggles" in the flow channel 702) and a serpentine "zig-zag" pattern where the flow channel 702b crisscrosses the lower member 720 of the TFF device from one end at the left of the device to the other end at the right of the device. The serpentine pattern allows for filtration over a high surface area relative to the device size and total channel volume, while the undulating contribution creates a secondary inertial flow to enable effective membrane regeneration preventing membrane fouling. Although an undulating geometry and serpentine pattern are exemplified here, other channel configurations 714 may be used as long as the flow channel 702 can be bifurcated by a membrane as discussed below, and as long as the channel configuration 714 provides for cell flow through the TFF module in alternating directions. Portals 704 and 706 are part of channel structure 716 by operation of the cells passing through flow channel 702. Generally, portals 704 collect cells passing through the flow channel 702 on one side of a membrane (not shown) (the "retentate"), and portals 706 collect the medium ("filtrate" or "permeate") passing through the flow channel 702 on the opposite side of the membrane (not shown). In this embodiment, recesses 708 accommodate screws or other fasteners (not shown) that allow the components of the TFF device to be secured to one another.

The length 710 and width 712 of the channel structure 716 may vary depending on the volume of the cell culture to be grown and the optical density of the cell culture to be concentrated. The length 710 of the channel structure 716 typically is from 1 mm to 300 mm, or from 50 mm to 250 mm, or from 60 mm to 200 mm, or from 70 mm to 150 mm, or from 80 mm to 100 mm. The width 712 of the channel structure 716 typically is from 1 mm to 120 mm, or from 20 mm to 100 mm, or from 30 mm to 80 mm, or from 40 mm to 70 mm, or from 50 mm to 60 mm. The cross-section configuration of the flow channel 702 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 702 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius.

Figure 7C:
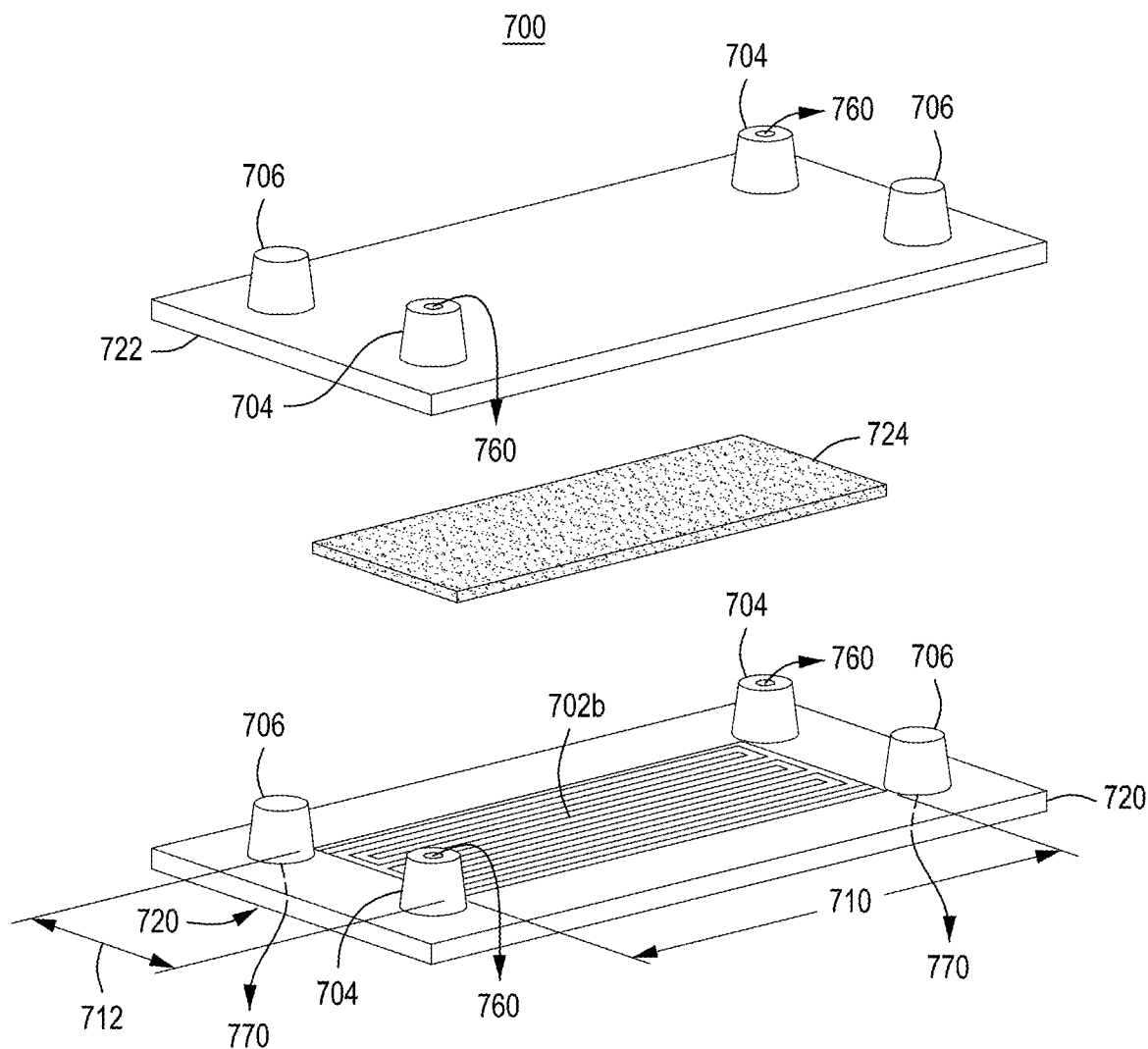
FIG. 7C depicts a top-down view of upper and lower members and a membrane of an exemplary TFF module.

When looking at the top view of lower member 720 of the TFF device/module of FIG. 7B, note that there are two retentate portals 704 and two filtrate portals 706, where there is one of each type of portal at both ends (e.g., the narrow edge) of the TFF device/module 700. In other embodiments, retentate and filtrate portals can be on the same surface of the same member (e.g., upper member 722 or lower member 720), or they can be arranged on the side surfaces of the assembly. Unlike other tangential flow filtration devices that operate continuously, the TFF device/module described herein uses an alternating flow method for concentrating cells. FIG. 7C depicts a top view of upper (722) and lower (720) members of an exemplary TFF module 700. The lower portion of the flow channel 702b is seen on the top surface of lower member 720. Again, portals 704 and 706 are seen. As noted above, recesses—such as the recesses 708 seen in FIG. 7B—provide a means to secure the components (upper member 722, lower member 720, and membrane 724) of the TFF device/membrane 700 to one another during operation via, e.g., screws or other like fasteners. However, in alternative embodiments, an adhesive—such as a pressure sensitive adhesive—or ultrasonic welding, or solvent bonding, may be used to couple the upper member 722, lower member 720, and membrane 724 together. Indeed, one of ordinary skill in the art given the guidance of the present disclosure can find yet other configurations for coupling the components of the TFF device 700, such as e.g., clamps; mated fittings disposed on the upper (722) and lower (720) members; combination of adhesives, welding, solvent bonding, and mated fittings; and other such fasteners and couplings.

Note that in FIG. 7C there is one retentate portal 704 and one filtrate portal 706 on each "end" (e.g., the narrow edges) of the TFF device/module 700. The retentate 704 and filtrate 706 portals on the left side of the TFF device/module 700 will collect cells (flow path at 760 from the upper member 722) and medium (flow path at 770 from the lower member 720), respectively, when the cells and medium flow from right to left in the TFF module 700. Likewise, the retentate 704 and filtrate 706 portals on the right side of the TFF device/module 700 will collect cells (flow path at 760) and medium (flow path at 770), respectively, when the cells and medium flow from left to right in the TFF device. In this embodiment, the retentate is collected from portals 704 on the top surface of the TFF device, and filtrate is collected from portals 706 on the bottom surface of the device. The cells are maintained in the TFF flow channel 702a (shown in FIG. 7D) above the membrane 724, while the filtrate (medium) flows through membrane 724 and then through filtrate portals 706; thus, the top/retentate portals 704 and bottom/filtrate portals 706 configuration is practical. It should be recognized, however, that other configurations of retentate 704 and filtrate 706 portals may be implemented such as positioning both the retentate 704 and filtrate 706 portals on the side surface (as opposed to the top and bottom surfaces) of the TFF device 700. In FIG. 7C, the flow channel 702*b* can be seen on the lower member 720 of the TFF device 700. However, in other embodiments, retentate 704 and filtrate 706 portals can reside on the same surface of the TFF device.

The overall work flow for cell concentration using the TFF device/module 700 involves flowing a cell culture or cell sample tangentially through the channel structure 716. The membrane 724 bifurcating the flow channels 702 retains the cells on one side of the membrane and allows unwanted medium or buffer to flow across the membrane into the filtrate side (e.g, lower member 720) of the TFF device 700. In this process, a fixed volume of cells in medium or buffer is driven through the device until the cell sample is collected into one of the retentate portals 704, and the medium/buffer that has passed through the membrane is collected through one or both of the filtrate portals 706. All types of prokaryotic and eukaryotic cells—both adherent and non-adherent cells—can be concentrated in the TFF device. Adherent cells may be grown on beads or other cell scaffolds suspended in medium in the rotating growth vial, then passed through the TFF device.

In the cell concentration process, passing the cell sample through the TFF device and collecting the cells in one of the retentate portals 404 while collecting the medium in one of the filtrate portals 706 is considered "one pass" of the cell sample. The transfer between retentate reservoirs "flips" the culture. The retentate and filtrate portals collecting the cells and medium, respectively, for a given pass reside on the same end of TFF device/module 700 with fluidic connections arranged so that there are two distinct flow layers (not shown) for the retentate and filtrate sides, but if the retentate portal 404 resides on the upper member 722 of the TFF device/module 700 (that is, the cells are driven through the flow channel 702*a* (not shown) above the membrane and the filtrate (medium) passes to the portion of the flow channel 702*b* below the membrane), the filtrate portal 706 will reside on the lower member of TFF device/module 700 and vice versa (that is, if the cell sample is driven through the flow channel 702*b* below the membrane, the filtrate (medium) passes to the portion of the flow channel 702*a* above the membrane). This configuration can be seen more clearly in FIGS. 7C-7D, where the retentate flow path 760 from the retentate portals 704 and the filtrate flow path 770 from the filtrate portals 706.

At the conclusion of a "pass", the cell sample is collected by passing through the retentate portal 704 and into the retentate reservoir (not shown). To initiate another "pass", the cell sample is passed again through the TFF device 700, this time in a flow direction that is reversed from the first pass. The cell sample is collected by passing through the retentate portal 704 and into retentate reservoir (not shown) on the opposite end of the TFF device/module 700 from the retentate portal 704 that was used to collect cells during the first pass. Likewise, the medium/buffer that passes through the membrane on the second pass is collected through the filtrate portal 706 on the opposite end of the TFF device/module 700 from the filtrate portal 706 that was used to collect the filtrate during the first pass, or through both portals. This alternating process of passing the retentate (the concentrated cell sample) through the TFF device/module 700 is repeated until the cells have been concentrated to a desired volume, and both filtrate portals 706 can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell concentration may (and typically do) take place simultaneously.

Returning to FIG. 7C, also seen is membrane or filter 724. Filters or membranes appropriate for use in the TFF device/module 700 are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 5 µm. Indeed, the pore sizes useful in the TFF device/module 700 include filters 724 with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters 724 may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching. The TFF device 700 shown in FIGS. 7C and 7D does not show a seat in the upper 722 and lower 720 members where the filter 724 can be seated or secured (for example, a seat half the thickness of the filter 724 in each of upper 722 and lower 720 members); however, such a seat is contemplated in some embodiments.

Figure 7E:
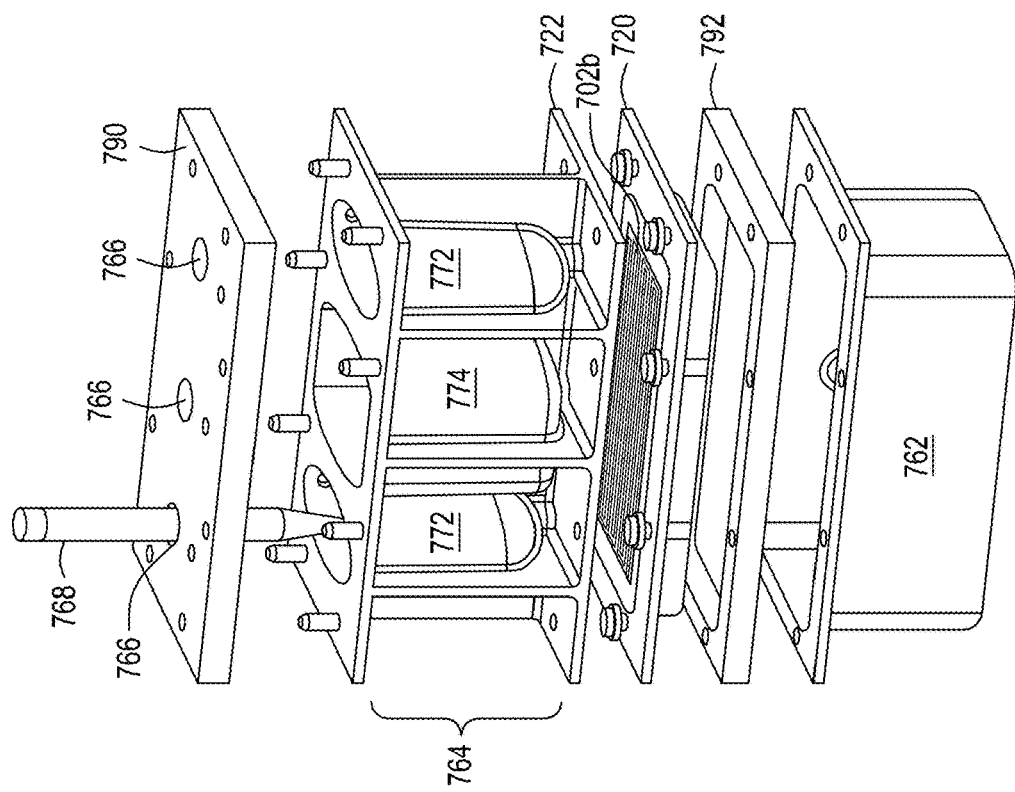
FIGS. 7E-7H depict various views of an embodiment of a TFF module having fluidically-coupled reservoirs for retentate, filtrate, and exchange buffer.
Figure 7D:
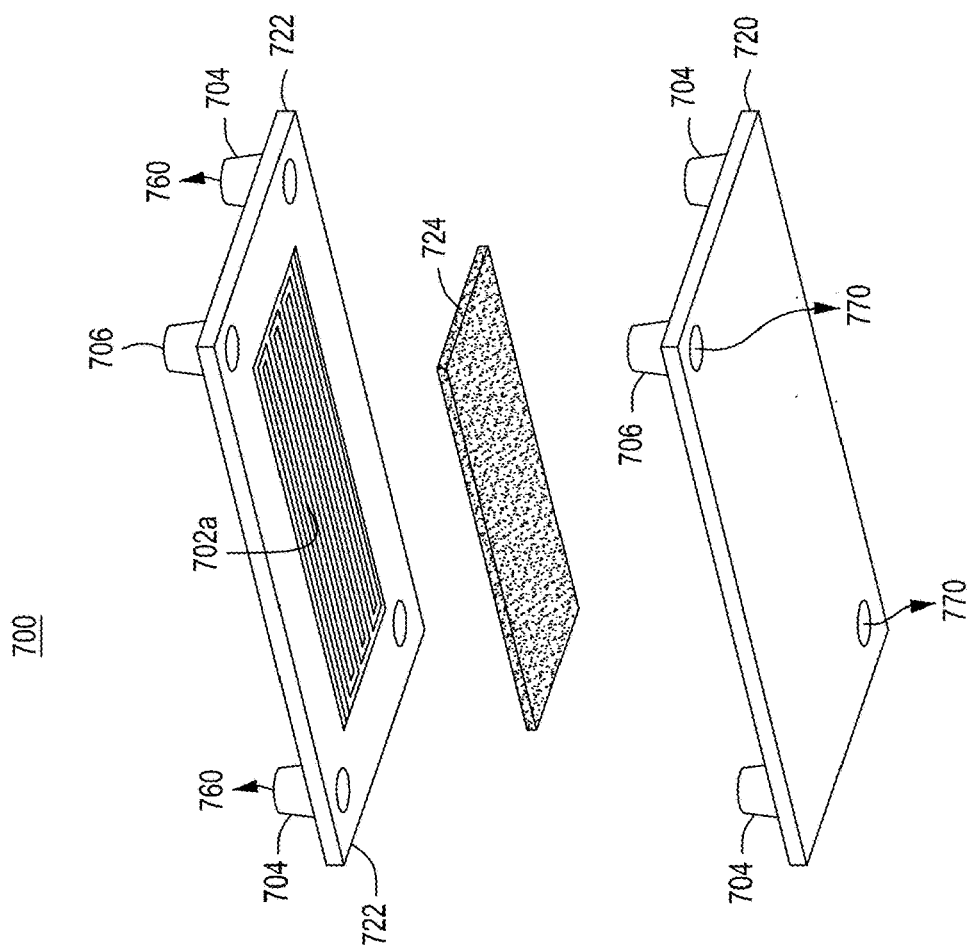
FIG. 7D depicts a bottom-up view of upper and lower members and a membrane of an exemplary TFF module.

FIG. 7D depicts a bottom-up view of upper member 722 and lower member 720 of the exemplary TFF module shown in FIG. 7C. Again portals 704 and 706 are seen. Note again that there is one retentate portal 704 and one filtrate portal 706 on each end of the upper member 722 and lower member 720 of the TFF device/module 700 (not all portals are seen in this view). On the left side of the TFF device 700, the retentate portals 704 will collect cells (flow path at 760) and the filtrate portals 706 will collect medium (flow path at 770), respectively, for the same pass. Likewise, on the right side of the TFF device 700, the retentate portals 704 will collect cells (flow path at 760) and the filtrate portals 706 will collect medium (flow path at 770), respectively, for the same pass. In FIG. 7D, the upper portion of flow channel 702*a* can be seen on the lower surface of upper member 722 of the TFF device 700. Thus, looking at FIGS. 7C and 7D, note that there is a flow channel 702 in both the upper member 722 (flow channel 702*a* in FIG. 7D) and lower member 722 (flow channel 702*b* in FIG. 7C) with a membrane 724 between the upper 722 and lower 720 members. Again, the flow channels 702*a* and 702*b* of the upper 722 and lower 720 members mate to create the flow channel 702 with the membrane 724 positioned horizontally between the upper and lower members of the TFF device/module thereby bifurcating the flow channel 702 (not shown).

Buffer exchange during cell concentration and/or rendering the cells competent is performed on the TFF device/module 700 by adding a desired buffer to the cells concentrated to a desired volume; for example, after the cells have been concentrated at least 20-fold, 30-fold, 40-fold, 50-fold, 60-fold, 70-fold, 80-fold, 90-fold, 100-fold, 150-fold, 200-fold or more. A desired exchange medium or exchange buffer is added to the cells by addition to a retentate reservoir (not shown) and the process of passing the cells through the TFF device 700 is repeated until the cells have been concentrated to a desired volume in the exchange medium or buffer. This process can be repeated any number of desired times so as to achieve a desired level of exchange of the buffer and a desired volume of cells. The exchange buffer may comprise, e.g., glycerol or sorbitol thereby rendering the cells competent for transformation in addition to decreasing the overall volume of the cell sample.

The TFF device 700 may be fabricated from any robust material in which flow channels may be milled including stainless steel, silicon, glass, aluminum, or plastics including cyclic-olefin copolymer (COC), cyclo-olefin polymer (COP), polystyrene, polyvinyl chloride, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module 700 is disposable, preferably it is made of plastic. In some embodiments, the material used to fabricate the TFF device/module 700 is thermally-conductive so that the cell culture may be heated or cooled to a desired temperature. In certain embodiments, the TFF device 700 is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to these mass production techniques.

FIG. 7E depicts an exploded perspective view of one exemplary embodiment of a TFF module having fluidically coupled reservoirs for retentate, filtrate, and exchange buffer. In this configuration, 790 is the top or cover of the TFF device, having three ports 766, where there is a pipette tip 768 disposed in the left-most port 766. The top 790 of the TFF device is, in operation, coupled with a combined reservoir and upper member structure 764. Combined reservoir and upper member structure 764 comprises a top surface that, in operation, is adjacent the top or cover 790 of the TFF device, a bottom surface which comprises the upper member 722 of the TFF device, where the upper member 722 of the TFF device defines the upper portion of the tangential flow channel (not shown). Combined reservoir and upper member structure 764 comprises two retentate reservoirs 772 and buffer or medium reservoir 774. The retentate reservoirs 772 are fluidically coupled to the upper portion of the flow channel, and the buffer or medium reservoir 774 is fluidically coupled to the retentate reservoirs 772. Also seen in this exploded view of the TFF device is lower member 720 which, as described previously, comprises on its top surface the lower portion of the tangential flow channel 702b (seen on the top surface of lower member 720), where the upper and lower portions of the flow channel 702 of the upper member 722 and lower member 720, respectively, when coupled mate to form a single flow channel 702 (the membrane that is interposed between the upper member 722 and lower member 720 in operation is not shown).

Beneath lower member 720 is gasket 792, which in operation is interposed between lower member 720 and a filtrate (or permeate) reservoir 762. In operation, top 790, combined reservoir and upper member structure 764, membrane (not shown), lower member 720, gasket 792, and filtrate reservoir 762 are coupled and secured together to be fluid- and air-tight. In FIG. 7E, fasteners are shown that can be used to couple the various structures (top 790, combined reservoir and upper member structure 764, membrane (not shown), lower member 720, gasket 792, and filtrate reservoir 762) together. However, as an alternative to screws or other like fasteners, the various structures of the TFF device can be coupled using an adhesive, such as a pressure sensitive adhesive; ultrasonic welding; or solvent bonding. Further, a combination of fasteners, adhesives, and/or welding types may be employed to couple the various structures of the TFF device. One of ordinary skill in the art given the guidance of the present disclosure could find yet other configurations for coupling the components of the TFF device, such as, e.g., clamps, mated fittings, and other such fasteners.

Figure 7F:
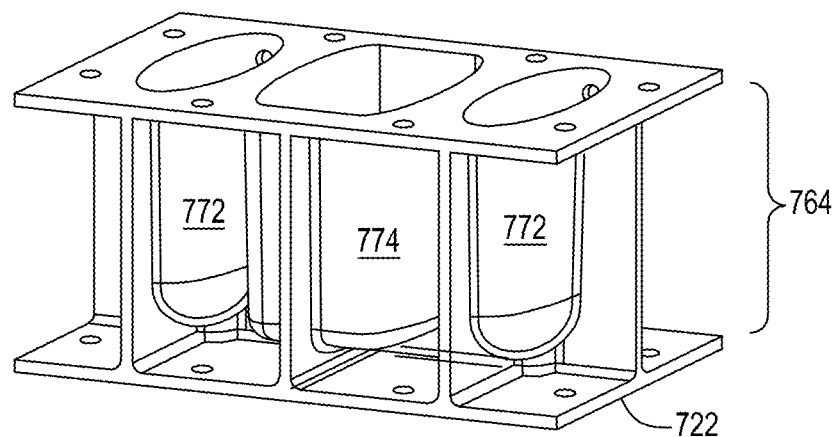
Figure 7G:
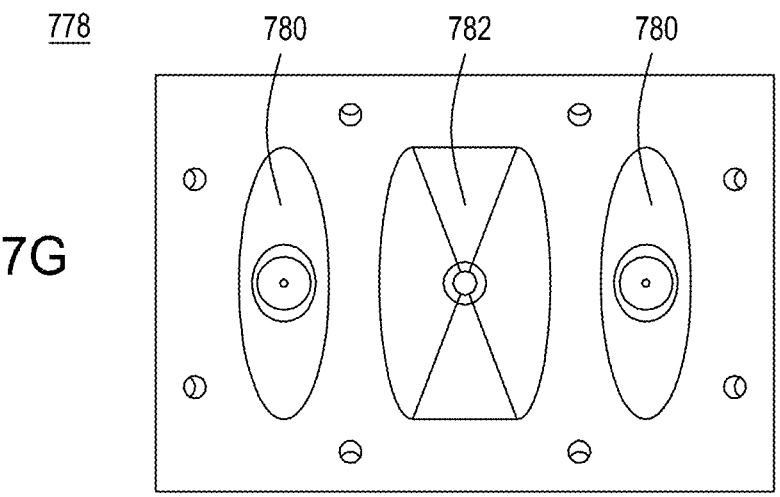
Figure 7H:
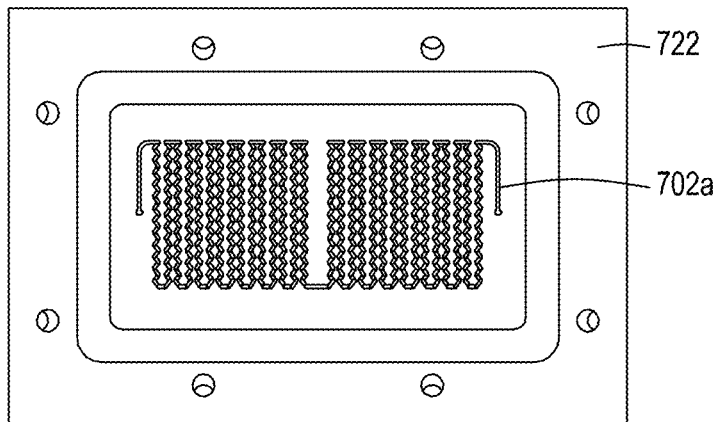

FIG. 7F depicts combined reservoir and upper member structure 764, comprising two retentate reservoirs 772 and buffer or medium reservoir 774, as well as upper member 722, which is disposed on the bottom of combined reservoir and upper member structure 764. Upper member 722 of the TFF device defines the upper portion of the tangential flow channel (not shown) disposed on the bottom surface of the combined reservoir and upper member structure 764. FIG. 7G is a top-down view of the upper surface 778 of combined reservoir and upper member structure 764, depicting the top 780 of retentate reservoirs 772 and the top 782 of buffer or medium reservoir 774. The retentate reservoirs 772 are fluidically coupled to the upper portion of the flow channel (not shown), and the buffer or medium reservoir 774 is fluidically coupled to the retentate reservoirs 772. FIG. 7H is a bottom-up view of the lower surface of combined reservoir and upper member structure 764, showing the upper member 722 with the upper portion of the tangential flow channel 702a disposed on the bottom surface of upper member 722. The flow channel 702a disposed on the bottom surface of upper member 722 in operation is mated to the bottom portion of the tangential flow channel 702b disposed on the top surface of the lower member 720 (not shown in this view, but see FIG. 7E), where the upper and lower portions of the flow channels 702a and 702b, respectively, mate to form a single flow channel 702 with a membrane or filter (not shown) interposed between the upper 702a and lower 702b portions of the flow channel.

Nucleic Acid Assembly Module

Certain embodiments of the automated multi-module cell editing instruments of the present disclosure optionally include a nucleic acid assembly module. The nucleic acid assembly module is configured to accept and assemble the nucleic acids necessary to facilitate the desired genome editing events. In general, the term "vector" refers to a nucleic acid molecule capable of transporting a desired nucleic acid to which it has been linked into a cell. Vectors include, but are not limited to, nucleic acid molecules that are single-stranded, double-stranded, or partially double-stranded; nucleic acid molecules that include one or more free ends, no free ends (e.g., circular); nucleic acid molecules that include DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, where virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors" or "editing vectors." Common expression vectors of utility in recombinant DNA techniques are often in the form of plasmids. Additional vectors include fosmids, phagemids, and synthetic chromosomes.

Recombinant expression vectors can include a nucleic acid in a form suitable for transcription, and for some nucleic acid sequences, translation and expression of the nucleic acid in a host cell, which means that the recombinant expression vectors include one or more regulatory elements—which may be selected on the basis of the host cells to be used for expression—that are operatively-linked to the nucleic acid sequence to be expressed. Within a recombinant expression vector, "operably linked" is intended to mean that the nucleotide sequence of interest is linked to the regulatory element(s) in a manner that allows for transcription, and for some nucleic acid sequences, translation and expression of the nucleotide sequence (e.g., in an in vitro transcription/translation system or in a host cell when the vector is introduced into the host cell). Appropriate recombination and cloning methods are disclosed in US Pub. No. 2004/0171156, the contents of which are herein incorporated by reference in their entirety for all purposes.

In some embodiments, a regulatory element is operably linked to one or more elements of a targetable nuclease system so as to drive transcription, and for some nucleic acid sequences, translation and expression of the one or more components of the targetable nuclease system.

In addition, the polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. In addition or alternatively, a vector may include a regulatory element operably liked to a polynucleotide sequence, which, when transcribed, forms a guide RNA.

The nucleic acid assembly module can be configured to perform a wide variety of different nucleic acid assembly techniques in an automated fashion. Nucleic acid assembly techniques that can be performed in the nucleic acid assembly module of the disclosed automated multi-module cell editing instruments include, but are not limited to, those assembly methods that use restriction endonucleases, including PCR, BioBrick assembly (U.S. Pat. No. 9,361,427), Type IIS cloning (e.g., GoldenGate assembly, European Patent Application Publication EP 2 395 087 A1), and Ligase Cycling Reaction (de Kok, ACS Synth Biol., 3(2): 97-106 (2014); Engler, et al., PLoS One, 3(11):e3647 (2008); and U.S. Pat. No. 6,143,527). In other embodiments, the nucleic acid assembly techniques performed by the disclosed automated multi-module cell editing instruments are based on overlaps between adjacent parts of the nucleic acids, such as Gibson Assembly®, CPEC, SLIC, Ligase Cycling etc. Additional assembly methods include gap repair in yeast (Bessa, Yeast, 29(10):419-23 (2012)), gateway cloning (Ohtsuka, Curr Pharm Biotechnol, 10(2):244- 51 (2009)); U.S. Pat. Nos. 5,888,732; and 6,277,608), and topoisomerase-mediated cloning (Udo, PLoS One, 10(9): e0139349 (2015); and U.S. Pat. No. 6,916,632). These and other nucleic acid assembly techniques are described, e.g., in Sands and Brent, Curr Protoc Mol Biol., 113:3.26.1-3.26.20 (2016).

The nucleic acid assembly module is temperature controlled depending upon the type of nucleic acid assembly used in the automated multi-module cell editing instrument. For example, when PCR is utilized in the nucleic acid assembly module, the module includes a thermocycling capability allowing the temperatures to cycle between denaturation, annealing and extension steps. When single temperature assembly methods (e.g., isothermal assembly methods) are utilized in the nucleic acid assembly module, the module provides the ability to reach and hold at the temperature that optimizes the specific assembly process being performed. These temperatures and the duration for maintaining these temperatures can be determined by a preprogrammed set of parameters executed by a script, or manually controlled by the user using the processing system of the automated multi-module cell editing instrument.

In one embodiment, the nucleic acid assembly module is a module to perform assembly using a single, isothermal reaction. Certain isothermal assembly methods can combine simultaneously up to 15 nucleic acid fragments based on sequence identity. The assembly method provides, in some embodiments, nucleic acids to be assembled which include an approximate 20-40 base overlap with adjacent nucleic acid fragments. The fragments are mixed with a cocktail of three enzymes—an exonuclease, a polymerase, and a ligase—along with buffer components. Because the process is isothermal and can be performed in a 1-step or 2-step method using a single reaction vessel, isothermal assembly reactions are ideal for use in an automated multi-module cell editing instrument. The 1-step method allows for the assembly of up to five different fragments using a single step isothermal process. The fragments and the master mix of enzymes are combined and incubated at 50° C. for up to one hour. For the creation of more complex constructs with up to fifteen fragments or for incorporating fragments from 100 bp up to 10 kb, typically the 2-step is used, where the 2-step reaction requires two separate additions of master mix; one for the exonuclease and annealing step and a second for the polymerase and ligation steps.

Transformation Module

Figure 8A:
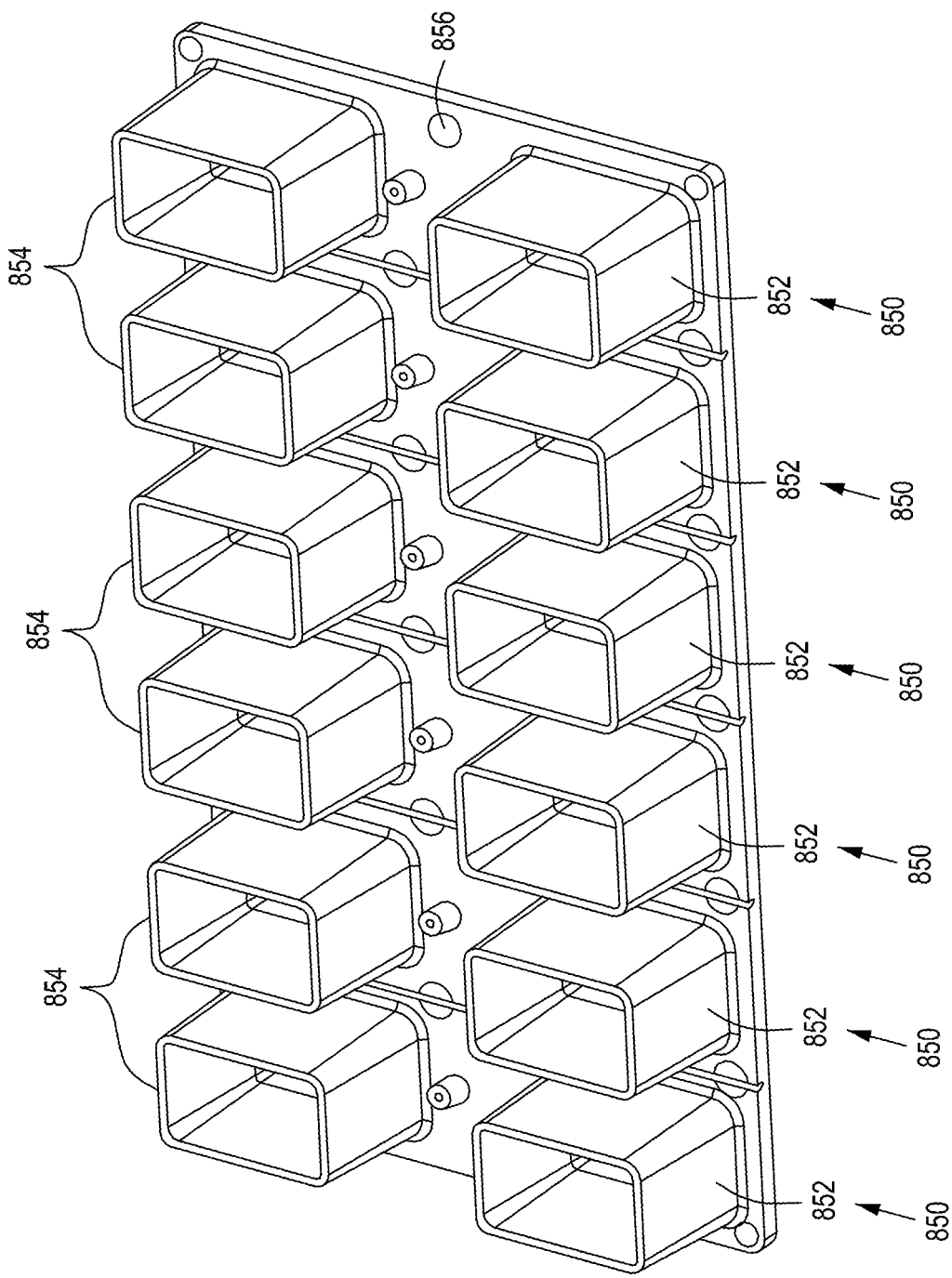
FIGS. 8A and 8B are top perspective and bottom perspective views, respectively, of flow-through electroporation devices (here, there are six such devices co-joined).
Figure 8B:
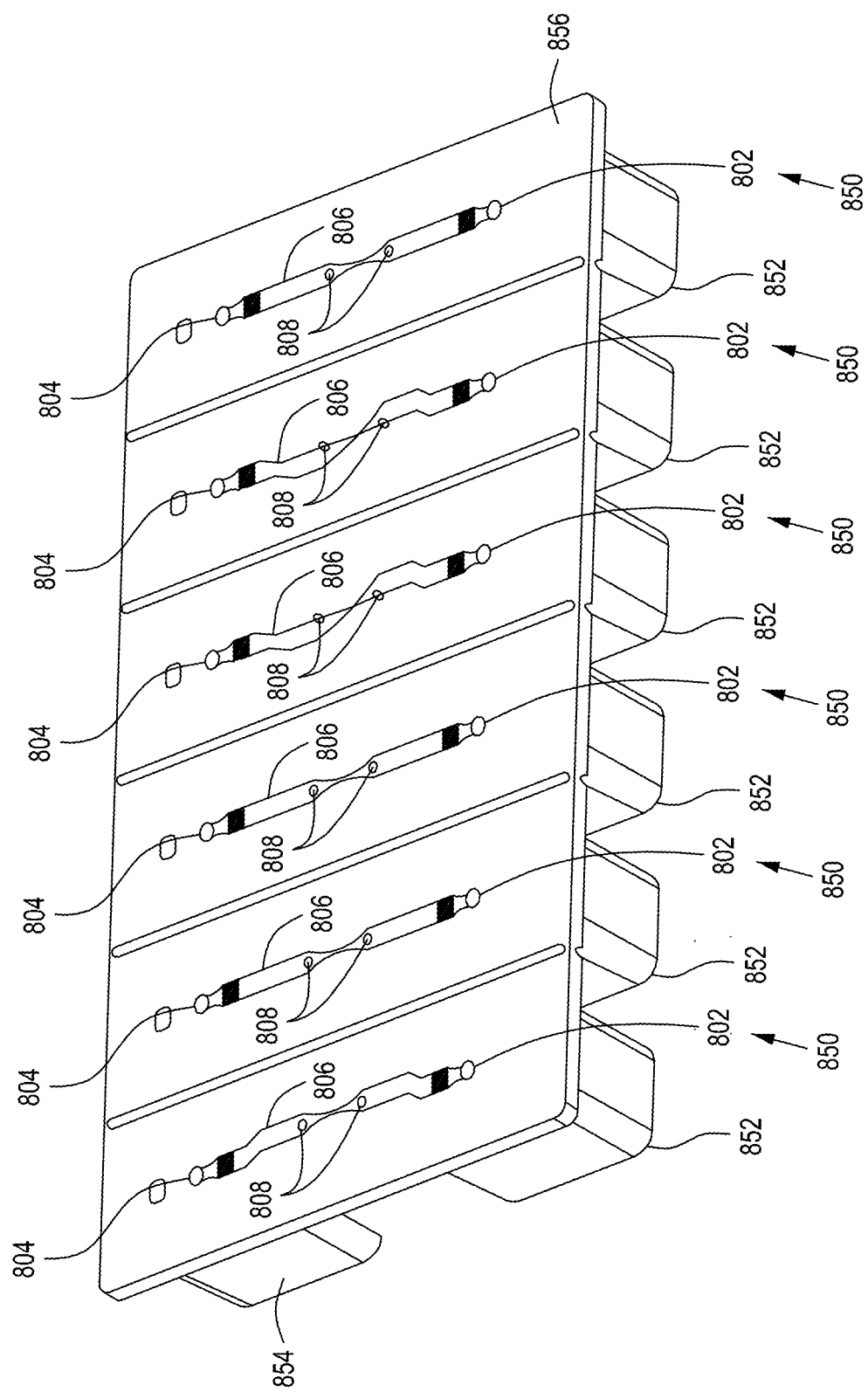

FIGS. 8A-8E depict variations on one embodiment of a cell transformation module (in this case, a flow-through electroporation device) that may be included in a cell growth/concentration/transformation instrument. FIGS. 8A and 8B are top perspective and bottom perspective views, respectively, of six co-joined flow-through electroporation devices 850. FIG. 8A depicts six flow-through electroporation units 850 arranged on a single substrate 856. Each of the six flow-through electroporation units 850 have inlet wells 852 that define cell sample inlets and outlet wells 854 that define cell sample outlets. FIG. 8B is a bottom perspective view of the six co-joined flow-through electroporation devices of FIG. 8A also depicting six flow-through electroporation units 850 arranged on a single substrate 856. Six inlet wells 852 can be seen, one for each flow-through electroporation unit 850, and one outlet well 854 can be seen (the outlet well of the left-most flow-through electroporation unit 850). Additionally seen in FIG. 8B are an inlet 802, outlet 804, flow channel 806 and two electrodes 808 on either side of a constriction in flow channel 806 in each flow-through electroporation unit 850. Once the six flow-through electroporation units 850 are fabricated, they can be separated from one another (e.g., "snapped apart") and used one at a time, or alternatively in embodiments where two or more flow-through electroporation units 850 can be used in parallel without separation.

The flow-through electroporation devices 850 achieve high efficiency cell electroporation with low toxicity. The flow-through electroporation devices 850 of the disclosure allow for particularly easy integration with robotic liquid handling instrumentation that is typically used in automated systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

Generally speaking, microfluidic electroporation—using cell suspension volumes of less than approximately 10 mL and as low as 1 µl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit electroporation device configurations; and integrated, automatic, multi-module cell processing and analysis.

In specific embodiments of the flow-through electroporation devices 850 of the disclosure, the toxicity level of the transformation results in greater than 10% viable cells after electroporation, preferably greater than 15%, 20%, 25%, 30%, 35%, 40%, 45%, 50%, 55%, 60%, 70%, 75%, 80%, 85%, 90%, or even 95% viable cells following transformation, depending on the cell type and the nucleic acids being introduced into the cells.

The flow-through electroporation device 850 described in relation to FIGS. 8A-8E comprises a housing with an electroporation chamber, a first electrode and a second electrode configured to engage with an electric pulse generator, by which electrical contacts engage with the electrodes of the electroporation device 850. In certain embodiments, the electroporation devices are autoclavable and/or disposable, and may be packaged with reagents in a reagent cartridge. The electroporation device 850 may be configured to electroporate cell sample volumes between 1 µl to 2 mL, 10 µl to 1 mL, 25 µl to 750 µl, or 50 µl to 500 µl. The cells that may be electroporated with the disclosed electroporation devices 850 include mammalian cells (including human cells), plant cells, yeasts, other eukaryotic cells, bacteria, archaea, and other cell types.

Figure 8C:
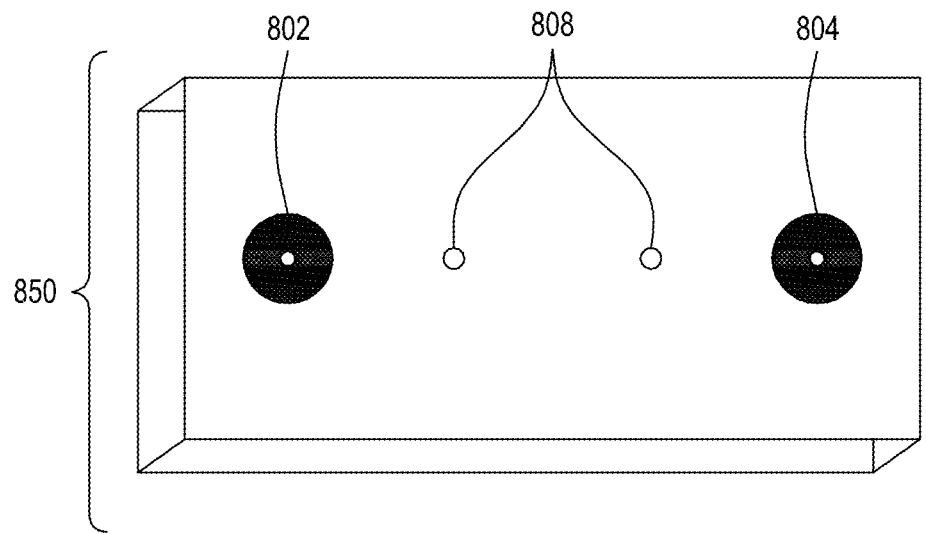
FIG. 8C is a top view of one embodiment of an exemplary flow-through electroporation device.
Figure 8D:
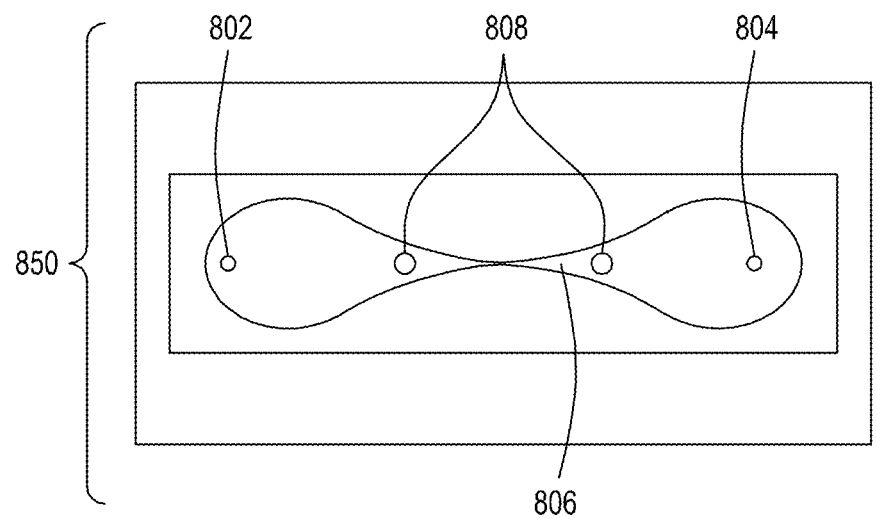
FIG. 8D depicts a top view of a cross section of the electroporation device of FIG. 8C.
Figure 8E:
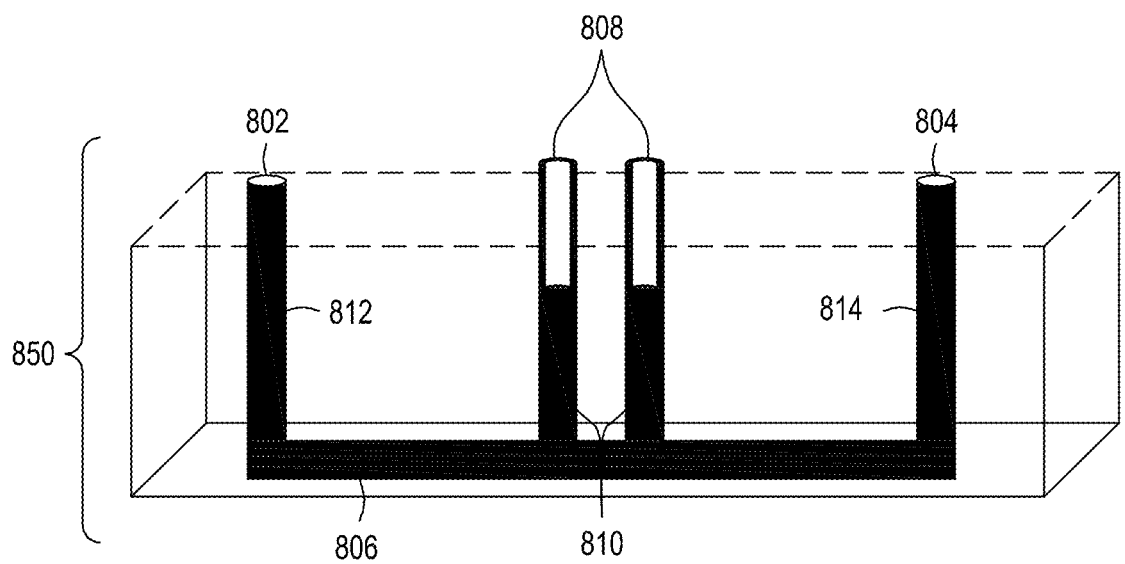
FIG. 8E is a side view cross section of a lower portion of the electroporation devices of FIGS. 8C and 8D.

In one exemplary embodiment, FIG. 8C depicts a top view of a flow-through electroporation device 850 having an inlet 802 for introduction of cells and an exogenous reagent to be electroporated into the cells ("cell sample") and an outlet 804 for the cell sample following electroporation. Electrodes 808 are introduced through electrode channels (not shown in this FIG. 8C) in the device. FIG. 8D shows a cutaway view from the top of flow-through electroporation device 850, with the inlet 802, outlet 804, and electrodes 808 positioned with respect to a constriction in flow channel 806. A side cutaway view of a lower portion of flow-through electroporation device 850 in FIG. 8E illustrates that electrodes 808 in this embodiment are positioned in electrode channels 810 and perpendicular to flow channel 806 such that the cell sample flows from the inlet channel 812 through the flow channel 806 to the outlet channel 814, and in the process the cell sample flows into the electrode channels 810 to be in contact with electrodes 808. In this aspect, the inlet channel 812, outlet channel 814 and electrode channels 810 all originate from the top planar side of the device; however, the flow-through electroporation architecture depicted in FIGS. 8C-8E is but one architecture useful with the reagent cartridges described herein. Additional electrode architectures are described, e.g., in U.S. Ser. No. 16/147,120, filed 24 Sep. 2018; Ser. No. 16/147,865, filed 30 Sep. 2018; and Ser. No. 16/147,871, filed 30 Sep. 2018.

Exemplary Workflows

Figure 9:
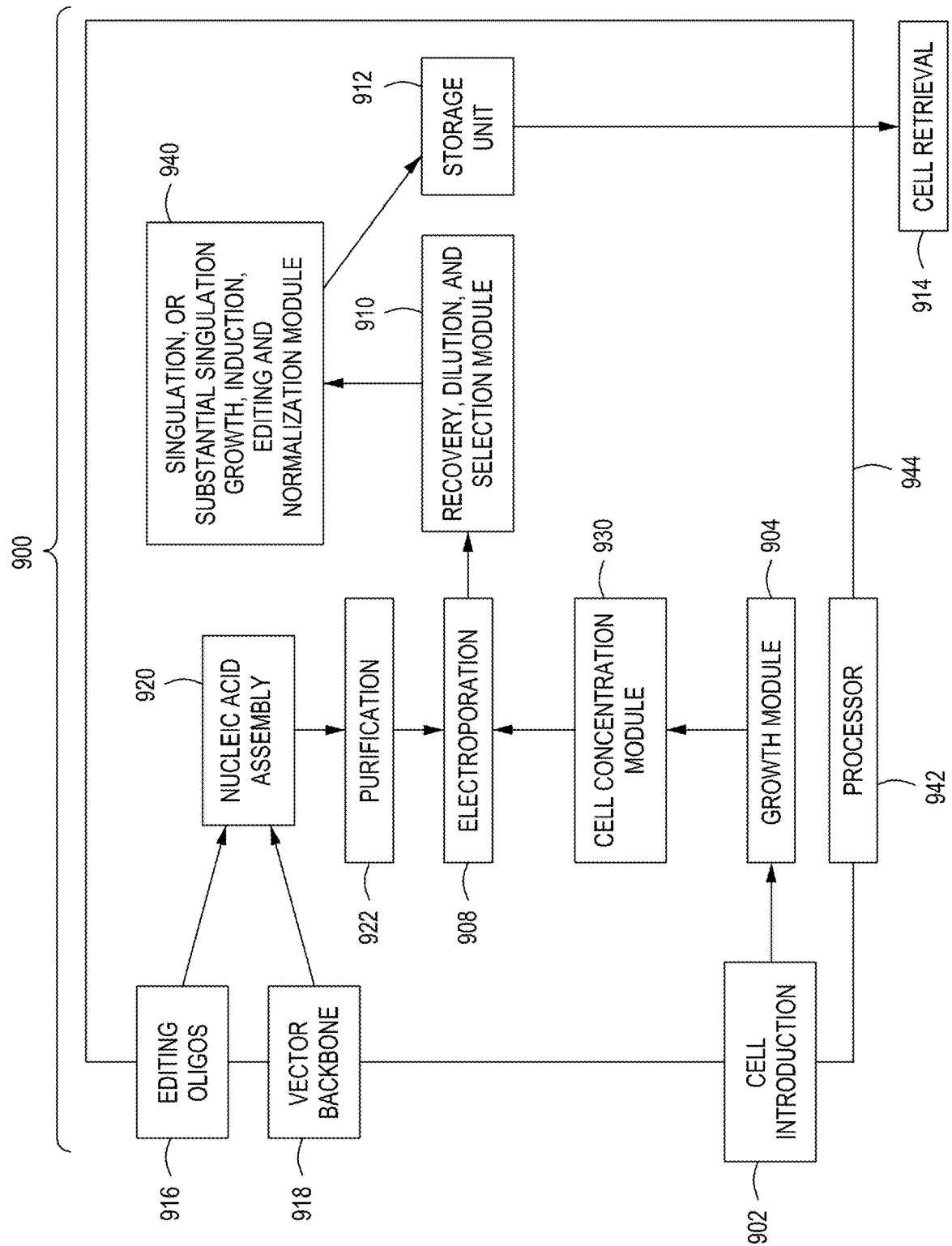
FIG. 9 is a simplified block diagram of an embodiment of an exemplary automated multi-module cell processing instrument comprising a singulation or substantial singulation/growth/editing and normalization or cherry picking module ("solid wall isolation/induction/normalization module" or "SWIIN").

FIG. 9 is a simplified block diagram of an embodiment of an exemplary automated multi-module cell processing instrument comprising a singulation or substantial singulation/growth/editing and normalization or cherry-picking module for enrichment or selection of edited cells. The cell processing instrument 900 may include a housing 944, a reservoir of cells to be transformed or transfected 902, and a growth module (a cell growth device) 904. The cells to be transformed are transferred from a reservoir to the growth module to be cultured until the cells hit a target OD. Once the cells hit the target OD, the growth module may cool or freeze the cells for later processing, or the cells may be transferred to a cell concentration module 930 where the cells are rendered electrocompetent and concentrated to a volume optimal for cell transformation. Once concentrated, the cells are then transferred to the electroporation device 908 (e.g., transformation/transfection module, with one exemplary module described above in relation to FIGS. 8A-8E). Exemplary electroporation devices of use in the automated multi-module cell processing instruments include flow-through electroporation devices such as those described in Ser. No. 16/147,120, filed 28 Sep. 2018; Ser. No. 16/147,353, filed 28 Sep. 2018; Ser. No. 16/147,865, filed 30 Sep. 2018; and Ser. No. 16/147,871, filed 30 Sep. 2018 all of which are herein incorporated by reference in their entirety.

In addition to the reservoir for storing the cells 930, the automated multi-module cell processing instrument 900 may include a reservoir for storing editing oligonucleotide cassettes 916 and a reservoir for storing an expression vector backbone 918. Both the editing oligonucleotide cassettes and the expression vector backbone are transferred from a reagent cartridge to a nucleic acid assembly module 920, where the editing oligonucleotide cassettes are inserted into the expression vector backbone. The assembled nucleic acids may be transferred into an optional purification module 922 for desalting and/or other purification and/or concentration procedures needed to prepare the assembled nucleic acids for transformation. Alternatively, pre-assembled nucleic acids, e.g., an editing vector, may be stored within reservoir 916 or 918. Once the processes carried out by the purification module 922 are complete, the assembled nucleic acids are transferred to, e.g., an electroporation device 908, which already contains the cell culture grown to a target OD and rendered electrocompetent via cell concentration module 930. In electroporation device 908, the assembled nucleic acids are introduced into the cells. Following electroporation, the cells are transferred into a combined recovery/selection module 910. For examples of multi-module cell editing instruments, see Ser. Nos. 16/024,816 and 16/024,831, filed 30 Jun. 2018; Ser. No. 16/147,865, filed 30 Sep. 2018; and Ser. No. 16/147,871, filed 30 Sep. 2018, all of which are herein incorporated by reference in their entirety.

Following recovery, and, optionally, selection, the cells are transferred to a singulation or substantial singulation, editing, and growth module 940, where the cells are diluted and compartmentalized such that there is an average of one cell per compartment. Once substantially or largely singulated, the cells are allowed to grow for a pre-determined number of doublings. Once these initial colonies are established, editing is induced and the edited cells are grown to establish colonies, which are grown to terminal size (e.g., the colonies are normalized). In some embodiments, editing is induced by one or more of the editing components being under the control of an inducible promoter. In some embodiments, the inducible promoter is activated by a rise in temperature and "deactivated" by lowering the temperature. Similarly, in embodiments where the solid wall device comprising a filter forming the bottom of the microwell, the solid wall device can be transferred to a plate (e.g., an agar plate or even to liquid medium) comprising a medium with a component that activates or induces editing, then transferred to a medium that deactivates editing. In solid wall devices with solid bottoms, induction of editing can deactivation of editing can take place by media exchange. Once the colonies are grown to terminal size, the colonies are pooled. Again, singulation or substantial singulation overcomes growth bias from unedited cells and growth bias resulting from fitness effects of different edits.

The recovery, selection, and singulation/induction/editing and normalization modules may all be separate, may be arranged and combined as shown in FIG. 9, or may be arranged or combined in other configurations. In certain embodiments, all of recovery, selection, singulation or substantial singulation, growth, editing, and normalization are performed in a single module such as on a substrate with nutrient agar, or on the solid wall device described in relation to FIGS. 3A-3E and 4A-4AA. Alternatively, recovery, selection, and dilution, if necessary, are performed in liquid medium in a separate vessel (module), then transferred to the singulation/growth/induction/editing and normalization module.

Once the normalized cell colonies are pooled, the cells may be stored, e.g., in a storage unit or module 912, where the cells can be kept at, e.g., 4° C. until the cells are retrieved for further study 914. Alternatively, the cells may be used in another round of editing. The multi-module cell processing instrument 900 is controlled by a processor 942 configured to operate the instrument based on user input, as directed by one or more scripts, or as a combination of user input or a script. The processor 942 may control the timing, duration, temperature, and operations of the various modules of the instrument 900 and the dispensing of reagents. For example, the processor 942 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

The automated multi-module cell processing instrument 900 is a nuclease-directed genome editing system and can be used in single editing systems (e.g., introducing one or more edits to a cellular genome in a single editing process). The system of FIG. 10, described below, is configured to perform sequential editing, e.g., using different nuclease-directed systems sequentially to provide two or more genome edits in a cell; and/or recursive editing, e.g. utilizing a single nuclease-directed system to introduce sequentially two or more genome edits in a cell.

Figure 10:
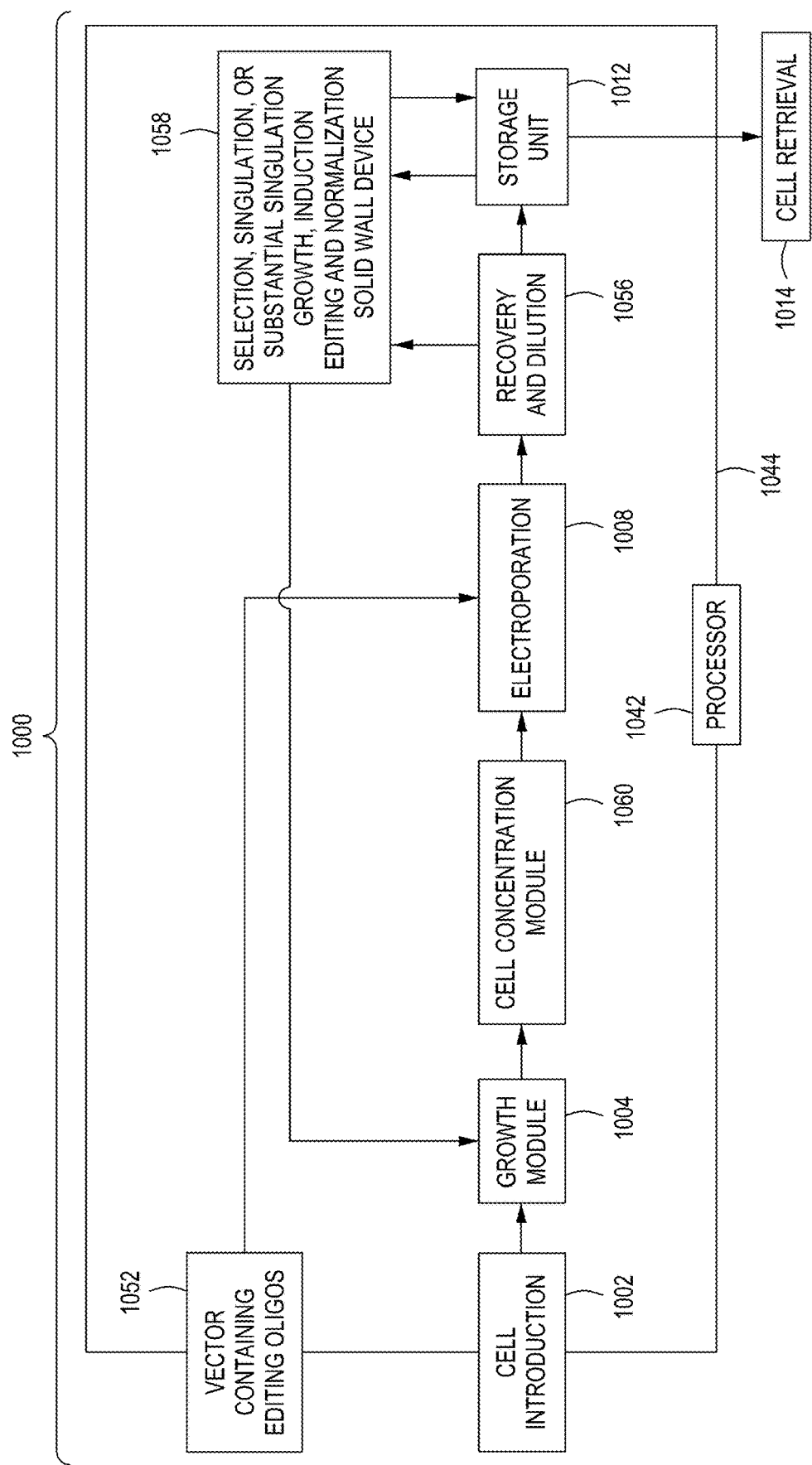
FIG. 10 is a simplified block diagram of an alternative embodiment of an exemplary automated multi-module cell processing instrument comprising a singulation or substantial singulation/growth/editing and normalization or cherry picking module ("solid wall isolation/induction/normalization module" or "SWIIN").

FIG. 10 illustrates another embodiment of an automated multi-module cell processing instrument configured to perform singulation or substantial singulation of cells, growth, induction of editing and normalization of cell colonies. This embodiment depicts an exemplary system that performs recursive gene editing on a cell population. As with the embodiment shown in FIG. 9, the cell processing instrument 1000 may include a housing 1044, a reservoir for storing cells to be transformed or transfected 1002, and a cell growth module (comprising, e.g., a rotating growth vial) 1004. The cells to be transformed are transferred from a reservoir to the cell growth module to be cultured until the cells hit a target OD. Once the cells hit the target OD, the growth module may cool or freeze the cells for later processing or transfer the cells to a cell concentration module 1060 where the cells are subjected to buffer exchange and rendered electrocompetent, and the volume of the cells may be reduced substantially. Once the cells have been concentrated to an appropriate volume, the cells are transferred to electroporation device 1008. In addition to the reservoir for storing cells, the multi-module cell processing instrument 1000 includes a reservoir for storing the vector pre-assembled with editing oligonucleotide cassettes 1052. The pre-assembled nucleic acid vectors are transferred to the electroporation device 1008, which already contains the cell culture grown to a target OD. In the electroporation device 1008, the nucleic acids are electroporated into the cells. Following electroporation, the cells are transferred into an optional recovery module 1056, where the cells are allowed to recover briefly post-transformation.

After recovery, the cells may be transferred to a storage unit or module 1012, where the cells can be stored at, e.g., 4° C. for later processing, or the cells may be diluted and transferred to a solid wall selection, singulation or substantial singulation/growth/induction/editing and normalization module 1058. In the multi-process module 1058, the cells are arrayed such that there is an average of one cell per microwell. The arrayed cells may be in selection medium to select for cells that have been transformed or transfected with the editing vector(s). Once substantially or largely singulated, the cells grow through 2-50 doublings and establish colonies. Once colonies are established, editing is induced by providing conditions (e.g., temperature, addition of an inducing or repressing chemical) to induce editing. Once editing is initiated and allowed to proceed, the cells are allowed to grow to terminal size (e.g., normalization of the colonies) in the microwells and then can be flushed out of the microwells and pooled, then transferred to the cell retrieval unit 1014 or can be transferred back to a growth module 1004 for another round of editing. In between pooling and transfer to a growth module, there may be one or more additional steps, such as cell recovery, medium exchange, cells concentration, etc., by, e.g., tangential flow filtration. Note that the selection/singulation or substantial singulation/growth/induction/editing and normalization modules may be the same module, where all processes are performed in the solid wall device, or selection and/or dilution may take place in a separate vessel before the cells are transferred to the solid wall singulation or substantial singulation/growth/induction/editing and normalization module (solid wall device). Once the putatively-edited cells are pooled, they may be subjected to another round of editing, beginning with growth, cell concentration and treatment to render electrocompetent, and transformation by yet another donor nucleic acid in another editing cassette via the electroporation module 1008.

In electroporation device 1008, the cells selected from the first round of editing are transformed by a second set of editing oligos (or other type of oligos) and the cycle is repeated until the cells have been transformed and edited by a desired number of, e.g., editing cassettes. The multi-module cell processing instrument 1000 exemplified in FIG. 10 is controlled by a processor 1042 configured to operate the instrument based on user input or is controlled by one or more scripts including at least one script associated with the reagent cartridge. The processor 1042 may control the timing, duration, and temperature of various processes, the dispensing of reagents, and other operations of the various modules of the automated multi-module cell processing instrument 1000. For example, a script or the processor may control the dispensing of cells, reagents, vectors, and editing oligonucleotides; which editing oligonucleotides are used for cell editing and in what order; the time, temperature and other conditions used in the recovery and expression module; the wavelength at which OD is read in the cell growth module, the target OD to which the cells are grown, and the target time at which the cells will reach the target OD. In addition, the processor may be programmed to notify a user (e.g., via an application to a smart phone or other device) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 10, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is to say that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries. In any recursive process, it is advantageous to "cure" the previous engine and editing vectors (or single engine+editing vector in a single vector system). "Curing" is a process in which one or more vectors used in the prior round of editing is eliminated from the transformed cells. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine plasmid.

Production of Cell Libraries Using Automated Editing Methods, Modules, Instruments and Systems In one aspect, the present disclosure provides automated editing methods, modules, instruments, and automated multi-module cell editing instruments for creating a library of cells that vary the expression, levels and/or activity of RNAs and/or proteins of interest in various cell types using various editing strategies, as described herein in more detail. Accordingly, the disclosure is intended to cover edited cell libraries created by the automated editing methods, automated multi-module cell editing instruments of the disclosure. These cell libraries may have different targeted edits, including but not limited to gene knockouts, gene knock-ins, insertions, deletions, single nucleotide edits, short tandem repeat edits, frameshifts, triplet codon expansion, and the like in cells of various organisms. These edits can be directed to coding or non-coding regions of the genome and are preferably rationally designed.

In other aspects, the present disclosure provides automated editing methods, automated multi-module cell editing instruments for creating a library of cells that vary DNA-linked processes. For example, the cell library may include individual cells having edits in DNA binding sites to interfere with DNA binding of regulatory elements that modulate expression of selected genes. In addition, cell libraries may include edits in genomic DNA that impact on cellular processes such as heterochromatin formation, switch-class recombination and VDJ recombination.

In specific aspects, the cell libraries are created using multiplexed editing of individual cells within a cell population, with multiple cells within a cell population are edited in a single round of editing, i.e., multiple changes within the cells of the cell library are in a single automated operation. The libraries that can be created in a single multiplexed automated operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

In other specific aspects, the cell libraries are created using recursive editing of individual cells within a cell population, with edits being added to the individual cells in two or more rounds of editing. The use of recursive editing results in the amalgamation of two or more edits targeting two or more sites in the genome in individual cells of the library. The libraries that can be created in an automated recursive operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

Examples of non-automated editing strategies that can be modified based on the present specification to utilize the automated systems can be found, e.g., U.S. Pat. Nos. 8,110,360, 8,332,160, 9,988,624, 20170316353, and 20120277120.

In specific aspects, recursive editing can be used to first create a cell phenotype, and then later rounds of editing used to reverse the phenotype and/or accelerate other cell properties.

In some aspects, the cell library comprises edits for the creation of unnatural amino acids in a cell.

In specific aspects, the disclosure provides edited cell libraries having edits in one or more regulatory elements created using the automated editing methods, automated multi-module cell editing instruments of the disclosure. The term "regulatory element" refers to nucleic acid molecules that can influence the transcription and/or translation of an operably linked coding sequence in a particular environment and/or context. This term is intended to include all elements that promote or regulate transcription, and RNA stability including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include, but are not limited to, promoters, operator sequences and a ribosome binding sites. Regulatory elements that are used in eukaryotic cells may include, but are not limited to, promoters, enhancers, insulators, splicing signals and polyadenylation signals.

Preferably, the edited cell library includes rationally designed edits that are designed based on predictions of protein structure, expression and/or activity in a particular cell type. For example, rational design may be based on a system-wide biophysical model of genome editing with a particular nuclease and gene regulation to predict how different editing parameters including nuclease expression and/or binding, growth conditions, and other experimental conditions collectively control the dynamics of nuclease editing. See, e.g., Farasat and Salis, PLoS Comput Biol., 29:12(1):e1004724 (2016).

In one aspect, the present disclosure provides the creation of a library of edited cells with various rationally designed regulatory sequences created using the automated editing instrumentation, systems and methods of the invention. For example, the edited cell library can include prokaryotic cell populations created using set of constitutive and/or inducible promoters, enhancer sequences, operator sequences and/or ribosome binding sites. In another example, the edited cell library can include eukaryotic sequences created using a set of constitutive and/or inducible promoters, enhancer sequences, operator sequences, and/or different Kozak sequences for expression of proteins of interest.

In some aspects, the disclosure provides cell libraries including cells with rationally designed edits comprising one or more classes of edits in sequences of interest across the genome of an organism. In specific aspects, the disclosure provides cell libraries including cells with rationally designed edits comprising one or more classes of edits in sequences of interest across a subset of the genome. For example, the cell library may include cells with rationally designed edits comprising one or more classes of edits in sequences of interest across the exome, e.g., every or most open reading frames of the genome. For example, the cell library may include cells with rationally designed edits comprising one or more classes of edits in sequences of interest across the kinome. In yet another example, the cell library may include cells with rationally designed edits comprising one or more classes of edits in sequences of interest across the secretome. In yet other aspects, the cell library may include cells with rationally designed edits created to analyze various isoforms of proteins encoded within the exome, and the cell libraries can be designed to control expression of one or more specific isoforms, e.g., for transcriptome analysis.

Importantly, in certain aspects the cell libraries may comprise edits using randomized sequences, e.g., randomized promoter sequences, to reduce similarity between expression of one or more proteins in individual cells within the library. Additionally, the promoters in the cell library can be constitutive, inducible or both to enable strong and/or titratable expression.

In other aspects, the present disclosure provides automated editing methods, automated multi-module cell editing instruments for creating a library of cells comprising edits to identify optimum expression of a selected gene target. For example, production of biochemicals through metabolic engineering often requires the expression of pathway enzymes, and the best production yields are not always achieved by the highest amount of the target pathway enzymes in the cell, but rather by fine-tuning of the expression levels of the individual enzymes and related regulatory proteins and/or pathways. Similarly, expression levels of heterologous proteins sometimes can be experimentally adjusted for optimal yields.

The most obvious way that transcription impacts on gene expression levels is through the rate of Pol II initiation, which can be modulated by combinations of promoter or enhancer strength and trans-activating factors (Kadonaga, et al., Cell, 116(2):247-57 (2004)). In eukaryotes, elongation rate may also determine gene expression patterns by influencing alternative splicing (Cramer et al., PNAS USA, 94(21):11456-60 (1997)). Failed termination on a gene can impair the expression of downstream genes by reducing the accessibility of the promoter to Pol II (Greger, et al., PNAS USA, 97(15):8415-20 (2000)). This process, known as transcriptional interference, is particularly relevant in lower eukaryotes, as they often have closely spaced genes.

In some embodiments the present disclosure provides methods for optimizing cellular gene transcription. Gene transcription is the result of several distinct biological phenomena, including transcriptional initiation (RNAp recruitment and transcriptional complex formation), elongation (strand synthesis/extension), and transcriptional termination (RNAp detachment and termination).

Site-Directed Mutagenesis

Cell libraries can be created using the automated editing methods, modules, instruments, and systems employing site-directed mutagenesis, i.e., when the amino acid sequence of a protein or other genomic feature may be altered by deliberately and precisely by mutating the protein or genomic feature. These cell lines can be useful for various purposes, e.g., for determining protein function within cells, the identification of enzymatic active sites within cells, and the design of novel proteins. For example, site-directed mutagenesis can be used in a multiplexed fashion to exchange a single amino acid in the sequence of a protein for another amino acid with different chemical properties. This allows one to determine the effect of a rationally designed or randomly generated mutation in individual cells within a cell population. See, e.g., Berg, et al. Biochemistry, Sixth Ed. (New York: W.H. Freeman and Company) (2007).

In another example, edits can be made to individual cells within a cell library to substitute amino acids in binding sites, such as substitution of one or more amino acids in a protein binding site for interaction within a protein complex or substitution of one or more amino acids in enzymatic pockets that can accommodate a cofactor or ligand. This class of edits allows the creation of specific manipulations to a protein to measure certain properties of one or more proteins, including interaction with other cofactors, ligands, etc. within a protein complex.

In yet another examples, various edit types can be made to individual cells within a cell library using site specific mutagenesis for studying expression quantitative trait loci (eQTLs). An eQTL is a locus that explains a fraction of the genetic variance of a gene expression phenotype. The libraries of the invention would be useful to evaluate and link eQTLs to actual diseased states.

In specific aspects, the edits introduced into the cell libraries of the disclosure may be created using rational design based on known or predicted structures of proteins. See, e.g., Chronopoulou and Labrou, Curr Protoc Protein Sci.; Chapter 26: Unit 26.6 (2011). Such site-directed mutagenesis can provide individual cells within a library with one or more site-directed edits, and preferably two or more site-directed edits (e.g., combinatorial edits) within a cell population.

In other aspects, cell libraries of the disclosure are created using site-directed codon mutation "scanning" of all or substantially all of the codons in the coding region of a gene. In this fashion, individual edits of specific codons can be examined for loss-of-function or gain-of-function based on specific polymorphisms in one or more codons of the gene. These libraries can be a powerful tool for determining which genetic changes are silent or causal of a specific phenotype in a cell or cell population. The edits of the codons may be randomly generated or may be rationally designed based on known polymorphisms and/or mutations that have been identified in the gene to be analyzed. Moreover, using these techniques on two or more genes in a single in a pathway in a cell may determine potential protein:protein interactions or redundancies in cell functions or pathways.

For example, alanine scanning can be used to determine the contribution of a specific residue to the stability or function of given protein. See, e.g., Lefèvre, et al., Nucleic Acids Research, Volume 25(2):447-448 (1997). Alanine is often used in this codon scanning technique because of its non-bulky, chemically inert, methyl functional group that can mimic the secondary structure preferences that many of the other amino acids possess. Codon scanning can also be used to determine whether the side chain of a specific residue plays a significant role in cell function and/or activity. Sometimes other amino acids such as valine or leucine can be used in the creation of codon scanning cell libraries if conservation of the size of mutated residues is needed.

In other specific aspects, cell libraries can be created using the automated editing methods, automated multi-module cell editing instruments of the invention to determine the active site of a protein such as an enzyme or hormone, and to elucidate the mechanism of action of one or more of these proteins in a cell library. Site-directed mutagenesis associated with molecular modeling studies can be used to discover the active site structure of an enzyme and consequently its mechanism of action. Analysis of these cell libraries can provide an understanding of the role exerted by specific amino acid residues at the active sites of proteins, in the contacts between subunits of protein complexes, on intracellular trafficking and protein stability/half-life in various genetic backgrounds.

Saturation Mutagenesis

In some aspects, the cell libraries created using the automated editing methods and automated multi-module cell editing instruments of the disclosure may be saturation mutagenesis libraries, in which a single codon or set of codons is randomized to produce all possible amino acids at the position of a particular gene or genes of interest. These cell libraries can be particularly useful to generate variants, e.g., for directed evolution. See, e.g., Chica, et al., Current Opinion in Biotechnology 16 (4): 378-384 (2005); and Shivange, Current Opinion in Chemical Biology, 13 (1): 19-25 (2009).

In some aspects, edits comprising different degenerate codons can be used to encode sets of amino acids in the individual cells in the libraries. Because some amino acids are encoded by more codons than others, the exact ratio of amino acids cannot be equal. In certain aspects, more restricted degenerate codons are used. 'NNK' and 'NNS' have the benefit of encoding all 20 amino acids, but still encode a stop codon 3% of the time. Alternative codons such as 'NDT', 'DBK' avoid stop codons entirely, and encode a minimal set of amino acids that still encompass all the main biophysical types (anionic, cationic, aliphatic hydrophobic, aromatic hydrophobic, hydrophilic, small).

In specific aspects, the non-redundant saturation mutagenesis, in which the most commonly used codon for a particular organism is used in the saturation mutagenesis editing process.

Promoter Swaps and Ladders

One mechanism for analyzing and/or optimizing expression of one or more genes of interest is through the creation of a "promoter swap" cell library, in which the cells comprise genetic edits that have specific promoters linked to one or more genes of interest. Accordingly, the cell libraries created using the methods, automated multi-module cell editing instruments of the disclosure may be promoter swap cell libraries, which can be used, e.g., to increase or decrease expression of a gene of interest to optimize a metabolic or genetic pathway. In some aspects, the promoter swap cell library can be used to identify an increase or reduction in the expression of a gene that affects cell vitality or viability, e.g., a gene encoding a protein that impacts on the growth rate or overall health of the cells. In some aspects, the promoter swap cell library can be used to create cells having dependencies and logic between the promoters to create synthetic gene networks. In some aspects, the promoter swaps can be used to control cell to cell communication between cells of both homogeneous and heterogeneous (complex tissues) populations in nature.

The cell libraries can utilize any given number of promoters that have been grouped together based upon exhibition of a range of expression strengths and any given number of target genes. The ladder of promoter sequences vary expression of at least one locus under at least one condition. This ladder is then systematically applied to a group of genes in the organism using the automated editing methods, automated multi-module cell editing instruments of the disclosure.

In specific aspects, the cell library formed using the automated editing processes, modules and systems of the disclosure include individual cells that are representative of a given promoter operably linked to one or more target genes of interest in an otherwise identical genetic background.

Examples of non-automated editing strategies that can be modified to utilize the automated systems can be found, e.g., in U.S. Pat. No. 9,988,624.

In specific aspects, the promoter swap cell library is produced by editing a set of target genes to be operably linked to a pre-selected set of promoters that act as a "promoter ladder" for expression of the genes of interest. For example, the cells are edited so that one or more individual genes of interest are edited to be operably linked with the different promoters in the promoter ladder. When an endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context.

The promoters are generally selected to result in variable expression across different loci, and may include inducible promoters, constitutive promoters, or both.

The set of target genes edited using the promoter ladder can include all or most open reading frames (ORFs) in a genome, or a selected subset of the genome, e.g., the ORFs of the kinome or a secretome. In some aspects, the target genes can include coding regions for various isoforms of the genes, and the cell libraries can be designed to expression of one or more specific isoforms, e.g., for transcriptome analysis using various promoters.

The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

Editing of other functional genetic elements, including insulator elements and other genomic organization elements, can also be used to systematically vary the expression level of a set of target genes, and can be introduced using the methods, automated multi-module cell editing instruments of the disclosure. In one aspect, a population of cells is edited using a ladder of enhancer sequences, either alone or in combination with selected promoters or a promoter ladder, to create a cell library having various edits in these enhancer elements. In another aspect, a population of cells is edited using a ladder of ribosome binding sequences, either alone or in combination with selected promoters or a promoter ladder, to create a cell library having various edits in these ribosome binding sequences.

In another aspect, a population of cells is edited to allow the attachment of various mRNA and/or protein stabilizing or destabilizing sequences to the 5' or 3' end, or at any other location, of a transcript or protein.

In certain aspects, a population of cells of a previously established cell line may be edited using the automated editing methods, modules, instruments, and systems of the disclosure to create a cell library to improve the function, health and/or viability of the cells. For example, many industrial strains currently used for large scale manufacturing have been developed using random mutagenesis processes iteratively over a period of many years, sometimes decades. Unwanted neutral and detrimental mutations were introduced into strains along with beneficial changes, and over time this resulted in strains with deficiencies in overall robustness and key traits such as growth rates. In another example, mammalian cell lines continue to mutate through the passage of the cells over periods of time, and likewise these cell lines can become unstable and acquire traits that are undesirable. The automated editing methods, automated multi-module cell editing instruments of the disclosure can use editing strategies such as SNP and/or STR swapping, indel creation, or other techniques to remove or change the undesirable genome sequences and/or introducing new genome sequences to address the deficiencies while retaining the desirable properties of the cells.

When recursive editing is used, the editing in the individual cells in the edited cell library can incorporate the inclusion of "landing pads" in an ectopic site in the genome (e.g., a CarT locus) to optimize expression, stability and/or control.

In some embodiments, each library produced having individual cells comprising one or more edits (either introducing or removing) is cultured and analyzed under one or more criteria (e.g., production of a chemical or product of interest). The cells possessing the specific criteria are then associated, or correlated, with one or more particular edits in the cell. In this manner, the effect of a given edit on any number of genetic or phenotypic traits of interest can be determined. The identification of multiple edits associated with particular criteria or enhanced functionality/robustness may lead to cells with highly desirable characteristics.

Knock-Out or Knock-In Libraries

In certain aspects, the present disclosure provides automated editing methods, modules, instruments and systems for creating a library of cells having "knock-out" (KO) or "knock-in" (KI) edits of various genes of interest. Thus, the disclosure is intended to cover edited cell libraries created by the automated editing methods, automated multi-module cell editing instruments of the disclosure that have one or more mutations that remove or reduce the expression of selected genes of interest to interrogate the effect of these edits on gene function in individual cells within the cell library.

The cell libraries can be created using targeted gene KO (e.g., via insertion/deletion) or KOs (e.g., via homologous directed repair). For example, double strand breaks are often repaired via the non-homologous end joining DNA repair pathway. The repair is known to be error prone, and thus insertions and deletions may be introduced that can disrupt gene function. Preferably the edits are rationally designed to specifically affect the genes of interest, and individual cells can be created having a KI or KI of one or more locus of interest. Cells having a KO or KI of two or more loci of interest can be created using automated recursive editing of the disclosure.

In specific aspects, the KO or KI cell libraries are created using simultaneous multiplexed editing of cells within a cell population, and multiple cells within a cell population are edited in a single round of editing, i.e., multiple changes within the cells of the cell library are in a single automated operation. In other specific aspects, the cell libraries are created using recursive editing of individual cells within a cell population, and results in the amalgamation of multiple edits of two or more sites in the genome into single cells.

SNP or Short Tandem Repeat Swaps

In one aspect, cell libraries are created using the automated editing methods, automated multi-module cell editing instruments of the disclosure by systematic introducing or substituting single nucleotide polymorphisms ("SNPs") into the genomes of the individual cells to create a "SNP swap"

cell library. In some embodiments, the SNP swapping methods of the present disclosure include both the addition of beneficial SNPs, and removing detrimental and/or neutral SNPs. The SNP swaps may target coding sequences, non-coding sequences, or both.

In another aspect, a cell library is created using the automated editing methods, modules, instruments, instruments, and systems of the disclosure by systematic introducing or substituting short tandem repeats ("STR") into the genomes of the individual cells to create an "STR swap" cell library. In some embodiments, the STR swapping methods of the present disclosure include both the addition of beneficial STRs, and removing detrimental and/or neutral STRs. The STR swaps may target coding sequences, non-coding sequences, or both.

In some embodiments, the SNP and/or STR swapping used to create the cell library is multiplexed, and multiple cells within a cell population are edited in a single round of editing, i.e., multiple changes within the cells of the cell library are in a single automated operation. In other embodiments, the SNP and/or STR swapping used to create the cell library is recursive, and results in the amalgamation of multiple beneficial sequences and/or the removal of detrimental sequences into single cells. Multiple changes can be either a specific set of defined changes or a partly randomized, combinatorial library of mutations. Removal of detrimental mutations and consolidation of beneficial mutations can provide immediate improvements in various cellular processes. Removal of genetic burden or consolidation of beneficial changes into a strain with no genetic burden also provides a new, robust starting point for additional random mutagenesis that may enable further improvements.

SNP swapping overcomes fundamental limitations of random mutagenesis approaches as it is not a random approach, but rather the systematic introduction or removal of individual mutations across cells.

Splice Site Editing

RNA splicing is the process during which introns are excised and exons are spliced together to create the mRNA that is translated into a protein. The precise recognition of splicing signals by cellular machinery is critical to this process. Accordingly, in some aspects, a population of cells is edited using a systematic editing to known and/or predicted splice donor and/or acceptor sites in various loci to create a library of splice site variants of various genes. Such editing can help to elucidate the biological relevance of various isoforms of genes in a cellular context. Sequences for rational design of splicing sites of various coding regions, including actual or predicted mutations associated with various mammalian disorders, can be predicted using analysis techniques such as those found in Nalla and Rogan, Hum Mutat, 25:334-342 (2005); Divina, et al., Eur J Hum Genet, 17:759-765 (2009); Desmet, et el., Nucleic Acids Res, 37:e67 (2009); Faber, et al., BMC Bioinformatics, 12(suppl 4):S2 (2011).

Start/Stop Codon Exchanges and Incorporation of Nucleic Acid Analogs

In some aspects, the present disclosure provides for the creation of cell libraries using the automated editing methods, modules, instruments and systems of the disclosure, where the libraries are created by swapping start and stop codon variants throughout the genome of an organism or for a selected subset of coding regions in the genome, e.g., the kinome or secretome. In the cell library, individual cells will have one or more start or stop codons replacing the native start or stop codon for one or more gene of interest.

For example, typical start codons used by eukaryotes are ATG (AUG) and prokaryotes use ATG (AUG) the most, followed by GTG (GUG) and TTG (UUG). The cell library may include individual cells having substitutions for the native start codons for one or more genes of interest.

In some aspects, the present disclosure provides for automated creation of a cell library by replacing ATG start codons with TTG in front of selected genes of interest. In other aspects, the present disclosure provides for automated creation of a cell library by replacing ATG start codons with GTG. In other aspects, the present disclosure provides for automated creation of a cell library by replacing GTG start codons with ATG. In other aspects, the present disclosure provides for automated creation of a cell library by replacing GTG start codons with TTG. In other aspects, the present disclosure provides for automated creation of a cell library by replacing TTG start codons with ATG. In other aspects, the present disclosure provides for automated creation of a cell library by replacing TTG start codons with GTG.

In other examples, typical stop codons for S. cerevisiae and mammals are TAA (UAA) and TGA (UGA), respectively. The typical stop codon for monocotyledonous plants is TGA (UGA), whereas insects and E. coli commonly use TAA (UAA) as the stop codon (Dalphin. et al., Nucl. Acids Res., 24: 216-218 (1996)). The cell library may include individual cells having substitutions for the native stop codons for one or more genes of interest.

In some aspects, the present disclosure provides for automated creation of a cell library by replacing TAA stop codons with TAG. In other aspects, the present disclosure provides for automated creation of a cell library by replacing TAA stop codons with TGA. In other aspects, the present disclosure provides for automated creation of a cell library by replacing TGA stop codons with TAA. In other aspects, the present disclosure provides for automated creation of a cell library by replacing TGA stop codons with TAG. In other aspects, the present disclosure provides for automated creation of a cell library by replacing TAG stop codons with TAA. In other aspects, the present invention teaches automated creation of a cell library by replacing TAG stop codons with TGA.

Terminator Swaps and Ladders

One mechanism for identifying optimum termination of a pre-spliced mRNA of one or more genes of interest is through the creation of a "terminator swap" cell library, in which the cells comprise genetic edits that have specific terminator sequences linked to one or more genes of interest. Accordingly, the cell libraries created using the methods, modules, instruments and systems of the disclosure may be terminator swap cell libraries, which can be used, e.g., to affect mRNA stability by releasing transcripts from sites of synthesis. In other embodiments, the terminator swap cell library can be used to identify an increase or reduction in the efficiency of transcriptional termination and thus accumulation of unspliced pre-mRNA (e.g., West and Proudfoot, Mol Cell.; 33(3-9); 354-364 (2009)) and/or 3' end processing (e.g., West, et al., Mol Cell. 29(5):600-10 (2008)). In the case where a gene is linked to multiple termination sites, the edits may edit a combination of edits to multiple terminators that are associated with a gene. Additional amino acids may also be added to the ends of proteins to determine the effect on the protein length on terminators.

The cell libraries can utilize any given number of edits of terminators that have been selected for the terminator ladder based upon exhibition of a range of activity and any given number of target genes. The ladder of terminator sequences vary expression of at least one locus under at least one condition. This ladder is then systematically applied to a group of genes in the organism using the automated editing methods, modules, instruments and systems of the disclosure.

In some aspects, the present disclosure provides for the creation of cell libraries using the automated editing methods, modules, instruments and systems of disclosure, where the libraries are created to edit terminator signals in one or more regions in the genome in the individual cells of the library. Transcriptional termination in eukaryotes operates through terminator signals that are recognized by protein factors associated with the RNA polymerase II. For example, the cell library may contain individual eukaryotic cells with edits in genes encoding polyadenylation specificity factor (CPSF) and cleavage stimulation factor (CstF) and or gene encoding proteins recruited by CPSF and CstF factors to termination sites. In prokaryotes, two principal mechanisms, termed Rho-independent and Rho-dependent termination, mediate transcriptional termination. For example, the cell library may contain individual prokaryotic cells with edits in genes encoding proteins that affect the binding, efficiency and/or activity of these termination pathways.

In certain aspects, the present disclosure provides methods of selecting termination sequences ("terminators") with optimal properties. For example, in some embodiments, the present disclosure teaches provides methods for introducing and/or editing one or more terminators and/or generating variants of one or more terminators within a host cell, which exhibit a range of activity. A particular combination of terminators can be grouped together as a terminator ladder, and cell libraries of the disclosure include individual cells that are representative of terminators operably linked to one or more target genes of interest in an otherwise identical genetic background. Examples of non-automated editing strategies that can be modified to utilize the automated instruments can be found, e.g., in U.S. Pat. No. 9,988,624 to Serber et al., entitled "Microbial strain improvement by a HTP genomic engineering platform."

In specific aspects, the terminator swap cell library is produced by editing a set of target genes to be operably linked to a pre-selected set of terminators that act as a "terminator ladder" for expression of the genes of interest. For example, the cells are edited so that the endogenous promoter is operably linked to the individual genes of interest are edited with the different promoters in the promoter ladder. When the endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context. The terminator ladder in question is then associated with a given gene of interest.

The terminator ladder can be used to more generally affect termination of all or most ORFs in a genome, or a selected subset of the genome, e.g., the ORFs of a kinome or a secretome. The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

EXAMPLES

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Other equivalent methods, steps and compositions are intended to be included in the scope of the invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1: Assessing the Fitness of a Model Inducible System

Figure 11A:
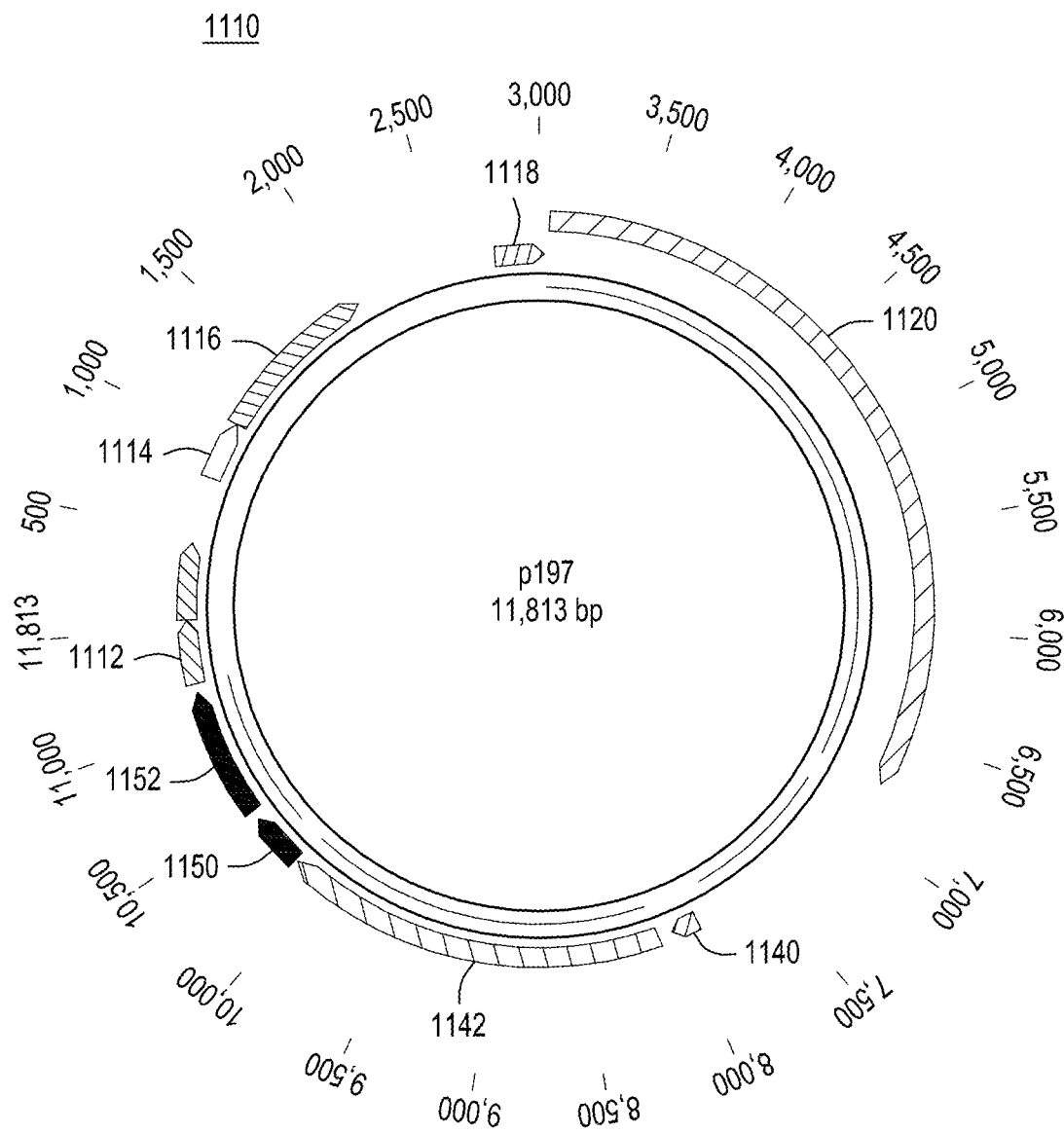
FIG. 11A is a map of an exemplary engine vector that may be used in the methods described herein.
Figure 11B:
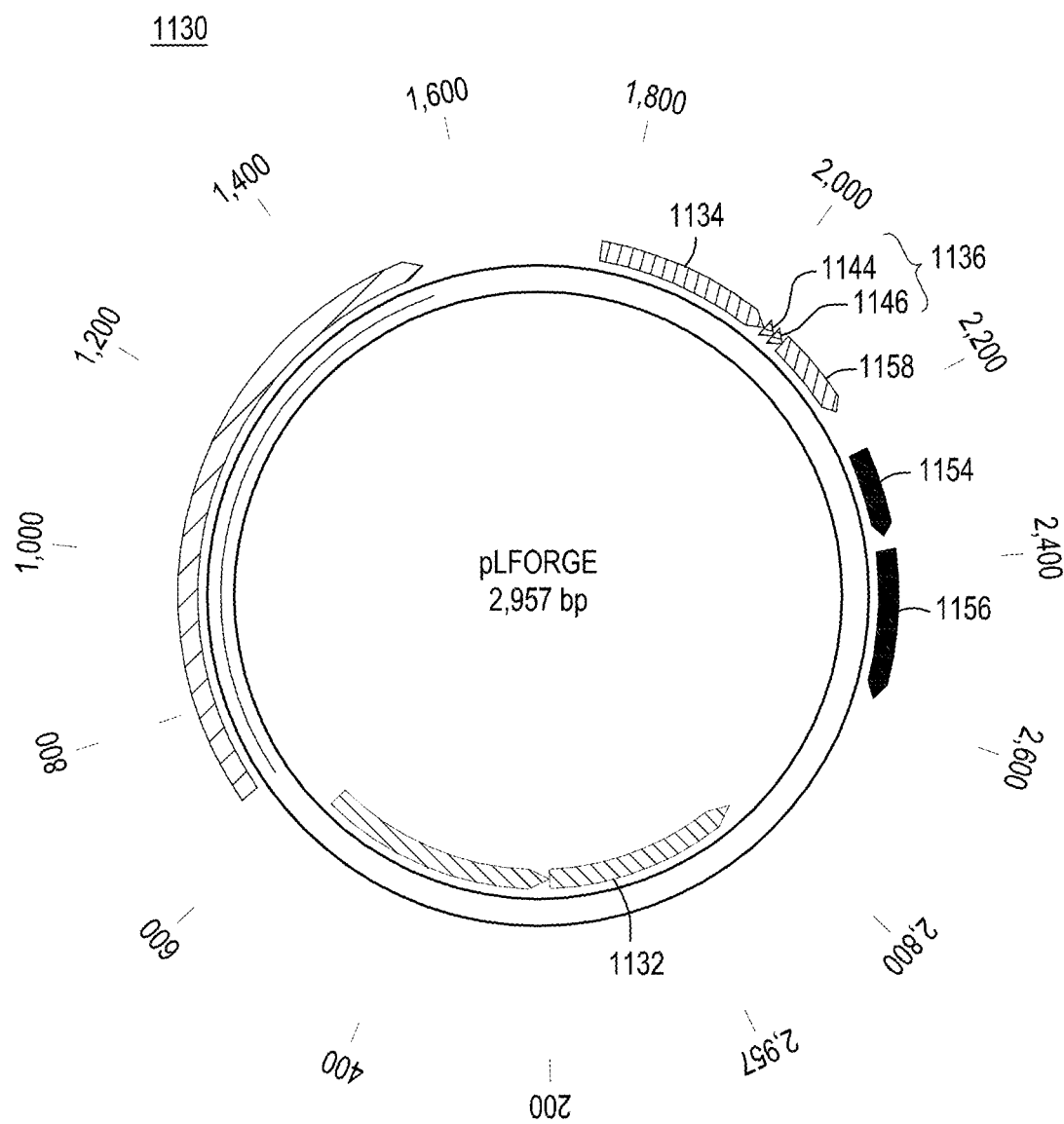
FIG. 11B is a map of an exemplary editing vector (with an editing cassette) that may be used in the methods described herein.

Basic components of a model system were assessed. The model system comprised E. coli cells transformed with an engine vector, where the engine vector comprised a coding sequence for a MAD nuclease (i.e., MAD 4 or MAD 7 nuclease) under the control of the pL temperature inducible promoter, a chloramphenicol resistance marker, and the λ Red recombineering system under the control of the pBAD promoter (induced by addition of arabinose to the growth medium). The E. coli cells were also transformed with an editing vector comprising an editing oligonucleotide, which in this model system was a library of editing oligonucleotides each configured to inactivate galK, where successful editing results in white (versus red) colonies when plated on MacConkey agar supplemented with galactose as the sole carbon source. In addition, the editing vector comprised a gRNA coding sequence under the control of the pL temperature inducible promoter, a carbenicillin resistance marker, and a sequence to remove, mutate, or otherwise render inactive the PAM region in the target sequence. FIGS. 11A and 11B depict an exemplary engine vector (FIG. 11A) and editing vector (FIG. 11B) that may be employed in the exemplary editing workflows described herein. In FIG. 11A, the exemplary engine vector 1110 (p197) comprises an origin of replication 1112, and a promoter 1114 driving expression of the gene coding for the c1857 repressor 1116 which regulates the pL promoter. A first pL promoter in this exemplary embodiment drives the transcription of the gRNA on the editing vector as described in relation to FIG. 11B below, and a second pL promoter 1118 on the engine vector drives expression of the nuclease 1120. The promoter driving nuclease 1120 may be an inducible or a constitutive promoter; however, the tightest regulation of the nucleic acid-guided nuclease system is achieved by using an inducible promoter to drive expression of the nuclease as well as the guide nucleic acid. Again, like inducible promoters and different inducible promoters may be used to drive the transcription of the guide nucleic acid and the nuclease. The pL promoter can be regulated (e.g., repressed or induced) by the thermolabile c1857 repressor 1116 which is active at permissive temperatures (e.g., 30° C.) and inactive at higher temperatures (e.g., 42° C.). The regulation of the pL promoter is shown in more detail in relation to FIG. 1C above.

The engine vector in FIG. 11A further comprises a pBAD promoter 1140 driving expression of the components of the λ Red recombineering system 1142. The pBAD promoter, like the pL promoter, is an inducible promoter, where the pBAD promoter is regulated (induced) by the addition of arabinose to the growth medium. Note that in this exemplary bacterial editing system, a recombineering system such as the λ Red recombineering system is provided as a component of the nucleic acid-guided nuclease editing system to repair the DNA breaks that occur during editing. In some embodiments, however, the cells to be edited may already comprise a recombineering system (e.g., episomally, integrated into the cellular genome, or naturally). Also, although the λ Red recombineering system is exemplified here, it should be understood that other recombineering systems may be employed. Further, cells—such as yeast, plant and animal cells—do not require a recombineering system equivalent to the λ Red recombineering system to repair the DNA breaks that result from editing. Thus the nucleic acid-guided nuclease editing components for, e.g., yeast, plant and animal cells do not need to include a heterologous recombineering system. Finally, exemplary engine vector 1110 comprises a promoter 1150 driving expression of a chloramphenicol selectable marker 1152. Additionally, the engine vector and all other vectors or constructs used in the disclosed method comprise appropriate control elements (e.g., polyadenylation signals, enhancers) operably-linked to the nucleic acid-guided nuclease editing system components.

FIG. 11B depicts an exemplary editing vector 1130 (pL-FORGE). Editing vector 1130 comprises an origin of replication 1132, and a pL promoter 1134 driving expression of an editing cassette 1136. The editing cassette comprises a coding sequence for a gRNA 1144, a spacer 1146, and a donor DNA 1158 (comprising homology arms flanking a desired edit to be made to the target sequence). Editing vector 1130 also comprises a promoter 1154 driving expression of a carbenicillin selectable marker 1156. Note that the pL inducible promoter 1134 is encoded on the vector backbone and is not part of the editing cassette 1136; however, in other embodiments the inducible promoter driving transcription of the gRNA may be part of the editing cassette. FIGS. 11A and 11B depict exemplary engine and editing vectors, respectively, but it should be recognized by one of ordinary skill in the art given the guidance of the present description that all elements of the nucleic acid-guided nuclease editing system may be contained on a single plasmid, or the elements shown on the engine and editing vectors of FIGS. 11A and 11B may reside on a different vector than shown. For example, the pBAD promoter and λ Red recombineering system may be contained on the editing vector rather than the engine vector; likewise, the gene for the c1857 repressor may be contained on the editing vector rather than the engine vector.

Figure 12:
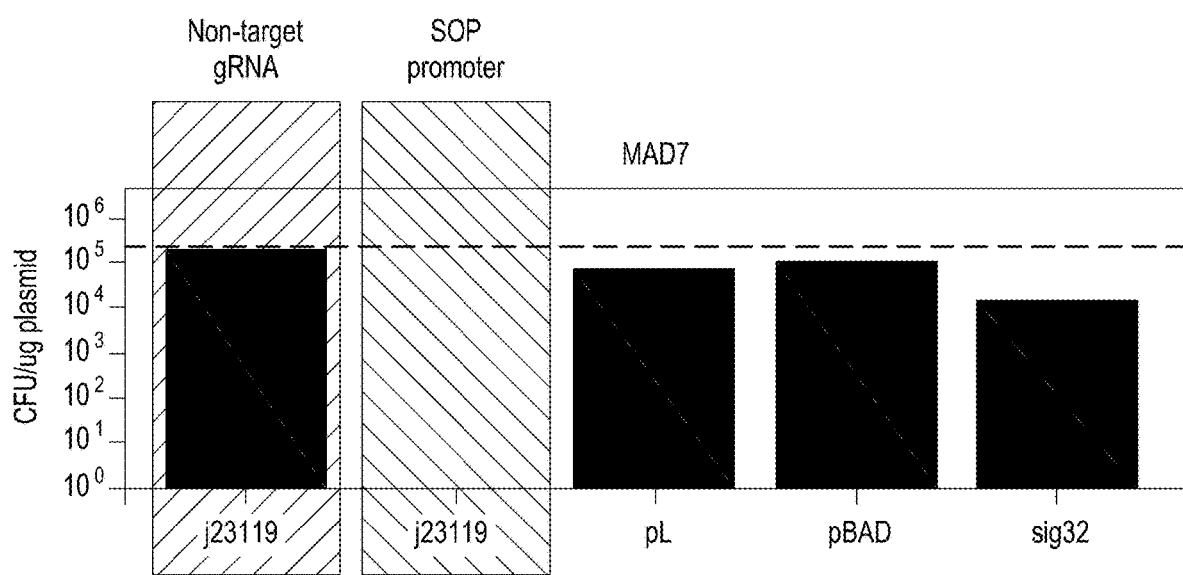
FIG. 12 is a bar graph showing the transformation efficiencies observed for galK gRNA targeting cassettes under a variety of promoters.

FIG. 12 is a bar graph showing the transformation efficiencies observed for galK gRNA targeting cassettes under a variety of promoters. Transformation efficiency of uninduced promoters provides a proxy for promoter leakiness. If there is high basal expression of gRNA (e.g., "leakiness"), there will be low CFU. If there is a low basal expression of gRNA (e.g., tight regulation), there will be high CFU. The non-target gRNAs experiment was performed with a pool of cassettes designed to target inactive PAM sequences that are unable to promote gRNA and nuclease binding and cleavage. For each of the promoters depicted (pL, pBAD, and sigma32) a cassette targeting galK with a TTTC PAM and a spacer configured to make a stop codon insertion at amino acid D70 was cloned downstream of the promoter. Plasmid concentrations were normalized to 50 ng/pL and transformed in equal cell volumes. CFU from serial dilution platings were used to derive the transformation efficiencies expressed as CFU/n. The J23119 promoter is a constitutive promoter, the pL promoter is inducible by high temperature, the pBAD promoter is induced by the presence of arabinose in the growth medium, and the sigma32 promoter is induced in stationary phase cells. For the MAD7 nuclease, the sigma32 promoter shows leaky expression, while both the pL and pBAD promoters are tightly repressed.

Figure 13:
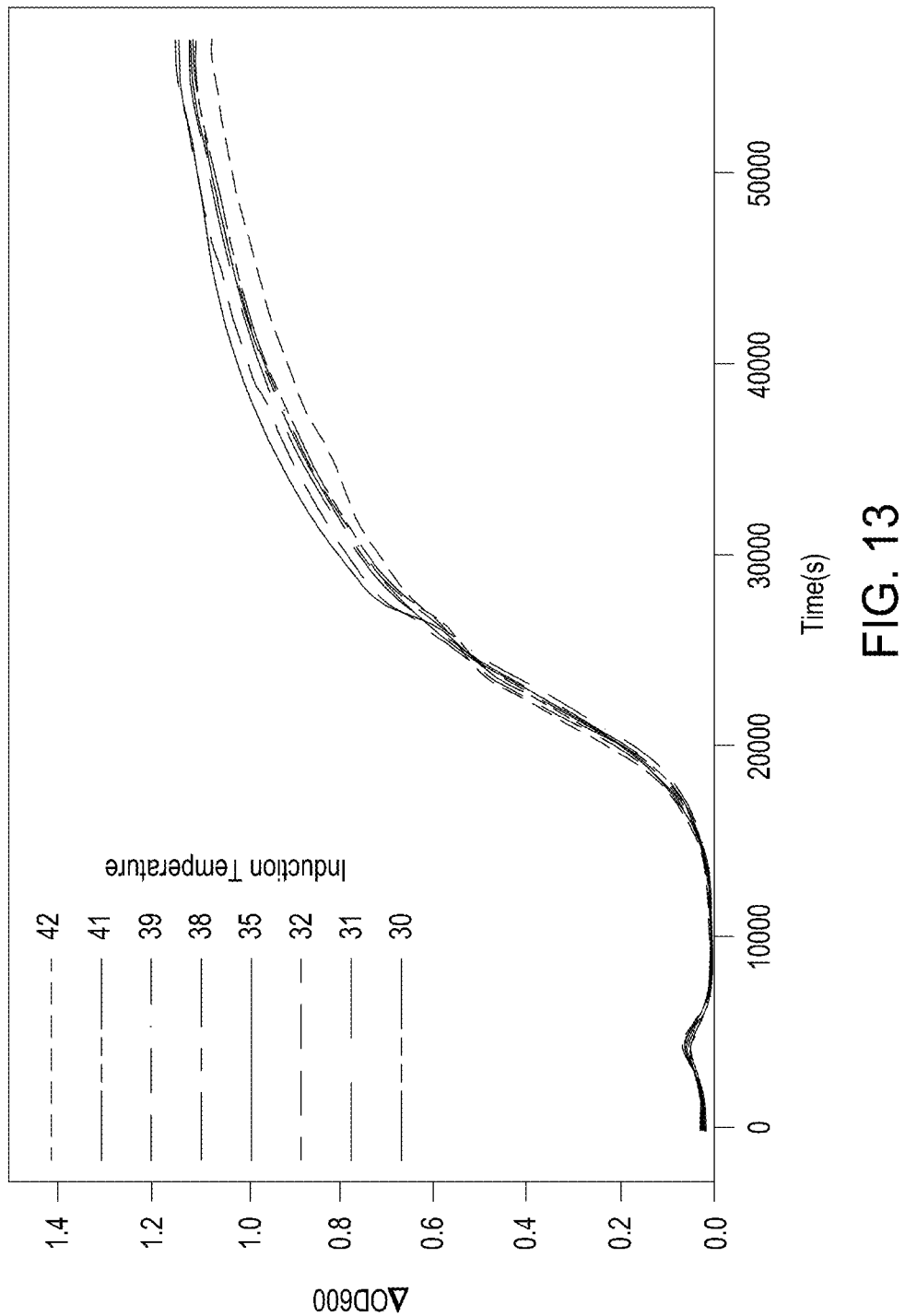
FIG. 13 is a plot of cell growth vs. time, demonstrating that thermal induction of editing does not impact cell growth or viability.

FIG. 13 is a graph showing the effects of thermal induction on cell viability. In this experiment, a pool of cassettes were designed to target an inactive PAM sequence. Cells were diluted 1/50 v:v into microtiter plates containing 200 µL LB+chlor/carb. Diluted cultures were induced for 1 hour at the indicated temperatures before shifting back to 30° C. with continuous shaking in an Infinite M Nano+ plate reader. To corresponds to the time of the induction step and growth was monitored by measuring the OD600 at 10 minute intervals. Note that high temperature (42° C.) induction has no impact on cell viability or growth rate.

Figure 14:
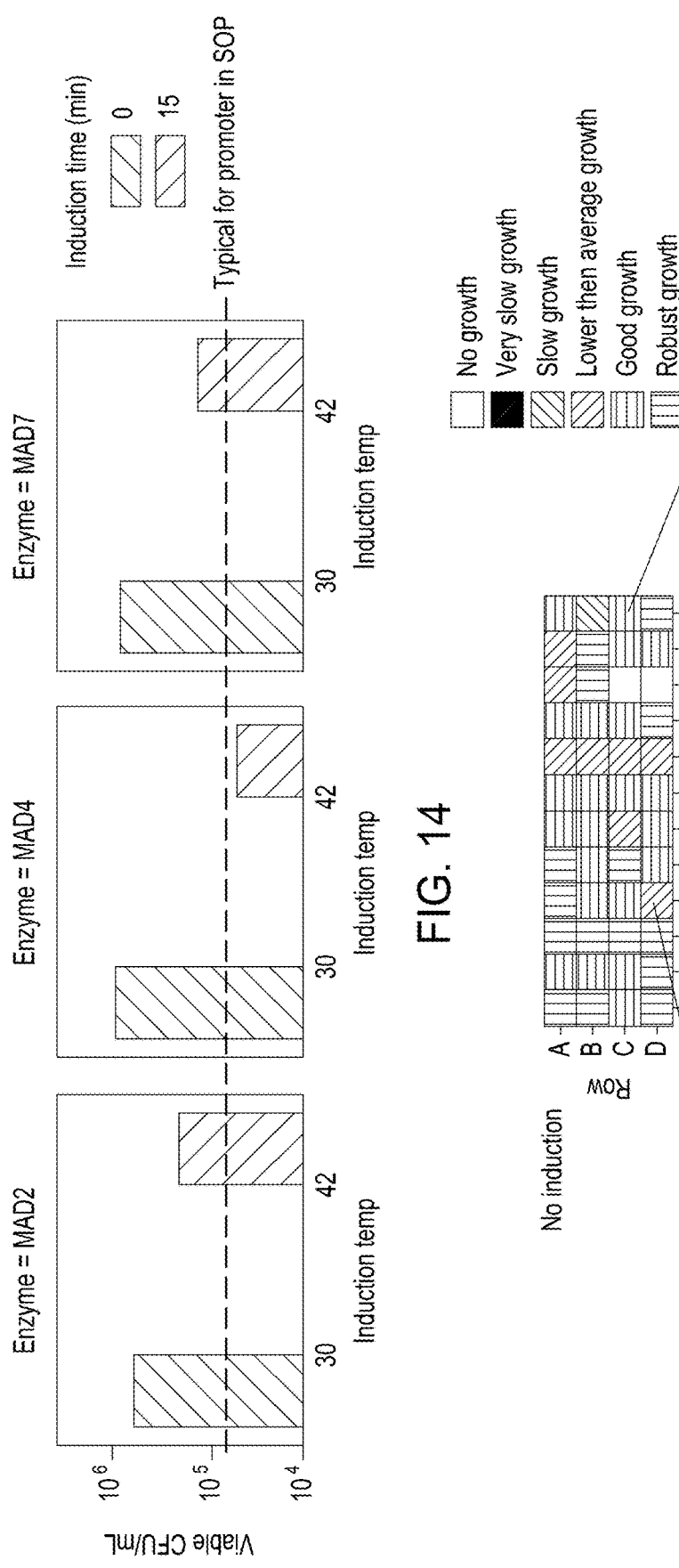
FIG. 14 depicts results demonstrating repressed gRNA cassettes yield high cell viability/transformation efficiency for three exemplary nucleases.

FIG. 14 shows the results of pooled induction experiments using a single sequence verified editing cassette that targets the galK locus and introduces a stop codon at amino acid D70. Following a three-hour outgrowth, cells were either induced at 42° C. for 15 minutes or retained at 30° C. prior to serial dilution plating. CFU/mL was calculated based on the plating volumes. For reference the dashed line in FIG. 14 shows the typical CFU obtained in an equivalent experiment using the constitutive J23119 promoter (data not shown). As can be seen, the absence of induction (i.e., the absence of editing) enables high efficiency transformation (10-100 fold) due to the lack of toxic dsDNA breaks.

Figure 15:
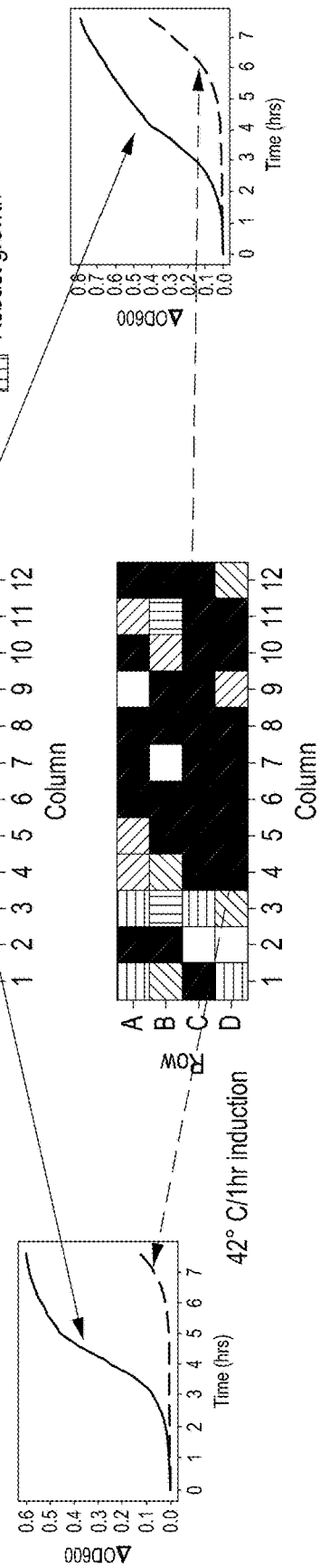
FIG. 15 illustrates heat maps and growth curves showing the OD at 6 hours for uninduced and induced cell populations.

FIG. 15 shows the growth profiles of randomly picked variants from a silent PAM mutation (SPM) library. This 500-member library targets regions located across the entire *E. coli* organism and integrates synonymous mutations that have no expected fitness effects. Colonies were picked from agar plates of uninduced transformed cells. Cells were picked from an agar plate and grown up in 200 µL LB+chlor/carb overnight in a 96-well microtiter plate format. 10 µL of the well content of the parent microtiter plate was then transferred to two replica daughter microtiter plates that received either no induction (top) or gRNA and nuclease induction (via the pL inducible promoter) for 1 hour at 42° C. (bottom). The well maps show the relative OD at 6 hours. The inserts show examples of the full growth curves for the indicated wells as a reference. The replica wells represent growth observed from the same cassette design with or without gRNA induction. While the majority of the wells for the no-induction plate show normal growth profiles, the induced plate shows that a large fraction of the gRNA designs are still active when induced, indicated by a large lag phase before the cells reach exponential growth. That is, the actively-editing cells have reduced viability due to DNA damage such that many in the colonies die off, and those edited cells that do survive grow slowly to begin with as the cellular machinery works to repair the edit. This characteristic of edited cells can be exploited to screen for active editing in a high-throughput manner.

Example 2: Editing Cassette and Backbone Amplification and Assembly

Editing Cassette Preparation:

5 nM oligonucleotides synthesized on a chip were amplified using Q5 polymerase in 50 μL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 30 μL SPRI mix was added to the 50 μL PCR reactions and incubated for 2 minutes. The tubes were subjected to a magnetic field for 2 minutes, the liquid was removed, and the beads were washed 2× with 80% ethanol, allowing 1 minute between washes. After the final wash, the beads were allowed to dry for 2 minutes, 50 μL 0.5×TE pH 8.0 was added to the tubes, and the beads were vortexed to mix. The slurry was incubated at room temperature for 2 minutes, then subjected to the magnetic field for 2 minutes. The eluate was removed and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation:

A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 μL ddH$_2$O and quantified before Gibson Assembly®.

Gibson Assembly:

150 ng backbone DNA was combined with 100 ng cassette DNA. An equal volume of 2× Gibson Master Mix was added, and the reaction was incubated for 45 minutes at 50° C. After assembly, the assembled backbone and cassettes were subjected to SPRI cleanup, as described above.

Example 3: Transformation of Editing Vector Library into E Cloni®

Transformation:

20 μL of the prepared editing vector Gibson Assembly reaction was added to 30 μL chilled water along with 10 μL E Cloni® (Lucigen, Middleton, Wis.) supreme competent cells. An aliquot of the transformed cells were spot plated to check the transformation efficiency, where >100× coverage was required to continue. The transformed E Cloni® cells were outgrown in 25 mL SOB+100 μg/mL carbenicillin (carb). Glycerol stocks were generated from the saturated culture by adding 500 μL 50% glycerol to 1000 μL saturated overnight culture. The stocks were frozen at −80° C. This step is optional, providing a ready stock of the cloned editing library. Alternatively, Gibson or another assembly of the editing cassettes and the vector backbone can be performed before each editing experiment.

Example 4: Preparation of Competent Cells

A 1 mL aliquot of a freshly-grown overnight culture of EC1 cells transformed with the engine vector was added to a 250 mL flask containing 100 mL LB/SOB+25 μg/mL chlor medium. The cells were grown to 0.4-0.7 OD, and cell growth was halted by transferring the culture to ice for 10 minutes. The cells were pelleted at 8000×g in a JA-18 rotor for 5 minutes, washed 3× with 50 mL ice cold ddH$_2$0 or 10% glycerol, and pelleted at 8000×g in JA-18 rotor for 5 minutes. The washed cells were resuspended in 5 mL ice cold 10% glycerol and aliquoted into 200 μL portions. Optionally at this point the glycerol stocks could be stored at −80° C. for later use.

Example 5: Creation of New Cell Line Transformed With Engine Vector

Transformation:

1 μL of the engine vector DNA (comprising a coding sequence for MAD7 nuclease under the control of the pL inducible promoter, a chloramphenicol resistance gene, and the λ Red recombineering system) was added to 50 μL EC1 strain E. coli cells. The transformed cells were plated on LB plates with 25 μg/mL chloramphenicol (chlor) and incubated overnight to accumulate clonal (or substantially clonal) isolates. The next day, a colony was picked, grown overnight in LB+25 μg/mL chlor, and glycerol stocks were prepared from the saturated overnight culture by adding 500 μL 50% glycerol to 1000 μL culture. The stocks of EC1 comprising the engine vector were frozen at −80° C.

Example 6: High Throughput Clonal Editing

The following protocols address cell growth/survival bias due to dsDNA breaks:

Transformation:

100 ng of the editing vector cloned library or editing vector Gibson Assembly® reaction was transformed by electroporation into 100 μL competent EC1 cells containing the engine vector. The electroporator was set to 2400 V in 2 mm cuvette. Following transformation, the cells were allowed to recover for 3 hours in SOB medium. A 10-fold dilution series of recovered cells (in H$_2$0) was spot plated and the resulting CFU counts/dilution ratios were used to calculate transformation efficiency.

Plating and Colony Arraying:

100 μL of the appropriate dilution was plated on LB medium+25 μg/mL chlor and grown at 30° C. overnight. Colonies were picked and grown overnight to saturation at 30° C. in 96-well microtiter plates.

Induced Cutting, Editing, and Edit Validation:

A replicator was used to transfer colonies in wells from the overnight growth to 200 μL fresh SOB+1% arabinose in replicate 96-well microtiter plates. The replicator transfers approximately 1-2 μL per well resulting in a 100-fold dilution for outgrowth. The microtiter plates were incubated at 250 rpm shaking for 3-4 hours to allow the cells to reach mid-log phase. The plates were then transferred to a static incubator at 42° C. and incubated for 2 hours, then placed in a 30° C. incubator for 1 hour to recover. At this point, the replicate cells were ready for genomic prep and were validated via sequencing analysis. As described in relation to FIG. 2B, additional replica plates of fresh SOB without arabinose may be used to enable functional deconvolution of inactive cut designs from the population.

Example 7: Rearray and Pooled Editing Using Inducible gRNAs

Transformation:

100 ng of the editing vector cloned library or Gibson Assembly® reaction was transformed by electroporation into 100 μL competent EC1 cells containing the engine vector. The electroporator was set to 2400 V in 2 mm cuvette. Following transformation, the cells were allowed to recover for 3 hours in SOB medium. A 10-fold dilution series of recovered cells (in $H_2O$) was spot plated and the resulting CFU counts/dilution ratios were used to calculate transformation efficiency.

Plating and Colony Arraying:

100 μL of the appropriate dilution was plated on LB medium+25 μg/mL chlor and grown at 30° C. overnight. Colonies were picked and grown overnight to saturation in 1 mL SOB+25 μg/mL chlor/100 μg/mL carb at 30° C. in 96-well microtiter plates.

Identification of Active Cassettes and Rearray:

A replicator was used to transfer colonies in wells from the overnight growth to 200 μL fresh SOB without arabinose in replicate 96-well microtiter plates. The replicator transfers approximately 1-2 μL per well resulting in a 100-fold dilution for outgrowth. The replicate microtiter plates were incubated at 250 rpm shaking for 3-4 hours to allow the cells to reach mid-log growth. The plates were then transferred to a static incubator at 42° C. and incubated for 2 hours, then placed in a 30° C. incubator for 1 hour to recover. The replicator was then used to transfer cells from the replicate microtiter plates to agar plates with LB medium+25 μg/mL chlor/100 μg/mL carb and allowed to grow overnight. Wells with active gRNAs were identified and 50 μL of cells from these colonies from the original 96-well microtiter plate were re-arrayed into "functionally-corrected" plates (e.g., the cells identified as having functional gRNAs were transferred (cherry picked) into a 96-well plate).

Pooled Editing Using Pooled Cassettes Identified as Active:

100 μL of cells identified as having functional gRNAs were transferred into 5 mL SOB medium and grown until the culture was saturated. 1% arabinose was added to the tube and the tube was incubated for 2 hours at 30° C. Cutting/editing was induced by transferring the tube to a 42° C. shaking water bath for 2 hours. The tube was then removed from the water bath and allowed to recover for 2 hours at 30° C. in a 250 rpm shaking incubator. A diluted culture (approximately $10^{-4}$ to $10^{-5}$) was plated on LB medium+25 μg/mL chlor/100 μg/mL carb resulting in isolated clonal colonies. Editing was assessed/validated by targeted or whole genome sequencing.

Example 8: Error Correction: Re-Array and Cloning

Transformation:

100 ng of the editing vector cloned library or Gibson Assembly® reaction was transformed by electroporation into 100 μL competent EC1 cells containing the engine vector. The electroporator was set to 2400 V in 2 mm cuvette. Following transformation, the cells were allowed to recover for 3 hours in SOB medium. A 10-fold dilution series of recovered cells (in $H_2O$) was spot plated and the resulting CFU counts/dilution ratios were used to calculate transformation efficiency.

Plating and Colony Arraying:

100 μL of the appropriate dilution was plated on LB medium+25 μg/mL chlor and grown at 30° C. overnight. Colonies were picked and grown overnight to saturation in 1 mL SOB+25 μg/mL chlor and 100 μg/mL carb at 30° C. in 96-well microtiter plates.

Identification of Active Cassettes and Rearray:

A replicator was used to transfer colonies in wells from the overnight growth to 200 μL fresh SOB without arabinose in replicate 96-well microtiter plates. The replicator transfers approximately 1-2 μL per well resulting in a 100-fold dilution for outgrowth. The replicate microtiter plates were incubated at 250 rpm shaking for 3-4 hours to allow the cells to reach mid-log growth. The plates were then transferred to a static incubator at 42° C. and incubated for 2 hours, then placed in a 30° C. incubator for 1 hour to recover. The replicator was then used to transfer cells from the replicate microtiter plates to plates with LB medium+25 μg/mL chlor/100 μg/mL carb and allowed to grow overnight. Wells with active gRNAs were identified and 50 μL of cells from these colonies from the original 96-well microtiter plate were re-arrayed into "functionally-corrected" plates (e.g., the cells identified as having functional gRNAs were transferred into a 96-well plate).

Library Re-amplification, Cloning, and Validation:

Cells identified as having functional gRNAs were pooled and DNA was extracted and isolated. Serial dilutions were made of the isolated DNA, and amplification was conducted with primers designed to amplify the editing cassettes. PCR was performed under the following conditions: 95° C. for 1 minute; 18 rounds of 95° C. for 30 seconds/60° C. for 30 seconds/72° C. for 2.5 minutes; with a final hold at 72° C. for 5 minutes. Amplicons were checked on a 1% agarose gel and pools with the cleanest output(s) were identified. The amplified cassettes were mini-prepped and eluted into 50 μL dd$H_2O$. Next, a Gibson Assembly® reaction containing 150 ng backbone DNA with 100 ng cassette inserts was performed. An equal volume 2× Master Mix was added to the backbone and insert, and the reaction was incubated for 45 min @ 50° C., then dialyzed for 30 min in sitting droplet with 0.25 μm filter disc. 100 ng of the Gibson Assembly® reaction was transformed by electroporation into competent EC1 cells containing the engine vector as described above. Following transformation, the cells were allowed to recover for 3 hours in SOB medium. A 10-fold dilution series of recovered cells (in $H_2O$) was spot plated and the resulting CFU counts/dilution ratios were used to calculate transformation efficiency. 100 μL of an appropriate dilution of cells were plated on LB medium+25 μg/mL chlor and grown at 30° C. overnight. Editing was assessed/validated by, e.g., sequencing.

Example 9: Enrichment of Editing Cells by Growth Lag Identification

Transformation:

100 ng of the editing vector cloned library or Gibson Assembly® reaction was transformed by electroporation into 100 μL competent EC1 cells containing the engine vector. The electroporator was set to 2400 V in 2 mm cuvette. Following transformation, the cells were allowed to recover for 3 hours in SOB medium. A 10-fold dilution series of recovered cells (in $H_2O$) was spot plated and the resulting CFU counts/dilution ratios were used to calculate transformation efficiency.

Plating and Colony Arraying:

100 µL of the appropriate dilution was plated on LB agar medium+25 µg/mL chlor and +arabinose and grown at 30° C. for 6-8 hours. Alternatively, the cells may be grown in liquid culture in LB medium+25 µg/mL chlor at 30° C. to saturation and diluted to the appropriate concentration before plating on LB agar medium+25 µg/mL chlor+arabinose and grown at 30° C. for 6-8 hours. Following the 6-8 hour growth, the temperature of the plate was adjusted to 42° C. and the plates were incubated for two hours. The temperature was then adjusted back to 30° C. and the cells were allowed to recover overnight.

Edited Cell Identification:

Small-size colonies were identified. The small colony-size phenotype indicates cell viability was compromised during the induced-editing procedure. Efficient recovery of edited cells from the initial pool was accomplished by identifying and picking small colonies and arraying cells from these small colonies onto a 96-well plate to create a library of edited cells, or the cells from the colonies were pooled generating highly-edited cell populations for recursive editing. Editing was assessed/validated by sequencing. It was found that 85% of the small colonies were edited cells.

Example 10: Standard Plating Protocol Control

This protocol describes a standard plating protocol for enriching for nucleic acid-guided nuclease editing of bacterial cells by singulation or substantial singulation, growth, editing, and normalization. This protocol was used to leverage the inducible system for both the nuclease and gRNAs to allow for a phenotypic difference in colonies. From the resulting agar plates, it was possible to select edited cells with a high degree (~80%) of confidence. Though clearly this protocol can be employed for enriching for edited cells, in the experiments described herein this "standard plating protocol," or "SPP," was used to compare efficiencies of singulation or substantial singulation, editing, and normalization with the solid wall device. Materials: Outside of standard molecular biology tools, the following will be necessary:

TABLE 1

| Product | Vendor |
| --- | --- |
| SOB | Teknova |
| LB | Teknova |
| LB agar plate with chloramphenicol/carbenicillin and 1% arabinose | Teknova |

Protocol: Inputs for this protocol are frozen electrocompetent cells and purified nucleic acid assembly product. Immediately after electroporation, the cell/DNA mixture was transferred to a culture tube containing 2.7 mL of SOB medium. Preparing 2.7 mL aliquots in 14 mL culture tubes prior to electroporation allowed for a faster recovery of cells from the electroporation cuvette; the final volume of the recovery was 3 mL. All culture tubes were placed into a shaking incubator set to 250 rpm and 30° C. for three hours. While the cultures were recovering, the necessary number of LB agar plates with chloramphenicol and carbenicillin+1% arabinose were removed from the refrigerator and warmed to room temperature. Multiple dilutions were used for each plating so as to have countable and isolated colonies on the plates. Plating suggestions:

TABLE 2

| Sequencing type | Dilution(s) suggested | Volume to plate |
| --- | --- | --- |
| SinglePlex Amplicon | $10^{-1}$ through $10^{-3}$ None | 300 µL 300 µL (= 1/10$^{th}$ recovery) |

After three hours, the culture tubes were removed from the shaking incubator. First, plating for amplicon sequencing was performed by following the above table. Plating beads were used to evenly distribute the culture over the agar. The beads were removed from the plate and the plate was allowed to dry uncovered in a laminar flow cabinet. While the plates were drying, the remaining culture was used to perform serial dilutions, where the standard dilutions were 50 µL of culture into 450 µL of sterile, 0.8% NaCl. The plate/tubes used for these dilutions (as well as the original culture) were maintained at 4° C. in case additional dilutions were needed to be performed based on colony counts. Plating for SinglePlex was performed according to the Table 2. Additional or fewer dilutions may be used based on library/competent cell knowledge. The cultures were evenly spread across the agar using sterile, plating beads. The beads were then removed from the plate and the plates were allowed to dry uncovered in the laminar flow cabinet. While the plates were drying, an incubator was programmed according to the following settings: 30° C. for 9 hours→42° C. for 2 hours→30° C. for 9 hours. The agar plates were placed in the pre-set incubator, and after the temperature cycling was complete (~21 hours), the agar plates were removed from the incubator. Induction of editing was successful as indicated by the size differences in the resulting cell colonies.

Example 11: Singulation and Culture of *E. coli* in a Solid Wall Device

Electrocompetent *E. coli* cells were transformed with a cloned library, an isothermal assembled library, or a process control sgRNA plasmid (escapee surrogate) as described in Examples 2-5 above. The *E. coli* strain carried the appropriate endonuclease and lambda red components and editing induction system (e.g., on an engine plasmid or integrated into the bacterial genome or a combination). Transformations routinely used 150 ng of plasmid DNA (or Gibson Assembly reactions) with 150 ng of pL sgRNA backbone DNA. Following electroporation, the cells were allowed to recover in 3 mL SOB and incubated at 30° C. with shaking for 3 hours. In parallel with processing samples through the solid wall device, samples were also processed with the solid plating protocol (see Example 10 above), so as to compare "normalization" in the sold wall device with the standard benchtop process. Immediately before cells the cells were introduced to the permeable-bottom solid wall device, the 0.2 µm filter forming the bottom of the microwells was treated with a 0.1% TWEEN (polysorbate or, IUPAC, polyoxyethylene (20) sorbitan monolaurate) solution to effect proper spreading/distribution of the cells into the microwells of the solid wall device. The filters were placed into a Swinnex Filter Holder (47 mm, Millipore®, SX0004700) and 3 mL of a solution with 0.85% NaCl, and 0.1% TWEEN (polysorbate or, IUPAC, polyoxyethylene (20) sorbitan monolaurate) was pulled through the solid wall device and filter through using a vacuum. Different TWEEN (polysorbate or, IUPAC, polyoxyethylene (20) sorbitan monolaurate) concentrations were evaluated, and it was determined that for a 47 mm diameter solid wall device with a 0.2 µM filter forming the bottom of the microwells, a pre-treatment of the solid wall device+filter with 0.1% TWEEN (polysorbate or, IUPAC, polyoxyethylene (20) sorbitan monolaurate) was preferred (data not shown).

After the 3-hour recovery in SOB, the transformed cells were diluted and a 3 mL volume of the diluted cells was processed through the TWEEN (polysorbate or, IUPAC, polyoxyethylene (20) sorbitan monolaurate)-treated solid wall device and filter, again using a vacuum. The number of successfully transformed cells was expected to be approximately 1.0E+06 to 1.0E+08, with the goal of loading approximately 10,000 transformed cells into the current 47 mm permeable-bottom solid wall device (having ~30,000 wells). Serial dilutions of $10^{-1}$, $10^{-2}$, and $10^{-3}$ were prepared, then 100 µL volumes of each of these dilutions were combined with 3 mL 0.85% NaCl, and the samples were loaded onto solid wall devices. Each permeable-bottom solid wall device was then removed from the Swinnex filter holder and transferred to an LB agar plate containing carbenicillin (100 µg/mL), chloramphenicol (25 µg/mL) and arabinose (1% final concentration). The solid wall devices were placed metal side "up," so that the permeable-bottom membrane was touching the surface of the agar such that the nutrients from the plate could travel up through the filter "bottom" of the wells. The solid wall devices on the LB agar plates were incubated for 9 hours at 30° C., at 42° C. for 2 hours, then returned to incubation at 30° C., for 12-16 hour, and, in another experiment for 36-40 hours.

At the end of the incubation the perforated disks and filters (still assembled) were removed from the supporting nutrient source (in this case an agar plate) and were photographed with a focused, "transilluminating" light source so that the number and distribution of loaded microwells on the solid wall device could be assessed (data not shown). To retrieve cells from the permeable-bottom solid wall device, the filter was transferred to a labeled sterile 100 mm petri dish which contained 15 mL of sterile 0.85% NaCl, then the petri dish was placed in a shaking incubator set to 30° C./80 RPM to gently remove the cells from the filter and resuspend the cells in the 0.85% NaCl. The cells were allowed cells to shake for 15 minutes, then were transferred to a sterile tube, e.g., a 50 mL conical centrifuge tube. The OD600 of the cell suspension was measured and at this point, the cells can be processed in different ways depending on the purpose of the study. For example, if the plasmids or libraries are designed to target a sugar metabolism pathway gene such as galK, then the resuspended cells can be spread onto MacConkey agar plates containing galactose (1% final concentration) and the appropriate antibiotics. On this differential medium, colonies that are the result of successfully-edited cells are expected to be phenotypically white in color, whereas unedited colonies are red in color. This red/white phenotype can then be used to assess the percentage of edited cells and the extent of normalization of edited and unedited cells. The results of one experiment are shown below in Table 3. In all replicates, the transformed cells were allowed to grow in the solid wall devices for 9 hours at 30° C., 2 hours at 42° C., and overnight at 30° C.

TABLE 3

| TWEEN (poly sorbate or IUPAC, polyoxytheylene (20) sorbitan monolaurate) | Dilution counted | Red colonies | White colonies | % edit |
|---|---|---|---|---|
| No TWEEN | $10^{-4}$ | 72 | 5 | 6% |
| No TWEEN | $10^{-4}$ | 89 | 3 | 3% |
| No TWEEN | $10^{-3}$ | 64 | 5 | 7% |

TABLE 3-continued

| TWEEN (poly sorbate or IUPAC, polyoxytheylene (20) sorbitan monolaurate) | Dilution counted | Red colonies | White colonies | % edit |
|---|---|---|---|---|
| Pre-treatment TWEEN | $10^{-4}$ | 71 | 5 | 7% |
| Pre-treatment TWEEN | $10^{-3}$ | 443 | 29 | 6% |
| Pre-treatment TWEEN | $10^{-3}$ | 149 | 12 | 7% |
| Pre-treatment TWEEN | $10^{-3}$ | 83 | 21 | 20% |
| Pre-treatment TWEEN | $10^{-2}$ | 318 | 112 | 26% |
| Pre-treatment TWEEN + TWEEN in cell loading buffer | $10^{-3}$ | 163 | 25 | 13% |
| Pre-treatment TWEEN + TWEEN in cell loading buffer | $10^{-4}$ | 132 | 10 | 7% |
| Pre-treatment TWEEN + TWEEN in cell loading buffer | $10^{-4}$ | 31 | 9 | 23% |
| Pre-treatment TWEEN + TWEEN in cell loading buffer | $10^{-3}$ | 147 | 18 | 10.9% |
| Pre-treatment TWEEN + TWEEN in cell loading buffer | $10^{-2}$ | 720 | 150 | 17% |
| Pre-treatment TWEEN + TWEEN in cell loading buffer | $10^{-3}$ | 55 | 15 | 21% |

Figure 16:
FIG. 16 shows the results of cell colony normalization for E. coli cells under various conditions.

FIG. 16 is a graph showing the extent of normalization of cells (% edited cells) for different dilutions of transformed cells, and no treatment with TWEEN (polysorbate or IUPAC, polyoxytheylene (20) sorbitan monolaurate) vs. pre-treatment with TWEEN (polysorbate or, IUPAC, polyoxyethylene (20) sorbitan monolaurate) vs. pre-treatment with TWEEN (polysorbate or, IUPAC, polyoxyethylene (20) sorbitan monolaurate)+TWEEN (polysorbate or, IUPAC, polyoxyethylene (20) sorbitan monolaurate) in the buffer when loading the cells into the microwells of the solid wall device. A standard plating protocol (SPP) was conducted in parallel with the solid wall singulation experiments as a benchmark (first bar on the left in the graph). Note that the percentage of edits for the standard plating protocol was approximately 27.5%, and the percentage of edits for two replicates of the $10^{-3}$ dilution of cells with pre-treatment with TWEEN (polysorbate or, IUPAC, polyoxyethylene (20) sorbitan monolaurate) was approximately 20% and 26%, respectively.

Example 12: Singulation of Yeast Colonies in a Solid Wall Device

Electrocompetent yeast cells were transformed with a cloned library, an isothermal assembled library, or a process control sgRNA plasmid (escapee surrogate) as described in Examples 2-5 above. Electrocompetent *Saccharomyces cerevisiae* cells were prepared as follows: The afternoon before transformation was to occur, 10 mL of YPAD was inoculated with the selected *Saccharomyces cerevisiae* strain. The culture was shaken at 250 RPM and 30° C. overnight. The next day, 100 mL of YPAD was added to a 250-mL baffled flask and inoculated with the overnight culture (around 2 mL of overnight culture) until the OD600 reading reached 0.3+/−0.05. The culture was placed in the 30° C. incubator shaking at 250 RPM and allowed to grow for 4-5 hours, with the OD checked every hour. When the culture reached an OD600 of approximately 1.5, 50 mL volumes were poured into two 50-mL conical vials, then centrifuged at 4300 RPM for 2 minutes at room temperature. The supernatant was removed from all 50 ml conical tubes, while avoiding disturbing the cell pellet. 50 mL of a Lithium Acetate/Dithiothreitol solution was added to each conical tube and the pellet was gently resuspended. Both suspensions were transferred to a 250 mL flask and placed in the shaker; then shaken at 30° C. and 200 RPM for 30 minutes. After incubation was complete, the suspension was transferred to two 50-mL conical vials. The suspensions then were centrifuged at 4300 RPM for 3 minutes, then the supernatant was discarded.

Following the Lithium Acetate/Dithiothreitol treatment step, cold liquids were used and the cells were kept on ice until electroporation. 50 mL of 1 M sorbitol was added and the pellet was resuspended, then centrifuged at 4300 RPM, 3 minutes, 4° C., after which the supernatant was discarded. The 1M sorbitol wash was repeated twice for a total of three washes. 50 µL of 1 M sorbitol was added to one pellet, cells were resuspended, then transferred to the other tube to suspend the second pellet. The volume of the cell suspension was measured and brought to 1 mL with cold 1 M sorbitol. At this point the cells were electrocompetent and could be transformed with a cloned library, an isothermal assembled library, or process control sgRNA plasmids. In brief, a required number of 2-mm gap electroporation cuvettes were prepared by labeling the cuvettes and then chilling on ice. The appropriate plasmid—or DNA mixture—was added to each corresponding cuvette and placed back on ice. 100 µL of electrocompetent cells was transferred to each labelled cuvette, and each sample was electroporated using appropriate electroporator conditions. 900 µL of room temperature YPAD Sorbitol media was then added to each cuvette. The cell suspension was transferred to a 14 mL culture tube and then shaken at 30° C., 250 RPM for 3 hours. After a 3 hr recovery, 9 mL of YPAD containing the appropriate antibiotic, e.g., geneticin or Hygromycin B, was added.

At this point the transformed cells were processed in parallel in the solid wall device and the standard plating protocol (see Example 10 above), so as to compare "normalization" in the sold wall device with the standard benchtop process. Immediately before cells the cells were introduced to the permeable-bottom solid wall device, the 0.45 µM filter forming the bottom of the microwells was treated with a 0.1% TWEEN (polysorbate or, IUPAC, polyoxyethylene (20) sorbitan monolaurate) solution to effect proper spreading/distribution of the cells into the microwells of the solid wall device. The filters were placed into a Swinnex Filter Holder (47 mm, Millipore®, SX0004700) and 3 mL of a solution with 0.85% NaCl and 0.1% TWEEN (polysorbate or, IUPAC, polyoxyethylene (20) sorbitan monolaurate) was pulled through the solid wall device and filter through using a vacuum. Different TWEEN (polysorbate or, IUPAC, polyoxyethylene (20) sorbitan monolaurate) concentrations were evaluated, and it was determined that for a 47 mm diameter solid wall device with a 0.45 µM filter forming the bottom of the microwells, a pre-treatment of the solid wall device+filter with 0.1% TWEEN (polysorbate or, IUPAC, polyoxyethylene (20) sorbitan monolaurate) was preferred (data not shown).

After the 3-hour recovery in SOB, the transformed cells were diluted and a 3 mL volume of the diluted cells was processed through the TWEEN (polysorbate or, IUPAC, polyoxyethylene (20) sorbitan monolaurate)-treated solid wall device and filter, again using a vacuum. The number of successfully transformed cells was expected to be approximately 1.0E+06 to 1.0E+08, with the goal of loading approximately 10,000 transformed cells into the current 47 mm permeable-bottom solid wall device (having ~30,000 wells). Serial dilutions of $10^{-1}$, $10^{-2}$, and $10^{-3}$ were prepared, then 100 µL volumes of each of these dilutions were combined with 3 mL 0.85% NaCl, and the samples were loaded onto solid wall devices. Each permeable-bottom solid wall device was then removed from the Swinnex filter holder and transferred to an LB agar plate containing carbenicillin (100 µg/mL), chloramphenicol (25 µg/mL) and arabinose (1% final concentration). The solid wall devices were placed metal side "up," so that the permeable-bottom membrane was touching the surface of the agar such that the nutrients from the plate could travel up through the filter "bottom" of the wells. The solid wall devices on the YPD agar plates were incubated for 2-3 days at 30° C.

Figure 17A:
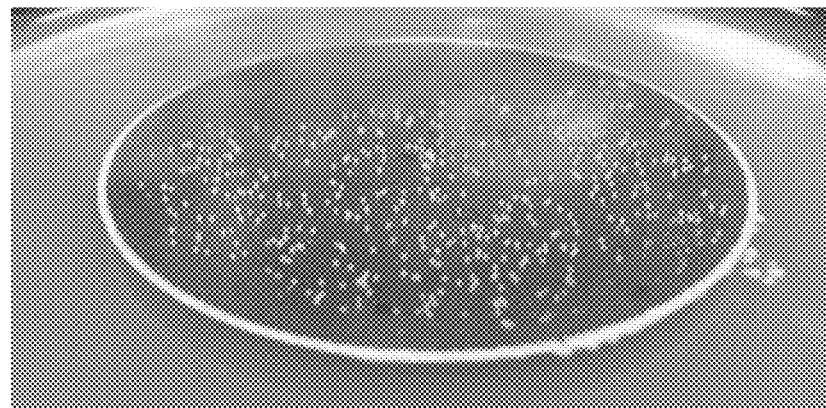
FIG. 17A is a photograph of a solid wall device with a permeable bottom on agar, on which yeast cells have been substantially singulated and grown into clonal colonies.
Figure 17B:
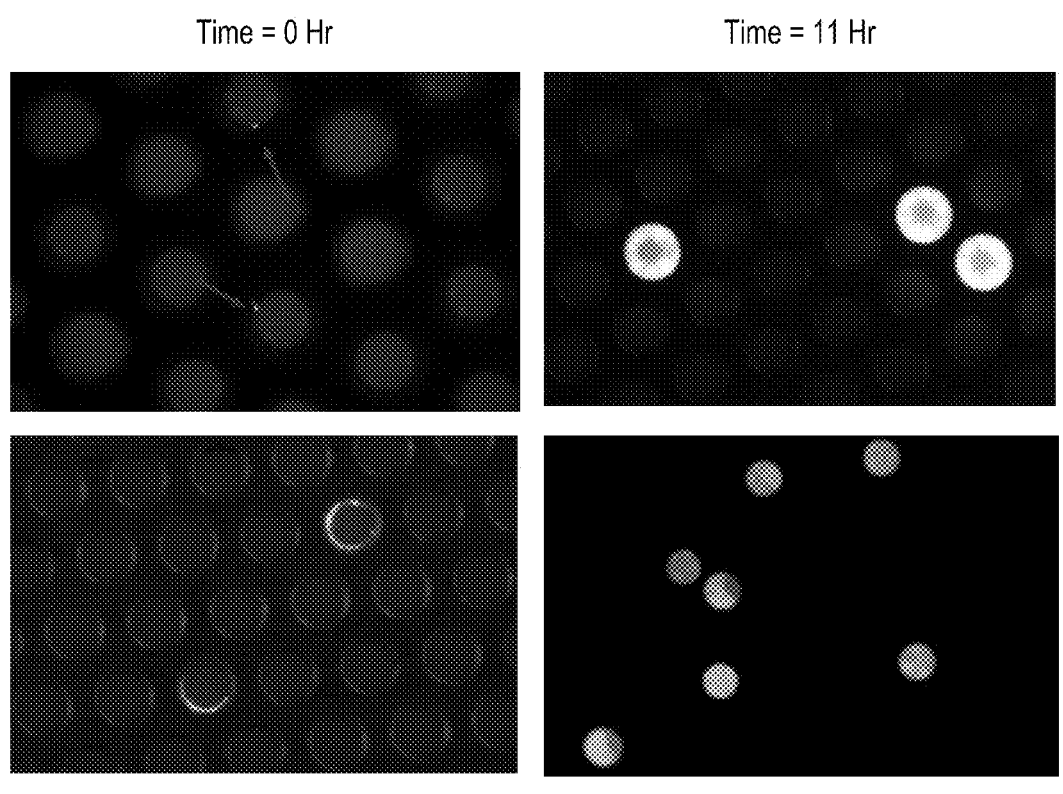
FIG. 17B presents photographs of yeast colony growth at various time points.

At the end of the incubation, the perforated disks and filters (still assembled) were removed from the supporting nutrient source (in this case an agar plate) and were photographed with a focused, "transilluminating" light source so that the number and distribution of loaded microwells on the solid wall device could be assessed (see FIGS. 17A and 17B). To retrieve cells from the permeable-bottom solid wall device, the filter was transferred to a labeled sterile 100 mm petri dish which contained 15 mL of sterile 0.85% NaCl, then the petri dish was placed in a shaking incubator set to 30° C./80 RPM to gently remove the cells from the filter and resuspend the cells in the 0.85% NaCl. The cells were allowed to shake for 15 minutes, then were transferred to a sterile tube, e.g., a 50 mL conical centrifuge tube. The OD600 of the cell suspension was measured; at this point the cells can be processed in different ways depending on the purpose of the study. For example, if an ADE2 stop codon mutagenesis library is used, successfully-edited cells should result in colonies with a red color phenotype when the resuspended cells are spread onto YPD agar plates and allowed to grow for 4-7 days. This phenotypic difference allows for a quantification of percentage of edited cells and the extent of normalization of edited and unedited cells.

Example 13: Singulation, Growth and Editing of *E. coli* in 200K SWIIN

Singleplex automated genomic editing using MAD7 nuclease, a library with 94 different edits in a single gene (yagP) and employing a 200K singulation device such as those exemplified in FIGS. 4F-4R was successfully performed. The engine vector used was substantially similar to that depicted in FIG. 11A (with MAD7 under the control of the pL inducible promoter), and the editing vector used was substantially similar to that depicted in FIG. 11B—including the editing cassette being under the control of the pL inducible promoter, and the λ Red recombineering system under control of the pBAD inducible promoter pBAD—with the exception that the editing cassette comprises the 94 yagP gene edits (donor DNAs) and the appropriate corresponding gRNAs. Two SWIIN workflows were compared, and further were benchmarked against the standard plating protocol (see Example 7). The SWIIN protocols different from one another that in one set of replicates LB medium containing arabinose was used to distribute the cells in the SWIIN (arabinose was used to induce the λ Red recombineering system (which allows for repair of double-strand breaks in *E. coli* that are created during editing), and in the other set of replicates SOB medium without arabinose was used to distribute the cells in the SWIIN and for initial growth, with medium exchange performed to replace the SOB medium without arabinose with SOB medium with arabinose. Approximately 70K cells were loaded into the 200K SWIIN.

Figure 18:
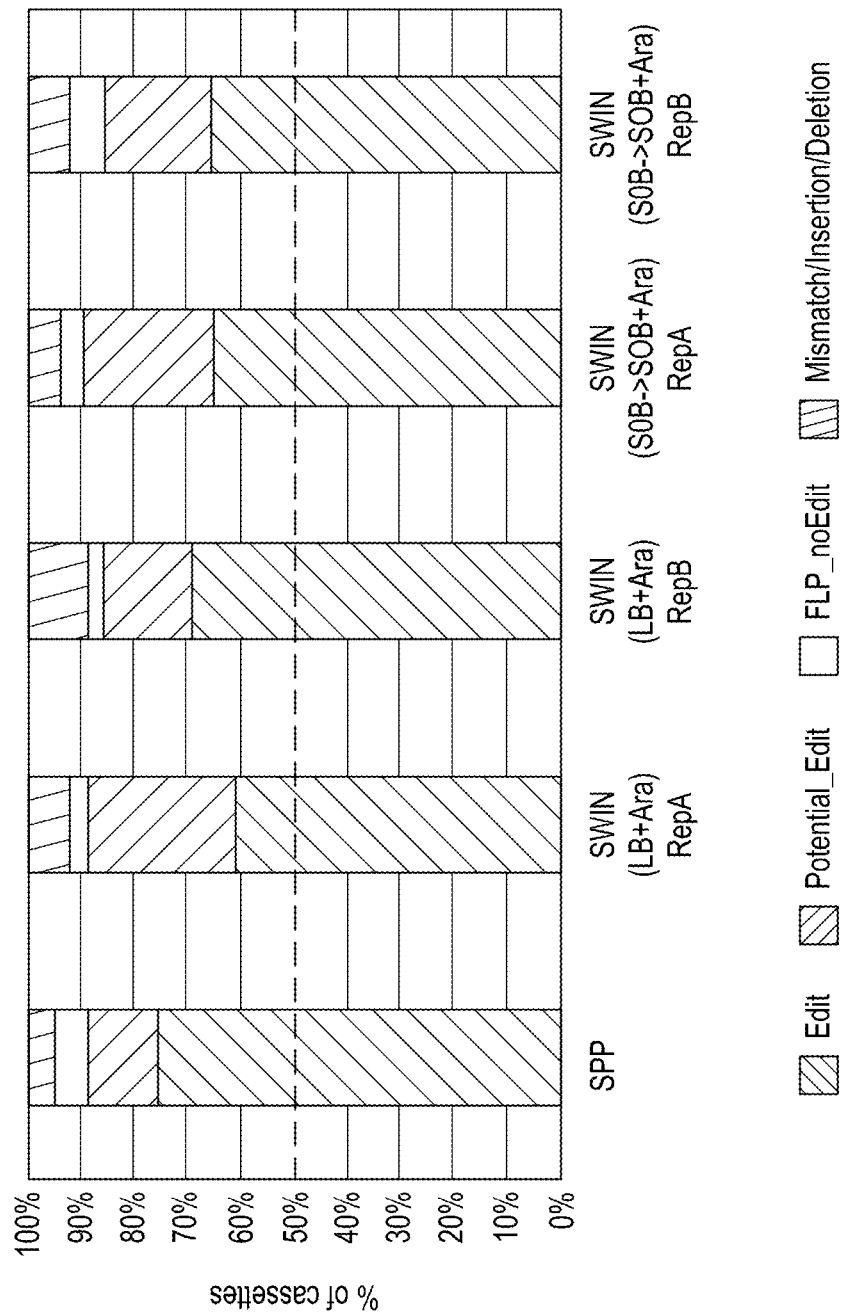
FIG. 18 is a graph comparing the percentage of editing obtained for a standard plating protocol (SPP), and replicates samples using two different conditions in a singulation in a solid wall isolation, induction, and normalization device (SWIIN): the first with LB+arabinose; and the second with SOB followed by SOB+arabinose.

In all protocols (standard plating, LB-SWIIN, and SOB-SWIIN), the cells were allowed to grow at 30° C. for 9 hours and editing was induced by raising the temperature to 42° C. for 2.5 hours, then the temperature was returned to 30° C. and the cells were grown overnight. The results of this experiment are shown in FIG. 18 and in Table 4 below. Note that similar editing performance was observed with the four replicates of the two SWIIN workflows, indicating that the performance of SWIIN plating with and without arabinose in the initial medium is similar. Editing percentage in the standard plating protocol was approximately 77%, in bulk liquid was approximately 67%, and for the SWIIN replicates ranged from approximately 63% to 71%. Note that the percentage of unique edit cassettes divided by the total number of edit cassettes was similar for each protocol.

TABLE 4

|  | Standard Plating | SWIIN LB/Ara Rep. A | SWIIN LB/Ara Rep. B | SWIIN SOB then SOB/Ara Rep. A | SWIIN SOB then SOB/Ara Rep. B |
|---|---|---|---|---|---|
| 40006 edit calls/identified wells | 0.777 | 0.633 | 0.719 | 0.663 | 0.695 |
| Unique edit cassettes/total edit cassettes | 0.49 | 0.49 | 0.43 | 0.50 | 0.51 |

Example 14: Fully-Automated Singleplex RGN-Directed Editing Run

Singleplex automated genomic editing using MAD7 nuclease was successfully performed with an automated multi-module instrument such as that shown in FIGS. 5A-5D. See U.S. Pat. No. 9,982,279, issued 29 May 2018 and Ser. No. 10/240,167, issued 9 Apr. 2019.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example 15: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

TABLE 5

| | | | | | | | | | | | | SV9- | SV10- | |
| Description of step | Step | Manifold/arm | pump | SV1-PR1 | SV2-PR2 | SV3-RR1 | SV4-RR2 | SV5-PR3 | SV6-PR4 | SV7-PR5 | SV8-RR4 | PUMP "P" | PUMP "V" | psi |
|---|---|---|---|---|---|---|---|---|---|---|---|---|---|---|
| Valve Status and Pressure | | | | | | | | | | | | | | |
| Load SWIIN module on instrument | 1 | open | 0 | 0 | 0 | 0 | 0 | 0 | 0 | 0 | 0 | 0 | 0 | 0 |
| Load 7.5 ml of cell suspension into RR1 and RR3 | 2 | open | 0 | 0 | 0 | 0 | 0 | 0 | 0 | 0 | 0 | 0 | 0 | 0 |
| Fill retentate layer with cell suspension | 3 | closed | 1 | 0 | 0 | 1 | 0 | 0 | 0 | 1 | 0 | 0 | 0 | 0.5 |
| Let cells settle to the vicinity of the perforated sheet and into microwells | 4 | closed | 0 | 0 | 0 | 0 | 0 | 0 | 0 | 0 | 0 | 0 | 0 | 0 |
| Drive medium in the retentate layer across membrane | 5 | closed | 1 | 1 | 1 | 0 | 0 | 1 | 1 | 0 | 0 | 1 | 1 | −5 |
| Open manifold | 6 | open | 0 | 0 | 0 | 0 | 0 | 0 | 0 | 0 | 0 | 0 | 0 | 0 |
| Remove excess medium from PRs with pipettor | 7 | open | 0 | 0 | 0 | 0 | 0 | 0 | 0 | 0 | 0 | 0 | 0 | 0 |
| Load 7.5 ml growth medium into PR1 and PR3 | 8 | open | 0 | 0 | 0 | 0 | 0 | 0 | 0 | 0 | 0 | 0 | 0 | 0 |
| Close manifold | 9 | closed | 0 | 0 | 0 | 0 | 0 | 0 | 0 | 0 | 0 | 0 | 0 | 0 |
| Flush permeate layer with growth medium from PR1 to PR2 and PR3 | 10 | closed | 0 | 0 | 0 | 0 | 0 | 0 | 0 | 0 | 0 | 0 | 0 | 0 |
| Open manifold | 11 | open | 0 | 0 | 0 | 0 | 0 | 0 | 0 | 0 | 0 | 0 | 0 | 0 |
| Remove excess medium from PRs with pipettor | 12 | open | 0 | 0 | 0 | 0 | 0 | 0 | 0 | 1 | 0 | 0 | 0 | 0.5 |
| Load 7.5 ml growth medium into PR1 and PR3 | 13 | open | 0 | 0 | 0 | 0 | 0 | 0 | 0 | 0 | 0 | 0 | 0 | 0 |
| Close manifold | 14 | closed | 0 | 0 | 0 | 0 | 0 | 0 | 1 | 0 | 0 | 1 | 1 | −5 |
| Flush permeate layer with growth medium from PR1 to PR2 and PR3 and PR4 via gravity | 15 | closed | 0 | 0 | 0 | 0 | 0 | 0 | 0 | 0 | 0 | 0 | 0 | 0 |
| Open manifold | 16 | open | 0 | 0 | 0 | 0 | 0 | 0 | 0 | 0 | 0 | 0 | 0 | 0 |
| Remove excess medium from PRs with pipettor | 17 | open | 0 | 0 | 0 | 0 | 0 | 0 | 0 | 0 | 0 | 0 | 0 | 0 |
| Close manifold | 18 | closed | 0 | 0 | 0 | 0 | 0 | 0 | 0 | 0 | 0 | 0 | 0 | 0 |
| Incubate at 30° C. for 4.5 hours | 19 | closed | 1 | 0 | 0 | 1 | 0 | 0 | 0 | 1 | 0 | 0 | 0 | 0.25 |
| Open manifold | 20 | open | 0 | 0 | 0 | 0 | 0 | 0 | 0 | 0 | 0 | 0 | 0 | 0 |

TABLE 5-continued

Valve Status and Pressure

| Description of step | Step | Mani-fold/arm | pump | SV1-PR1 | SV2-PR2 | SV3-RR1 | SV4-RR2 | SV5-PR3 | SV6-PR4 | SV7-PR5 | SV8-RR4 | SV9-PUMP "P" | SV10-PUMP "V" | psi |
|---|---|---|---|---|---|---|---|---|---|---|---|---|---|---|
| Load 7.5 ml growth medium into PR1 and PR3 | 21 | open | 0 | 0 | 0 | 0 | 0 | 0 | 0 | 0 | 0 | 0 | 0 | 0 |
| Close manifold | 22 | closed | 0 | 0 | 0 | 0 | 0 | 0 | 0 | 0 | 0 | 0 | 0 | 0 |
| Incubate at 30° C. for 4.5 hours | 23 | closed | 1 | 0 | 0 | 1 | 0 | 0 | 0 | 1 | 0 | 0 | 0 | 0.25 |
| Induce at 42° C. for 2 hours | 24 | closed | 1 | 0 | 0 | 1 | 0 | 0 | 0 | 1 | 0 | 0 | 0 | 0.25 |
| Incubate at 30° C. for 9 hours | 25 | closed | 1 | 0 | 0 | 1 | 0 | 0 | 0 | 1 | 0 | 0 | 0 | 0.25 |
| Aspirate cells into RR1 and RR2 | 26 | closed | 1 | 0 | 0 | 1 | 0 | 0 | 1 | 0 | 0 | 1 | 1 | −5 |
| Open manifold | 27 | open | 1 | 0 | 0 | 0 | 0 | 0 | 0 | 0 | 0 | 0 | 0 | 0 |
| Recover cells from RR1 and RR3 with pipettor | 28 | open | 1 | 0 | 0 | 0 | 0 | 0 | 0 | 0 | 0 | 0 | 0 | 0 |
| Remove remaining medium from PR1 and PR2 and PR3 and PR4 | 29 | open | 1 | 0 | 0 | 0 | 0 | 0 | 0 | 0 | 0 | 0 | 0 | 0 |

TABLE 6

Reservoir Volumes

| Description of step | Step | RR1 and RR3 Initial/Final | RR2 and RR4 Initial/Final | PR1 and PR3 Initian/Final | PR2 and PR4 Initial/Final | Temperature (° C.) |
|---|---|---|---|---|---|---|
| Load SWIIN module on instrument | 1 | 0/0 | 0/0 | 0/0 | 0/0 | 25 |
| Load 7.5 ml of cell suspension into RR1 and RR3 | 2 | 0/7.5 | TBD/TBD | 0/0 | 0/0 | 25 |
| Fill retentate layer with cell suspension | 3 | 7.5/0 | TBD/TBD | 0/0 | 0/0 | 25 |
| Let cells settle to the vicinity of the perforated sheet and into microwells | 4 | 0/0 | TBD/TBD | 0/0 | 0/0 | 4 |
| Drive medium in the retentate layer across membrane | 5 | 0/0 | TBD/TBD | 0/1 | 0/1 | 30 |
| Open manifold | 6 | 0/0 | TBD/TBD | 1/1 | 1/1 | 30 |
| Remove excess medium from PRs with pipettor | 7 | 0/0 | TBD/TBD | 1/0 | 1/0 | 30 |
| Load 7.5 ml growth medium into PR1 and PR3 | 8 | 0/0 | TBD/TBD | 0/7.5 | 0/0 | 30 |
| Close manifold | 9 | 0/0 | TBD/TBD | 7.5/7.5 | 0/0 | 30 |
| Flush permeate layer with growth medium from PR1 to PR2 and PR3 | 10 | 0/0 | TBD/TBD | 7.5/3.75 | 0/3.75 | 30 |
| Open manifold | 11 | 0/0 | TBD/TBD | 3.75/3.75 | 3.75/3.75 | 30 |
| Remove excess medium from PRs with pipettor | 12 | 0/0 | TBD/TBD | 3.75/0 | 3.75/0 | 30 |
| Load 7.5 ml growth medium into PR1 and PR3 | 13 | 0/0 | TBD/TBD | 0/7.5 | 0/0 | 30 |
| Close manifold | 14 | 0/0 | TBD/TBD | 7.5/7.5 | 0/0 | 30 |
| Flush permeate layer with growth medium from PR1 to PR2 and PR3 to PR4 via gravity | 15 | 0/0 | TBD/TBD | 7.5/3.75 | 0/3.75 | 30 |
| Open manifold | 16 | 0/0 | TBD/TBD | 3.7/3.75 | 3.75/3.75 | 30 |
| Remove excess medium from PRs with pipettor | 17 | 0/0 | TBD/TBD | 3.75/0 | 3.75/0 | 30 |
| Close manifold | 18 | 0/0 | TBD/TBD | 0/0 | 0/0 | 30 |
| Incubate at 30° C. for 4.5 hours | 19 | 0/0 | TBD/TBD | 0/0 | 0/0 | 30 |
| Open manifold | 20 | 0/0 | TBD/TBD | 0/0 | 0/0 | 30 |
| Load 7.5 ml growth medium into PR1 and PR3 | 21 | 0/0 | TBD/TBD | 0/7.5 | 0/0 | 30 |

TABLE 6-continued

Reservoir Volumes

| Description of step | Step | RR1 and RR3 Initial/Final | RR2 and RR4 Initial/Final | PR1 and PR3 Initian/Final | PR2 and PR4 Initial/Final | Temperature (° C.) |
|---|---|---|---|---|---|---|
| Close manifold | 22 | 0/0 | TBD/TBD | 7.5/3.75 | 0/3.75 | 30 |
| Incubate at 30° C. for 4.5 hours | 23 | 0/0 | TBD/TBD | 3.75/3.75 | 3.75/3.75 | 30 |
| Induce at 42° C. for 2 hours | 24 | 0/0 | TBD/TBD | 3.75/3.75 | 3.75/3.75 | 42 |
| Incubate at 30° C. for 9 hours | 25 | 0/0 | TBD/TBD | 3.75/3.75 | 3.75/3.75 | 30 |
| Aspirate cells into RR1 and RR2 | 26 | 0/5 | TBD/TBD | 3.75/1.25 | 3.75/1.25 | RT |
| Open manifold | 27 | 5/5 | TBD/TBD | 1.25/1.25 | 1.25/1.25 | RT |
| Recover cells from RR1 and RR3 with pipettor | 28 | 5/0 | TBD/TBD | 1.25/1.25 | 1.25/1.25 | RT |
| Remove remaining medium from P1 | 29 | 0/0 | TBD/TBD | 1.25/0 | 1.25/0 | RT |

We claim:

1. An automated multi-module cell editing instrument for creating edited cell libraries comprising:
a growth module;
a transformation module; and
a singulation or substantial singulation, growth, induction of editing, and normalization or cherry-picking (SWIIN) module, wherein the SWIIN module comprises a singulation assembly, wherein the singulation assembly comprises:
a retentate member comprising an upper surface and a lower surface, wherein the retentate member comprises at least one retentate distribution channel which traverses the retentate member from its upper surface to its lower surface; wherein the lower surface of the retentate member comprises a first portion of a serpentine channel; wherein the retentate member further comprises one or more retentate member ports configured to supply cells and fluid to and remove cells and fluid from the retentate member; and wherein the retentate member ports are fluidically-connected to the at least one retentate distribution channel and the first portion of the serpentine channel;
the permeate member comprising the upper surface and a lower surface, wherein the permeate member comprises at least one permeate distribution channel which traverses the permeate member from its lower surface to its upper surface; wherein the upper surface of the permeate member comprises a second portion of the serpentine channel; wherein the permeate member further comprises one or more permeate member ports configured to supply fluid to and remove fluid from the permeate member; wherein the permeate member ports are fluidically-connected to the second portion of the serpentine channel and permeate flow directors; and wherein the first and second portions of the serpentine channel mate to create the serpentine channel;
a gasket disposed between the retentate member and the permeate member;
means to couple the retentate member and permeate member;
a reservoir assembly comprising at least two reservoirs wherein
a first reservoir is 1) fluidically-coupled to at least a first reservoir access aperture into which fluids and/or cells flow from outside the SWIIN module into the first reservoir, 2) fluidically-coupled to a reservoir/channel port from which fluids and/or cells flow from the first reservoir into the one or more retentate member ports; and 3) pneumatically-coupled via a first pneumatic access aperture to a pressure source;
a second reservoir is 1) fluidically-coupled to at least a second reservoir access aperture into which fluids flow from outside the SWIIN module into the second reservoir, 2) fluidically-coupled to a reservoir/channel port from which fluids and/or cells flow from the second reservoir into the one or more permeate member ports; and 3) pneumatically-coupled via a second pneumatic access aperture to a pressure source; and
a SWIIN cover.

2. The automated multi-module cell editing instrument for creating edited cell libraries of claim 1, wherein the SWIIN module further comprises:
two additional reservoirs wherein
a third reservoir is 1) fluidically-coupled to a third reservoir access aperture into which fluids and/or cells flow from outside the SWIIN module into the third reservoir, 2) fluidically-coupled to a reservoir/channel port from which fluids and/or cells flow from the third reservoir into the one or more retentate member ports; and 3) pneumatically-coupled via a third pneumatic access aperture to a pressure source; and
a fourth reservoir is 1) fluidically-coupled to a fourth reservoir access aperture into which fluids and/or cells flow from outside the SWIIN module into the fourth reservoir, 2) fluidically-coupled to a reservoir/channel port from which fluids and/or cells flow from the reservoir into the one or more permeate member ports; and 3) pneumatically-coupled via a fourth pneumatic access aperture to a pressure source.

3. The automated multi-module cell editing instrument for creating edited cell libraries of claim 1, wherein the means to couple the retentate member and perforated member is a pressure sensitive adhesive.

4. The automated multi-module cell editing instrument for creating edited cell libraries of claim 1, wherein the retentate and permeate members of the singulation assembly are from 75 mm to 350 mm in length, from 50 mm to 250 mm in width, and from 2 mm to 15 mm in thickness.

5. The automated multi-module cell editing instrument for creating edited cell libraries of claim 1, wherein a volume of the singulation assembly is from 5 mL to 100 mL.

6. The automated multi-module cell editing instrument for creating edited cell libraries of claim 5, wherein the volume of the singulation assembly is from 10 mL to 40 mL.

7. The automated multi-module cell editing instrument for creating edited cell libraries of claim 1, further comprising a cell concentration module.

8. The automated multi-module cell editing instrument for creating edited cell libraries of claim 1, wherein the transformation module comprises a flow-through electroporation device.

9. The automated multi-module cell editing instrument for creating edited cell libraries of claim 1, wherein the edited cell library is a promoter or terminator swap library.

10. The automated multi-module cell editing instrument for creating edited cell libraries of claim 1, wherein the edited cell library created is a saturation mutagenesis library.

11. An automated multi-module cell editing instrument for creating edited cell libraries comprising:
   a growth module;
   a transformation module comprising a flow-through electroporation device; and
   a singulation or substantial singulation, growth, induction of editing, and normalization or cherry-picking (SWIIN) module, wherein the SWIIN module comprises a singulation assembly, wherein the singulation assembly comprises:
      a retentate member comprising an upper surface and a lower surface, wherein the retentate member comprises at least one retentate distribution channel which traverses the retentate member from its upper surface to its lower surface; wherein the lower surface of the retentate member comprises a first portion of a serpentine channel; wherein the retentate member further comprises one or more retentate member ports configured to supply cells and fluid to and remove cells and fluid from the retentate member; and wherein the retentate member ports are fluidically-connected to the at least one retentate distribution channel and the first portion of the serpentine channel;
      the permeate member comprising the upper surface and a lower surface, wherein the permeate member comprises at least one permeate distribution channel which traverses the permeate member from its lower surface to its upper surface; wherein the upper surface of the permeate member comprises a second portion of the serpentine channel; wherein the permeate member further comprises one or more permeate member ports configured to supply fluid to and remove fluid from the permeate member; wherein the permeate member ports are fluidically-connected to the at least one permeate distribution channel and the second portion of the serpentine channel; and wherein the first and second portions of the serpentine channel mate to create the serpentine channel;
      a gasket disposed between the retentate member and the permeate member;
      means to couple the retentate member and permeate member;
      a reservoir assembly comprising at least two reservoirs wherein
         a first reservoir is 1) fluidically-coupled to at least a first reservoir access aperture into which fluids and/or cells flow from outside the SWIIN module into the first reservoir, 2) fluidically-coupled to a reservoir/channel port from which fluids and/or cells flow from the first reservoir into the one or more retentate member ports; and 3) pneumatically-coupled via a first pneumatic access aperture to a pressure source;
         a second reservoir is 1) fluidically-coupled to at least a second reservoir access aperture into which fluids flow from outside the SWIIN module into the second reservoir, 2) fluidically-coupled to a reservoir/channel port from which fluids and/or cells flow from the second reservoir into the one or more permeate member ports; and 3) pneumatically-coupled via a second pneumatic access aperture to a pressure source; and
      a SWIIN cover.

12. The automated multi-module cell editing instrument for creating edited cell libraries of claim 11, wherein the SWIIN module further comprises:
   two additional reservoirs wherein
      a third reservoir is 1) fluidically-coupled to a third reservoir access aperture into which fluids and/or cells flow from outside the SWIIN module into the third reservoir, 2) fluidically-coupled to a reservoir/channel port from which fluids and/or cells flow from the third reservoir into the one or more retentate member ports; and 3) pneumatically-coupled via a third pneumatic access aperture to a pressure source; and
      a fourth reservoir is 1) fluidically-coupled to a fourth reservoir access aperture into which fluids and/or cells flow from outside the SWIIN module into the fourth reservoir, 2) fluidically-coupled to a reservoir/channel port from which fluids and/or cells flow from the reservoir into the one or more permeate member ports; and 3) pneumatically-coupled via a fourth pneumatic access aperture to a pressure source.

13. The automated multi-module cell editing instrument for creating edited cell libraries of claim 1, wherein the means to couple the retentate member and perforated member is a pressure sensitive adhesive.

14. The automated multi-module cell editing instrument for creating edited cell libraries of claim 1, wherein the retentate and permeate members of the singulation assembly are from 75 mm to 350 mm in length, from 50 mm to 250 mm in width, and from 2 mm to 15 mm in thickness.

15. The automated multi-module cell editing instrument for creating edited cell libraries of claim 1, further comprising a cell concentration device.

16. The automated multi-module cell editing instrument for creating edited cell libraries of claim 11, wherein the cell library created comprises at least 5,000,000 edited cells.

17. The automated multi-module cell editing instrument for creating edited cell libraries of claim 11, wherein a liquid handling device performs transfer steps between modules.

18. The automated multi-module cell editing instrument for creating edited cell libraries of claim 17, wherein the liquid handling device is controlled by a processor.

* * * * *